(12) United States Patent
Herrmann et al.

(10) Patent No.: US 6,642,369 B1
(45) Date of Patent: Nov. 4, 2003

(54) NUCLEIC ACIDS INVOLVED IN THE RESPONDER PHENOTYPE AND APPLICATIONS THEREOF

(75) Inventors: Bernhard Herrmann, Freiburg (DE); Birgit Koschorz, Freiburg (DE); Andreas Kispert, Freiburg (DE)

(73) Assignee: Max-Planck-Gesellschaft zur Forderung der Wissenschaften e. V., Berlin (DE)

( * ) Notice: Subject to any disclaimer, the term of this patent is extended or adjusted under 35 U.S.C. 154(b) by 0 days.

(21) Appl. No.: 09/554,726

(22) PCT Filed: Nov. 18, 1998

(86) PCT No.: PCT/EP98/07395
§ 371 (c)(1),
(2), (4) Date: Jul. 26, 2000

(87) PCT Pub. No.: WO99/25815
PCT Pub. Date: May 27, 1999

(30) Foreign Application Priority Data

Nov. 18, 1997 (EP) .............................................. 97120190
Feb. 3, 1998 (EP) .............................................. 98103596

(51) Int. Cl.[7] .......................... C12N 15/11; C12N 15/02; C12N 15/09; C12N 15/74; C12P 21/06; A01N 65/00

(52) U.S. Cl. .................. 536/23.1; 435/320.1; 435/69.1; 435/325; 435/455; 424/93.1

(58) Field of Search ...................... 536/23.1; 435/320.1, 435/69.1, 325, 455; 424/93.1

(56) References Cited

FOREIGN PATENT DOCUMENTS

| EP | 291 533 B1 | 11/1988 |
|---|---|---|
| EP | 321 201 B1 | 6/1989 |
| EP | 321 201 A3 | 6/1989 |
| EP | 321 201 A2 | 6/1989 |
| EP | 360 257 A2 | 3/1990 |
| EP | 360 257 A3 | 3/1990 |
| EP | 360 257 B1 | 3/1990 |
| WO | WO 88/04300 | 6/1988 |
| WO | WO 93/06859 | 4/1993 |

OTHER PUBLICATIONS

JU Bowie et al., Science, "Deciphering the Message in Protein Sequences:Tolerance to Amino Acid Substitutions," Mar. 1990, vol. 247, pp. 1306–1310.*
JC Schimenti, Mammalian Genome, "ORFless, intronless, and mutant transcription units in the mouse t complex responder (Tcr) Locus, " 1999, 10,969–976.*
MF Lyon, American Naturalist, "The Genetic Basis of Transmission–Ratio Distortion and Male Sterility Due to the t Complex," Mar. 1991, vol. 137, No. 3, pp. 349–358.*
Encyclopedia Britannica Online, "chemical compound." Jan. 2001.*

Albanesi et al., "A cell– and developmental stage–specific promoter drives the expression of a truncated c–kit protein during mouse spermatid elongation," *Development*. Apr. 1996;122(4):1291–302.
Auffray et al., "Purification of mouse immunoglobulin heavy–chain messenger RNAs from total myeloma tumor RNA," *Eur J Biochem*. Jun. 1980;107(2):303–14.
Ausubel et al., eds., *Current Protocols in Molecular Biology*, vols. 1–4, John Wiley & Sons, Inc., New York, NY, updated 1987–1998; title page, publisher's page and table of contents only (12 pages).
Beal et al., "Second structural motif for recognition of DNA by oligonucleotide–directed triple–helix formation," *Science*. Mar 15, 1991;251(4999):1360–3.
Bennett et al., "Genetic analysis of transmission ratio distortion by t–haplotypes in the mouse," *Genet Res*. Feb. 1983;41(1):29–45.
Bullard et al., "Functional analysis of a t complex responder locus transgene in mice," *Mamm Genome*. 1992;3(10):579–87.
Cebra–Thomas et al., "Allele– and haploid–specific product generated by alternative splicing from a mouse t complex responder locus candidate," *Nature*. Jan. 17, 1991; 349(6306):239–41.
Church et al., "Genomic sequencing," *Proc Natl Acad Sci U S A*. Apr. 1984; 81(7):1991–5.
Cooney et al., "Site–specific oligonucleotide binding represses transcription of the human c–myc gene in vitro," *Science*. Jul. 22, 1988;241(4864):456–9.
Ehrich et al., "A family of cosmid vectors with the multi–copy R6K replication origin," *Gene*. 1987;57(2–3):229–37.
Ewulonu et al., "Targeted mutagenesis of a candidate t complex responder gene in mouse t haplotypes does not eliminate transmssion ratio distortion," *Genetics*. Oct. 1996;144(2):785–92.
Faisst et al., "Compilation of vertebrate–encoded transcription factors," *Nucleic Acids Res*. Jan. 11, 1992;20(1):3–26.

(List continued on next page.)

Primary Examiner—Anne M. Wehbe'
Assistant Examiner—Janice Li
(74) Attorney, Agent, or Firm—Mueting, Raasch & Gebhardt, P. A.

(57) ABSTRACT

The present invention relates to nucleic acid molecules encoding expression products involved in the Responder function, which contributes to the phenomenon of transmission ratio distortion. The present invention also relates to regulatory regions of the genes corresponding to the nucleic acid molecules. The present invention further relates to recombinant DNA molecules and vectors comprising the nucleic acid molecules and/or regulatory regions as well as to host cells transformed therewith. Additionally, the present invention relates to transgenic animals, comprising the nucleic acid molecules, recombinant DNA molecules or vectors stably integrated into their genome. The various embodiments of the invention have a significant impact on breeding strategies by allowing for the specific selection of genetic traits and in particular of sex. Further, the present invention finds applications in the development of contraceptive.

9 Claims, 37 Drawing Sheets

OTHER PUBLICATIONS

Figure 1A:
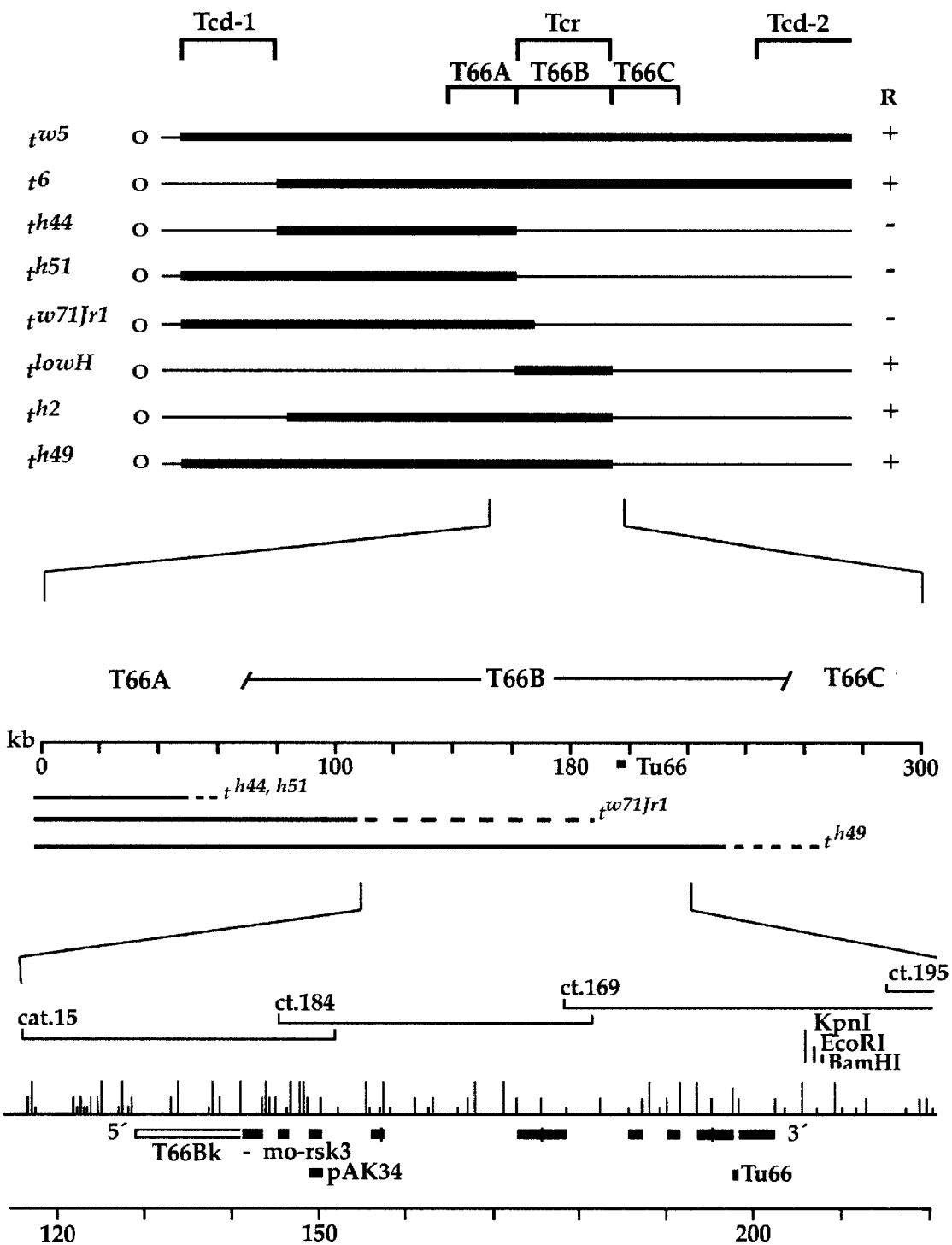

Fox et al., "Molecular probes define different regions of the mouse t complex," *Cell.* Jan. 1985;40(1):63–9.

Friedrich et al., "Promoter traps in embryonic stem cells: a genetic screen to identify and mutate developmental genes in mice," *Genes Dev.* Sep. 1991;5(9):1513–23.

Ghattas et al., "The encephalomyocarditis virus internal ribosome entry site allows efficient coexpression of two genes from a recombinant provirus in cultured cells and in embryos," *Mol Cell Biol.* Dec. 1991;11(12):5848–59.

Gossen et al., "Tight control of gene expression in mammalian cells by tetracycline–responsive promoters," *Proc Natl Acad Sci U S A.* Jun. 15, 1992;89(12):5547–51.

Gossen et al., "Control of gene activity in higher eukaryotic cells by prokaryotic regulatory elements," *Trends Biotechnol.* Feb. 1994;12(2):58–62.

Hames et al., eds., *Nucleic Acid Hybridisation: a Practical Approach*; IRL Press Limited, Oxford, England; title page, publisher's page and table of contents only (8 pgs) 1985.

Herrmann et al., "Genetic analysis of the proximal portion of the mouse t complex: evidence for a second inversion within t haplotypes," *Cell.* Feb. 14, 1986;44(3):469–76.

Herrmann et al., "Isolation of genomic DNA," *Methods Enzymol.* 1987;152:180–3.

Herrmann et al., "A large inverted duplication allows homologous recombination between chromosomes heterozygous for the proximal t complex inversion," *Cell.* Mar. 13, 1987;48(5):813–25.

Howard et al., "Transcription of testicular angiotensin–converting enzyme (ACE) is initiated within the 12th intron of the somatic ACE gene," *Mol Cell Biol.* Aug. 1990;10(8):4294–302.

Huang et al., "The simian virus 40 small–t intron, present in many common expression vectors, leads to aberrant splicing," *Mol Cell Biol.* Apr. 1990;10(4):1805–10.

Kay et al., "CD24, a signal transducer modulating B cell activation responses, is a very short peptide with a glycosyl phosphatidylinositol membrane anchor," *J Immunol.* Aug. 15, 1991;147(4):1412–6.

Langford et al., "Transgenic mice demonstrate a testis–specific promoter for angiotensin–converting enzyme," *J Biol Chem.* Aug. 25, 1991;266(24):15559–62.

Lee et al., "Complexes formed by (pyrimidine)$_n$ · (purine)$_n$ DNAs on lowering the pH are three–stranded," *Nucleic Acids Res.* Jul. 11, 1979;6(9):3073–91.

Lyon, "Transmission ratio distortion in mouse t–haplotypes is due to multiple distorter genes acting on a responder locus," *Cell.* Jun. 1984;37(2):621–8.

Lyon, "Male sterility of the mouse t–complex is due to homozygosity of the distorter genes," *Cell.* Jan. 31, 1986;44(2):357–63.

Melani et al., "Inhibition of proliferation by c–myb antisense oligodeoxynucleotides in colon adenocarcinoma cell lines that express c–myb," *Cancer Res.* Jun. 1, 1991; 51(11):2897–901.

Nadeau et al., "Genetic evidence for two t complex tail interaction (tct) loci in t haplotypes," *Genetics.* Aug. 1989;122(4):895–903.

Nagy et al., "Derivation of completely cell cultured–derived mice from early–passage embryonic stem cells," *Proc Natl Acad Sci U S A.* Sep. 15, 1993;90(18):8424–8.

Peschon et al., "Spermatid–specific expression of protamine 1 in transgenic mice," *Proc Natl Acad Sci U S A.* Aug. 1987;84(15):5316–9.

Rackwitz et al., "Analysis of cosmids using linearization by phage lambda terminase," *Gene.* 1985;40(2–3):259–66.

Rossi et al., "A novel c–kit transcript, potentially encoding a truncated receptor, originates within a kit gene intron in mouse spermatids," *Dev Biol.* Jul. 1992; 152(1):203–7.

Rugh, *The Mouse, Its Reproduction and Development* (Oxford University Press, Oxford, England); title page, publisher's page and table of contents only (6 pages) 1990.

Sambrook et al., *Molecular Cloning: A Laboratory Manual, Books 1–3*, Cold Spring Harbor Laboratory Press, Cold Spring Harbor, NY, 1989; title page, publisher's page and table of contents only (30 pgs).

Schimenti et al., "An unstable family of large DNA elements in the center of the mouse t complex," *J Mol Biol.* Apr. 20, 1987;194(4):583–94.

Schimenti et al., "A candidate gene family for the mouse t complex responder (Tcr) locus responsible for haploid effects on sperm function," *Cell.* Oct. 7, 1988;55(1):71–8.

Schimenti et al., "Rapid identification of mouse t–haplotypes by PCR polymorphism (PCRP)," *Mouse Genome* 1990:87:108.

Silver et al., "Five of the nine genetically defined regions of mouse t haplotypes are involved in transmission ratio distortion," *Genet Res.* Feb. 1987;49(1):51–6.

Steinecke et al., "Ribozymes," *Methods Cell Biol.* 1995;50:449–60.

Wassarman et al., eds., "Guide to Techniques in Mouse Development," *Methods Enzymol.* 225:title page, publisher page, table of contents, and pages xxxiii–xxxviii only (9 pages) 1993.

Willison et al., "Mammalian spermatogenic gene expression," *Trends Genet.* 1987; 3:351–355.

Wilmut et al., "Viable offspring derived from fetal and adult mammalian cells," *Nature.* Feb. 27, 1997;385(6619):810–3.

Zlokarnik et al., "Quantitation of transcription and clonal selection of single living cells with β–lactamase as reporter," *Science.* Jan. 2, 1998;279(5347):84–8.

D. Bullard et al., "Molecular Cloning and Genetic Mapping of the t complex repsonder Candidate Gene Family," *Genetics*, 124:957–966 (1990).

G. Drewes et al., "MARK, a Novel Family of Protein Kinases That Phosphorylate Microtubule–Associated Proteins and Trigger Microtubule Disruption," *Cell*, 89:297–308 (1997).

U. Ewulonu et al., "Promoter Mapping of the Mouse Tcp–10b$^t$ Gene in Transgenic Mice Identifies Essential Male Germ Cell Regulatory Sequences," *Molecular Reprod. Dev.*, 43:290–297 (1996).

L. Fraser et al., "New insights into the t–complex and control of sperm function," *BioEssays*, 21:304–312 (1999).

L. Rosen et al., "Molecular Cloning of the t complex responder Genetic Locus," *Genomics*, 8:134–140 (1990).

L. Snyder et al., "Distortion of transmission ratio by candidate t complex responder locus transgene," *Mammalian Genome*, 3:588–596 (1992).

Y. Zhao et al., "RSK3 Encodes a Novel pp90$^{rsk}$ Isoform with a Unique N–Terminal Sequences: Growth Factor–Stimulated Kinase Function and Nuclear Translocation," *Mol. Cell. Biol.*, 15:4353–4363 (1995).

\* cited by examiner

Sequence of pCRth2-161/144

```
     161 ---------------------- 3'
             GTT TGG GAG GAG CTT GTG TGT GTG AGT TGT GTT TTA AGT TTA TTT GCG TGT GAG
                  9       18      27      36      45      54
TAC CTT TGG GTT TTT GTG TGT GTC TGT GTG TGT TTG TGT GTG TAT AAC TGT GGG TGA CTG
     63      72      81      90      99     108
TAA GTG CAC CTG TGT GTT TGT ACG TGA GTG TGT AAG ACT GTG TGT GTG CAC AAG AGC GTG
    123     132     141     150     159     168
TGT AGG TGC ACG TGT TGT AGG TGT GAG AAC ACC TGT TGT GTT TAG GCC ATC AGT CAG CTT
    183     192     201     210     219     228
GGT CAT TGT TTC TAA GGT AGC ATT TAT ACT TTG TTA CCT CAA GTG GGC TCT GGG AGT CAA
    243     252     261     270     279     288

M   E   K   F   H   A
CAG AAG TCA GAA AAG CTC AGA TCC AAG CCC CCT TTT TCT GAC ATG GAG AAA TTT CAT GCT
    303     312     321     330     339     348

Q   Y   E   M   L   E   T   I   G   Q   G   G   C   A   Q   V   K   L   A   R
CAA TAT GAG ATG CTA GAG ACT ATT GGC CAG GGA GGC TGC GCC CAG GTG AAG CTG GCC CGA
    363     372     381     390     399     408

H   R   L   T   G   T   H   V   A   V   K   V   I   V   K   R   E   C   W   F
CAC CGC CTC ACA GGC ACC CAC GTG GCT GTC AAA GTG ATT GTA AAG AGG GAG TGT TGG TTC
    423      432     441     450     459     468

N   P   V   M   S   E   A   E   L   L   M   M   T   D   H   P   N   I   I   S
AAC CCT GTC ATG TCT GAG GCA GAG TTA CTG ATG ATG ACC GAT CAT CCG AAT ATC ATC TCT
    483     492     501     510     519     528

L   L   Q   V   I   E   T   K   K   V   Y   L   I   M   E   L   C   E   G
CTC CTT CAA GTC ATT GAG ACC AAG AAG AAA GTA TAC CTC ATT ATG GAG TTG TGC GAG GGT
    543     552     561     570     579     588

K   S   L   Y   Q   H   I   Q   N   A   G   Y   L   Q   E   D   E   A   R   P
AAA TCA CTT TAC CAA CAC ATC CAA AAT GCT GGC TAC CTG CAG GAG GAT GAA GCA CGC CCA
    603     612     621     630     639     648

L   F   K   Q   L   L   S   A   M   N   Y   C   H   N   Q   G   I   V   H   R
TTA TTC AAG CAG CTC TTA AGT GCT ATG AAC TAC TGC CAC AAC CAG GGT ATA GTT CAC AGG
    663     672     681     690     699     708

D   L   T   P   D   N   I   M   V   E   K   D   G   K   V   K   I   I   D   F
GAC CTG ACA CCT GAC AAT ATT ATG GTA GAA AAA GAT GGG AAA GTG AAG ATC ATT GAT TTT
    723     732     741     750     759     768

G   L   G   T   Q   E   K   P   G   Q   N   H   N   L   F   C   E   I   Y   P
GGA CTC GGC ACC CAA GAG AAG CCA GGG CAA AAC CAC AAC TTA TTC TGT GAG ATT TAC CCA
    783     792     801     810     819     828
                                                                  155 ----------
  F   S   T   P   E   V   L   F   N   R   P   Y   D   M   R   K   I   D   V   W
TTT AGT ACT CCT GAG GTG CTC TTT AAC AGA CCC TAT GAT ATG CGC AAG ATC GAT GTG TGG
    843     852     861     870     879     888
------- 3'
  G   L   G   V   V   L   Y   F   M   V   T   G   K   I   L   F   D   T   A   S
GGT CTT GGA GTT GTG CTG TAT TTT ATG GTA ACT GGA AAG ATT CTG TTT GAT ACT GCC AGC
    903     912     921     930     939     948

V   E   K   L   R   K   Q   I   V   A   E   K   C   S   V   P   C   R   L   S
GTA GAA AAG CTG CGA AAG CAA ATT GTT GCA GAA AAG TGT TCT GTT CCC TGT AGA CTG TCA
    963     972     981     990     999     1008
```

Fig. 4a

```
      V    E    L    Q    D    L    I    R    L    L    M    T    D    I    P    E    L    R    P    T
     GTA  GAG  CTC  CAA  GAC  CTG  ATT  AGA  CTT  TTA  ATG  ACG  GAC  ATC  CCC  GAA  CTT  AGG  CCC  ACT
          1023           1032           1041           1050           1059           1068

V    A    E    V    M    V    H    P    W    V    T    E    G    S    G    V    L    P    D    P
     GTT  GCT  GAA  GTT  ATG  GTG  CAT  CCC  TGG  GTC  ACA  GAA  GGC  TCA  GGG  GTG  TTA  CCA  GAT  CCT
          1083           1092           1101           1110           1119           1128

C    E    E    H    I    P    L    K    P    D    P    A    I    A    K    A    M    G    F    I
     TGT  GAA  GAA  CAT  ATA  CCC  CTC  AAG  CCA  GAC  CCT  GCG  ATT  GCA  AAA  GCA  ATG  GGA  TTT  ATC
          1143           1152           1161           1170           1179           1188
                                                                                             181 --
      G    F    Q    A    Q    D    I    E    D    S    L    C    Q    R    K    F    N    E    T    M
     GGG  TTC  CAA  GCT  CAA  GAC  ATT  GAA  GAT  TCG  TTA  TGT  CAG  AGA  AAA  TTC  AAC  GAA  ACC  ATG
          1203           1212           1221           1230           1239           1248
     ---------------------- 3'
      A    S    Y    C    L    L    K    K    Q    I    L    K    E    C    D    R    P    I    R    A
     GCA  TCT  TAT  TGT  CTA  CTG  AAA  AAA  CAG  ATT  CTT  AAG  GAA  TGT  GAC  AGG  CCA  ATC  CGG  GCT
          1263           1272           1281           1290           1299           1308

Q    P    M    N    P    S    V    T    P    L    S    S    L    V    D    A    P    T    F    H
     CAG  CCC  ATG  AAT  CCA  TCT  GTG  ACC  CCA  CTC  TCT  TCC  CTT  GTT  GAT  GCT  CCT  ACT  TTC  CAT
          1323           1332           1341           1350           1359           1368

L    G    L    R    R    T    E    T    E    P    T    G    L    R    L    S    D    N    K    E
     CTC  GGA  CTT  CGG  AGG  ACA  GAG  ACT  GAA  CCC  ACA  GGT  CTC  AGA  TTA  TCT  GAC  AAT  AAG  GAA
          1383           1392           1401           1410           1419           1428

V    P    V    C    G    N    S    T    S    K    K    R    E    R    S    F    S    G    P    G
     GTG  CCT  GTC  TGT  GGC  AAT  AGT  ACT  AGT  AAG  AAA  AGA  GAG  AGA  AGT  TTC  AGT  GGG  CCG  GGT
          1443           1452           1461           1470           1479           1488

V    L    S    R    P    I    N    T    T    P    T    M    D    Q    T    H    T    R    T    W
     GTT  CTC  AGC  AGG  CCG  ATT  AAC  ACA  ACA  CCC  ACA  ATG  GAC  CAA  ACA  CAC  ACC  CGT  ACT  TGG
          1503           1512           1521           1530           1539           1548

S    G    P    C    I    Y    S    N    V    C    T    I    H    P    N    S    I    N    E    S
     AGT  GGT  CCC  TGC  ATT  TAC  TCA  AAT  GTT  TGC  ACA  ATC  CAT  CCA  AAC  AGC  ATC  AAT  GAG  AGT
          1563           1572           1581           1590           1599           1608

T    E    G    H    I    S    T    S    A    E    D    K    P    V    H    S    R    G    W    P
     ACA  GAA  GGC  CAC  ATC  AGT  ACC  TCA  GCA  GAG  GAT  AAG  CCT  GTC  CAC  AGC  AGA  GGC  TGG  CCC -
          1623           1632           1641           1650           1659           1668

R    G    I    K    G    W    T    R    K    I    G    N    A    M    R    K    L    C    C    C
     AGA  GGC  ATC  AAG  GGC  TGG  ACT  AGG  AAG  ATA  GGA  AAT  GCA  ATG  AGG  AAG  CTC  TGT  TGC  TGT
          3'---------------------- 170
          1683           1692           1701           1710           1719           1728

I    P    S    K    E    T    S    H    L    G    Q    R    R    V    C    P    K    I
     ATC  CCA  TCC  AAA  GAG  ACA  TCT  CAC  CTG  GGG  CAG  AGA  AGA  GTC  TGC  CCA  AAA  ATT  TAA  GAC
          1743           1752           1761           1770           1779           1788
     ACA  GGA  AGG  ATG  TCA  GGA  GAA  TGA  GCA  TCC  AGC  ATG  GCC  CAG   *   CCT  TTC  AGA  CCG  AAG  GCA
          1803           1812           1821           1830           1839           1848
     AGC  TCT  ACC  TGA  TCC  TGG  ACT  TCC  TGC  GGG  GAG  GTG  ACC  TCT  TCA  CCA  GGC  TTT  CCA  AAG
          1863           1872           1881           1890           1899           1908
     AGG  TGA  TGT  TCA  CGG  AGG  AGG  ATG  TCA  AGT  TCT  ACC  TGG  CTG  AGC  TGG  CCT  TGG  CTC  TAG
          1923           1932           1941           1950           1959           1968
     ACC  ACC  TCC  ATG  GCC  TGG  GGA  TCA  TCT  ACA  GGG  ATC  TGA  AGC  CAG  AGA  ATA  TCC  TCC  TGG
          1983           1992           2001           2010           2019           2028
     ATG  AAG  AGG  GAC  ATA  TTA  AGA  TCA  CAG  ATT  TTG  GCT  TGA  GCA
                                                   3'---------------------- 144
          2043           2052           2061           2070
```

Fig. 4b

Sequence of ptlib0.7

```
                161 -------------------- 3´
5´GTGTATCAGT GTGTGTTTGG GAGGAGCTTG TGTGTGTGAG TTGTGTTTTA AGTTTATTTG      60
3´CACATAGTCA CACACAAACC CTCCTCGAAC ACACACACTC AACACAAAAT TCAAATAAAC

TGTGTTAGTA CCTTTGGGTT TGTGTGTGTG TCTCTGTGTG TTTGTGTGTG TATAACTGTG    120
   ACACAATCAT GGAAACCCAA ACACACACAC AGAGACACAC AAACACACAC ATATTGACAC

GGTGACTGTA AGTGCACCTG TGTGTTTGTA CGTGAGTGTG TAAGACTGTG TGTGTGCACA    180
   CCACTGACAT TCACGTGGAC ACACAAACAT GCACTCACAC ATTCTGACAC ACACACGTGT

AGAGCGTGTG TAGGTGCTCG TGTTGTAGGT GTGAGAACAC CTGTTGTGTT TAGGCCATCA    240
   TCTCGCACAC ATCCACGAGC ACAACATCCA CACTCTTGTG GACAACACAA ATCCGGTAGT

TTCAGCTTGG CCATTGTTTC TAAGC*TGCGA GACCGGGTCA GATCTAAGAT GGAGAGAGAC   300
   AAGTCGAACC GGTAACAAAG ATTCG*ACGCT CTGGCCCAGT CTAGATTCTA CCTCTCTCTG

ATCCTGGCAG AGGTGAATCA CCCTTTCATT GTCAAGCTGC ATTATGCCTT TCAGACCGAA    360
   TAGGACCGTC TCCACTTAGT GGGAAAGTAA CAGTTCGACG TAATACGGAA AGTCTGGCTT

GGCAAGCTCT ACCTGATCCT GGACTTCCTG CGGGGAGGTG ACCTCTTCAC CAGGCTTTCC    420
   CCGTTCGAGA TGGACTAGGA CCTGAAGGAC GCCCCTCCAC TGGAGAAGTG GTCCGAAAGG

AAAGAGGTGA TGTTCACGGA GGAGGATGTC AAGTTCTACC TGGCTGAGCT GGCCTTGGCT    480
   TTTCTCCACT ACAAGTGCCT CCTCCTACAG TTCAAGATGG ACCGACTCGA CCGGAACCGA

CTAGACCACC TCCATGGCCT GGG.3´
   GATCTGGTGG AGGTACCGGA CCC 5´
```

Fig. 4c

Fig. 7a

Genomic t^w12 DNA Sequence of T66Bk-2

```
                GTA GCA TTT ATA CTT TGT TAC CTC AAA TGG GCT CTG GGA GTC AAC AGA AGT CAG
                 9          18          27          36          45          54

M   E   K   F   H   A   Q   Y
AAA AGC TCA GAT CCA AGC CCC CTT TAT CTG ACT GAC ATG GAG AAA TTT CAT GCT CAA TAT
            232 5´ -------------------- 3´
     63          72          81          90          99         108

E   M   L   E   T   I   G   Q   G   G   C   A   K   V   K   L   A   R   H   R
GAG ATG CTA GAG ACT ATT GGC CAG GGA GGC TGC GCA AAG GTG AAG CTG GCC CGA CAC CGC
    123         132         141         150         159         168

L   T   G   T   H   V   A   V   K   M   I   P   K   R   E   Y   W   C   K   L
CTC ACA GGC ACC CAC GTG GCT GTC AAA ATG ATT CCA AAG AGG GAG TAT TGG TGC AAA CTT
    183         192         201         210         219         228

L   M   F   E   A   E   L   L   M   M   F   N   H   P   N   I   I   S   L   L
CTG ATG TTT GAG GCA GAG TTA CTG ATG ATG TTC AAT CAT CCT AAT ATC ATC TCT CTC CTT
    243         252         261         270         279         288

Q   V   I   E   T   K   K   K   V   Y   L   I   M   E   L   C   E   G   K   S
CAA GTC ATT GAG ACC AAG AAG AAA GTA TAT CTC ATT ATG GAG TTG TGC GAG GGT AAA TCA
    303         312         321         330         339         348

L   Y   Q   H   I   Q   N   A   G   Y   L   Q   E   D   E   A   R   P   L   F
CTT TAC CAA CAC ATC CAA AAT GCT GGC TAC CTG CAG GAG GAT GAA GCA CGC CCA TTA TTC
    363         372         381         390         399         408

K   Q   L   S   A   M   N   Y   C   H   N   Q   G   I   V   H   R   D   L
AAG CAG CTC TTA AGT GCT ATG AAC TAC TGC CAC AAC CAG GGT ATA GTT CAC AGG GAC CTG
    423         432         441         450         459         468

T   P   D   N   I   M   V   E   K   D   G   R   V   K   N   I   D   F   G   L
ACA CCT GAC AAT ATT ATG GTA GAA AAA GAT GGG AGA GTG AAG AAC ATT GAT TTT GGA CTC
    483         492         501         510         519         528

S   T   H   V   K   P   G   Q   K   L   N   L   F   C   G   T   Y   P   F   S
AGC ACC CAC GTG AAA CCA GGG CAA AAA CTC AAC TTA TTC TGT GGG ACT TAC CCA TTT AGT
    543         552         561         570         579         588

A   P   E   V   L   L   S   R   P   Y   G   G   P   K   I   D   V   W   T   L
GCT CCT GAG GTG CTC CTT AGC AGA CCC TAT GGT GGG CCC AAG ATC GAT GTA TGG ACT CTT
    603         612         621         630         639         648

G   V   V   L   Y   F   M   V   I   G   K   I   P   F   D   A   A   S   I   E
GGA GTT GTG TTG TAT TTT ATG GTA ATT GGA AAG ATC CCA TTT GAT GCT GCC AGC ATA GAA
                                                  3´ -------------------- 5´ 237
    663         672         681         690         699         708

K   L   R   K   Q   I   V   A   G   K   Y   S   A   P   C   R   L   S   V   K
AAG CTG CGG AAG CAA ATT GTT GCA GGA AAG TAT TCT GCT CCC TGT AGA CTG TCA GTA AAG
    723         732         741         750         759         768

L   Q   H   L   I   N   L   L   M   T   D   N   P   E   L   R   P   T   V   A
CTT CAA CAC CTG ATT AAT CTT TTA ATG ACG GAC AAC CCC GAA CTT AGG CCC ACT GTT GCT
    783         792         801         810         819         828

E   V   M   V   H   P   W   I   T   K   G   S   G   V   F   P   D   P   C   E
GAA GTT ATG GTG CAT CCC TGG ATC ACA AAA GGC TCA GGG GTG TTC CCA GAT CCT TGT GAA
    843         852         861         870         879         888
```

Genomic t^{w12} DNA Sequence of T66Bk-2 continued

```
E   Q   I   P   L   K   P   D   P   A   I   V   K   P   M   G   H   I   G   F
GAA CAG ATA CCC CTC AAG CCA GAC CCT GCG ATT GTA AAA CCA ATG GGA CAT ATT GGG TTC
        903         912         921         930         939         948

Q   A   Q   D   I   E   D   S   L   R   Q   R   K   F   N   E   T   M   A   S
CAA GCT CAA GAC ATT GAA GAT TCG TTA CGT CAG AGA AAA TTC AAT GAA ACC ATG GCA TCT
        963         972         981         990         999         1008

Y   C   L   L   K   K   Q   I   L   K   E   C   D   R   P   I   R   D   Q   P
TAT TGT CTA CTG AAA AAA CAG ATT CTT AAG GAA TGT GAC AGG CCA ATC CGG GAT CAG CCC
        1023        1032        1041        1050        1059        1068

M   N   P   S   V   T   P   F   P   S   L   V   D   T   P   T   F   H   L   G
ATG AAT CCA TCA GTG ACC CCA TTC CCT TCC CTT GTT GAT ACT CCT ACT TTC CAT CTC GGA
        1083        1092        1101        1110        1119        1128

L   R   R   R   E   T   E   P   T   G   L   R   L   S   A   N   R   Q   V   S
CTT CGG AGG AGA GAG ACT GAA CCC ACA GGT CTC AGA TTA TCT GCC AAT AGG CAA GTG TCT
        1143        1152        1161        1170        1179        1188

V   C   G   K   S   T   S   K   K   R   D   R   S   F   I   W   P   G   V   L
GTC TGT GGA AAA AGT ACA AGT AAG AAA AGA GAC AGA AGT TTC ATT TGG CCC GGT GTT CTC
        1203        1212        1221        1230        1239        1248

S   R   P   I   N   T   T   P   T   M   D   Q   T   H   T   R   T   R   S   V
AGC AGG CCG ATT AAC ACA ACA CCC ACA ATG GAC CAA ACA CAC ACC CGT ACT AGG AGT GTT
        1263        1272        1281        1290        1299        1308

P   C   I   Y   S   N   V   C   T   I   H   P   N   S   I   D   E   S   T   E
CCC TGC ATT TAC TCA AAT GTT TGC ACA ATC CAT CCA AAC AGC ATC GAT GAG AGT ACA GAA
        1323        1332        1341        1350        1359        1368

G   H   T   S   A   S   A   E   D   K   P   V   H   S   R   G   W   P   R   G
GGC CAC ACC AGT GCC TCA GCA GAG GAT AAG CCT GTC CAC AGC AGA GGC TGG CCC AGA GGC
        1383        1392        1401        1410        1419        1428

I   K   G   W   T   R   K   I   G   N   A   M   R   K   L   C   C   C   I   P
ATC AAG GGC TGG ACT AGG AAG ATA GGA AAT GCA ATG AGG AAG CTC TGT TGC TGT ATC CCA
        1443        1452        1461        1470        1479        1488

S   K   E   T   S   H   L   G   Q   S   R   V   C   P   K   K
TCC AAA GAG ACA TCT CAC CTG GGG CAG AGC AGA GTC TGC CCA AAA AAA TAA GAC ACA GGA
        1503        1512        1521        1530        1539        1548

AGG GTG TCA GGA GAA CGA GCA TCC GGC ACG GCC CAG
        1563        1572        1581        1590
```

Fig. 7b

Fig. 7c cDNA T66k-8 sequence

```
                    G   EAG TTT GGT GGA GTT GGT GGA GTT GGT GGT GCC CTT TGT GAT TTC GTT GTA TCT
                            10          19          28          37          46          55
                                                                        161 5'----------------
AGT GAG TTG TGT GTG TGT GTG TGT GTG TGT GTG TGT AGT TCA GTG TGT GTT TGG GAG GAG
            64          73          82          91         100         109
-------- 3'
CTT GTG TGT GTG AGT TGT GAA TTA AGT TTA CTT GCG TGT GAA TAC CTT TGT GTT TTT GTG
           124         133         142         151         160         169
TGT GTC TGT GTG TAT CCA TGT GGG TGA CTG TAA GTG CAC CTG TGT GAT AGT TCG AAA GTG
           184         193         202         211         220         229
TAT GAG AGA GTG TGT GTG GGC ACA AGA GTG TGT GTA GGT GCA CGT GTG GTA GGT GTG AGA
           244         253         262         271         280         289
ACA CCT CTT GTG TTG AGG CCG TCA GTC AGC TTG GCC ATT GTT TCT AAG GTA GCA TTT ATA
           304         313         322         331         340         349
CTT TGT TAC CTC AAA TGG GCT CTG GGA GTC AAC AGA AGT CAG AAA AGC TCA GAT CCA AGC
           364         373         382         391         400         409

M   E   K   F   H   A   Q   Y   E   M   L   E   T   L
CCC CTT TAT CTG ACT GAC ATG GAG AAA TTT CAT GCT CAA TAT GAG ATG CTA GAG ACT ATT
           424         433         442         451         460         469

G   Q   G   G   C   A   K   V   K   L   A   R   H   R   L   T   G   T   H   V
GGC CAG GGA GGC TGC GCA AAG GTG AAG CTG GCC CGA CAC CGC CTC ACA GGC ACC CAC GTG
           484         493         502         511         520         529

A   V   K   M   I   P   K   R   E   Y   W   C   K   L   L   M   F   E   A   E
GCT GTC AAA ATG ATT CCA AAG AGG GAG TAT TGG TGC AAA CTT CTG ATG TTT GAG GCA GAG
           544         553         562         571         580         589

L   L   M   M   F   N   H   P   N   I   I   S   L   L   Q   V   I   E   T   K
TTA CTG ATG ATG TTC AAT CAT CCT AAT ATC ATC TCT CTC CTT CAA GTC ATT GAG ACC AAG
           604         613         622         631         640         649

K   K   V   Y   L   I   M   E   L   C   E   G   K   S   L   Y   Q   H   I   Q
AAG AAA GTA TAT CTC ATT ATG GAG TTG TGC GAG GGT AAA TCA CTT TAC CAA CAC ATC CAA
           664         673         682         691         700         709

N   A   G   Y   L   Q   E   D   E   A   R   P   L   F   K   Q   L   L   S   A
AAT GCT GGC TAC CTG CAG GAG GAT GAA GCA CGC CCA TTA TTC AAG CAG CTC TTA AGT GCT
           724         733         742         751         760         769

M   N   Y   C   H   N   Q   G   I   V   H   R   D   L   T   P   D   N   I   M
ATG AAC TAC TGC CAC AAC CAG GGT ATA GTT CAC AGG GAC CTG ACA CCT GAC AAT ATT ATG
           784         793         802         811         820         829

V   E   K   D   G   R   V   K   N   I   D   F   G   L   S   T   H   V   K   P
GTA GAA AAA GAT GGG AGA GTG AAG AAC ATT GAT TTT GGA CTC AGC ACC CAC GTG AAA CCA
           844         853         862         871         880         889

G   Q   K   L   N   L   F   C   G   T   Y   P   F   S   A   P   E   V   L   L
GGG CAA AAA CTC AAC TTA TTC TGT GGG ACT TAC CCA TTT AGT GCT CCT GAG GTG CTC CTT
           904         913         922         931         940         949

S   R   P   Y   G   G   P   K   I   D   V   W   T   L   G   V   V   L   Y   F
AGC AGA CCC TAT GGT GGG CCC AAG ATC GAT GTA TGG ACT CTT GGA GTT GTG TTG TAT TTT
           964         973         982         991        1000        1009

M   V   I   G   K   I   P   F   D   A   A   S   I   E   K   L   R   K   Q   I
ATG GTA ATT GGA AAG ATC CCA TTT GAT GCT GCC AGC ATA GAA AAG CTG CGG AAG CAA ATT
                               3'----------------------- 5' 237
          1024        1033        1042        1051        1060        1069
``` cDNA T66k-8 sequence continued

```
  V   A   G   K   Y   S   A   P   C   R   L   S   V   K   L   Q   H   L   I   N
 GTT GCA GGA AAG TAT TCT GCT CCC TGT AGA CTG TCA GTA AAG CTT CAA CAC CTG ATT AAT
      1084        1093        1102        1111        1120        1129

L   L   M   T   D   N   P   E   L   R   P   T   V   A   E   V   M   V   H   P
 CTT TTA ATG ACG GAC AAC CCC GAA CTT AGG CCC ACT GTT GCT GAA GTT ATG GTG CAT CCC
      1144        1153        1162        1171        1180        1189

W   I   T   K   G   S   G   V   F   P   D   P   C   E   E   Q   I   P   L   K
 TGG ATC ACA AAA GGC TCA GGG GTG TTC CCA GAT CCT TGT GAA GAA CAG ATA CCC CTC AAG
      1204        1213        1222        1231        1240        1249

P   D   P   A   I   V   K   P   M   G   H   I   G   F   Q   A   Q   D   I   E
 CCA GAC CCT GCG ATT GTA AAA CCA ATG GGA CAT ATT GGG TTC CAA GCT CAA GAC ATT GAA
      1264        1273        1282        1291        1300        1309

D   S   L   R   Q   R   K   F   N   E   T   M   A   S   Y   C   L   L   K   K
 GAT TCG TTA CGT CAG AGA AAA TTC AAT GAA ACC ATG GCA TCT TAT TGT CTA CTG AAA AAA
      1324        1333        1342        1351        1360        1369

Q   I   L   K   E   C   D   R   P   I   R   D   Q   P   M   N   P   S   V   T
 CAG ATT CTT AAG GAA TGT GAC AGG CCA ATC CGG GAT CAG CCC ATG AAT CCA TCA GTG ACC
      1384        1393        1402        1411        1420        1429

P   F   P   S   L   V   D   T   P   T   F   H   L   G   L   R   R   R   E   T
 CCA TTC CCT TCC CTT GTT GAT ACT CCT ACT TTC CAT CTC GGA CTT CGG AGG AGA GAG ACT
      1444        1453        1462        1471        1480        1489

E   P   T   G   S   D   Y   L   P   I   G   K   C   L   S   V   E   K   V   Q
 GAA CCC ACA GGC TCA GAT TAT CTG CCA ATA GGC AAG TGT CTG TCT GTG GAA AAA GTA CAA
      1504        1513        1522        1531        1540        1549

V   R   K   E   T   E   V   S   F   G   P   V   F   S   A   G   R   L   T   Q
 GTA AGA AAA GAG ACA GAA GTT TCA TTT GGC CCG GTG TTC TCA GCA GGC CGA TTA ACA CAA
      1564        1573        1582        1591        1600        1609

H   P   Q   W   T   K   H   T   P   V   L   G   V   F   P   A   F   T   Q   M
 CAC CCA CAA TGG ACC AAA CAC ACA CCC GTA CTA GGA GTG TTC CCT GCA TTT ACT CAA ATG
      1624        1633        1642        1651        1660        1669

F   A   Q   S   I   Q   T   A   S   M   R   V   Q   K   A   T   P   V   P   Q
 TTT GCA CAA TCC ATC CAA ACA GCA TCG ATG AGA GTA CAG AAG GCC ACA CCA GTG CCT CAG
      1684        1693        1702        1711        1720        1729

Q   R   I   S   L   S   T   A   E   A   G   P   E   A   S   R   A   G   L   G
 CAG AGG ATA AGC CTG TCC ACA GCA GAG GCT GGC CCA GAG GCA TCA AGG GCT GGA CTA GGA
      1744        1753        1762        1771        1780        1789

R
 AGA TAG GAA ATG CAA TGA GGA AGC TCT GTT GCT GTA TCC ATC CAA AGA GAC ATC TCA CC
      1804        1813        1822        1831        1840        1849
 TGG GGC AGA GCA GAG TCT GCC AAA AAT AAG ACA GAG GAA GGG TGT CAG GAG AAC GAG
      1864        1873        1882        1891        1900        1909
 CAT CCG GCA CGG CCC AGA AGA TCA CCA GAG GAT GCC GGA TGC TAC GAT TCA ACA GTT ATA
      1924        1933        1942        1951        1960        1969
 ATA TTG GAA AGG ACC CAT GTA TAG ACA TGG ACC TGC AAA AGG GAA CCT TGT GGA AAG GCA
      1984        1993        2002        2011        2020        2029
```

Fig. 7d

```
cDNA T66k-8 sequence continued

TCA TGT TCT GGG TTC AGC ATG TTT CAC TCA GAG CCC CGG GTC CAG CCA GGG GGA AGA AAG
    2044         2053         2062         2071         2080         2089
CAA ATG ATG AAA TCC CAG ATG GTG TCT GGG ATC ACC ATT CAG AGC AGG GGC TGA AAG CCT
    2104         2113         2122         2131         2140         2149
GTC CAA AGC TGG TAG AGA CAG AAG CCC CTC TGC CTA CCC AGG GTC ATA ATC AGA CTC CTG
    2164         2173         2182         2191         2200         2209
CTC TGA GAA TAA AAT AGA TGT TTG TGA AAG ATG AAA AAA AAA
    2224         2233         2242         2251
```

Fig. 7e

Antisense cDNA clone T66k-7 as

```
EcoRI SmaI    SalI       MluI
GAATTCCCGG GTCGACCCAC GCGTCCGGCA GGAATTCACA GAGTTACCGT GCTTGCCTCT GTGGAAGTGG
----------------------------3'-----------------------------------------------
         10         20         30         40         50         60         70

GTCAAGCTGA TGGTATCTAA TATTCTCTCT GGTCCTTCTG ATCATGCTGC TGGGTCCAGA AGTACCCAGA
-----------------------------------------------------------------------------
         80         90        100        110        120        130        140

TTCCACACCC AGCTTCTACA CTCCCCCACT TCAGGTACCT GAAAGCTTGG TCCCTTCAAA GGCACTTTTA
-----------------------------------------------------------------------------
        150        160        170        180        190        200        210

ATGATCTGGT GGTTTGGGGT GTGAAGTTAT TCTACCTGGG GCTTTTGTAC ACCACAGGAA CAATTTTCCT
-----------------------------------------------------------------------------
        220        230        240        250        260        270        280

CTTACTTCTC CCACTTCCTC TCCCTAGCAT GGTCAGTTCT CCTCCTTGTT CAACGTGCAT GATACACACA
-----------------------------------------------------------------------------
        290        300        310        320        330        340        350

GGAGATACTT TCTGGGATGT TAGATCTGTT GGCAGGTTCG ATTTAACCAC CATCCCATGG TGTCTAGACC
-----------------------------------------------------------------------------
        360        370        380        390        400        410        420

TAGCTTCCCC ATGCATCACA CCATATACAT ATACATAAGT ATAATCTGCC AGTTTACACA GACATGAGTA
-----------------------------------------------------------------------------
        430        440        450        460        470        480        490

ACATAGATAC ATTCAAATAC AGAAATGTAC CTGGGCCGTG CCAGATGCTC ATTCTCCTGA CAACCTTCCT
----------------------------5' 3'============================================
        500        510        520        530        540        550        560

GTGTCTTATT TTTTGGGGAG ACTCTGCTGT GCCCCACGTG AGCTGTCTCT TTTGATGGGA TACAGCAACA
=============================================================================
        570        580        590        600        610        620        630

GAGTTTCCTC ATTGCATTTC CTATCTTCCT AGTCCAGCCC TTGATGCCTC TGGGCCAGCC TCTGCTGCGG
=============================================================================
        640        650        660        670        680        690        700

ACAGGCTTAT CCTCTGCTGA GGCACTGGTG TGGCCTTCTG TACTCTCATC ACTGCTATTT GGATGGATTG
=============================================================================
        710        720        730        740        750        760        770

TGCAAACATT TGAGTAAATG CAGGGAACAC TCCTAGTATG GGTGTGTCTG TGGTCCATTG TGGATGTTAT
=============================================================================
        780        790        800        810        820        830        840

GTGGAGTGGC CTGCCGGAAA CACTGGGCCA ACTGAATCTT CTGTCTCTTT TTTTACTAGT ACACTTGCCA
=============================================================================
        850        860        870        880        890        900        910

CAGACAGACA CTTGCCTATT GCCAGATGAC CAGAGACCTG TGGGTTCAGT CTCTCCCCTC CAAAGTCTGA
=============================================================================
        920        930        940        950        960        970        980

GATGGAAAGT AGGAGTATCA ACAAGGGAAG GGAATGGGGT CAGCGACAGA TTCATGGGCT GAGCCCGGAT
=============================================================================
        990       1000       1010       1020       1030       1040       1050
```

Fig. 7f

Antisense cDNA clone T66k-7as continued

```
TGGCCTGTCA CATTCCTTAA GAATCTGTTT TTTCAGTAGA CAATAAGATG CCATGGTTTC ATTGAATTTT
========== ========== ========== ========== ========== ========== ==========
    1060       1070       1080       1090       1100       1120       1130

CTCTGACATA ACGAATCTTC AATGTCTTGA GCTTGGAACC CGATATATCC CATTGCTTTT ACAATCGCAG
========== ========== ========== ========== ========== ========== ==========
    1130       1140       1150       1160       1170       1180       1190

GGTCTGGCTT GAGGGGTATC TGTTCTTCAC AAGGATCTGG GAACACGCCT GAGCCTTCTG TGACCCAGGG
========== ========== ========== ========== ========== ========== ==========
    1200       1210       1220       1230       1240       1250       1260

ATGCACCATA ACTTCAGCAA CAGTGGGCCT AAGTTCGGGG TTGTCCGTCA TTAAAAGTCT AATCAGGTCT
========== ========== ========== ========== ========== ========== ==========
    1270       1280       1290       1300       1310       1320       1330

TGGAGCTCTA CTGACAGTCT ACAGGGAACA GAACACTTTC CTGCAACAAT TTGCTTTCGC AGCTTTTCTA
========== ========== ========== ========== ========== ========== ==========
    1340       1350       1360       1370       1380       1390       1400

TGCTGGCAGC ATCAAACAGA ATCTTTCCAG TTACCATAAA ATACAGCACA ACTCTAAGAC CCCACACATC
========== ========== ========== ========== ========== ========== ==========
    1410       1420       1430       1440       1450       1460       1470

GATCTTGCGC ATATCATAGG GTCTGCTAAG GAGCACCTCA GGAGTACTAA ATGGGTAAGT CTCACAGAAT
========== ========== ========== ========== ========== ========== ==========
    1480       1490       1500       1510       1520       1530       1540

AAGTTGAGTT TTTGCCCTGG CTTCTCTTGG GTGCCGAGTC CAAAATCAAT GATCTTCACT TTCCCATCTT
========== ========== ========== ========== ========== ========== ==========
    1550       1560       1570       1580       1590       1600       1610
                                    14 base pairs deleted
TTTCTACCAT AATATTGTCA GGTGTCAGGT CCCTG GTTGT GGCAGTAGTT CATAGCACTT AAGAGCTGCT
========== ========== ========== ===== ===== ========== ========== ==========
    1620       1630       1640       1650       1660       1670       1680

TGAATAATGG GCGTGCTTCA TCCTCCTGCA GGTAGCCAGC GTTTCAGATG TGTTGGTAAA GTGATTTACC
========== ========== ========== ========== ========== ========== ==========
    1690       1700       1710       1720       1730       1740       1750

CTCTCACAAC TCCATAATGA GGTATACTTT CTTCTTGGTC TCAATGACTT GAAGGAGAGA GATGATATTT
========== ========== ========== ========== ========== ========== ==========
    1760       1770       1780       1790       1800       1810       1820

GGATGATCGG CCATCATCAG TAACTCTGCC TCAGACATGA CAGGGTTGCA CCAATACTCC CTCTTTCGAA
========== ========== ========== ========== ========== ========== ==========
    1830       1840       1850       1860       1870       1880       1890

TCACTTTGAC AGCCACGTGG GTGCCTGTGA GGCGGTGCCT GGCCAGCTTC ACCTTGGCAC AGCCTCCATC
========== ========== ========== ========== ========== ========== ==========
    1900       1910       1920       1930       1940       1950       1960

GCCGATAGTC TCTAGCATCT CATATTGAGC ATGAAATTTC GCCATGTCAG AGAAGGGGG CTTGGATCTG
========== ========== ========== ========== ========== ========== ==========
    1970       1980       1990       2000       2010       2020       2030

AGCTTTTCTG ATTTCTGTTG ACTCCCAGAG CCCACTTGAG GTAACAAAGT ATAAATGCTA CCTAAGGGGG
========== ========== ========== ========== ========== ========== ========== 5' 3' --
    2040       2050       2060       2070       2080       2090       2100
```

Fig. 7g

Antisense cDNA clone T66k-7 as continued

```
CGGGGAGAAA TAAAGGGAAG AAAGAAAGGT AAGATAAAAA TTAAAATAGT GAAAAATAAG CAAAACAGAA
-----------------------------------------------------------------------------
     2110       2120       2130       2140       2150       2160       2170

AATTAAAACC CAACAAAAAA TAATAACAGC AGAAACCCAG AAGAGCAAAA CCACACACAA AGCCAAGAAA
-----------------------------------------------------------------------------
     2180       2190       2200       2210       2220       2230       2240

ATCCAAATTA AAAAACCTAG CTGCAAGTCC CTAGGAGAGA GGGGCACAGC TCAGCAACAC TAAGAAGAAA
-----------------------------------------------------------------------------
     2250       2260       2270       2280       2290       2300       2310

TATTACTAAG TGAGGAGCCA AGTGTGTTGG CGCACACCTT TAATCCCCTG ACTCGGGAGG CCGAGGCAGG
-----------------------------------------------------------------------------
     2320       2330       2340       2350       2360       2370       2380

TGGATTTCTG AGTTCGGGGC CAGCCTGGTC TACAGAGTGA ATTCCAGGAC AGCCAGAGCT ATACAGAGAA
-----------------------------------------------------------------------------
     2390       2400       2410       2420       2430       2440       2450

ATCAAACTCA AAAAAACAAA CAAACAAACA AACAAAAAAC TCTACTAGGA AATATATAAA TGATTAGTAT
-----------------------------------------------------------------------------
     2460       2470       2480       2490       2500       2510       2520

AACAAACTCA TCAAAACTTC TAGAATATAC AAAGAACTAA AAAAAAAAAA AAAAGGGCGG CCGCTCTAGA
-----------------------------------------------------------------------------
     2530       2540       2550       2560       2570       2580       2590
BamHI
GGATCC
------
```

Fig. 7h

Sequence of T66k-20

```
            AGT TCG TGG AGT TGG TGG AGT TTG GTG GAG TTG GTG GTG CCC TTT GCG ATT TCG
                  9              18              27              36              45              54
TTG TAT CTA GTG AGC TGT GTG TGG ATT TTG TGT TTG ATT GGT TTG TGT GTG AGC TTG TGT
        63              72              81              90              99             108
GTG TGT GTG TGT GTG TGT GTG TGT GTG TGT CTA GAT CAG TGT GTG TTT GGG AGG AGC GTT
       123             132             141             150             159             168
GTC TGT GTT TGT GAG TTG AGT TTT AAG TTT ACT TGC GTG TGA GTA ACT TTG TGT TGT GTG
       183             192             201             210             219             228
TGG GTG TGT GTG TGT AGG TAT ACC CGT GGG TGA CTC TAA GTG CAC CTG TGT GTT TGT GAC
       243             252             261             270             279             288
CGA GTG TGT GAG AGT GTG TGT GTG TGA GCA CAC AAG AGT GTG TGT AGG TGC ACG TGT AGC
       303             312             321             330             339             348
AGG TGT GAG AAC ATC TGT TGT GTT GAG GCC GTC AGT CAG CTT GGC CAT TGT TTC TAA GGT
       363             372             381             390             399             408

M   G   P   G   S   Q   Q   K   S   E   K   L
AGC ATT TAT ACT TGG TTA CCT CAA ATG GGC CCT GGG AGT CAA CAG AAG TCA GAA AAG CTC
       423             432             441             450             459             468

R   S   K   S   P   L   A   D   M   D   G   L   H   A   Q   Y   V   M   L   E
AGA TCC AAG TCC CCT TTG GCT GAC ATG GAT GGT TTG CAT GCT CAA TAT GTG ATG CTA GAG
       483             492             501             510             519             528

T   I   G   H   G   G   C   A   T   V   K   L   A   Q   H   R   L   T   G   T
ACT ATC GGC CAT GGA GGC TGT GCC ACA GTG AAG CTG GCC CAG CAC CGC CTC ACA GGC ACT
       543             552             561             570             579             588

H   V   A   V   K   T   I   R   K   R   E   Y   W   C   N   R   V   I   S   E
CAC GTG GCT GTC AAA ACG ATT CGA AAG AGG GAG TAT TGG TGC AAC CGT GTC ATT TCT GAG
       603             612             621             630             639             648

V   E   L   L   M   M   A   D   H   P   N   I   I   S   L   L   Q   V   I   E
GTA GAG TTA CTG ATG ATG GCC GAT CAT CCG AAT ATC ATC TCT CTC CTT CAA GTC ATT GAG
       663             672             681             690             699             708

T   K   K   K   V   Y   L   I   M   E   L   C   K   G   K   S   L   Y   Q   H
ACC AAG AAG AAA GTA TAC CTC ATT ATG GAG TTG TGC AAG GGT AAA TCA CTT TAC CAA CAC
       723             732             741             750             759             768

I   R   K   A   G   Y   L   Q   E   H   E   A   R   A   L   F   K   Q   L   L
ATC CGA AAA GCT GGC TAC CTG CAG GAG CAT GAA GCA CGC GCA TTA TTC AAG CAG CTC TTA
       783             792             801             810             819             828

S   A   M   N   Y   C   H   N   Q   G   I   V   H   R   D   L   K   P   D   N
AGT GCT ATG AAC TAC TGC CAC AAC CAG GGT ATA GTT CAC AGG GAC CTG AAA CCG GAC AAT
       843             852             861             870             879             888

I   M   V   E   K   D   G   K   V   K   I   I   D   F   G   L   G   T   K   V
ATC ATG GTT GAA AAA GAT GGG AAA GTG AAG ATC ATT GAT TTT GGA CTC GGC ACC AAA GTG
       903             912             921             930             939             948

K   P   G   Q   K   L   N   L   F   C   G   T   Y   P   F   S   A   P   E   V
AAG CCA GGG CAA AAA CTC AAC TTA TTC TGT GGG ACT TAC CCA TTT AGT GCT CCT GAG GTG
       963             972             981             990             999            1008

L   L   S   T   P   Y   D   G   P   K   I   D   V   W   T   L   G   V   V   L
CTC CTT AGC ACA CCC TAT GAT GGG CCC AAG ATC GAT GTA TGG ACT CTT GGA GTT GTG CTG
      1023            1032            1041            1050            1059            1068
```

Fig. 7i

Sequence of T66k-20 continued

```
  Y   F   M   V   T   G   K   I   P   F   D   A   C   S   I   K   K   L   V   K
 TAT TTT ATG GTA ACT GGA AAG ATC CCG TTT GAT GCT TGC AGC ATA AAA AAG CTG GTA AAG
         1083        1092        1101        1110        1119        1128

R   I   L   A   G   K   Y   S   I   P   S   R   L   S   A   E   L   Q   D   L
 CGA ATT CTT GCA GGA AAG TAT TCT ATT CCC TCT AGA CTG TCA GCA GAG CTC CAA GAC CTG
         1143        1152        1161        1170        1179        1188

L   S   L   L   M   T   A   N   P   K   L   R   P   T   V   A   E   V   M   V
 CTT AGT CTT TTA ATG AGG GCC AAC CCC AAA CTC AGG CCC ACT GTT GCT GAG GTT ATG GTG
         1203        1212        1221        1230        1239        1248

H   P   W   V   T   E   G   S   G   V   F   P   D   P   C   E   E   Q   T   P
 CAT CCC TGG GTC ACA GAA GGC TCA GGG GTG TTC CCA GAT CCT TGT GAA GAA CAG ACC CCC
         1263        1272        1281        1290        1299        1308

L   K   P   D   P   A   I   V   K   A   M   G   H   I   G   F   Q   A   Q   D
 CTC AAG CCA GAC CCT GCA ATT GTA AAA GCA ATG GGA CAT ATC GGG TTC CAA GCT CAA GAT
         1323        1332        1341        1350        1359        1368

I   E   D   S   L   R   Q   R   K   F   N   Q   T   M   A   S   Y   C   L   L
 ATT GAA GAT TCG TTA CGT CAG AGA AAA TTC AAC CAA ACC ATG GCG TCT TAT TGT CTA CTG
         1383        1382        1401        1410        1419        1428

K   K   Q   I   L   K   E   C   D   R   P   T   R   A   R   P   V   N   P   S
 AAA AAA CAG ATT CTT AAG GAA TGT GAC AGG CCA ACC CGG GCT AGG CCC GTG AAC CCA TCG
         1443        1452        1461        1470        1479        1488

V   T   P   F   P   S   L   V   D   T   A   T   T   R   L   G   L   R   R   R
 GTG ACC CCA TTC CCT TCC CTT GTT GAT ACT GCT ACT ACC CGT CTC GGA CTT CGC AGG AGA
         1503        1512        1521        1530        1539        1548

E   N   E   P   T   C   P   W   S   S   A   N   R   Q   V   S   V   C   G   K
 GAG AAT GAA CCC ACA TGT CCC TGG TCA TCC GCC AAT AGG CAA GTG TCT GTG TGT GGC AAG
         1563        1572        1581        1590        1599        1608

S   T   S   K   K   R   D   R   R   V   S   W   P   S   V   L   G   R   P   R
 AGT ACT AGT AAG AAA AGA GAC AGA AGA GTC AGT TGG CCC AGT GTT CTC GGC AGG CCA CGC
         1623        1632        1641        1650        1659        1668

H   T   A   P   T   M   D   H   T   R   T   R   T   R   S   V   P   C   I   C
 CAC ACG GCA CCC ACA ATG GAC CAC ACA CGC ACC CGT ACT AGG AGT GTA CCC TGC ATT TGC
         1683        1692        1701        1710        1719        1728

S   M   F   C   T   V   Q   P   N   S   S   E   E   S   T   Q   G   H   T   R
 TCA ATG TTT TGC ACA GTC CAG CCA AAC AGC AGC GAA GAG AGC ACA CAA GGC CAC ACC AGA
         1743        1752        1761        1770        1779        1788

A   S   A   A   D   K   P   V   H   S   R   G   W   P   R   G   I   K   G   W
 GCC TCA GCA GCA GAT AAG CCT GTC CAC AGC AGG GGC TGG CCC AGA GGC ATC AAG GGC TGG
         1803        1812        1821        1830        1839        1848

T   R   M   I   G   N   A   M   R   K   L   C   C   C   I   P   S   K   E   T
 ACG AGG ATG ATA GGA AAT GCG ATG AGG AAG CTC TGT TGC TGT ATC CCA TCC AAA GAG ACA
         1863        1872        1881        1890        1899        1908

S   H   L   G   Q   N   R   V   S   P   K   K
 TCT CAC CTG GGG CAG AAC AGA GTC TCC CCC AAA AAA TAA GAC ACA GGA AGG GTG TCA GGA
         1923        1932        1941        1950        1959        1968
```

Fig. 7j

Sequence of T66k-20 continued

```
GAA CAA GCA TCC GGC ACG GCC CAG GTA CAT TTC TGC ATT TGA ATG TAT CTA TGT TAC TCA
    1983         1992         2001         2010         2019         2028
TGT CTG TGT CAA CTG GCA GAT GAT ACT TAT GTA TAT GGT GCA AAG CAT GAA GGG GCT AGG
    2043         2052         2061         2070         2079         2088
TGT AGA CAC CGT GGG ATG ATG GGT AAA TCT AAC CTG CCA ACA TAC CTA GCA TCC CAG AAG
    2103         2112         2121         2130         2139         2148
GTA TCT CCT GCG TGT ATC CTG CAT GTT GAA CAA CGA GGG GAA CTG ACC ATG CTA GGG GGA
    2163         2172         2181         2190         2199         2208
GGA AGT GGG AGA AGG AAG AGG AGG AGA TGC TGA GGG AGG AGA GGA TGG TAT GTG ATG GGA
    2223         2232         2241         2250         2259         2268
GCT AGG AGA TGG GGG GAA GAG GTT GAG ACA GGA GGA GGC AAC TTG GGG GAG CAG TGT GAA
    2283         2292         2301         2310         2319         2328
ACA GGG TAA CCA CAG CTG GAG AGA TGC CCT GTG CAG CTG AGG TTC TCA GAG TCC CTC TCA
    2342         2352         2361         2370         2379         2388
CGT GTG CTT TGC ATT TTA GAA GAT CAC CAG AGG ATG CCG GAT GCT ACG ATT CTA CAG TTA
    2403         2412         2421         2430         2439         2448
TAG TAT TGG AAA GGA CCC GTG TAT AGA CAC GGA CCT GAA AAA GGG AAC CTT GTG GAA AGG
    2463         2472         2481         2490         2499         2508
CAT CAT GTT CTG GGT TCA GCG TGC TTC ACT CAG AGC CCC CAG TCC AGC CAG GGG GCA AGA
    2523         2532         2541         2550         2559         2568
AAG CAA ATG ATG AAA TCC CAG ATG GGC TCT GGG ATC ACC ATT CAG AGA AGT GGC TTA AAG
    2583         2592         2601         2610         2619         2628
CAT GTC CAA AGC TGA TAG AGA CAG CCC CTC TGC CTG CCC AAG CTC ATA ATC AGA CTC CTC
    2643         2652         2661         2670         2679         2688
CTC TGA GAA TAA AAT AGA TGT TTG TGA AAA AAA AAA AAA AAA AA
    2703         2712         2721         2730
```

Fig. 7k

Amino acid sequence alignment of putative T66Bk gene products

```
T66Bk     1 _____MEKFHAQYEMLETIGQGGCAQVKLARHRLTGTHVAVKVIV
T66Bk-2   1 --------------------*****************K*****************M*P
T66k-20   1 MGPGSQQKSEKLRSKSPLAD*DGL****V*****H****T****Q*************T*R
T66k-8    1 _____*****************K*****************M*P

T66Bk    41 KRECWFNPVMSEAELLMMTDHPNIISLLQVIETKKKVYLIMELCEGKSLYQHIQNAGYLQ
T66Bk-2  41 ***Y*CKLL*F******FN*****************************************
T66k-20  61 ***Y*C*R*IV*A************K****RK**
T66k-8   41 ***Y*CKLL*F******FN*****************************************

T66Bk   101 EDEARPLFKQLLSAMNYCHNQGIVHRDLTPDNIMVEKDGKVKIIDFGLGTQEKPGQNHNL
T66Bk-2 101 ****************************************RN*****S*HV**KL
T66k-20 121 *H***A************************************K**************KV***KL**
T66k-8  101 ****************************************RN*****S*HV**KL

T66Bk   161 FCEIYPFSTPEVLFNRPYDMRKIDVWGLGVVLYFMVTGKILFDTASVEKLRKQIVAEKCS
T66Bk-2 161 GTALS*GGP**T*****I*PA*************G*Y*
T66k-20 181 GTALST*GP**T***********PAC*IK**V*R*L*G*Y*
T66k-8  161 GTALS*GGP**T*****I*PAI***********G*Y*

T66Bk   221 VPCRLSVELQDLIRLLMTDIPELRPTVAEVMVHPWVTEGSGVLPDPCEEHIPLKPDPALA
T66BK-2 221 A****KHN*N**********I*K**F*Q*******V
T66K-20 241 I*S***A*****LS****AN*K*******************F*****QT********V
T66K-8  221A****KHN*N************I8KF*Q*******V

T66Bk   281 KAMGFIGFQAQDIEDSLCQRKFNETMASYCLLKKQILKECDRPIRAQPMNPSVTPLSSLV
T66Bk-2 281 *PH*********R************************D****FP*
T66k-20 301 ****H*************R****Q***********************T**R*V*****FP***
T66k-8  281 *PH*********R************************D****FP*

T66Bk   341 DAPTFHLGLRRTETWPTGLRLSDNKEVPVCGNSTSKKRERSFSGPGVLSRPINTTPTMDQ
T66Bk-2 341 *T*********R**********A*RQ*S***K******D***IW***************
T66k-20 361 *TA*TR*****R*N****CPWS*A*RQ*S*K****D*RV*W*SGRH*A****_
T66k-8  341 *T*********R******SDYLPIGKCLSVEKVQVRKETEVSFGPVFSAGRLTQHPQWTK

T66Bk   401 THTRT__WSGPCIYSNVCTIHPNSINESTEGHISTSA__EDKPVHSRGWPRGIKGWTRKI
T66Bk-2 401 *****__R*V*************D*****__***SA*********************
T66k-20 420 _****RTR*V***C*MFVQ*SEQTRA__A*****************M*
T66k-8  401 MTPVLGVFPAFTQMFAQSIQTASMRVQKATPVPQQRISLSTAEAGPEASRAGLGR

T66Bk   457 GNAMRKLCCCIPSKETSHLGQRRVCPKI
T66Bk-2 457 *********************S*****K
T66k-20 477 *******************NS**K
```

Fig. 71

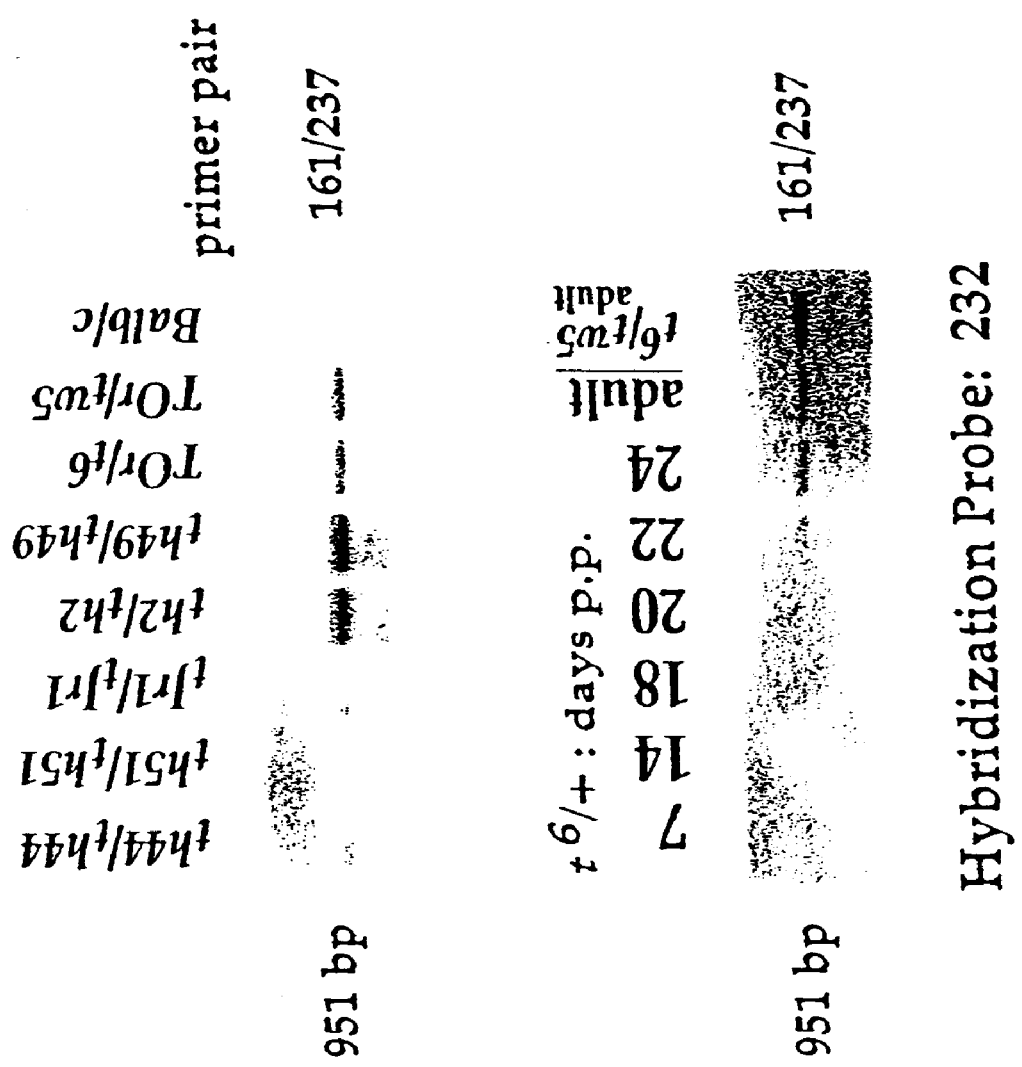

Fig. 9a

Sequence of cDNA pSV-T66Bk

```
      G AGA GGA GTT GGT GGA GTT GGT GGA GTT TGG TGG ATT TGG TGG AGT TGG TGG TGC
             10          19          28          37          46          55
CCT TTG CGA TTT CGT TGT ATC TAG TGA GCC GTG TGT GGA TTT TGT GTT TGA TTG GTT CGT
     64          73          82          91         100         109
GTG TGA GCT TTT GTG TGT GTG TGT GTG TGT GTG TGT GTG TGT GTG TGT GTG TGT GTG TGT
    124         133         142         151         160         169
AGA TCA GTG TGT GTT TGG GAG GAG CTT GTG TGT GTG AGT TGT GTT TTA AGT TTA TTT GCG
    184         193         202         211         220         229
TGT GAG TAC CTT TGG GTT TTT GTG TGT GTC TGT GTG TGT TTG TGT GTG TAT AAC TGT GGG
    244         253         262         271         280         289
TGA CTG TAA GTG CAC CTG TGT GTT TGT ACG TGA GTG TGT AAG ACT GTG TGT GTG CAC AAG
    304         313         322         331         340         349
AGC GTG TGT AGG TGC ACG TGT TGT AGG TGT GAG AAC ACC TGT TGT GTT TAG CCA TCA GT
    364         373         382         391         400         409
CAG CTT GGT CAT TGT TTC TAA G * GT AGC ATT TAT ACT TTG TTA CCT CAA GTG GGC TCT GGG
    424         433            442         451         460         469
                                                                  M   E   K   F
AGT CAA CAG AAG TCA GAA AAG CTC AGA TCC AAG CCC CCT TTT TCT GAC ATG GAG AAA TTT
    484         493         502         511         520         529
 H   A   Q   Y   E   M   L   E   T   I   G   Q   G   G   C   A   Q   V   K   L
CAT GCT CAA TAT GAG ATG CTA GAG ACT ATT GGC CAG GGA GGC TGC GCC CAG GTG AAG CTG
    544         553         562         571         580         589
 A   R   H   R   L   T   G   T   H   V   A   V   K   V   I   V   K   R   E   C
GCC CGA CAC CGC CTC ACA GGC ACC CAC GTG GCT GTC AAA GTG ATT GTA AAG AGG GAG TGT
    604         613         622         631         640         649
 W   F   N   P   V   M   S   E   A   E   L   L   M   M   T   D   H   P   N   I
TGG TTC AAC CCT GTC ATG TCT GAG GCA GAG TTA CTG ATG ATG ACC GAT CAT CCG AAT ATC
    664         673         682         691         700         709
 I   S   L   L   Q   V   I   E   T   K   K   K   V   Y   L   I   M   E   L   C
ATC TCT CTC CTT CAA GTC ATT GAG ACC AAG AAG AAA GTA TAC CTC ATT ATG GAG TTG TGC
    724         733         742         751         760         769
 E   G   K   S   L   Y   Q   H   I   Q   N   A   G   Y   L   Q   E   D   E   A
GAG GGT AAA TCA CTT TAC CAA CAC ATC CAA AAT GCT GGC TAC CTG CAG GAG GAT GAA GCA
    784         793         802         811         820         829
 R   P   L   F   K   Q   L   L   S   A   M   N   Y   C   H   N   Q   G   I   V
CGC CCA TTA TTC AAG CAG CTC TTA AGT GCT ATG AAC TAC TGC CAC AAC CAG GGT ATA GTT
    844         853         862         871         880         889
 H   R   D   L   T   P   D   N   I   M   V   E   K   D   G   K   V   K   I   I
CAC AGG GAC CTG ACA CCT GAC AAT ATT ATG GTA GAA AAA GAT GGG AAA GTG AAG ATC ATT
    904         913         922         931         940         949
 D   F   G   L   G   T   Q   E   K   P   G   Q   N   H   N   L   F   C   E   I
GAT TTT GGA CTC GGC ACC CAA GAG AAG CCA GGG CAA AAC CAC AAC TTA TTC TGT GAG ATT
    964         973         982         991        1000        1009
 Y   P   F   S   T   P   E   V   L   F   N   R   P   Y   D   M   R   K   I   D
TAC CCA TTT AGT ACT CCT GAG GTG CTC TTT AAC AGA CCC TAT GAT ATG CGC AAG ATC GAT
   1024        1033        1042        1051        1060        1069
 V   W   G   L   G   V   V   L   Y   F   M   V   T   G   K   I   L   F   D   T
GTG TGG GGT CTT GGA GTT GTG CTG TAT TTT ATG GTA ACT GGA AAG ATT CTG TTT GAT ACT
   1084        1093        1102        1111        1120        1129
 A   S   V   E   K   L   R   K   Q   I   V   A   E   K   C   S   V   P   C   R
GCC AGC GTA GAA AAG CTG CGA AAG CAA ATT GTT GCA GAA AAG TGT TCT GTT CCC TGT AGA
   1144        1153        1162        1171        1180        1189
 L   S   V   E   L   Q   D   L   I   R   L   L   M   T   D   I   P   E   L   R
CTG TCA GTA GAG CTC CAA GAC CTG ATT AGA CTT TTA ATG ACG GAC ATC CCC GAA CTT AGG
   1204        1213        1222        1231        1240        1249
 P   T   V   A   E   V   M   V   H   P   W   V   T   E   G   S   G   V   L   P
CCC ACT GTT GCT GAA GTT ATG GTG CAT CCC TGG GTC ACA GAA GGC TCA GGG GTG TTA CCA
   1264        1273        1282        1291        1300        1309
 D   P   C   E   E   H   I   P   L   K   P   D   P   A   I   A   K   A   M   G
GAT CCT TGT GAA GAA CAT ATA CCC CTC AAG CCA GAC CCT GCG ATT GCA AAA GCA ATG GGA
   1324        1333        1342        1351        1360        1369
```

Fig. 9b

Sequence of cDNA pSV-T66Bk continued

```
 F   I   G   F   Q   A   Q   D   I   E   D   S   L   C   Q   R   K   F   N   E
TTT ATC GGG TTC CAA GCT CAA GAC ATT GAA GAT TCG TTA TGT CAG AGA AAA TTC AAC GAA
    1384        1393        1402        1411        1420        1429
 T   M   A   S   Y   C   L   L   K   K   Q   I   L   K   E   C   D   R   P   I
ACC ATG GCA TCT TAT TGT CTA CTG AAA AAA CAG ATT CTT AAG GAA TGT GAC AGG CCA ATC
    1444        1453        1462        1471        1480        1489
 R   A   Q   P   M   N   P   S   V   T   P   L   S   S   L   V   D   A   P   T
CGG GCT CAG CCC ATG AAT CCA TCT GTG ACC CCA CTC TCT TCC CTT GTT GAT GCT CCT ACT
    1504        1513        1522        1531        1540        1549
 F   H   L   G   L   R   R   T   E   T   E   P   T   G   L   R   L   S   D   N
TTC CAT CTC GGA CTT CGG AGG ACA GAG ACT GAA CCC ACA GGT CTC AGA TTA TCT GAC AAT
    1564        1573        1582        1591        1600        1609
 K   E   V   P   V   C   G   N   S   T   S   K   K   R   E   R   S   F   S   G
AAG GAA GTG CCT GTC TGT GGC AAT AGT ACT AGT AAG AAA AGA GAG AGA AGT TTC AGT GGG
    1624        1633        1642        1651        1660        1669
 P   G   V   L   S   R   P   I   N   T   T   P   T   M   D   Q   T   H   T   R
CCG GGT GTT CTC AGC AGG CCG ATT AAC ACA ACA CCC ACA ATG GAC CAA ACA CAC ACC CGT
    1684        1693        1702        1711        1720        1729
 T   W   S   G   P   C   I   Y   S   N   V   C   T   I   H   P   N   S   I   N
ACT TGG AGT GGT CCC TGC ATT TAC TCA AAT GTT TGC ACA ATC CAT CCA AAC AGC ATC AAT
    1744        1753        1762        1771        1780        1789
 E   S   T   E   G   H   I   S   T   S   A   E   D   K   P   V   H   S   R   G
GAG AGT ACA GAA GGC CAC ATC AGT ACC TCA GCA GAG GAT AAG CCT GTC CAC AGC AGA GGC
    1804        1813        1822        1831        1840        1849
 W   P   R   G   I   K   G   W   T   R   K   I   G   N   A   M   R   K   L   C
TGG CCC AGA GGC ATC AAG GGC TGG ACT AGG AAG ATA GGA AAT GCA ATG AGG AAG CTC TGT
    1864        1873        1882        1891        1900        1909
 C   C   I   P   S   K   E   T   S   H   L   G   Q   R   R   V   C   P   K   I
TGC TGT ATC CCA TCC AAA GAG ACA TCT CAC CTG GGG CAG AGA AGA GTC TGC CCA AAA ATT
    1924        1933        1942        1951        1960        1969
TAA GAC ACA GGA AGG ATG TCA GGA GAA TGA GCA TCC AGC ATG GCC CAG * CCT TTC AGA CCG
    1984        1993        2002        2011        2020        2029
AAG GCA AGC TCT ACC TGA TCC TGG ACT TCC TGC GGG GAG GTG ACC TCT TCA CCA GGC TTT
    2044        2053        2062        2071        2080        2089
CCA AAG AGG TGA TGT TCA CGG AGG AGG ATG TCA AGT TCT ACC TGG CTG AGC TGG CCT TGG
    2104        2113        2122        2131        2140        2149
CTC TAG ACC ACC TCC ATG GCC TGG GGA TCA TCT ACA GGG ATC TGA AGC CAG AGA ATA TCC
    2164        2173        2182        2191        2200        2209
TCC TGG ATG AAG AGG GAC ATA TTA AGA TCA CAG ATT TTG GCT GAG CAG GAG GCC ACC G
    2224        2233        2242        2251        2260        2269
ACC ATG ACA AGA GAG CCT ATT CAT TTT GTG GGA CTA TTG AAT ACA TGG CGC CCG AGG TGG
    2284        2293        2302        2311        2320        2329
TGA ACC GGC GTG GAC ACA CAC AGA GTG CCG ACT GGT GGT CCT CGT GTG CTC ATG TCG
    2344        2353        2362        2371        2380        2389
AGA TGC TCA CAG GGT CCC TGC CAT TCC AGG GGA AGG ACA GGA AGG AAA CAA TGG CCC GCA
    2404        2413        2422        2431        2440        2449
TCC TCA AAG CAA AGC TGG GTA TGC CTT AGT TCC TCA GTG CGG AGG CTC AGA GCC TGC TCA
    2464        2473        2482        2491        2500        2509
GGG CCC TTT TCA AGC GGA ACC CCT GCA ACC GGC TAG GTA AGG GTC CCT GTG ACA CCC CCA
    2524        2533        2542        2551        2560        2569
CCC CAG GAA TGC AAT GAG GCT GCC CTC TAG ACC CCC TTA GGA ATG TGA GAG GCA CAC CAT
    2584        2593        2602        2611        2620        2629
TCT GTT CCC CAC GGG ATG TGG AGG ACT TCC TCC TTA TGC CCC AAC TCT GAA CTG TAT GCT
    2644        2653        2662        2671        2680        2689
TTT CCT TGC TAA GGT TGC AGG AAG CAG AGG TAC CCC GAC GCT GGG GAA ACA CTC ACA TGT
    2704        2713        2722        2731        2740        2749
GGC CTG GCG CCC ACA GGC ACG TGG ACT TAT CAG GAT GCT GAA AAG GCA TTT GAA AAA AAA
    2764        2773        2782        2791        2800        2809
AAA AAA AAA AAA
    2824
```

Sequence of cDNA pCR.Balb-66k

```
          C   ACG TGT GGT AGG TGT GAG AAC ACC TCT TGT GTT GAG GCC GTC AGT CAG CTT GGC
                      10          19          28          37          46          55
                                                              M   G   S   G   S   Q   Q
CAT TGT TTC TAA GGT AGC ATT TAT ACT TTG TTA CCT CAA ATG GGG TCT GGG AGT CAA CAG
         64          73          82          91         100         109
 K   S   E   K   L   R   S   K   P   P   F   S   E   M   E   N   F   H   A   Q
AAG TCA GAA AAG CTC AGA TCC AAG CCC CCT TTC TCT GAA ATG GAG AAC TTT CAT GCT CAA
        124         133         142         151         160         169
 Y   E   M   L   G   T   I   G   H   G   G   S   T   K   V   K   L   A   R   H
TAT GAG ATG CTA GGG ACT ATT GGC CAT GGA GGC AGC ACA AAG GTG AAG CTG GCC CGA CAC
        184         193         202         211         220         229
 R   L   T   G   T   H   V   A   V   K   M   I   P   K   R   E   Y   W   C   K
CGC CTC ACA GGC ACC CAC GTG GCT GTC AAA ATG ATT CCA AAG AGG GAG TAT TGG TGC AAA
        244         253         262         271         280         289
 P   L   M   S   E   A   E   L   L   M   M   A   D   H   P   N   I   I   S   L
CCT CTC ATG TCT GAG GCA GAG TTA CTG ATG ATG GCC GAT CAT CCG AAT ATC ATC TCT CTC
        304         313         322         331         340         349
 L   Q   V   I   E   T   K   K   K   V   Y   L   I   M   E   L   C   E   G   K
CTT CAA GTC ATT GAG ACC AAG AAG AAA GTA TAC CTC ATT ATG GAG TTG TGT GAG GGT AAA
        364         373         382         391         400         409
 S   L   Y   Q   H   I   R   N   A   G   Y   L   Q   E   D   E   A   R   A   L
TCA CTT TAC CAA CAC ATC AGA AAC GCT GGC TAC CTG CAG GAG GAT GAA GCA CGA GCA TTA
        424         433         442         451         460         469
 F   K   Q   L   L   S   A   I   N   Y   C   R   N   Q   G   I   V   H   R   D
TTC AAG CAG CTC TTA AGT GCT ATA AAC TAC TGC CGC AAC CAG GGT ATA GTT CAC AGG GAC
        484         493         502         511         520         529
 L   K   P   D   N   I   M   V   E   K   D   G   R   V   K   I   I   D   F   G
CTG AAA CCC GAC AAT ATT ATG GTA GAA AAA GAT GGG AGA GTA AAG ATC ATT GAT TTT GGG
        544         553         562         571         580         589
 L   G   I   Q   V   K   P   G   Q   K   L   N   L   F   C   G   T   Y   P   F
CTT GGC ATC CAA GTG AAG CCA GGG CAA AAA CTA AAC TTA TTC TGT GGG ACT TAC CCA TTT
        604         613         622         631         640         649
 S   A   P   E   V   L   L   S   R   P   Y   D   G   P   K   I   D   V   W   T
AGT GCT CCT GAG GTG CTC CTT AGC AGA CCC TAT GAT GGG CCC AAG ATC GAT GTA TGG ACT
        664         673         682         691         700         709
 L   G   V   V   L   Y   F   M   V   T   G   K   I   P   F   D   A   A   S   I
CTT GGA GTT GTG CTA TAC TTT ATG GTA ACT GGA AAG ATC CCA TTT GAT GCT GCC AGC ATA
        724         733         742         751         760         769
 E   K   L   R   K   Q   I   V   A   G   K   Y   S   V   P   C   R   L   S   V
GAA AAG CTG CGG AAG CAA ATT GTT GCA GGA AAG TAT TCT GTT CCC TGT AGA CTG TCA GTA
        784         793         802         811         820         829
 K   L   H   H   L   I   T   L   L   M   T   D   N   P   E   L   R   P   T   V
AAG CTT CAT CAC CTG ATT ACT CTT TTA ATG ACA GAC AAC CCT GAA CTT AGG CCC ACT GTT
        844         853         862         871         880         889
 A   E   V   M   M   H   P   W   V   T   K   G   S   G   V   F   P   D   P   C
GCT GAA GTT ATG ATG CAT CCC TGG GTC ACA AAA GGC TCA GGG GTG TTC CCA GAT CCT TGT
        904         913         922         931         940         949
 E   E   Q   I   P   L   K   P   D   P   A   I   V   K   A   M   G   H   I   G
GAA GAA CAG ATA CCC CTC AAG CCA GAC CCT GCG ATT GTA AAA GCA ATG GGA CAT ATT GGG
        964         973         982         991        1000        1009
 F   Q   A   Q   D   I   E   D   S   L   R   Q   R   K   F   N   E   T   M   A
TTC CAA GCT CAA GAC ATT GAA GAT TCT TTA CGT CAG AGA AAA TTC AAC GAA ACC ATG GCA
       1024        1033        1042        1051        1060        1069
 S   Y   C   L   L   K   K   Q   L   L   K   E   C   D   R   P   I   R   A   Q
TCT TAT TGT CTA CTG AAA AAA CAG CTT CTT AAG GAA TGT GAC AGG CCA ATC CGG GCT CAG
       1084        1093        1102        1111        1120        1129
 P   M   N   P   S   V   T   P   F   P   S   L   V   D   T   P   T   F   H   L
CCC ATG AAT CCA TCG GTG ACC CCA TTC CCC TCC CTT GTT GAT ACT CCT ACT TTC CAT CTC
       1144        1153        1162        1171        1180        1189
```

Fig. 10a

Sequence of cDNA pCR.Balb-66k continued

```
 G   L   R   R   R   E   T   E   P   T   S   L   R   L   S   A   N   R   Q   M
GGA CTT CGG AGG AGA GAG ACT GAA CCC ACG AGT CTC AGA TTA TCT GCT AAT AGG CAA ATG
        1204        1213        1222        1231        1240        1249
 S   V   C   G   R   S   T   S   K   K   R   D   R   S   F   S   W   P   G   V
TCT GTC TGT GGA AGG AGT ACT AGT AAG AAA AGA GAC AGA AGT TTC AGT TGG CCC GGT GTT
        1264        1273        1282        1291        1300        1309
 L   S   R   P   I   N   I   T   P   T   M   D   Q   T   H   T   C   T   R   S
CTC AGC AGG CCG ATT AAC ATA ACA CCC ACA ATG GAC CAA ACA CAC ACC TGT ACT AGG AGT
        1324        1333        1342        1351        1360        1369
 V   P   C   I   N   S   N   F   C   I   I   H   P   N   S   S   D   E   S   T
GTT CCC TGC ATT AAC TCA AAT TTT TGC ATA ATC CAT CCA AAC AGC AGC GAC GAG AGT ACA
        1384        1393        1402        1411        1420        1429
 E   G   H   T   S   A   S   A   E   D   K   P   V   R   S   R   G   W   P   R
GAA GGC CAC ACC AGT GCC TCA GCA GAG GAT AAG CCT GTC CGC AGC AGA GGC TGG CCC AGA
        1444        1453        1462        1471        1480        1489
 G   I   K   G   W   T   S   K   I   G   N   A   M   R   K   L   C   C   C   I
GGC ATC AAG GGC TGG ACT AGC AAG ATA GGA AAT GCG ATG AGG AAG CTC TGT TGC TGT ATC
        1504        1513        1522        1531        1540        1549
 P   S   N   E   T   S   H   L   G   Q   R   R   V   S   P   K   K
CCA TCA AAT GAG ACA TCT CAC CTG GGG CAG AGG AGA GTC TCC CCC AAA AAA TAA GAC ACA
        1564        1573        1582        1591        1600        1609
GGA AGG GTG TCA GGA AAC CGA GCA TTC GGC TCG GCA CAG AAG ATC ACT AGA GGA TGC CGG
        1624        1633        1642        1651        1660        1669
ATG CTA TGA TTC AAC AGT TAT AGT ATT GGA AAG GAC CCA TGT ATA GAC ATG GAC CTG CAA
        1684        1693        1702        1711        1720        1729
AAG GGA ACC TTG TGG AAA GGC ATC ATG TTC TGG GTC CAG CCA GGG GGA AGA A
        1744        1753        1762        1771        1780
```

Fig. 10b

Sequence of pCR.C3H-66k

```
            GTG TGG GAG GAG CTT GTG TGT GTG AGT TGT GTT TTA AGT TTA TTT GCG TCT CGT
                 9          18          27          36          45          54
GAG TAC CTT TGG GTT TGT GTG TGT GTG TCT GTG TGT GTT TGT GTG TGT ATA ACT GTG GGT
     63          72          81          90          99          108
GAC TGT TAA GAG CAC CTG TGT GTT TGT ACG TGA GTG TGT AAG ACT GTG TGT GTG CAC AAG
     123         132         141         150         159         168
AGC GTG TGT AGG TGC ACA TGT TGT AGG TGT GAG AAC ACC TGT TGT GTT TAG GCC ATC AGT
     183         192         201         210         219         228
CAG CTT GGC CAT TGT TTC TAA GGT AGC ATT TAT ACT TTG TTA CCT CAA GTG GGC TCT GGG
     243         252         261         270         279         288
                                                                 M   E   K   F
AGT CAA GAG AAA TCA GAA AAG CTC AGA TCC AAG CCC CCT TTC TCT GAC ATG GAG AAA TTT
     303         312         321         330         339         348
 H   A   Q   Y   E   M   L   E   T   I   G   Q   G   G   C   A   Q   V   K   L
CAT GCT CAA TAT GAA ATG CTA GAG ACT ATC GGC CAG GGA GGC TGC GCC CAG GTG AAG CTG
     363         372         381         390         399         408
 A   Q   H   R   L   T   G   T   H   V   A   V   K   V   I   V   K   R   E   C
GCC CAG CAC CGC CTC ACA GGC ACC CAC GTG GCT GTC AAA GTG ATT GTA AAG AGG GAG TGT
     423         432         441         450         459         468
 W   F   N   P   V   M   S   E   A   E   L   L   M   M   T   D   H   P   N   I
TGG TTC AAC CCT GTC ATG TCT GAG GCA GAG TTA CTG ATG ATG ACC GAT CAT CCG AAT ATC
     483         492         501         510         519         528
 I   S   L   L   Q   V   I   E   T   K   K   K   L   Y   L   I   M   E   L   C
ATC TCT CTC CTT CAA GTC ATC GAG ACC AAG AAG AAA TTA TAC CTC ATT ATG GAG TTG TGC
     543         552         561         570         579         588
 E   G   K   S   L   Y   Q   H   I   Q   N   A   G   Y   L   Q   E   D   E   A
GAG GGT AAA TCA CTT TAC CAA CAC ATC CAA AAT GCT GGC TAC CTG CAG GAG GAT GAA GCA
     603         612         621         630         639         648
 C   P   L   F   K   Q   L   L   S   A   V   N   Y   C   H   N   Q   G   I   V
TGC CCA TTA TTC AAG CAG CTC TTA AGT GCT GTG AAC TAC TGC CAC AAC CAG GGT ATA GTT
     663         672         681         690         699         708
 H   R   D   L   T   P   D   N   I   M   V   E   K   D   G   K   V   K   I   I
CAC AGG GAC CTG ACA CCT GAC AAT ATT ATG GTA GAA AAA GAT GGG AAA GTG AAG ATC ATT
     723         732         741         750         759         768
 D   F   G   L   G   T   Q   E   K   P   A   Q   K   L   N   L   F   C   E   N
GAT TTT GGA CTC GGC ACC CAA GAG AAG CCA GCG CAA AAA CTC AAC TTA TTC TGT GAG AAT
     783         792         801         810         819         828
 Y   P   F   S   T   P   E   V   L   L   S   R   P   Y   D   M   R   K   I   D
TAC CCA TTT AGT ACC CCT GAG GTG CTC CTT AGC AGA CCC TAT GAT ATG CGC AAG ATC GAT
     843         852         861         870         879         888
 V   W   G   L   G   V   V   L   Y   F   M   V   T   G   K   I   L   F   D   A
GTG TGG GGT CTT GGA GTT GTG CTG TAT TTT ATG GTA ACT GGA AAG ATT CTG TTT GAT GCT
     903         912         921         930         939         948
 A   S   I   E   K   L   R   K   Q   I   V   A   G   K   C   S   V   P   C   R
GCC AGC ATA GAA AAG CTG CGA AAG CAA ATT GTT GCA GGA AAG TGT TCT GTT CCC TGT AGA
     963         972         981         990         999        1008
 L   S   V   E   L   Q   D   L   I   R   L   L   M   T   D   N   P   E   L   R
CTG TCA GTA GAG CTC CAA GAC CTG ATT AGA CTT TTA ATG ACG GAC AAC CCC GAA CTT AGG
     1023        1032        1041        1050        1059        1068
 P   T   V   A   E   V   M   V   H   P   W   V   T   V   G   S   G   V   F   P
CCC ACT GTT GCT GAA GTT ATG GTG CAT CCC TGG GTC ACA GTA GGC TCA GGG GTG TTC CCA
     1083        1092        1101        1110        1119        1128
 D   P   C   E   E   Q   I   S   L   K   P   D   P   A   I   V   K   A   M   G
GAT CCT TGT GAA GAA CAG ATA TCC CTC AAG CCA GAC CCT GCG ATT GTA AAA GCA ATG GGA
     1143        1152        1161        1170        1179        1188
 Y   I   G   F   R   A   Q   E   I   E   D   S   L   R   Q   R   K   F   N   E
TAT ATC GGG TTC CGA GCT CAA GAA ATT GAA GAT TCG TTA CGT CAG AGA AAA TTC AAC GAA
     1203        1212        1221        1230        1239        1248
 T   M   A   S   Y   C   L   L   K   K   Q   I   L   K   E   C   D   R   P   I
ACC ATG GCA TCT TAT TGT CTA CTG AAA AAA CAG ATT CTT AAG GAA TGT GAC AGG CCA ATC
     1263        1272        1281        1290        1299        1308
```

Fig. 10c

Sequence of pCR.C3H-66k continued

```
R   A   Q   P   M   N   P   S   L   T   P   F   P   S   L   V   D   T   P   T
CGG GCT CAG CCC ATG AAT CCA TCG CTG ACC CCA TTC CCT TCC CTT GTT GAT ACT CCT ACT
    1323        1332        1341        1350        1359        1368
S   H   L   G   L   R   R   R   E   T   E   P   T   G   L   S   L   S   A   N
TCC CAT CTC GGA CTT CGG AGG AGA GAG ACT GAA CCC ACA GGT CTC AGC TTA TCT GCC AAT
    1383        1392        1401        1410        1419        1428
R   Q   V   S   V   C   G   K   S   T   S   K   K   R   D   R   S   F   S   W
AGG CAA GTG TCT GTC TGT GGC AAG AGT ACT AGT AAG AAA AGA GAC AGA AGT TTC AGT TGG
    1443        1452        1461        1470        1479        1488
P   G   V   L   G   R   P   I   H   T   T   P   T   M   D   Q   T   H   T   R
CCC GGT GTT CTA GGC AGG CCG ATC CAC ACA ACA CCC ACA ATG GAC CAA ACA CAC ACC CGT
    1503        1512        1521        1530        1539        1548
T   R   S   V   P   C   I   Y   S   N   F   C   T   I   H   P   N   S   I   D
ACT AGG AGT GTT CCC TGC ATT TAC TCA AAT TTT TGC ACA ATC CAT CCA AAC AGC ATC GAT
    1563        1572        1581        1590        1599        1608
E   S   T   E   G   H   T   S   A
GAG AGT ACA GAA GGC CAC ACC AGT GCC TAA GCA GAG GAT AAG CCT GTC CGC AGC AGA GGC
    1623        1632        1641        1650        1659        1668
TGG CCC AGA GGC ATC AAG GGC TGG ACT AGG AAG ATA GGA AAT GCG ATG AGG AAG CTC TGT
    1683        1692        1701        1710        1719        1728
TGC TGT ATC CCA TCA AAA GAG ACA TCT CAC CTG GGG CAG AGC AAA GTC TCC CCA AAA AAA
    1743        1752        1761        1770        1779        1788
TAA GAC ACA GGA AGG GTG TCA GGA GAA AGA GCA TCT GGC ACG GCC CAG AAG ATC ACC AGA
    1803        1812        1821        1830        1839        1848
GGA TGC CGG ATG CTA TGA TTC GAC AGT TAT AAT ATT GGA AAG GAC CCA TGT ATA GAC ATT
    1863        1872        1881        1890        1899        1908
GTC CTG CAA AAG GGA ACC TTG TGG AAA GGC ATC ATG TTC TGG GTT CAG CGT GCT TCA CTC
    1923        1932        1941        1950        1959        1968
AGA GCC CCG GGT CCA GCC AGG GGG AAG
    1983        1992        2001
```

Fig. 10d

Sequence of pλ.129-66k

```
  C   TTA GGT AGC ATT TAT ACT TTG TTA CCT CAA GTG GGC TCT GGG AGT CAA GCG AAG
          10          19          28          37          46          55
                                                  M   E   K   F   H   S   Q   Y
TCA GAA AAG CTC AGA TCC AAG CCC CCT TTC TCT GAC ATG GAG AAA TTT CAT TCT CAA TAT
         64          73          82          91         100         109
 E   M   L   E   T   I   G   Q   G   S   C   A   Q   V   K   L   A   Q   H   R
GAG ATG CTA GAG ACT ATC GGC CAG GGA AGC TGC GCC CAG GTG AAG CTG GCC CAG CAC CGC
        124         133         142         151         160         169
 L   T   G   T   H   V   A   V   K   V   I   V   K   R   E   C   W   F   N   P
CTC ACA GGC ACC CAC GTG GCT GTC AAA GTG ATT GTA AAG AGG GAG TGT TGG TTC AAC CCT
        184         193         202         211         220         229
 V   M   S   E   A   E   L   L   M   M   T   D   H   P   N   I   I   S   L   L
GTC ATG TCT GAG GCA GAG TTA CTG ATG ATG ACC GAT CAT CCG AAT ATC ATC TCT CTC CTT
        244         253         262         271         280         289
 Q   V   I   E   T   K   K   K   L   Y   L   I   M   E   L   C   E   G   K   S
CAA GTC ATC GAG ACC AAG AAG AAA TTA TAC CTC ATT ATG GAG TTG TGC GAG GGT AAA TCA
        304         313         322         331         340         349
 L   Y   Q   H   I   Q   N   A   G   Y   L   Q   E   D   E   A   C   P   L   F
CTT TAC CAA CAC ATC CAA AAT GCT GGC TAC CTG CAG GAG GAT GAA GCA TGC CCA TTA TTC
        364         373         382         391         400         409
 K   Q   L   L   S   A   V   N   Y   C   H   N   Q   G   I   V   H   R   D   L
AAG CAG CTC TTA AGT GCT GTG AAC TAC TGC CAC AAC CAG GGT ATA GTT CAC AGG GAC CTG
        424         433         442         451         460         469
 T   P   D   N   I   M   V   E   K   D   G   K   V   K   I   I   D   F   G   L
ACA CCT GAC AAT ATT ATG GTA GAA AAA GAT GGG AAA GTG AAG ATC ATT GAT TTT GGA CTC
        484         493         502         511         520         529
 G   T   Q   E   K   P   A   Q   K   L   N   L   F   C   E   N   Y   P   F   S
GGC ACC CAA GAG AAG CCA GCG CAA AAA CTC AAC TTA TTC TGT GAG AAT TAC CCA TTT AGT
        544         553         562         571         580         589
 T   P   E   V   L   L   S   R   P   Y   D   M   R   K   I   D   V   W   G   L
ACC CCT GAG GTG CTC CTT AGC AGA CCC TAT GAT ATG CGC AAG ATC GAT GTG TGG GGT CTT
        604         613         622         631         640         649
 G   V   V   L   Y   F   M   V   T   G   K   I   L   F   D   A   A   S   I   E
GGA GTT GTG CTG TAT TTT ATG GTA ACT GGA AAG ATT CTG TTT GAT GCT GCC AGC ATA GAA
        664         673         682         691         700         709
 K   L   R   K   Q   I   V   A   G   K   C   S   V   P   C   R   L   S   V   E
AAG CTG CGA AAG CAA ATT GTT GCA GGA AAG TGT TCT GTT CCC TGT AGA CTG TCA GTA GAG
        724         733         742         751         760         769
 L   Q   D   L   I   R   L   L   M   T   D   N   P   E   L   R   P   T   V   A
CTC CAA GAC CTG ATT AGA CTT TTA ATG ACG GAC AAC CCC GAA CTT AGG CCC ACT GTT GCT
        784         793         802         811         820         829
 E   V   M   V   H   P   W   V   T   E   G   S   G   V   F   P   D   P   C   E
GAA GTT ATG GTG CAT CCC TGG GTC ACA GAA GGC TCA GGG GTG TTC CCA GAT CCT TGT GAA
        844         853         862         871         880         889
 E   Q   I   S   L   K   P   D   P   A   I   V   K   A   M   G   Y   I   G   F
GAA CAG ATA TCC CTC AAG CCA GAC CCT GCG ATT GTA AAA GCA ATG GGA TAT ATC GGG TTC
        904         913         922         931         940         949
 R   A   Q   E   I   E   D   S   L   R   Q   R   K   F   N   E   T   M   A   S
CGA GCT CAA GAA ATT GAA GAT TCG TTA CGT CAG AGA AAA TTC AAC GAA ACC ATG GCA TCT
        964         973         982         991        1000        1009
 Y   C   L   L   K   K   Q   I   L   K   E   C   D   R   P   I   R   A   Q   P
TAT TGT CTA CTG AAA AAA CAG ATT CTT AAG GAA TGT GAC AGG CCA ATC CGG GCT CAG CCC
       1024        1033        1042        1051        1060        1069
 M   N   P   S   L   T   P   F   P   S   L   V   D   T   P   T   S   H   L   G
ATG AAT CCA TCG CTG ACC CCA TTC CCT TCC CTT GTT GAT ACT CCT ACT TCC CAT CTC GGA
       1084        1093        1102        1111        1120        1129
 L   R   R   R   E   T   E   P   T   G   L   S   L   S   A   N   R   Q   V   S
CTT CGG AGG AGA GAG ACT GAA CCC ACA GGT CTC AGC TTA TCT GCC AAT AGG CAA GTG TCT
       1144        1153        1162        1171        1180        1189
 V   C   G   K   S   T   S   K   K   R   D   R   S   F   S   W   P   G   V   L
GTC TGT GGC AAG AGT ACT AGT AAG AAA AGA GAC AGA AGT TTC AGT TGG CCC GGT GTT CTA
```

Fig. 10e

Sequence of pλ.129-66k continued

```
          1204          1213          1222          1231          1240          1249
    G    R    P    I    H    T    T    P    T    M    D    Q    T    H    T    R    T    R    S    V
    GGC  AGG  CCG  ATC  CAC  ACA  ACA  CCC  ACA  ATG  GAC  CAA  ACA  CAC  ACC  CGT  ACT  AGG  AGT  GTT
          1264          1273          1282          1291          1300          1309
    P    C    I    Y    S    N    F    C    T    I    H    P    N    S    I    D    E    S    T    E
    CCC  TGC  ATT  TAC  TCA  AAT  TTT  TGC  ACA  ATC  CAT  CCA  AAC  AGC  ATC  GAT  GAG  AGT  ACA  GAA
          1324          1333          1342          1351          1360          1369
    G    H    T    S    A
    GGC  CAC  ACC  AGT  GCC  TAA  GCA  GAG  GAT  AAG  CCT  GTC  CGC  AGC  AGA  GGC  TGG  CCC  AGA  GGC
          1384          1393          1402          1411          1420          1429
    ATC  AAG  GGC  TGG  ACT  AGG  AAG  ATA  GGA  AAT  GCG  ATG  AGG  AAG  CTC  TGT  TGC  TGT  ATC  CCA
          1444          1453          1462          1471          1480          1489
    TCA  AAA  GAG  ACA  TCT  CAC  CTG  GGG  CAG  AGC  AGA  GTG  TCC  CCA  AAA  AAA  TAA  GAC  ACA  GGA
          1504          1513          1522          1531          1540          1549
    AGG  GTG  TCA  GGA  GAA  CGA  GCA  TGC  GGC  ACG  GCC  CAG
          1564          1573          1582          1591
```

Fig. 10f

Sequence of T66Bk-2 3´/T66Bk 5´region (putative promoter)

```
  *  GTA CAT TCT GTA TTT GAA TGT ATC TAT GTT ACT CAT GTC TGT GTC AAC TGG CAG
              9          18          27          36          45          54
ATT ATA CTT ATG TAT ATG TAT ATG TAT ATG TAT ATG TAT ATG TAT ATG TAT ATG
         63          72          81          90          99         108
TAT ATG TAT ATG TAT ATG GTG CAA TGC ATG GGG AAG CTA GGT CTA GAC ACC TTG GGA AAA
        123         132         141         150         159         168
TAG TTA AAT TGA ACC TGC CAA CAG ATC CAG CAT CCC AGA AGG TAT CTC CTG TGT GTA TCC
        183         192         201         210         219         228
TGC ACA TTG AAC AAG GAG GAG AAC TGA CCA TGC TAG GGA GAG GAA GTG GGA GAA GGA AGA
        243         252         261         270         279         288
GGA GGA GAT GCT GAG GGA GGA GAG GGT GGT ATG TGG TGG AAG CTA GGA GAA GAG GGG AAG
        303         312         321         330         339         348
AGG TTC AGA CAG GAG GAG GCA ACT TGG GGG AGC AGT GTG AAA CAG GGT AAC CCC AGC TGG
        363         372         381         390         399         408
AGA GAT GCC CTG TGC AGC TGA GGT TCT CAG AGT CCC TCT CAC GTG TGC TTT GGC ATT TTA
        423         432         441         450         459         468
G  *  AA GAT CAC CAG AGG ATG CCG GAT GCT ACG ATT CAA CAG TTA TAA TAT TGG AAA GGA CCC
              483         492         501         510         519         528
ATG TAT AGA CAT GGA CCT GCA AAA GGG AAC TTG TGA AAG GCA T CAT GTT CTG GGT TCA
        543         552         561         570         579         588
GCA TGT TTC ACT CAG AGC CCC GGG TCC AGC CAG GGG GAA GAA AGC AAA TGA TGA AAT CCC
        603         612         621         630         639         648
AGA TGG TGT CTG GGA TCA CCA TTC AGA GCA GGG GCT GAA AGC CTG TCC AAA GCT GGT AGA
        663         672         681         690         699         708
GAC AGA AGC CCC TCT GCC TAC CCA GGG TCA TAA TCA GAC TCC TGC TCT GAG AAT AAA ATA
        723         732         741         750         759         768
GAT GTT TGT GAA AGA TGA CCT CGG AGG TTT TCC TGC CTC TTC TTT ACA TAG GAA AAA CGT
        783         792         801         810         819         828
TCC TGT GGT GTT CAA AAT CCC CAG GTA GAA CAA CTT CAC ACC CCA AAC CAC CAG ATC ATT
        843         852         861         870         879         888
                                                KpnI
AAA AGT GCC TTT GAA GGG ACC AAG CTT TCA GGT ACC TGA AGT GGG GGA GTG TAG AAG CTG
        903         912         921         930         939         948
GGT GTG GAC TCT GGG TCC TTC TGG ACC CAG CAG CAT GAT CAG AAG GAC CAG AGA GAA CAT
        963         972         981         990         999        1008
TAG ATA CAA TCA GCT TGA CCC ACT TCC ACA GAG GCA AGC CCG GTC ACC CTG TGA ATT CCT
       1023        1032        1041        1050        1059        1068
GCA GAT GTG GCA TGT GTT GCA TCC CAG GGT CTC TGC CTA TGT AAG ATC AGA GAG CCT GGA
       1083        1092        1101        1110        1119        1128
GTT AGC TAA ATA TCA GTG TCC CTT GGC CTC AAG GGA GAA GGG AGG TTG GAT TCC AGC CCT
       1143        1152        1161        1170        1179        1188
AGC ATG GTC CTC TAA TAA GCA GTC CCC CTC AAA TGC AGA CAG CAA GGT CTA CAT GAT GTT
       1203        1212        1221        1230        1239        1248
CAC AGC TCC CCT GGC CTA AAA CCA TCC TGT GAT TGA TAC TAC AAA CCA GGA AGC AGG GAC
       1263        1272        1281        1290        1299        1308
TTG AAG TTG AGA TCA CTG ACT CAG GCT AGG GAG GGC TCC AGG GCA CCT GAT CTC AAC TAC
       1323        1332        1341        1350        1359        1368
AAT ATC AGA AGC TGA GCC ACA ATG ACC AGT GGT GGC AGG TTT TCT TTT CTG CTC TCA GGC
       1383        1392        1401        1410        1419        1428
CCG GCA ATG AAG TCC ACA TAT GAG GCT CTT TCC TCC CAG TCG TAC TGT CTG CAG ATA TGA
       1443        1452        1461        1470        1479        1488
GGT TCC TCA ACA GTG GAT TCA AAA CTC CAG AAA GGA AAG AGC TAC ACA TTG TAC TCT GAA
       1503        1512        1521        1530        1539        1548
AAG CAG AGG CCC ATT CAG GGT TTG AGC AAA TCA TCG CTC AAT AGT TAG ATT CCG GGT ACA
       1563        1572        1581        1590        1599        1608
CTA TGT GCT CAG GAG TAA CAC AGC AGC ATG GGT TCT GTG AGC TGA ATG TGG TTC AAA GTC
       1623        1632        1641        1650        1659        1668
TGT TTC AAG TGT GTC AGC AGC ACA GCT AAT CTG TTC ACG GTG TCC ACA GAG CTT CTG GTC
       1683        1692        1701        1710        1719        1728
```

Fig. 11a

Sequence of T66Bk-2 3´/T66Bk 5´region (putative promoter) continued

```
CTC GAA TGT GCC TGC TCC ACC TTT GGA CCT TAG AGT GTA AAG TGA GCC CTA CAC GCA GCA
    1743          1752          1761          1770          1779          1788
CGG ACT TGG TTT TCT ATA CAT CAT GCC AAC CTC TGT GTT TGA TGA CGG GGC GGG AGT GGG
    1803          1812          1821          1830          1839          1848
GGG TAT GTG GTG GGA GAG GTG AGA GAA AGG AGA GAG AGA GAG TCG GGT AGA GAA AGG GAA
    1863          1872          1881          1890          1899          1908
GGA AGG AGG GAG GGG AGA GGT AAA AGG AAA AGC TTC TAT GTA CAT GGT CAT GGA TAT GTC
    1923          1932          1941          1950          1959          1968
CCA CCA TGT GTG TGG AGG TTA GAG GAC ATT TTT CTC AGA TTT ACC TTC TAC TTT GTT TGA
    1983          1992          2001          2010          2019          2028
AAC TAG GTG TGT GGT TTG AGA CTA CAT ATG CCA AGG TGC CTG CCC CAC AAG CTC CCA GAC
    2043          2052          2061          2070          2079          2088
ATT TTC CTG TCT CTA ATG CTT TCC CTG CTT CCT AGG AGC TCT GAT ATT GCA AGT GTG TGC
    2103          2112          2121          2130          2139          2148
TCA GTG TCC ACA TGC ATT CAA TCT CAG GCC CTC CCT CTT TGC AGG GCA GGT GTT CTA ACC
    2163          2172          2181          2190          2199          2208
ACT TGT CTA TCC CCT AAG GCC CCT CCC ATG TTT TTG ATG AGA ATC CAA AAC CTT GGA AAT
    2223          2232          2241          2250          2259          2268
TAT GAG AAA CAC CTC TTT CTG TCA TCC TCA CAG GTG GTA ATA AGC TGC CCT ATT ATA TTT
    2283          2292          2301          2310          2319          2328
CAT AAG CAG AGT TGG GGT CCA GGA ATC ACC CCA CAA ACC ACT CAG CCA TCT AAG TCA AGC
    2343          2352          2361          2370          2379          2388
AGG GAT AGT TTA TTG AAC ATA TAC CCT GGG ACT GAT TGA TCA GGG ATG CAG ATC AGA CTC
    2403          2412          2421          2430          2439          2448
AGA AGT TTA GAC TGC AAC CCT GTT TCC CAA GGG TTG CTT ATA AAA GGC AAA AAC CAC AGG
    2463          2472          2481          2490          2499          2508
AGC TCA CGG CAA CCA TAA AAG CTC ACA CAC AGG TGC AGG AAG TCT TGC CAG GCA GTT GGG
    2523          2532          2541          2550          2559          2568
TGG CTG GTT CGA GTC CAA CCT TAT TTT TGC TAA CTG TAC AAA GCA ATT CCA ACT GAC TTT
    2583          2592          2601          2610          2619          2628
AGT TAT TAT GAT TGG CCC TAA ACG AGG GCA AGG GTC GGG GGT GTT TGC AAG AAC ACC AAA
    2643          2652          2661          2670          2679          2688
GCA TAA AGC TTA ATG GGA TAT GCA GTT AAT GGT TAG CTG GGC ATG AGA AAG GTC CTC TGT
    2703          2712          2721          2730          2739          2748
AAT AAT TTA AGA TGG CAG GCT ACA GGT ATA AAA TGA AAT GGC TAC AGT AAT GTC AGA AAG
    2763          2772          2781          2790          2799          2808
GCA GCA GCC ACC TAC GTC TTA ATG AGT AGG ACC TTT TTA TTT ATT TAT TTA TTT ATT TAT
    2823          2832          2841          2850          2859          2868
TTA TTT ATT TAT TTA ATG TTA AGT GGT GGC ATC ATC CTG GAC CCA TCA GTT GGA ATG CAA
    2883          2892          2901          2910          2919          2928
AGG TGA CAC ACA GAG TGT AGA CAT GAG GAC TTT AAA GCA GGA GGC ACA GCA AAC ATT CAA
    2943          2952          2961          2970          2979          2988
ACC AGA GAC CTA AGG ACA TCA GCA TGG CCT AGA GGT TTT GAT TTC TAA AAG CCT AAT GTC
    3003          3012          3021          3030          3039          3048
AGT CTC CAT AGC CCA CTT AAG CCA GAG CCT TGA GTC CCT CCT AGC CCT GCC AGG ACA GGT
    3063          3072          3081          3090          3099          3108
CCT GAT ATG ACC ACA TGA GGA GTG ACT ATG ATG CGG CCC AGC CAG CAG GTT TAA GCT GTG
    3123          3132          3141          3150          3159          3168
GCC ACA CCT AGA TTT CTT TGA GTG TGT TGA GAG GAG TTG GTG GAG TTG GTG GAG TTT GGT
    3183          3192          3201          3210          3219          3228
GGA TTT GGT GGA GTT GGT GGT GCC CTT GCA GAT TTC GTT GTA TCT AGT GAG CCG TGT GTG
    3243          3252          3261          3270          3279          3288
GAT TTT GTG TTT GAT TGG TTC GTG TGT GAG CTT TTG TGT GTG TGT GTG TGT GTG TGT GTG
    3303          3312          3321          3330          3339          3348
TGT GTG TGT GTG TGT GTG TGT GTG TAG ATC AGT GTG TGT TTG GGA GGA GCT TGT GTG TGT
    3363          3372          3381          3390          3399          3408
GAG TTG TGT TTT AAG TTT ATT TGC GTG TGA GTA CCT TTG GGT TTT TGT GTG TGT CTG TGT
    3423          3432          3441          3450          3459          3468
```

Fig. 11b

Sequence of T66Bk-2 3´/T66Bk 5´region (putative promoter) continued

```
GTG TTT GTG TGT GTA TAA CTG TGG GTG ACT GTA AGT GCA CCT GTG TGT TTG TAC GTG AGT
    3483        3492        3501        3510        3519        3528
                                                    PmlI
GTG TAA GAC TGT GTG TGT GCA CAA GAG CGT GTG TAG GTG CAC GTG TTG TAG GTG TGA GAA
    3543        3552        3561        3570        3579        3588
CAC CTG TTG TGT TTA GGC CAT CAG TCA GCT TGG TCA TTG TTT CTA AG *
    3603        3612        3621        3630        3639
```

Fig. 11c

Fig. 13a

Sequence of cDNA pSV-T66Bk with potential second ORF encoding RSK3 Polypeptide

```
        GAG AGG AGT TGG TGG AGT TGG TGG AGT TTG GTG GAT TTG GTG GAG TTG GTG GTG
                 9          18          27          36          45          54
CCC TTT GCG ATT TCG TTG TAT CTA GTG AGC CGT GTG TGG ATT TTG TGT TTG ATT GGT TCG
         63          72          81          90          99         108
TGT GTG AGC TTT TGT GTG TGT GTG TGT GTG TGT GTG TGT GTG TGT GTG TGT GTG TGT GTG
        123         132         141         150         159         168
TAG ATC AGT GTG TGT TTG GGA GGA GCT TGT GTG TGT GAG TTG TGT TTT AAG TTT ATT TGC
        183         192         201         210         219         228
GTG TGA GTA CCT TTG GGT TTT TGT GTG TGT CTG TGT GTG TTT GTG TGT GTA TAA CTG TGG
        243         252         261         270         279         288
GTG ACT GTA AGT GCA CCT GTG TGT TTG TAC GTG AGT GTG TAA GAC TGT GTG TGT GCA CAA
        303         312         321         330         339         348
GAG CGT GTG TAG GTG CAC GTG TTG TAG GTG TGA GAA CAC CTG TGT TTA GGC CAT CAG
        363         372         381         390         399         408
TCA GCT TGG TCA TTG TTT CTA AG * G TAG CAT TTA TAC TTT GTT ACC TCA AGT GGG CTC TGG
        423         432            441         450         459         468
GAG TCA ACA GAA GTC AGA AAA GCT CAG ATC AAG GCC CCC TTT TTC TGA CAT GGA GAA ATT
        483         492         501         510         519         528
TCA TGC TCA ATA TGA GAT GCT AGA GAC TAT TGG CCA GGG AGG CTG CGC CCA GGT GAA GCT
        543         552         561         570         579         588
GGC CCG ACA CCG CCT CAC AGG CAC CCA CGT GGC TGT CAA AGT GAT TGT AAA GAG GGA GTG
        603         612         621         630         639         648
TTG GTT CAA CCC TGT CAT GTC TGA GGC AGA GTT ACT GAT GAT GAC CGA TCA TCC GAA TAT
        663         672         681         690         699         708
CAT CTC TCT CCT TCA AGT CAT TGA GAC CAA GAA GAA AGT ATA CCT CAT TAT GGA GTT GTG
        723         732         741         750         759         768
CGA GGG TAA ATC ACT TTA CCA ACA CAT CCA AAA TGC TGG CTA CCT GCA GGA GGA TGA AGC
        783         792         801         810         819         828
ACG CCC ATT ATT CAA GCA GCT CTT AAG TGC TAT GAA CTA CTG CCA CAA CCA GGG TAT AGT
        843         852         861         870         879         888
TCA CAG GGA CCT GAC ACC TGA CAA TAT TAT GGT AGA AAA AGA TGG GAA AGT GAA GAT CAT
        903         912         921         930         939         948
TGA TTT TGG ACT CGG CAC CCA AGA GAA GCC AGG GCA AAA CCA CAA CTT ATT CTG TGA GAT
        963         972         981         990         999        1008
TTA CCC ATT TAG TAC TCC TGA GGT GCT CTT AAC AGA CCA TGA TAT GCG CAA GAT CGA
       1023        1032        1041        1050        1059        1068
TGT GTG GGG TCT TGG AGT TGT GCT GTA TTT TAT GGT AAC TGG AAA GAT CTG TTG ATA C
       1083        1092        1101        1110        1119        1128
TGC CAG CGT AGA AAA GCT GCG AAA GCA AAT TGT TGC AGA AAA GTG TTC TGT TCC CTG TAG
       1143        1152        1161        1170        1179        1188
ACT GTC AGT AGA GCT CCA AGA CCT GAT TAG ACT TTT AAT GAC GGA CAT CCC CGA ACT TAG
       1203        1212        1221        1230        1239        1248
GCC CAC TGT TGC TGA AGT TAT GGT GCA TCC CTG GGT CAC AGA AGG CTC AGG GGT GTT ACC
       1263        1272        1281        1290        1299        1308
AGA TCC TTG TGA AGA ACA TAT ACC CCT CAA GCC AGA CCC TGC GAT TGC AAA AGC AAT GGG
       1323        1332        1341        1350        1359        1368
ATT TAT CGG GTT CCA AGC TCA AGA CAT TGA AGA TTC GTT ATG TCA GAG AAA ATT CAA CGA
       1383        1392        1401        1410        1419        1428
AAC CAT GGC ATC TTA TTG TCT ACT GAA AAA ACA GAT TCT AAG GGA ATG TGA CAG GCC AAT
       1443        1452        1461        1470        1479        1488
CCG GGC TCA GCC ATG AAT CCA TCT GTG ACC CCA CTC TTC CCT TGT TGA TGC TCC TAC
       1503        1512        1521        1530        1539        1548
TTT CCA TCT CGG ACT TCG GAG GAC AGA GAC TGA ACC ACA GGT CTC AGA TTA TCT GAA CAA
       1563        1572        1581        1590        1599        1608
TAA GGA AGT GCC TGT CTG TGG CAA TAG TAC TAG TAA GAA AAG AGA GAG AAG TTT CAG TGG
       1623        1632        1641        1650        1659        1668
GCC GGG TGT TCT CAG CAG GCC GAT TAA CAC AAC ACC ACA ATT GGA CCA AAC ACA CAC CCG
       1683        1692        1701        1710        1719        1728
TAC TTG GAG TGG TCC CTG CAT TTA CTC AAA TGT TTG CAC AAT CCA TCC AAA CAG CAT CAA
       1743        1752        1761        1770        1779        1788
```

Sequence of cDNA pSV-T66Bk with potential second ORF encoding RSK3 Polypeptide - continued

```
TGA GAG TAC AGA AGG CCA CAT CAG TAC CTC AGC AGA GGA TAA GCC TGT CCA CAG CAG AGG
    1803        1812        1821        1830        1839        1848
CTG GCC CAG AGG CAT CAA GGG CTG GAC TAG GAA GAT AGG AAA TGC AAT GAG GAA GCT CTG
    1863        1872        1881        1890        1899        1908
TTG CTG TAT CCC ATC CAA AGA GAC ATC TCA CCT GGG GCA GAG AAG AGT CTG CCC AAA AAT
    1923        1932        1941        1950        1959        1968
                                             M   S   I   Q   H   G   P   A       F   Q   T
TTA AGA CAC AGG AAG GAT GTC AGG AGA ATG AGC ATC CAG CAT GGC CCA G * CC TTT CAG ACC
    1983        1992        2001        2010        2019              2028
 E   G   K   L   Y   L   I   L   D   F   L   R   G   G   D   L   F   T   R   L
GAA GGC AAG CTC TAC CTG ATC CTG GAC TTC CTG CGG GGA GGT GAC CTC TTC ACC AGG CTT
    2043        2052        2061        2070        2079        2088
 S   K   E   V   M   F   T   E   E   D   V   K   F   Y   L   A   E   L   A   L
TCC AAA GAG GTG ATG TTC ACG GAG GAG GAT GTC AAG TTC TAC CTG GCT GAG CTG GCC TTG
    2103        2112        2121        2130        2139        2148
 A   L   D   H   L   H   G   L   G   I   I   Y   R   D   L   K   P   E   N   I
GCT CTA GAC CAC CTC CAT GGC CTG GGG ATC ATC TAC AGG GAT CTG AAG CCA GAG AAT ATC
    2163        2172        2181        2190        2199        2208
 L   L   D   E   E   G   H   I   K   I   T   D   F   G   L   S   K   E   A   T
CTC CTG GAT GAA GAG GGA CAT ATT AAG ATC ACA GAT TTT GGC TTG AGC AAG GAG GCC ACC
    2223        2232        2241        2250        2259        2268
 D   H   D   K   R   A   Y   S   F   C   G   T   I   E   Y   M   A   P   E   V
GAC CAT GAC AAG AGA GCC TAT TCA TTT TGT GGG ACT ATT GAA TAC ATG GCG CCC GAG GTG
    2283        2292        2301        2310        2319        2328
 V   N   R   R   G   H   T   Q   S   A   D   W   W   S   F   G   V   L   M   F
GTG AAC CGG CGT GGA CAC ACA CAG AGT GCC GAC TGG TGG TCC TTC GGT GTG CTC ATG TTC
    2343        2352        2361        2370        2379        2388
 E   M   L   T   G   S   L   P   F   Q   G   K   D   R   K   E   T   M   A   R
GAG ATG CTC ACA GGG TCC CTG CCA TTC CAG GGG AAG GAC AGG AAG GAA ACA ATG GCC CGC
    2403        2412        2421        2430        2439        2448
 I   L   K   A   K   L   G   M   P
ATC CTC AAA GCA AAG CTG GGT ATG CCT TAG TTC CTC AGT GCG GAG GCT CAG AGC CTG CTC
    2463        2472        2481        2490        2499        2508
AGG GCC CTT TTC AAG CGG AAC CCC TGC AAC CGG CTA GGT AAG GGT CCC TGT GAC ACC CCC
    2523        2532        2541        2550        2559        2568
ACC CCA GGA ATG CAA TGA GGC TGC CCT CTA GAC CCC CCT AGA ATG TGA GAG GCA CCA
    2583        2592        2601        2610        2619        2628
TTC TGT TCC CCA CGG GAT GTG GAG GAC TTC CTC CTT ATG CCC CAA CTC TGA ACT GTA TGC
    2643        2652        2661        2670        2679        2688
TTT TCC TTG CTA AGG TTG CAG GAA GCA GAG GTA CCC CGA CGC TGG GGA AAC ACT CAC ATG
    2703        2712        2721        2730        2739        2748
TGG CCT GGC GCC CAC AGG CAC GTG GAC TTA TCA GGA TTG CTG AAA GGC ATT TGA AAA AAA
    2763        2772        2781        2790        2799        2808
AAA AAA AAA AAA A
    2823
```

Fig. 13b

NUCLEIC ACIDS INVOLVED IN THE RESPONDER PHENOTYPE AND APPLICATIONS THEREOF

The present application is a U.S. National Stage Application of PCT/EP 98/07395, filed Nov. 18, 1998. This application also claims the benefit under 35 U.S.C. §119 of foreign application nos. EP 97 12 0190.0, filed Nov. 18, 1997 and EP 98 10 3596.7 (Mar. 2, 1998).

The present invention relates to nucleic acid molecules encoding expression products involved in the Responder function, which contributes to the phenomenon of transmission ratio distortion. The present invention also relates to regulatory regions of the genes corresponding to said nucleic acid molecules. The present invention further relates to recombinant DNA molecules and vectors comprising said nucleic acid molecules and/or regulatory regions as well as to host cells transformed therewith. Additionally, the present invention relates to transgenic animals, comprising said nucleic acid molecules, recombinant DNA molecules or vectors stably integrated into their genome. The various embodiments of the invention have a significant impact on breeding strategies by allowing for the specific selection of genetic traits and in particular of sex. Further, the present invention finds applications in the development of contraceptive.

The mouse T/t-complex, a region of approximately 12 cM genetic distance on the proximal part of chromosome 17, contains several loci acting in concert to produce a phenomenon called transmission ratio distortion (TRD). The latter designation indicates the fact that the so-called t-haplotype form of this chromosomal region has a selective advantage over the wild type form in that it is transmitted to the offspring at non-mendelian ratios of up to 99%. This transmission at non-mendelian ratio is achieved by the concerted action of mainly four loci, the so-called Distorters Tcd-1 (D1), Tcd-2 (D2) and Tcd-3 (D3), and the Responder Tcr ($R^t$)(Lyon 1984). Two more Distorters have been postulated by other authors (Silver and Remis 1987).

According to Lyon's model (Lyon 1986) which formally explains the genetic interactions of these loci, the Distorters D1, D2 and D3 act strongly and harmfully on the wild type allele of the Responder and weakly on the t form of the Responder ($R^t$), leading to distortion in favor of $R^t$. $R^t$ might protect sperm carrying it from this harmful action of the Distorters. The Distorters act in trans while the Responder acts in cis. This means that the chromosome which contains $R^t$ is transmitted at non-mendelian ratio to the offspring. If D2 or all the Distorters are present, the chromosome containing $R^t$ is transmitted at a frequency of more than 50% up to 99% to the offspring. If no Distorter or only D1 or D3 are present, however, the chromosome containing $R^t$ is transmitted at less than 50% to the offspring ("low" phenotype). The Distorters are only transmitted at ratios over 50% if they are located on the same chromosome as is $R^t$. The cis-action of $R^t$ suggests that $R^t$ may be expressed at a stage of spermiogenesis when spermatids are no longer connected in a syncytium (Willison and Ashworth 1987). This would ensure that the product of $R^t$ would be restricted to the spermatozoon containing the t-haplotype form of the R locus. It is expected that expression in elongating spermatids or mature spermatozoa is compatible with this requirement. The trans-acting and cis-acting properties of the Distorters and the Responder, respectively, have been demonstrated by the transmission ratio properties of so-called partial t-haplotypes which carry only a subset of the above named loci (FIG. 1).

Genetic mapping of molecular markers on partial t-haplotypes allowed a more or less precise localization of D1, D2, D3 and $R^t$ to subregions of the T/t-complex and relative to these molecular markers (Lyon 1984; Fox et al. 1985; Herrmann et al. 1986; Silver and Remis 1987; Bullard et al. 1992). Only one locus, $R^t$ could be mapped fairly precisely to a region of appr. 200 kb, the so-called T66B region (Fox et al. 1985; Schimenti et al. 1987; Nadeau et al. 1989; Rosen et al. 1990; Bullard et al. 1992). The T66B region represents a chromosomal piece of the t-haplotype identified by a t-specific restriction fragment length polymorphism detected with the probe Tu66 (Fox et al. 1985). The T66B region is not present in the partial t-haplotypes $t^{h44}$ and $t^{h51}$, but is present in the partial t-haplotypes $t^{low}$, $t^{h2}$, $t^{h49}$, $t^6$, and in the complete t-haplotypes, e.g. $t^{w5}$ or $t^{w12}$ (FIG. 1). Another partial t-haplotype, $t^{w71Jr1}$ (abbr. $t^{Jr1}$) contains T66A and a part of T66B. The chromosomes $t^{h44}$, $t^{h51}$ and $t^{Jr1}$ do not contain the $R^t$ function, whereas the other partial and complete t-haplotypes named above do. The t-haplotypes containing $R^t$ function must have the t-form of R, whereas the haplotypes $t^{h44}$, $t^{h51}$ and $t^{Jr1}$ are expected to have the wild type form. The genomic region T66B has been cloned molecularly and analyzed. A partial restriction map covering appr. 145 kb of it has been published (Schimenti et al. 1987; Rosen et al. 1990; Bullard et al. 1992).

An extensive and careful search of this region for genes expressed during spermatogenesis has yielded a single gene, T66B-a or Tcp-10b$^t$ (Schimenti et al. 1988). Further mapping studies localized "sequences responsible for differential responder activity" to an interval of 40 kb at the telomeric end of the T66B region which includes Tcp-10b$^t$ (Bullard et al. 1992). No other transcription unit could be identified by these authors in the T66B region within the last 10 years. Tcp-10b$^t$ has been claimed to represent the candidate for $R^t$, but a careful analysis showed that it does not encode Responder properties (Schimenti et al. 1988; Cebra-Thomas et al. 1991; Bullard and Schimenti 1990; Ewulonu et al. 1996).

The combined teachings of the prior art thus did not provide any clue how the genetic elements responsible for the Responder phenomenon might be identified. More importantly, the analyses referred to above questioned the prior art discussions that the Responder is a transcription unit. Accordingly, they taught away from the possibility that a transcription unit encoding the Responder might be located in the T66B region. The technical problem underlying the present invention was, accordingly, to overcome these long standing prior art difficulties and provide a genetic entity encoding the Responder function.

The solution to said technical problem is achieved by providing the embodiments characterized in the claims.

Accordingly, the present invention relates to a nucleic acid molecule comprising a transcription unit encoding in its 5' portion a kinase having a homology to the MARK2 kinase (Drewes et al., 1997) as well as to other kinases whereas the 3' portion of the nucleotide sequence has a high homology to the rsk3 kinase (Zhao et al., 1995) as well as to expression products thereof. The term "homology" as used in accordance with the present invention relates to more than 25% and preferably about 38% identity on the amino acid level. Thus, in accordance with the present invention, 38% identity was found in a region of 291 amino acids between MARK2 and the protein encoded by the nucleic acid molecule shown in FIGS. 4a and b or 9a and b. Preferably, the kinase gene encoded by the 5' portion lacks its 3' end which is preferably an untranslated region whereas the kinase gene encoded by the 3' portion lacks the 5' end and is preferably not translated.

Preferably or alternatively, the present invention relates to a nucleic acid molecule encoding an expression product involved in the Responder phenotype, which contributes to the phenomenon of transmission ratio distortion, selected from the group consisting of (a) a nucleic acid molecule comprising the nucleic acid molecule as shown in FIGS. 4a and b or 9a and b, 7a and b, 7c, d, and e, 7f, g, and h, 7i, j, and k, 7l or a fragment thereof;

(b) a nucleic acid molecule being an allelic variant or a homologue of the nucleic acid sequence of (a);

(c) a nucleic acid molecule hybridizing to a nucleic acid molecule complementary to a nucleic acid molecule of (a) or (b); and (d) a nucleic acid molecule which is related to the nucleic acid molecule of (a), (b) or (c) by the degeneration of the genetic code.

The term "Responder" or "R" as used in accordance with the present invention relates to mutant as well as wild type forms of the Responder locus.

The term "involved in the Responder phenotype", in accordance with the present invention relates to the fact that transcripts of all genes displayed on FIGS. 4a and b or 9a and b, 7a and b, 7c, d, and e, 7i, j, and k and the antisense transcript of 7f, g, and h are detected in testis carrying complete t-haplotypes, whereas mapping of the genes displayed on FIGS. 4a and b or 9a and b and 7a and b to the t-Responder region suggests that gene 4a and b or 9a and b and/or 7a and b is (are) the one(s) encoding t-Responder activity. In accordance with the further biological data described in this specification, in particular the data relating to the transgenic animals, it is proposed that pursuant to this invention, the gene displayed in FIGS. 4a and b or 9a and b encodes t-Responder activity. The overall data suggest that several genes of the Responder (T66Bk) gene family may act in parallel within t-haplotype carrying spermatids and/or spermatozoa and are thus presumed to be involved in the Responder phenotype, whereby it is envisaged that t-Responder products may antagonize the negative effect of t-Distorter genes and antisense transcripts derived from Responder genes may reduce the activity of Responder genes encoding products with t-Responder as well as wild type or nearly wild-type Responder activity. The latter products may permit the negative action of t-Distorter genes. It is, furthermore, envisaged in accordance with the present invention that alternative translation products from one mRNA-transcript may also be involved in the Responder phenotype (see, e.g., FIGS. 13a and b).

Specifically the cDNA sequence of T66Bk shown in FIGS. 4a and b or 9a and b contains the MARK kinase and the rsk3 kinase homology regions. The cDNA sequence of T66Bk-2 shown in FIGS. 7a and b contains only the MARK kinase homology region. The cDNA sequence of T66k-8 shown in FIGS. 7c, d, and e contains the complete sequence of T66Bk-2 except for a single base deleted between nucleotide position 1508 and 1509 resulting in a frame shift. The cDNA sequence of T66k-7as shown in FIGS. 7f, g, and h corresponds to an antisense transcript of a T66Bk family member. The cDNA sequence of T66k-20 shown in FIGS. 7i, j, and k shows a strong similarity to the above members of the T66Bk gene family.

The term "fragment" as used in connection with the nucleic acid molecule of the invention relates to a fragment that retains the Responder function. Preferably, said fragment comprises the portion of the nucleic acid molecule that has a homology to the MARK kinase referred to above or a part thereof.

As has been indicated above, in one embodiment of the nucleic acid molecule of the invention said expression product is an antisense RNA.

The term "an allelic variant or a homologue" comprises forms of the wild type or t-allele of the Responder "gene" which have been manipulated in vitro in order to achieve an optimal transmission ratio distortion effect and/or to adapt it to the specific requirements of the breeding scheme employed, thus improving the selectability of genetic traits. A number of standard manipulations known in the field are taken into consideration, such as those resulting in the exchange of phosphorylation sites (Ser, Thr, Tyr) on the Responder (poly)peptide for acidic or neutral (Ala) amino acid residues, mutagenesis of the active center, overexpression or knock out mutagenesis of said gene, construction of hypomorphic (poly)peptides by mutagenesis of ATP and/or GTP binding site(s), deletion of phosphorylation sites on said (poly)peptide, deletion of binding sites for other (poly) peptides involved in the Responder/Distorter signaling cascade, synthesis of antisense RNA, N-terminal or C-terminal truncations, introduction of frame shifts which alter part of the amino acid sequence of the protein, etc., resulting either in null, hypomorphic, constitutively active, antimorphic or dominant negative alleles. It is also envisaged that a distortion of the transmission ratio can be achieved with several, if not all, manipulated forms of the Responder gene suggested above. Thus, a manipulated Responder allele affecting the transmission ratio most effectively will have to be identified empirically by employing activity assays in cell culture systems and by employing transgenic animal systems.

It is also envisaged that one or several members of the T66Bk kinase gene family might function as Distorter(s), provided it is (they are) expressed during the diploid or early haploid phase of spermatogenesis allowing distribution of the gene products to all spermatozoa, or can be altered in vitro such as to function as Distorters. The latter may be achieved by in vitro manipulations such as those resulting in the exchange of phosphorylation sites (Ser, Thr, Tyr) on said Responder (poly)peptide for acidic or neutral (Ala) amino acid residues, N- or C-terminal truncation, frame shift, deletion of phosphorylation sites, deletion of binding sites for other (poly)peptides, mutagenesis of the active center, or overexpression of said gene or of antisense transcripts, resulting in constitutively active, hypomorphic, antimorphic or dominant negative gene products and expression of said gene products during the diploid or early haploid phase of spermatogenesis allowing distribution of the gene products to all spermatozoa, e.g. under the control of the Pgk2 promoter. These manipulations are envisaged to have a negative effect on sperm motility and/or fertilization capability. This negative effect may then be balanced by Responder constructs having the opposite effect. The latter could be restricted to those spermatozoa carrying the construct by expressing it under the control of the Responder gene promoter. It is envisaged that both types of spermatozoa would be negatively affected by the Distorter construct expressed in the diploid phase of spermatogenesis, whereas the sperm carrying, in addition, the Responder construct expressed in spermiogenesis would be partially or completely protected by the (poly)peptide expressed in it, and would thus gain an advantage in sperm motility and/or fertilization capability over the other sperm. This would lead to a transmission ratio distortion in favor of the "protected" spermatozoa. Preferably the Distorter construct expressed in both types of spermatozoa would encode a hypermorphic or constitutively active (poly)peptide, whereas the Responder construct expressed only in those spermatozoa carrying it should encode a hypomorphic, antimorphic or dominant negative (poly)peptide. Both constructs could be integrated on the same or on different chromosomes. Preferably both constructs would be integrated together on the X- or the Y-chromosome, resulting in the preferential or exclusive transmission of the X- or Y-chromosome and thus the preferential or exclusive fathering of female or male offspring, respectively.

The term "hybridizing" as used in connection with the present invention relates to stringent or nonstringent hybridization conditions. Preferably, it relates to stringent conditions. Said hybridization conditions may be established according to conventional protocols described, for example, in Sambrook, "Molecular Cloning, A Laboratory Manual", Cold Spring Harbor Laboratory (1989) N.Y., Ausubel, "Current Protocols in Molecular Biology", Green Publishing Associates and Wiley Interscience, N.Y. (1989), or Hames et al., (eds) "Nucleic acid hybridisation, a practical approach" IRL Press Oxford, England, (1985).

Stringent hybridization conditions are, for example, hybridization in 6×SSC, 5×Denhardt's reagent, 0,5% SDS, and 100 µg/ml denatured DNA at 65° C. and washing in 0,1×SSC, 0,1% SDS at 65° C.

In accordance with the present invention and in contrast to the teachings of the prior art, it was surprisingly found that nucleic acid sequences responsible for the Responder phenotype are comprised at the centromere-close part of the T66 B region. It conforms with several criteria that would be expected for the Responder function:

a) it is located in the T66B region;
b) it is expressed in testis; and
c) it is expressed during spermatogenesis.

In accordance with the present invention, it is further envisaged that additional expression products may contribute to Responder function as has been indicated above which are not necessarily located in the B-region.

As has been indicated above, one of the transcription units (namely T66Bk) contributing to the Responder (R) phenotype apparently arises from two truncated genes. One of said genes has a high homology to the rsk3 gene, the second one has an homology to the MARK kinase recently identified (Drewes et al., 1997). Another transcription unit envisaged to contribute to the R phenotype, T66Bk-2, also has a homology to the MARK kinase, but lacks homology to the rsk3 gene as indicated above. The identification of the genetic basis underlying the R phenotype allows a number of genetic manipulations, in particular in connection with breeding schemes, to be conveniently carried out in the future. Such schemes will be addressed in more detail herein below.

In accordance with the present invention, it is envisaged that the expression products encoded by the nucleic acid sequences of the invention may contribute to the Responder phenotype in several different ways. Thus, in one embodiment one of the above indicated expression products are themselves sufficient to distort the transmission ratio. In another embodiment all of said expression products or combinations of them have to be provided in order to distort the transmission ratio, with certain combinations being more effective than others. In yet another embodiment of the present invention said expression products may work in an additive or synergistic manner. In a still further embodiment it is envisaged that antisense transcripts derived from one or several genes of the T66Bk gene family may contribute to the t-Responder function resulting in a lower level or abolishment of mRNA of one or several T66Bk genes and thus a lower level or abolishment of the corresponding (poly)peptides translated from said mRNA molecules. An example of such an antisense transcript is shown in FIGS. 7f, g, and h. Furthermore, it is suggested that the specifically identified nucleic acid sequences coding for expression products involved in the R phenotype may not be the only ones responsible for the Responder phenotype. Thus, it is envisaged that further nucleic acids encoding expression products that act in concert with the ones discussed above and that may contribute to the Responder phenotype are contained in the genome. Additionally, it is envisaged in accordance with the present invention that the nucleic acid molecules of the invention exert or enhance the Responder phenotype in conjunction with further sequences comprised, for example, in the T66A, T66B and T66C regions. Preferably, said additional regions encode MARK-related kinases.

Also, the person skilled in the art will, on the basis of the teachings of the present invention, be in a position to genetically manipulate the nucleic acid contributing to the Responder phenotype. He will further be in the position to screen the genome of an organism or cell of interest for additional nucleic acid sequences encoding Responder functions on the basis of the genetic organization of the Responder taught in accordance with the present invention. All these embodiments that are without further ado derivable from the specific teachings provided herein are also comprised by the present invention.

It is further envisaged in accordance with the present invention that the Responder may act as a component of a signaling cascade involved in sperm motility and/or the fertilization of oocytes. The t-Responder may act such as to protect the sperm carrying the t-form of the Responder from the negative actions of the t-Distorters whereas the sperm carrying the wild type form of the Responder is "poisoned" (see Lyon 1986). Therefore, the action of the t-form of the Responder somehow counteracts the t-Distorter function suggesting that the Distorters are part of the same signaling cascade. It is, thus, envisaged that the wild type gene or the products of any member of that signaling cascade, once molecularly known, can be manipulated such as to "poison" the sperm expressing either dominant active or dominant negative forms, or by overexpressing, reducing or abolishing the gene function of any member of said signaling cascade. Selection of genetic traits may then be easily achieved by manipulating the amino acid sequence, activity or expression level of any member of that signaling cascade and restricting the expression of the manipulated form preferentially or completely to those sperm carrying it, such as is the case for the Responder function. The promoter of the Responder or other promoters activating gene expression during the haploid phase of spermatogenesis would be a suitable means for achieving this restriction.

Accordingly, the present invention also relates to methods of influencing transmission ratio by manipulating the expression level or the protein activity of any other member of said signaling cascade. For the purposes of this invention, said cascade is termed "Responder/Distorter signal cascade". It is further envisaged in accordance with the present invention that other signaling cascades may exist besides the Responder/Distorter signaling cascade that may be involved in the motility and/or fertilization capability of spermatozoa. Thus, it is envisaged in accordance with the present invention that the expression level and/or activity of one or more of the proteins involved in said other signaling cascades may be also manipulated in order to influence the transmission ratio. Influencing transmission ratio implies that said ratio may be enhanced or reduced. Methods for manipulating said expression level or said protein activity are known in the art and comprise methods of manipulating amino acid sequences and/or, e.g., promoter strengths or expressing an inhibitor of any member of said signaling cascade. Alternatively, it is envisaged that the expression level may be modulated on the transcription level, the level of pre-mRNA processing, mRNA transport and/or stability, and/or the translation level. Preferably, the modification and/or replacement of elements does not alter the tissue specificity or the specificity for the developmental stage of the expression unit. It is also envisaged in accordance with the present invention that the genetic background of the host organism, the site of integration, and/or the number of integrated copies of a transgene construct may influence the expression efficiency of said transgene construct. Expression or activity of one or more of said members may (significantly) be altered or enhanced, (significantly) be reduced or abolished. Said members also include the Distorters. These methods of the invention can, either alone or in conjunction with other methods described below, advantageously be used for the generation of transgenic animals. Said transgenic animals provide a suitable assay system to test whether the above mentioned methods for manipulating said expression level or said protein activity were successful. Such a system is described in Example 6. Furthermore, said transgenic animals may be employed in any of the breeding schemes addressed below.

In another preferred embodiment of the invention, said nucleic acid molecule is a DNA molecule.

The deduction of the amino acid sequence from the nucleic acid sequence of the invention allows the conclusion that the polypeptide is the expression product that contributes to the Responder phenotype. However, it is not excluded that the mRNA contributes to or triggers said Responder phenotype. Also, it is envisaged in accordance with the present invention that the expression level, stage of expression during spermatogenesis or the copy number of said gene results in or contributes to the Responder phenotype. Therefore, in a preferred embodiment of the nucleic acid molecule of the invention said expression product is an RNA or a (poly)peptide.

A further preferred embodiment of the invention is a nucleic acid molecule, wherein said Responder function is the mouse-t-complex Responder function.

Although it is easily possible to identify mutated or wild-type Responders in animals other than the mouse on the basis of the genetic structure of the Responder that is provided in accordance with the present invention, the mouse t-complex Responder may find applications, for example in breeding, also when introduced into other animals. Specific applications of the Responder function are addressed herein below.

The invention further relates to a regulatory region of the gene corresponding to the nucleic acid molecule of the invention being capable of controlling expression of said nucleic acid molecule.

The term "corresponding" as used in accordance with the present invention also means that the gene comprises the nucleic acid molecule of the invention or fragments thereof.

The term "regulatory region" in the present application refers to sequences which influence the specificity and/or level of expression, for example in the sense that they confer cell and/or tissue specificity. Such regions can be located upstream of the transcription initiation site, but can also be located downstream of it, e.g., in transcribed leader sequences or in an intron.

The term "a regulatory region of the gene corresponding to the nucleic acid molecule" refers to a region with the above mentioned capabilities that controls expression of the bipartite nucleic acid molecule referred to herein also as a "gene".

Regulatory elements ensuring expression in eukaryotic cells, preferably mammalian cells, are well known to those skilled in the art. They usually comprise promoters ensuring initiation of transcription and optionally poly-A signals ensuring termination of transcription and stabilization of the transcript. Additional regulatory elements may include transcriptional as well as translational enhancers.

Preferably, said regulatory region is a naturally occurring regulatory region or a genetically engineered derivative thereof.

More preferably, said regulatory region comprises or is a promoter. Said promoter is preferably tissue specific and confers expression, for example, during spermiogenesis.

The term "promoter" refers to the nucleotide sequences necessary for transcription initiation, i.e. RNA polymerase binding, and also includes, for example, the TATA box.

In one embodiment, said promoter is or comprises a minimal promoter. According to the present invention, promoters from other species can be used that are functionally homologous to the regulatory sequences or the promoter of the murine gene, or promoters of genes that display an identical pattern of expression, in the sense of being expressed in sperm cells. As has been outlined above, it is possible for the person skilled in the art to isolate with the help of the known murine nucleic acid corresponding genes from other species, for example, human. This can be done by conventional techniques known in the art, for example, by using the nucleic acid molecule of the invention as a hybridization probe or by designing appropriate PCR primers. It is then possible to isolate the corresponding promoter region by conventional techniques and test it for its expression pattern. For this purpose, it is, for instance, possible to fuse the promoter to a reporter gene, such as the lacZ gene or green fluorescent protein (GFP) and assess the expression of the reporter gene in transgenic mice.

The present invention also relates to the use of promoter regions which are substantially identical to the murine promoter or to a promoter of a homologous gene or to parts thereof and which are able to confer specific expression in sperm cells.

Such promoters differ at one or more positions from the above-mentioned promoters but still have the same specificity, namely they comprise the same or similar sequence motifs responsible for the above described expression pattern. Preferably such promoters hybridize to one of the above-mentioned promoters, most preferably under stringent conditions. Particularly preferred are promoters which share at least 85%, more preferably 90–95%, and most preferably 96–99% sequence identity with one of the above-mentioned promoters and have the same specificity. Such promoters also comprise those which are altered, for example by deletion(s), insertion(s), substitution(s), addition (s), and/or recombination(s) and/or any other modification(s) known in the art either alone or in combination in comparison to the above-described nucleotide sequence. Methods for introducing such modifications in the nucleotide sequence of the promoter of the invention are well known to the person skilled in the art. It is also immediately evident to the person skilled in the art that further regulatory sequences may be added to the promoter of the invention. For example, transcriptional enhancers and/or sequences which allow for induced expression of the promoter of the invention may be employed. A suitable inducible system is for example tetracycline-regulated gene expression as described, e.g., by Gossen and Bujard (Proc. Natl. Acad. Sci. USA 89 (1992), 5547–5551) and Gossen et al. (Trends Biotech. 12 (1994), 58–62).

Most preferably, said regulatory region comprises the fragment from nucleotides 930 to 3576 of the sequence shown in FIG. 11.

Also comprised are fragments or variants of the above sequence wherein the regulatory function of said fragments or variants is essentially retained or even improved. This may be tested according to methods well known in the art in combination with the teaching of this specification.

The invention further relates to a recombinant DNA molecule comprising a nucleic acid molecule of the invention and/or a regulatory region of the invention and/or a regulatory region allowing expression during spermatogenesis/spermiogenesis.

Accordingly, the regulatory region may control expression of the nucleic acid molecule contributing to the Responder function. Alternatively, said recombinant DNA molecule may comprise said regulatory region which controls expression of a heterologous nucleic acid or which is not operatively linked to any nucleic acid and, thus, may be used for cloning purposes. In the first alternative, said regulatory region is operatively linked to a heterologous DNA sequence. For example, said regulatory region may be operatively linked to a naturally occurring or in vitro engineered DNA encoding a member of the Responder/Distorter cascade, for example, a Distorter or a member of another signaling cascade involved in sperm motility and/or fertilization. Also, in this embodiment of the invention, the nucleic acid molecule of the invention may be operatively linked to a different or to no regulatory region. The regulatory region may be the original regulatory region of the gene corresponding to the nucleic acid molecule of the invention or may be derived from a different copy of said gene or from a different gene. Furthermore, the regulatory region may be derived from a copy of the homologous gene (in case more than one copy exists) in a different species or may be derived from a different gene from said different species. The above-mentioned regulatory regions may also be modified in order to obtain optimum expression, which may be enhanced or reduced expression. Thus, it is envisaged in accordance with the present invention that e.g., the regulatory regions controlling expression of the gene comprising the T66k-20-cDNA (see FIGS. 7i, j, and k) or the cDNAs shown in FIG. 10 are used in unmodified or modified form in accordance with the present invention. Due to the teaching of the present invention, namely the cloning and the disclosure of the sequences of the cDNAs, it is routine experimentation for the person skilled in the art to clone and use said regulatory regions.

Advantageously, the recombinant DNA molecule of the invention may further comprise an expression unit encoding and expressing a desired genetic trait. Such a DNA molecule may be used to reduce, or enhance the inheritance of said desired genetic trait, provided that either the recombinant DNA molecule further comprises an expression unit encoding and expressing at least one Distorter or protein with Distorter activity, preferably D2, or the genetic background of the host provides such Distorter activity which may be naturally occurring in said host or which may have been introduced.

A particularly preferred embodiment of the invention relates to a recombinant DNA molecule, wherein said heterologous DNA sequence encodes a peptide, protein, antisense RNA, sense RNA and/or ribozyme. As regards the antisense RNA, it may find applications in methods of antisense therapy or antisense knockout strategies. Antisense therapy may be carried out by administering to an animal or a human patient, a recombinant DNA containing the regulatory sequences of the invention operably linked to a DNA sequence, i.e., an antisense template which is transcribed into an antisense RNA. The antisense RNA may be a short (generally at least 10, preferably at least 14 nucleotides, and optionally up to 100 or more nucleotides) nucleotide sequence formulated to be complementary to a portion of a specific mRNA sequence. Standard methods relating to antisense technology have been described (Melani, Cancer Res. 51 (1991), 2897–2901). Following transcription of the DNA sequence into antisense RNA, the antisense RNA binds to its target mRNA molecules within a cell, thereby inhibiting translation of the mRNA and down-regulating expression of the protein expected to be encoded by the mRNA. For example, an antisense sequence will be complementary to a portion of or all of the mRNA. In addition, ribozymes may advantageously be employed to eliminate wild-type Responder transcripts from cells.

The invention further relates to a recombinant DNA molecule, wherein said peptide, protein, antisense RNA, sense RNA, a toxin and/or ribozyme is capable of causing cell death.

In this embodiment of the invention, sperm which do not carry the R related transgene can be genetically selected.

For example, the promoter of the R gene can be used for the expression of a gene product inducing the destruction or apoptosis of said spermatocytes carrying said construct. Integration of such a construct on the X- or Y-chromosome will result in the transmission of the respectively other sex chromosome. Integration of the construct on the X chromosome will lead to the neutral transmission of the construct in female animals. Integration in the Y chromosome should, preferably, be in an inactive state that can be activated along the rules that will be laid down herein below.

A recombinant DNA molecule which further comprises DNA encoding an effector polypeptide is a further preferred embodiment of the invention.

It is particularly preferred that said effector polypeptide is capable of sequestering an ion selectively binding to a solid support, or binding to a preselected antigenic determinant or is a toxin, an enzyme, a ribozyme, a label or a remotely detectable moiety.

In accordance with the invention, it is most preferred that said effector polypeptide is calmodulin, methallothionein, a fragment thereof, green fluorescent protein (GFP), β-lactamase (Zlokamik et al., 1998), hCD24, myc, FLAG, hemagglutinin or an amino acid sequence rich in at least one of glutamic acid, aspartic acid, lysine, histidine or arginine.

Accordingly and in other words, the above embodiments of the invention relate to the use of the R promoter for the expression of a (poly)peptide being or having a tag. Said tag may be expressed in the cytoplasm of sperm. An example of such a tag is GFP or β-lactamase. Said tag is alternatively located on the surface of sperm and thus, may be recognized by specific antibodies. This enables the separation of sperm carrying a transgene expressed under the control of the R promoter from sperm not carrying said transgene. The person skilled in the art is familiar with a variety of methods for the separation of sperm carrying said tag on its surface. Preferably, said tag is selected by affinity chromatography or by using a cell sorter. After separation, sperm carrying the transgene or sperm without the transgene can be used for fertilization of eggs. This embodiment includes integration of transgene in either autosomes or sex chromosomes. Advantageously, the solid support referred to above is a membrane or the surface of an ELISA plate.

Further, the invention relates to a vector comprising the nucleic acid molecule of the invention, the regulatory region of the invention or the recombinant DNA molecule of the invention.

The vector of the invention may simply be used for propagation of the genetic elements comprised therein. Advantageously, it is an expression vector and/or a targeting vector. Expression vectors such as Pichia pastoris derived vectors or vectors derived from viruses such as CMV, SV-40, baculovirus or retroviruses, vaccinia virus, adeno-associated virus, herpes viruses, or bovine papilloma virus, may be used for delivery of the recombinant DNA molecule or vector of the invention into targeted cell population. Methods which are well known to those skilled in the art can be used to construct recombinant viral vectors; see, for example, the techniques described in Sambrook, loc. cit. and Ausubel, loc. cit. Alternatively, the recombinant DNA molecules and vectors of the invention can be reconstituted into liposomes for delivery to target cells.

It is preferred according to one further embodiment that said vector comprises a heterologous promoter.

Said heterologous promoter not naturally operatively linked with the nucleic acid contributing to the Responder function may be used to determine a certain time point of the onset of Responder expression. This time point may be the same or a different one that is set when the natural Responder transcription unit is employed. For example, said heterologous promoter may also be active in the early or late haploid phase of spermatogenesis.

It is particularly preferred that said heterologous promoter is controlling gene expression in spermatogenesis and/or in spermiogenesis.

Most preferably, said heterologous promoter is the testis promoter of c-kit or of Angiotensin-Converting-Enzyme (ACE), both of which are well known in the art.

The invention further relates to a host cell transformed or transfected with the nucleic acid molecule, the recombinant DNA molecule or the vector of the invention. The host cell can be any prokaryotic or eukaryotic cell, such as a bacterial, insect, fungal, plant, animal or human cell. Prokaryotic host cells will usually only be employed for the propagation of the nucleic acid molecule of the invention and sometimes for the production of the expression product. Suitable mammalian, fish or bird cell lines are well known or can easily be determined by the person skilled in the art and comprise COS cells, Hela cells, primary embryonic cell lines etc.

The term "transfected or transformed" is used herein in its broadest possible sense and also refers to techniques such as electroporation, infection or particle bombardment.

Furthermore, the invention relates to a method of recombinantly producing an expression product as defined herein above comprising the steps of culturing the host cell of the invention under conditions to cause expression of the protein and recovering said protein from the culture.

The method of the invention is most advantageously carried out along conventional protocols which have been described, for example, in Sambrook, loc. cit.

The invention further relates to an expression product encoded by the nucleic acid molecule of the invention or which is obtainable by the production method of the invention.

In accordance with the invention, said expression product may either be an mRNA or a polypeptide. Said expression product is, in accordance with the present invention, involved in the Responder phenotype and contributes to the phenomenon of transmission ratio distortion.

A further embodiment of the invention relates to an antibody specifically recognizing the expression product of the invention.

The antibody of the invention may be a monoclonal antibody or an antibody comprised in a polyclonal serum. Accordingly, the term "antibody" as used herein also relates to a polyclonal antiserum. In addition, said term relates to antibody fragments or fusion proteins comprising antibody binding sites such as Fab, Fv, scFv fragments etc. The antibody of the invention has a number of applicabilities including purification or diagnostic processes.

The invention additionally relates to a nucleic acid molecule specifically hybridizing with the nucleic acid molecule of the invention translatable into said MARK related kinase or to an intron of said nucleic acid molecule or with the regulatory region of the invention or with a complementing strand thereof.

Said nucleic acid molecules comprise at least 15 nucleotides in length and hybridize specifically with a nucleic acid or regulatory sequence as described above or with a complementary strand thereof. Specific hybridization occurs preferably under stringent conditions and implies no or very little cross-hybridization with nucleotide sequences having no or substantially different regulatory properties. Such nucleic acid molecules may be used as probes and/or for the control of gene expression. Nucleic acid probe technology is well known to those skilled in the art who will readily appreciate that such probes may vary in length. Preferred are nucleic acid probes of 17 to 35 nucleotides in length. Of course, it may also be appropriate to use nucleic acids of up to 100 and more nucleotides in length. The nucleic acid probes of the invention are useful for various applications. On the one hand, they may be used as PCR primers for amplification of regulatory sequences according to the invention. In this embodiment, one of the primers may hybridize to the 3' portion of the Responder having a high homology to the rsk3 gene. Another application is the use as a hybridization probe to identify regulatory sequences hybridizing to the regulatory sequences of the invention by homology screening of genomic DNA libraries. Nucleic acid molecules according to this preferred embodiment of the invention which are complementary to a regulatory sequence as described above may also be used for repression of expression of a gene comprising such regulatory sequences, for example due to an aniisense or triple helix effect or for the construction of appropriate ribozymes (see, e.g., EP-B1 0 291 533, EP-A1 0 321 201, EP-A2 0 360 257) which specifically cleave the (pre)-mRNA of a gene comprising a regulatory sequence of the invention. Selection of appropriate target sites and corresponding ribozymes can be done as described for example in Steinecke, Ribozymes, Methods in Cell Biology 50, Galbraith et al. eds Academic Press, Inc. (1995), 449–460. Furthermore, the person skilled in the art is well aware that it is also possible to label such a nucleic acid probe with an appropriate marker for specific applications, such as for the detection of the presence of a nucleic acid molecule of the invention in a sample derived from an organism.

The above described nucleic acid molecules may either be DNA or RNA or a hybrid thereof. Furthermore, said nucleic acid molecule may contain, for example, thioester bonds and/or nucleotide analogues, commonly used in oligonucleotide anti-sense approaches. Said modifications may be useful for the stabilization of the nucleic acid molecule against endo- and/or exonucleases in the cell. Said nucleic acid molecules may be transcribed by an appropriate vector containing a chimeric gene which allows for the transcription of said nucleic acid molecule in the cell. Such nucleic acid molecules may further contain ribozyme sequences which specifically cleave the (pre)-mRNA comprising the regulatory sequence of the invention. Furthermore, oligonucleotides can be designed which are complementary to a regulatory sequence of the invention (triple helix; see Lee, Nucl. Acids Res. 6 (1979), 3073; Cooney, Science 241 (1988), 456 and Beal et al., Science 251 (1991), 1360), thereby preventing transcription and the production of the encoded mRNA and/or protein.

Furthermore, the invention relates to a pharmaceutical composition comprising the DNA molecule, the regulatory region, the recombinant DNA, the vector, the host cell, the expression product or the antibody of the invention.

Said pharmaceutical composition comprises at least one of the aforementioned compounds of the invention, either alone or in combination, and optionally a pharmaceutically acceptable carrier or excipient. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by conventional methods. These pharmaceutical compositions can be administered to subject in need thereof at a suitable dose. Administration of the suitable compositions may be effected by different ways, e.g., by intravenous, intraperitoneal, subcutaneous, intramuscular, topical, intradermal, intranasal or intrabronchial administration. The dosage regimen will be determined by the attending physician and other clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 μg (or of nucleic acid for expression or for inhibition of expression in this range); however, doses below or above this exemplary range are envisioned, especially considering the aforementioned factors. Generally, the regimen as a regular administration of the pharmaceutical composition should be in the range of 1 μg to 10 mg units per day. If the regimen is a continuous infusion, it should also be in the range of 1 μg to 10 mg units per kilogram of body weight per minute, respectively. Progress can be monitored by periodic assessment. Dosages will vary but a preferred dosage for intravenous administration of DNA is from approximately $10^6$ to $10^{22}$ copies of the nucleic acid molecule. The compositions of the invention may be administered locally or systematically. Administration will generally be parenterally, e.g., intravenously; DNA may also be administered directly to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents such as interleukins or interferons depending on the intended use of the pharmaceutical composition.

It is envisaged by the present invention that in particular the various recombinant nucleic acid/DNA molecules and vectors of the invention are administered either alone or in any combination using standard vectors and/or gene delivery systems, and optionally together with an appropriate compound and/or together with a pharmaceutically acceptable carrier or excipient. Subsequent to administration, said molecules may be stably integrated into the genome of the mammal, fish or bird. On the other hand, viral vectors may be used which are specific for certain cells or tissues, preferably for pancreatic cells and persist in said cells. Suitable pharmaceutical carriers and excipients are well known in the art.

The invention further relates to a diagnostic composition comprising the nucleic acid molecule, the regulatory region, the recombinant DNA molecule, the vector, the host cell, the expression product or a primer or an oligonucleotide hybridizing to the nucleic acid molecule or regulatory region of the invention or to a complementary strand thereof and preferably to the regions identified herein above or the antibody of the invention. Comprised by the above definition of the term "primer" are also pairs of primers such as forward and reverse primers that may be used for PCR. One of said primers of said pair of primers may hybridize in the region of the rsk-related nucleic acid sequence.

In one embodiment, said diagnostic composition is manufactured in the form of a kit.

Said compositions may additionally contain further compounds such as plasmids, antibiotics and the like for screening animals or cells for the presence of nucleic acid sequences or regulatory elements corresponding to those identified in the appended examples or described herein above. The components of the diagnostic composition and/or kit of the present invention may be packaged in containers such as vials, optionally in buffers and/or solutions. If appropriate, one or more of said components may be packaged in one and the same container. Additionally or alternatively, one or more of said components may be adsorbed to a solid support such as, e.g., a nitrocellulose filter or nylon membrane, or to the well of a microtiter plate.

The invention further relates to a method for the production of a transgenic non human mammal, fish or bird comprising introducing the nucleic acid molecule, the regulatory region, the recombinant DNA molecule or the vector of the invention into a cell, preferably germ cell, embryonic cell or an egg cell or a cell derived therefrom.

Methods for the generation of such transgenic animals are well known in the art and are described, for example, in "Guide to techniques in mouse development" (ed. Wassarman & DePamphilis) Methods in Enzymology Vol. 225 (Academic Press, 1993). The method of the invention also comprises embodiments related to the cloning of such animals. These embodiments include the steps of introducing said nucleic acid molecule, recombinant DNA molecule or vector of the invention into the nucleus of a cell, preferably an embryonic cell, replacing the nucleus of an oocyte, a zygote or an early embryo with said nucleus comprising said nucleic acid molecule, recombinant DNA molecule or vector of the invention, transferring either said ooyte, zygote or early embryo into a foster mother or first in vitro or in vivo culturing said oocyte, zygote or early embryo and subsequently transferring the resulting embryo into a foster mother and allowing the embryo to develop to term; see, for example, Wilmut I. et al. (1997) "Viable offspring derived from fetal and adult mammalian cells", Nature 385, 810–813.

In a preferred embodiment of the method of the invention, said chromosome is an X chromosome or the corresponding sex chromosome in birds or fish or an autosome.

In an alternative preferred embodiment of the method of the invention, said chromosome is a Y chromosome, or the corresponding sex chromosome in birds or fish.

It is particularly preferred that the nucleic acid molecule, the regulatory region, the recombinant DNA molecule or the vector of the invention, a heterologous promoter controlling expression in spermiogenesis and/or a DNA sequence encoding an effector (poly)peptide as defined hereinabove alone or in combination is/are integrated in said Y chromosome in a reversible inactive state of expressibility.

In accordance with the method of the invention, it is most preferred that said nucleic acid molecule, regulatory region, recombinant DNA molecule, vector of the invention, a heterologous promoter controlling expression in spermiogenesis and/or a DNA sequence encoding an effector (poly)peptide as defined hereinabove alone or in combination is/are flanked by lox P sites or FRT sites.

In all the above embodiments, at least one Distorter may be present on the same or on different chromosome.

An additional particularly preferred embodiment of the method of the invention further comprises introducing a nucleic acid molecule encoding at least one Distorter into the same or a different chromosome or introducing a chromosomal fragment comprising at least one Distorter into said cell. Advantageously, said Distorters are the mouse t-complex Distorter loci.

It is most preferred that said Distorter is/are D2 and/or D1.

Said method of the invention and its various preferred embodiments provide a wide range of applications in particular in the breeding of animals. Thus, as has been outlined above, the nucleic acid sequence encoding a molecule contributing to the Responder and/or an effector (poly)peptide as defined hereinabove may be under the regulation of the promoter naturally associated with said nucleic acid sequence. Integration of such a construct into a chromosome will, in the absence of a Distorter function result in a disadvantage in a chromosome if it comes to transmission of said chromosome. This disadvantage may be in the range of 49 to 0% transmission ratio. In the case that the Responder effect results in a very low or no transmission of the corresponding chromosome and if, in addition, the above recited construct comprising the nucleic acid molecule of the invention or the effector (poly)peptide is integrated into the Y chromosomes, the Y chromosome and the Responder function would hardly or not be transmitted by male animals. In order to provide for male animals, the Y chromosome should advantageously comprise an inactive construct that can, however, be activated. Said inactive construct should be without influence on the transmission ratio. One embodiment of said construct comprises loxP or FRT sites which flank an intervening sequence located between said promoter or a heterologous promoter controlling expression in spermiogenesis and effector (poly)peptide encoding sequences and/or sequences conferring Responder activity. The intervening sequence would be designed in such a way as to prevent the expression of effector and/or Responder activity. Activation of the effector and/or Responder activity may be effected by excision of the intervening sequence due to activity of the Cre or flp protein comprised in the same cell. Another embodiment of said construct comprises loxP or FRT sites flanking said promoter or a heterologous promoter controlling expression in spermiogenesis whereby the promoter is oriented away from the construct comprising the nucleic acid of the invention or the effector sequences encoding the above mentioned (poly)peptides. The activity of Cre or flp would allow the promoter to be inverted resulting in the transcription of the effector sequences or the sequences contributing to Responder activity during spermiogenesis. Another embodiment of said construct comprises loxP or FRT sites flanking said nucleic acid sequences reversely oriented towards the promoter such that the antisense strand is transcribed during spermiogenesis. Activation may be effected by flipping the effector sequences or the sequences contributing to Responder activity due to the activity of Cre or flp comprised in the same cell. Expression of the Cre or flp protein would advantageously be effected prior to spermiogenesis. The activation of the Responder or effector function is in such cases effected during spermatogenesis under the control of the R promoter or another promoter controlling expression during spermatogenesis/spermiogenesis. Preferably, the Cre gene is integrated on an autosome and may be expressed under the control of one of the following promoters: cytomegalovirus immediate early enhancer-chicken beta-actin hybrid (CAG) promoter, wherein site specific recombination occurs in the zygote; adenovirus Ella promoter, wherein expression is triggered during early embryogenesis; CMV, wherein expression is triggered during embryogenesis; OCT4, wherein expression is also triggered during embryogenesis and in germ line cells; HSV-TK or Pgk, wherein expression is ubiquitous; or Pgk2, wherein the construct is expressed during spermatogenesis. In the above embodiment, the Responder and/or effector encoding construct is transmitted by male animals in an inactive state. Mating with a female carrier of the Cre construct will result in male progeny having their Responder and/or effector activated during spermatogenesis. Progeny of these male animals inherit predominantly or exclusively the X chromosome of the father and are accordingly female progeny. In the case that the X chromosome is exclusively transmitted, the Responder and/or effector function is not inherited by the progeny. However, in cases of a less strong effect of the Responder and/or effector (poly)peptide leading to, for example, 10 to 20% transmission, the inactivation of the construct is not necessary because this low transmission is sufficient for the generation of male carriers. The frequency of inheritance of the R gene of the mouse, without the interaction of t-Distorters, is naturally in the range of about 20%.

In an alternative preferred embodiment of the method of the invention that has been identified above, the Responder and/or effector is integrated on the X chromosome or on an autosome. In this case, no inactive construct is necessary, since the Responder and/or effector encoding construct is transmitted in female animals in a neutral state, because Responder function only acts during spermatogenesis. Mating with wild type male animals leads to the generation of male animals carrying an active R and/or effector encoding gene on the X chromosome or an autosome. The chromosome carrying the R and/or effector encoding gene has a disadvantage in transmission. This means less than 50% to 0% of the progeny inherit said chromosome. In the case that the R and/or effector encoding construct is integrated into the X chromosome, no female progeny or only a low percentage of female progeny will be generated.

Furthermore, the invention relates to a method for the production of a male transgenic non human mammal, fish or bird having integrated in its Y or corresponding sex chromosome the nucleic acid molecule, the regulatory region, the recombinant DNA molecule or the vector of the invention, a heterologous promoter controlling expression in spermiogenesis and/or a DNA sequence encoding an effector (poly)peptide as defined hereinabove alone or in combination in an active state of expressibility, said method comprising in vitro fertilization or injection of spermatozoa into eggs using sperm from said male transgenic non human mammal, fish or bird. In a preferred embodiment of the present invention, said method prior to in vitro fertilization or injection further comprises allowing expression of said effector (poly)peptide and selecting for sperm expressing said effector (poly)peptide and, thus, containing said Y or corresponding sex chromosome. The above method is useful in case the transmission of the construct from male carriers by natural mating or artificial insemination is close to 0%. The production of transgenic male carriers can be achieved by the method of the invention using in vitro fertilization since it has been shown in mice that transmission ratio distortion of t/+ sperm does not occur during in vitro fertilization. The efficiency of the method of the invention can be further enhanced by selection for sperm carrying a Y or corresponding sex chromosome prior to in vitro fertilization as described above. Selection can be effected, e.g., by cell sorting.

Alternatively, male carriers of the R and/or effector function which are used for the generation of predominantly female progeny result from mating of hemizygous male animals carrying an inactive R and/or effector encoding construct with hemizygous female animals carrying a locus encoding a site specific recombinase and preferably the Cre locus. Progeny of such matings may be used for the maintenance of the strain as well as for the generation of the desired female progeny. It is worthwhile noting that from a single male carrier of the R and/or effector encoding construct many female progeny can be obtained.

A further embodiment of the invention that has been referred to above relates to the use of the R gene in combination with Distorter 2 (D2) preferably in combination with Distorter 1 (D1). In this embodiment, the chromosome carrying the R construct is transmitted predominantly or exclusively.

Distorters D1 and D2 (and possibly D3 as well as further postulated Distorters) act in trans to the advantage of the chromosome carrying the R construct. Whereas the applicant does not wish to be bound by any scientific theory, it is presently assumed that D1 and D2 are expressed in the diploid phase of spermatogenesis. Whereas the Distorter genes have not yet been identified it is well known that their gene products lead to the predominant or exclusive transmission of the chromosome carrying the R function. The Distorter function can be provided, for example, by a chromosome carrying a partial t-haplotype containing, e.g., Distorter D1 or D2 or both. It is further presumed that the expression products of the Distorter genes exert a negative influence on sperm not carrying the R function. In contrast, the sperm carrying the R function are protected by the R function. It is also suggested that such sperm may have a selective advantage as regards motility and thus faster reach the egg cell to be fertilized.

It is envisaged in accordance with the present invention that D2, D1 and further Distorters are located on the same or one or more different chromosomes than that or those which carry/carries the R construct. If R is integrated on the Y chromosome, mating will predominantly result in male progeny. Integration on the X chromosome, in contrast, will yield predominantly or exclusively female progeny. Integration in an autosome will result in a high transmission of said chromosome and thus any trait linked to said R construct. The high transmission of the R construct guarantees the maintenance of the R function. A practical advantage of the embodiment, in the case that the R encoding construct is integrated in the X chromosome, is that only few male wild type animals are necessary for the maintenance of the Y chromosome, i.e., of the male sex. Said male wild type animals may be generated by mating transgenic hemizygous female animals, carrying both the Distorter(s) and the R function with wild type males.

The subject-matter of the invention relates also to a transgenic non human mammal, fish or bird having stably integrated in its genome the nucleic acid molecule, the regulatory region, the recombinant DNA molecule or the vector of the invention or which is regenerated from a host cell of the invention or which is obtainable by the method of the invention referred to above.

Said transgenic animal is advantageously mouse, cattle, sheep, pig, goat, rat, rabbit, horse, dog, cat, camel, chicken, duck, salmon or trout.

Said transgenic animals may be used for producing offspring at a non mendelian ratio comprising breeding, in vitro fertilization or artificial insemination.

The invention additionally relates to a pair of transgenic non human mammals, fish or bird, wherein the male is a transgenic animal having integrated in its Y chromosome the nucleic acid molecule, the regulatory region, the recombinant DNA molecule, or the vector of the invention in a reversible inactive state of expressibility and optionally at least one Distorter in its genome, and the female is a transgenic animal having stably integrated into its genomic DNA a nucleic acid molecule encoding a site specific DNA recombinase.

The pair of transgenic animals should of course be preferably of the same species in order to allow a successful mating.

Preferably, in said female of said pair of animals, said DNA recombinase is Cre or flp.

Most advantageously, said DNA recombinase is controlled by regulatory elements that are active prior to spermiogenesis.

Further, the present invention relates to sperm obtainable from a male of the transgenic non-human mammal, fish or bird as defined herein before. Said sperm may be comprised in a composition suitable, for example, for deep freezing.

The invention also relates to a method for the selection of the sperm of the invention comprising allowing expression of the effector (poly)peptide and selecting for the presence or absence of said (poly)peptide.

In accordance with this method of the invention, the effector (poly)peptide is preferably selected for by cell sorting or affinity chromatography. Sperm either carrying or not carrying the effector (poly)peptide and thus the nucleic acid molecule of the invention may then be used for the further desired purpose.

Additionally, the invention relates to a method for the selection against sperm of the invention comprising (a) allowing expression of the recombinant DNA molecule defined herein above that is capable of causing cell death; and (b) selecting for viable sperm.

Cell death can advantageously also be caused by the in vivo expression of an effector molecule comprising a tag and the addition of a specific antibody binding to the tag and of complement to sperm in vitro, resulting in the inactivation or lysis of the spermatozoa carrying the construct.

Said methods find applicability in cases where sperm carrying the R promoter function is to be selected against.

A further object of the invention is the use of the sperm for the production of offspring. Such a production may comprise breeding, in vitro fertilization or artificial insemination.

An additional object of the present invention relates to the use of the nucleic acid molecule of the invention, the regulatory region of the invention, the recombinant DNA of the invention, the vector of the invention, the host cell of the invention, the expression product of the invention or the antibody of the invention for the isolation of receptors on the surface of sperm recognizing attractants of the egg cell for the development and/or production of contraceptive.

Further, the present invention relates to the use of the nucleic acid molecule of the invention, the regulatory region of the invention, the recombinant DNA of the invention, the vector of the invention, the host cell of the invention, the expression product of the invention or the antibody of the invention for the identification of chemicals or biological compounds able to trigger the (premature) activation or inhibition (repression) of the signaling cascade in which the Responder function is envisaged to be involved in. Such compounds could be applicable as potent contraceptiva since it is envisaged that the activation or inhibition (repression) of said signaling cascade may affect the motility of sperm, due to rapid exhaustion of their energy reserve, and/or by inhibiting sperm movement and/or affect the ability of sperm to fertilize ovulated eggs.

The identification of said chemical or biological compounds could be achieved by standard screening technology using the activation of the wild type Responder protein expressed in cell culture cells as an assay. It is e.g. envisaged that activation of said protein may trigger microtubule disruption in cell culture cells similar to the effect obtained by overexpression of the MARK kinase. Compounds triggering or inhibiting such an effect could then be tested for their effect on the motility and/or fertilization ability of sperm. Alternatively, a similar screening system for said compounds could also be envisaged for sperm without prior employment of a screening assay in cell culture cells.

Furthermore, the nucleic acid molecule of the invention, the regulatory region of the invention, the recombinant DNA of the invention, the vector of the invention, the host cell of the invention, the expression product of the invention or the antibody of the invention can be used for the isolation of receptor molecules and/or other members of the Responder/Distorter signaling cascade to which said expression product which would be expected to be a (poly)peptide may bind. Said signal transducing molecules may be identified by immunoprecipitation of protein complexes involving the Responder (poly)peptide and cloning of the corresponding genes encoding them, or by Two Hybrid Screening techniques in yeast employing standard technology. In particular, most preferably the Responder gene or (poly) peptide may be used to isolate the membrane receptor of the signaling molecule which is envisaged to activate said Responder/Distorter signaling cascade. Said membrane receptor is envisaged to be most preferable as a target for the development of novel contraceptives.

Additionally, the present invention relates to a method for the detection of the nucleic acid molecule, the regulatory region, the recombinant DNA molecule, the vector, or the expression product of the invention or a different heterologous expression product encoded by said DNA molecule or vector in the transgenic non human mammal, fish or bird of the invention or a part thereof comprising identifying said nucleic acid molecule, regulatory region, recombinant DNA molecule or vector of the invention or a portion thereof in said transgenic animal or said part thereof. The method of the invention allows the identification of animals of the invention on the basis of the genetic constructs they carry in accordance with the invention. Moreover, the method allows the identification of such animals e.g. after slaughtering by analyzing parts thereof. It should be noted that sperm, egg cells and embryos are also to be considered as parts of said animals. Detection may be effected by PCR using primers specified herein above. Nucleic acid hybridization with a detectably labeled probe constitutes a different method of detection. It is further most important to note that any portion or component of the nucleic acid, recombinant DNA molecule or vector may be identified in accordance with the method of the invention as long as it is indicative thereof. Thus, for example, the vector may comprise a nucleic acid sequence without any biological function that is nevertheless indicative of said vector and thus, of the invention. In another embodiment the effector (poly)peptide may be used for detection. Of course, the nucleic acid molecule of the invention or a portion thereof may itself be detected. All embodiments conceivable by the person skilled in the art that comprise the above step underfall the method of the invention as long as they allow the detection of the above mentioned genetic material.

Also, the present invention relates to a method of distorting the transmission ratio of genetic traits comprising manipulating the sequence or expression level of a different member of the Responder/Distorter signal cascade than the t-Responder, and restricting the expression of the manipulated form of said different member preferentially or completely to those sperm carrying it.

Preferred embodiments and various applications of this method as well as methods of manipulating said sequence or expression level have been addressed herein before.

The invention also relates to a transgenic animal having a recombinantly manipulated altered sequence or expression level of a member of the Responder/Distorter signal cascade, and wherein the expression of said member has been restricted preferentially or completely to those sperm carrying it.

Preferably, said member of said signal cascade is not the Responder.

In these embodiments of the invention, the sequence or expression level of a preferably different member of the cascade than the Responder is altered or abolished. Simultaneously, it is expected that the activity of the Responder and/or one or more of the Distorters is affected. Depending on the type of alteration/abolishment of Responder/Distorter functions, these transgenic animals may be used in breeding schemes corresponding to the ones addressed above.

Finally, the present invention relates to a method for the distortion, to a non-Mendelian ratio, of the transmission of a genetic trait from male mammals to their offspring comprising expressing during spermatogenesis/spermiogenesis a gene involved in sperm motility and/or fertilization.

In a preferred embodiment of the invention said genetic trait determines the sex.

In another preferred embodiment of the method of the invention said gene is under the control of a promoter that allows expression during spermatogenesis/spermiogenesis.

The promoter may be the original promoter of said gene or may be derived from a different copy of said gene or from a different gene. Furthermore, the promoter may be derived from a copy of the homologous gene (in case more than one exists) from a different species or may be derived from a different gene from said different species. The promoters may also be modified in order to obtain optimum expression, which may be enhanced or reduced expression.

In a particularly preferred embodiment of the method of the invention said promoter allows the preferential or exclusive expression of said gene in sperm carrying said gene.

In a further preferred embodiment of the method of the invention said gene is engineered such as to interfere with the function of its wild type allele or with the function of other genes involved in sperm motility and/or fertilization, wherein said gene inhibits the function of one or more genes involved in sperm motility and/or fertilization, and/or wherein said gene causes cell death in spermatocytes/spermatids expressing it, and/or wherein said gene encodes a tag allowing the in vitro selection of sperm carrying said tag.

In a further preferred embodiment of the method of the invention said gene encodes an inhibitor of cAMP dependent protein kinase A.

In a particularly preferred embodiment said inhibitor is PKI or a functionally active derivative or fragment thereof.

As used in accordance with the present invention the term "functionally active derivative or fragment" denotes molecules that deviate from PKI by one or more amino acid substitutions, deletions, and/or additions but essentially retain the biologically activity/activities of PKI, i.e. retain at least the inhibitory activity on cAMP dependent protein kinase A. Examples of functionally active derivatives or fragments of PKI are well known to the person skilled in the art and can be found, e.g., in catalogues of biotechnology companies (see, e.g., the Promega catalogue of 1998).

In another embodiment, the present invention relates to a transgenic animal comprising a gene as defined hereinabove.

Finally, the present invention relates to a sperm obtainable from the transgenic animal of the present invention.

The references cited in the present specification are herewith incorporated by reference.

THE FIGURES SHOW

Figure 1B:
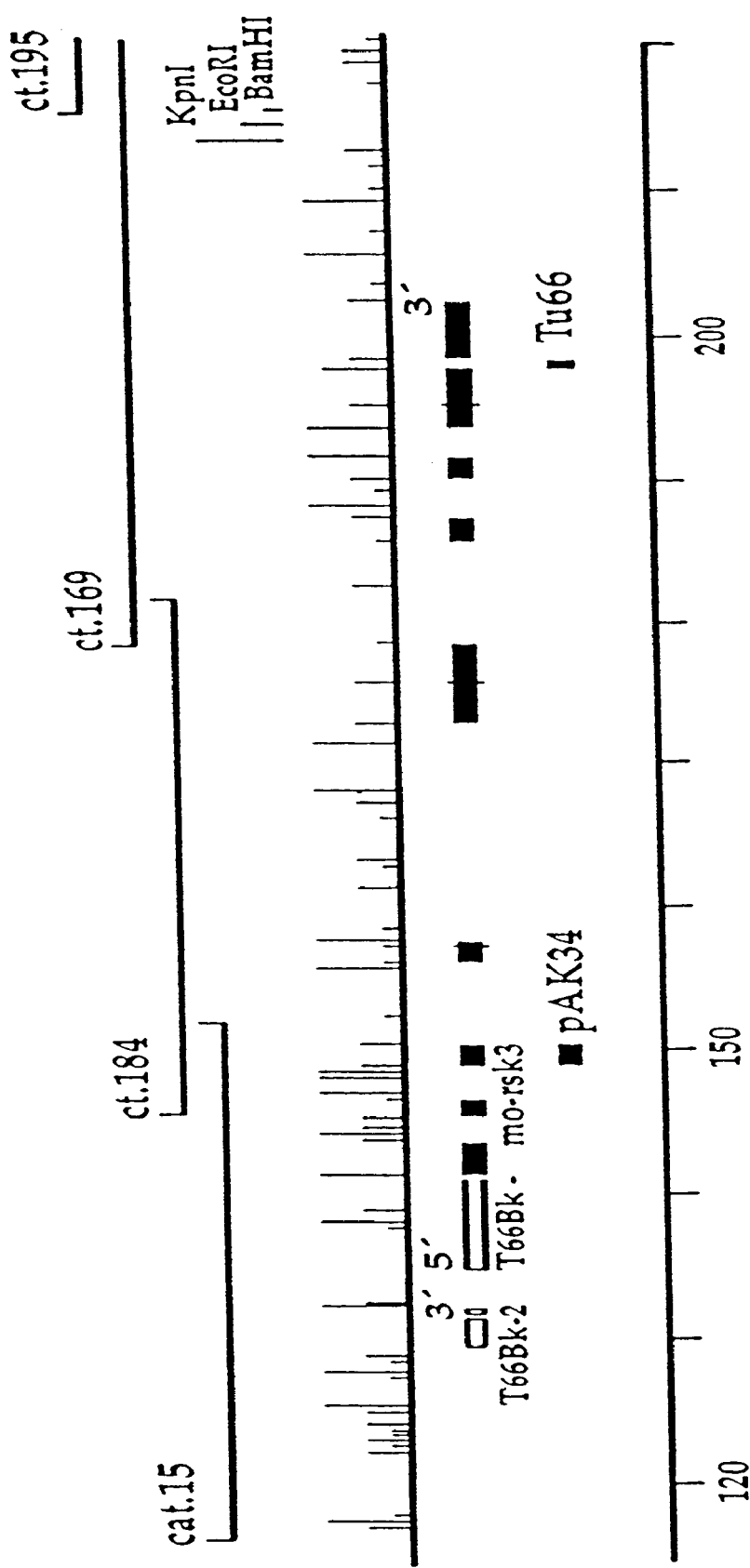

FIGS. 1a–1b:

(a) The upper panel shows a schematical drawing of the extend of the t-chromosome region (thick bars) of complete and partial t-haplotypes on chromosome 17 of the mouse, as well as the mapping positions of the Responder (R$^r$) and two Distorters (D1, D2) contributing to the transmission ratio distortion phenomenon (TRD) in mice (Lyon 1984; Fox et al. 1985; Herrmann et al. 1986; Bullard et al. 1992). The Responder function maps to the T66B genomic region shown in more detail in the middle panel (Schimenti et al. 1987; Nadeau et al. 1989; Rosen et al. 1990; Bullard et al. 1992). The region carrying R is defined by the recombination breakpoints of the partial t-haplotypes $t^{h44}$, $t^{h51}$, $t^{Jr1}$ which do not contain R$^r$, and $t^{h49}$ or $t^{h2}$ which do contain R$^r$. The breakpoints of $t^{h2}$ and $t^{h49}$ coincide (Bullard et al. 1992). The intervals within which the breakpoints must have occurred are not sharply defined (as indicated by broken lines); only t-haplotype DNA is indicated. The position of the marker Tu66 serves as an anchor point for correlating the mapping of the Responder with the genetic fine map shown on the lower panel. The genomic clones (cosmids cat.15, ct.184, ct.169, ct.195), restriction map and gene structure of the fusion of T66Bk and mouse rsk3 demonstrate that the Responder candidate T66Bk lies well within the region defined as carrying R$^r$. The exon-intron structure of T66Bk has not been determined; black bars indicate restriction fragments containing exons of mouse rsk3 located in the T66B region (Kispert 1990). The fragments encoding T66Bk and T66Bk-2 sequences have been determined by hybridisation of $\alpha$-$^{32}$P labelled fragment pCRt$^{h2}$-161/170 to cosmid DNA, restriction digested, electrophoresed and blotted onto Nylon membrane according to standard techniques and as described in figure legend 2, as well as by sequencing as described in figure legend 4.

(b) The analysis of the BamHI fragment B9.1 of cosmid cat.15 demonstrated that another T66Bk gene family member, T66Bk-2, is located on the centromere-close side of B9.1, whereas the telomere-close side contains the putative promoter and first exon of the T66Bk-rsk3 fusion gene. B9.1 contains the complete putative protein coding region on one exon and a single 3'-exon (indicated as 3') encoding untranslated sequences of T66Bk-2. The putative promoter region and first exon encoding untranslated sequences of T66Bk-2 is located at the centromere-close side of B9.1 probably within the 6.1 kb BamHI fragment of cat.15, but the exact position has not been determined.

Methods:

The cosmids cat.15, ct.169, ct.184 and ct.195 were isolated from a cosmid library constructed from $t^{w12}/t^{w12}$ genomic DNA prepared according to conventional techniques in the vector pcos2EMBL (Ehrich et al. 1987). Library screening and cosmid mapping were performed as described (Herrmann et al. 1987; Rackwitz et al. 1985; Kispert 1990). The restriction map as well as the structure and sequence of mouse rsk3 have been determined previously (mouse rsk3 was initially named Tck; Kispert, 1990). The chromosomal localization of genomic restriction fragments hybridizing to subfragments derived from cosmids or to cDNA probes was done by restriction fragment length polymorphism (RFLP) mapping (Fox et al. 1985; Herrmann et al. 1986). Polymorphic restriction fragments specific to t-haplotypes were assigned to the T66B region if present in genomic DNA from $t^{h2}$, $t^{h49}$, $t^{low}$, $t^6$, $t^{w5}$ or other complete t-haplotypes, but not in DNA from $t^{h44}$, $t^{h51}$, or wild type inbred strains, according to previous characterizations of these t-haplotypes (Lyon 1984; Fox et al. 1985; Herrmann et al. 1986; Bullard et al. 1992).

FIG. 2:

Southern blot hybridization of genomic or cosmid DNA of various t-haplotype carrying mice, or wild type mouse strains. The DNA was digested with BamHI endonuclease, blotted on Nylon membrane and hybridized with the probe pCRt$^{h2}$-161/170. Two fragments, B7.8 and B9.1 (marked by an asterisk), are visualized in t-haplotypes carrying the Responder, but are absent from t-haplotypes without R function as well as from wild type strains. Both fragments are present in the cosmid cat.15 and together contain the transcription unit of the gene T66Bk, as shown on FIG. 1 (bottom left). B9.1 additionally contains the protein coding and 3'-untranslated region of T66Bk-2. A third hybridizing fragment on cosmid cat.15 of about 6.1 kb is likely to contain part of the T66Bk-2 gene. The 6.1 kb BamHI fragment is located at the proximal (centromere close) end of cosmid cat.15; it is truncated by the cloning event and thus, it is not identical in size with and cannot be correlated to any of the fragments identified in the hybridizations of total genomic DNA.

Abbreviations: $t^{Jr1}=t^{w71Jr1}$; $t^{low}=t^{lowH}$; $T^{Or}$=deletion chromosome T Oak Ridge 4. 129/Sv, C57BL/6 and DBA/2 are mouse inbred strains.

Methods:

Genomic DNA was prepared as described (Herrmann and Frischauf, 1987), digested with BamHI, blotted by an alkaline capillary transfer onto Hybond N+ membrane (Amersham) as described (Herrmann et al. 1986; Sambrook et al. 1989), UV treated in a UV Stratalinker 2400 (Stratagene) according to Church and Gilbert (1984), hybridized in 0.5M NaPi pH 6.8/7%SDS at 68° C. over night with $2\times10^6$ cpm/ml of probe, washed in 40 mM NaPi pH 6.8/1%SDS at 68° C., and exposed on Kodak X-AR5 X-ray film and an intensifying screen at −80° C. The probe was prepared by random primer extension using the T7 QuickPrime kit (Pharmacia Biotech), 50 ng of probe DNA and 5 µl of $\alpha$-$^{32}$P dCTP (Amersham) at 3000 Ci/mmole according to the suppliers instructions.

The cDNA probe fragment pCRt$^{h2}$-161/170 was prepared by standard PCR amplification in 20 mM Tris pH8.4, 50 mM KCl, 1.5 mM MgCl2, 0.2 mM dATP/dCTP/dGTP/dTTP each, using 1 unit of the Taq DNA polymerase, approximately 50 ng of the cDNA pCRt$^{h2}$-161/144 as template, 20 pmole of primer 161 and 170 each. 15 cycles of 30 seconds at 94° C., 30 seconds at 50° C. and 2 minutes at 72°C. with a final extension of 5 min. at 72° C. were performed, the product was loaded on a 1% agarose gel in TAE buffer (Sambrook et al. 1989), electrophoresed, the amplified fragment cut out under long wave length UV light (366 nm) and purified by centrifugation through an EZ Enzyme Removers column (Amicon) and ethanol precipitation (Sambrook et al. 1989). The DNA was dissolved in TE.

Figure 3A:
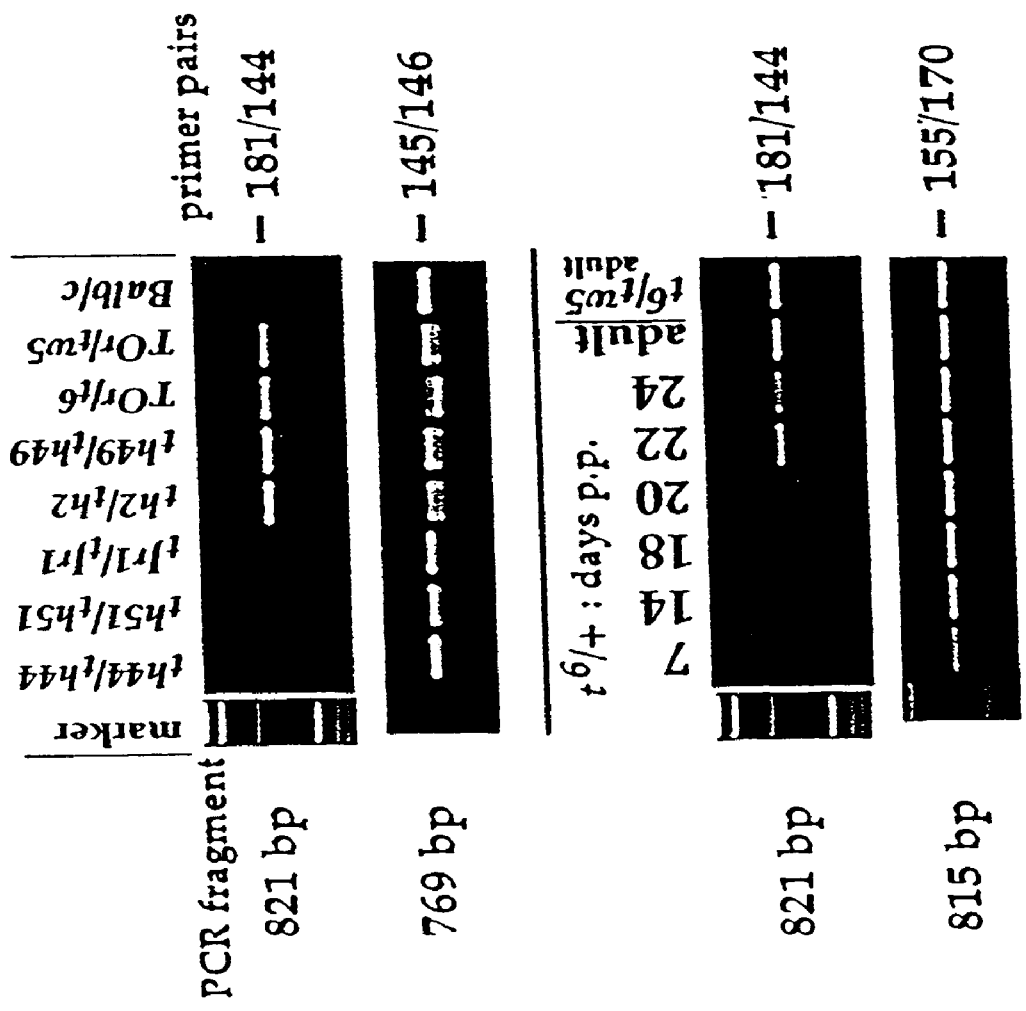
Figure 3B:
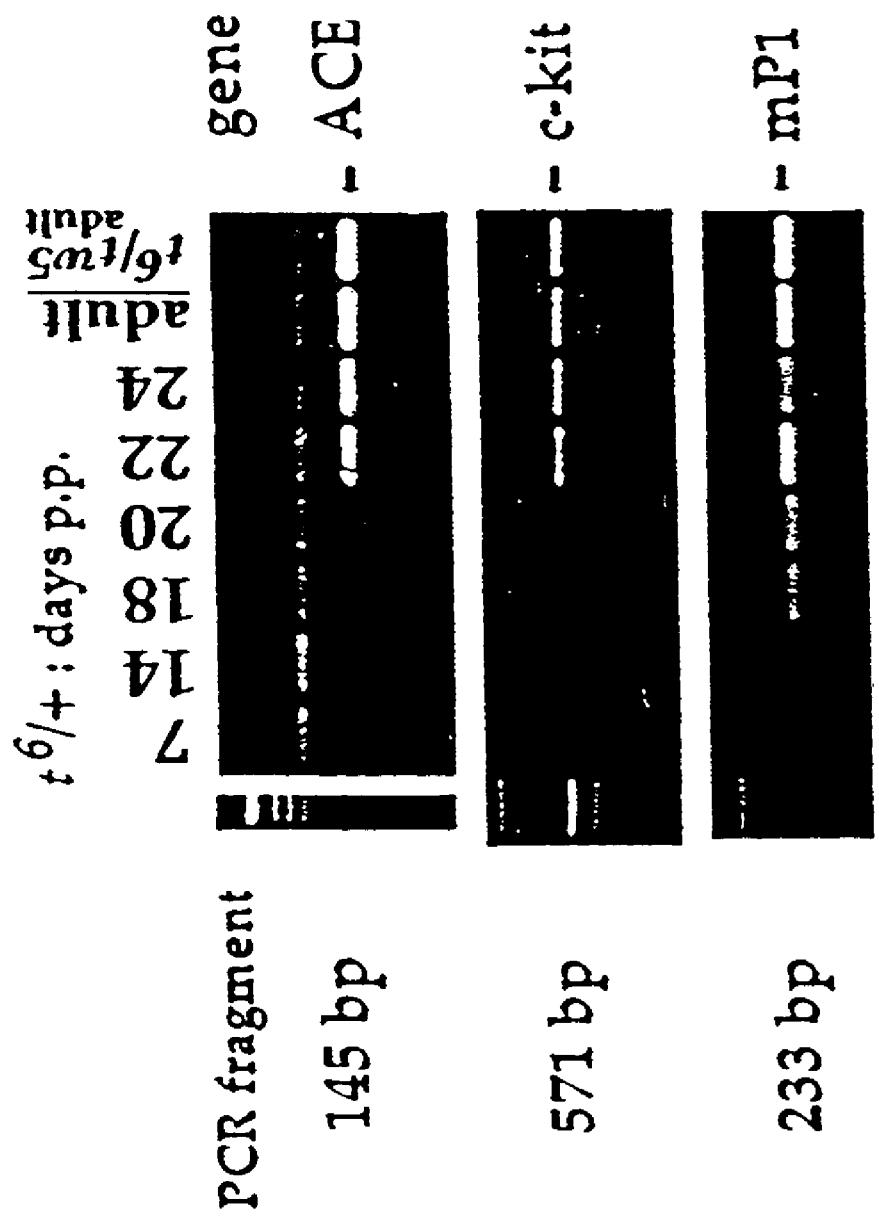

FIGS. 3a–3b:

RT-PCR analyses verify that T66Bk maps to the Responder region and is transcribed during spermiogenesis. a) RT-PCR of testis RNA with the primer pair 181/144 which is specific for the T66Bk-rsk3 fusion gene amplifies a cDNA fragment of 821 bp from RNA of t-haplotypes carrying the t-Responder (for comparison see FIG. 1) confirming that this gene is present in the t-Responder carrying region and is expressed in testis (upper panel). The quality of the RNA and first strand cDNA used for the assay was confirmed by RT-PCR with the primer pair 145/146 which amplifies a cDNA fragment of 769 bp from the mouse rsk3 gene (Tck, see Kispert 1990). The latter RT-PCR also produces a smaller fragment in t-haplotypes containing the T66B region, but not in wild type or t-haplotypes which do not contain the T66B region. This smaller cDNA fragment is due to the deletion of an exon in the T66B-copy of rsk3. A substantial level of transcription of the T66Bk-rsk3 fusion gene is first detectable in 22 days p.p. testis (lower panel). At this stage haploid spermatids have formed and are undergoing the transformation process into spermatozoa called spermiogenesis (Rugh 1990). The primer pair 155/170 amplifies a cDNA fragment of 815 bp derived from T66Bk as well as related genes. The presence of RNA at all stages of spermatogenesis tested with the primer pair 155/170 suggests an early onset of the transcription of one or several members of the T66Bk gene family. A very low (basal) level of transcript from the T66Bk-rsk3 fusion gene is also detectable in early stages of spermatogenesis. b) Comparative RT-PCR of testis RNA with primer pairs specific for testis specific transcripts of angiotensin converting enzyme (ACE, Howard et al. 1990), c-kit (Rossi et al. 1992) and mouse protamine 1 (mP1, Peschon et al. 1987) allows a correlation of the transcription of the T66Bk-rsk3 fusion gene with that of known genes. The promoters of all three genes have been analyzed in transgenic mice (Langford et al. 1991; Albanesi et al. 1996; Peschon et al. 1987). mP1 is supposed to be transcribed in round, ACE and c-kit in elongating spermatids. Since, in our RT-PCR analysis the T66Bk-rsk3 fusion gene appears to be transcribed slightly later than ACE and c-kit we conclude that expression of the T66Bk-rsk3 fusion gene most likely commences in elongating spermatids.

Methods:

Total RNA of testis tissue was prepared following homogenization of the tissue in LiCl/urea according to a published procedure (Auffray and Rougeon 1980). After ethanol precipitation the RNA was dissolved in 50 µl 10 mM Tris-HCV1 mM EDTA pH7.6 (TE) per approximately 100 mg starting material. 2 µl total RNA (appr. 6 µg RNA) were used for cDNA synthesis with an oligo(dT) primer according to the instructions of the SuperScript plasmid cDNA synthesis kit of Gibco/BRL. After first strand synthesis the reaction was diluted to 50 µl with TE. For PCR amplification 0.5 µl of the first strand cDNA stock solution was added to 20 µl of the reaction mix containing 20 pmole of each primer, 20 mM Tris pH8.4, 50 mM KCl, 1.5 mM MgCl2, 0.2 mM dATP/dCTP/dGTP/dTTP each, and 1 unit Taq DNA polymerase. Reaction mixes were overlayed with mineral oil and 35 cycles of 30 seconds at 94° C., 30 seconds at 50° C. and 30 seconds at 72° C. were performed using a PTC-100 thermocycler (MJ Research, Inc.). The reaction products were electrophoresed in 1% or 2% agarose gels, as applicable, containing 0.4 µg/ml ethidium bromide in TAE buffer (Sambrook et al. 1989), and photographed on a UV light box. The 1 kb ladder of Gibco/BRL was used as marker, as shown on the left margin of each photograph.

FIGS. 4a–4c:

a and b) Nucleic acid (SEQ ID NO:1) and amino acid sequence (SEQ ID NO:2) of pCRt$^{h2}$-161/144, representing a partial cDNA of the T66Bk-rsk3 fusion gene encoding a putative protein of 484 amino acid residues. Several in frame stop codons 5' to the first methionine (start codon) and the stop codon at the end of the single long open reading frame suggest that the protein coding region of this cDNA is complete. However, the 5' and 3' non-coding sequences are most likely incomplete. An asterisk indicates the junction between the T66Bk gene and the truncated mouse rsk3 gene. Nucleic acid sequences of primers used for RT-PCR detection and cloning 30 of T66Bk sequences are indicated. The primer number and 3' end are given.

c) Partial nucleic acid sequence (SEQ ID NO:3) of a cDNA fragment, ptlib0.7, consisting of a fragment from the 5' end of a T66Bk-related gene fused to part of a mouse rsk3-related gene. This partial cDNA was isolated by PCR amplification with a plasmid vector anchor primer (seq5lib) and primer 144, from clone pools of a total of approximately 200,000 clones of a cDNA plasmid library constructed with RNA extracted from testis of a t$^{w5}$/t$^{w12}$ adult male. Another 380,000 cDNA clones were screened by cDNA filter hybridization. From those clones another partial cDNA containing a sequence homologous to the one shown here, fused to rsk3 sequences, was obtained. A primer (161) located at the 5' end of the cDNA sequence shown was designed and used in combination with primer 1.44 (rsk3) to amplify the cDNA fragment of T66Bk shown on FIGS. 4a and b, from testis cDNA of a t$^{h2}$/t$^{h2}$ adult mouse.

Methods:

A cDNA library of testis RNA of an adult male carrying the complete t-haplotypes t$^{w5}$/tw$^{12}$ was constructed in the plasmid vector pSV-Sport1 using the SuperScript Plasmid cDNA synthesis kit (Gibco/BRL) according to the suppliers instructions. RNA isolation was performed as described in the legend to FIG. 3, mRNA purification was done using Oligotex beads according to the supplier's instructions (Qiagen). DNA preparations of library pools of a total of appr. 200,000 clones were prepared with the Qiagen plasmid midi kit (Qiagen) and tested by PCR amplification as described in figure legend 3 using primer pair seq5lib/144. A fragment of 0.7 kb was obtained and cloned in the vector pCR2.1 using the TA cloning kit of Invitrogen according to the instruction manual. Another 380,000 cDNA clones were plated on filters and screened by hybridization as described (Herrmann et al. 1987).

The partial cDNA pCRt$^{h2}$-161/144 was obtained by PCR amplification of cDNA, prepared and amplified as described in figure legend 3, except that the primer extension time at 72° C. was 2 minutes per cycle, from testis RNA of an adult male homozygous for the t-haplotype t$^{h2}$, with the primer pair 161/144. The cDNA fragment was purified from a 1% agarose gel as described in figure legend 3, and cloned in the plasmid vector pCR2.1.

Plasmid DNA was prepared with the Qiagen Plasmid Midi kit. Sequencing reactions were performed using the RR DyeDeoxy Terminator Cycle Sequencing kit (PE Applied Biosystems) according to the instructions and gene specific primers (MWG Biotech) designed with the OLIGO Primer Analysis Software (NBI), the reactions were purified by centrifugation through Centri-Sep columns (Princeton Separations) according to the instructions, and run on an automatic ABI Prism 310 Genetic Analyzer (PE Applied Biosystems). Sequences were evaluated with the MacMolly Tetra programs set (Soft Gene, Berlin) on a Power Macintosh computer.

FIG. 5:

Northern blot hybridization demonstrating the transcription of T66Bk-gene family members. Transcripts are detectable in adult testis from all t-haplotype or wild type strains tested, but not in RNA from any other organ tested. During spermatogenesis a detectable level of transcript first appears at 22 days p.p. For a control the blot was re-hybridized with a probe for GAPDH (Kispert 1990).

Methods:

RNA was extracted as described (Auffray and Rougeon 1979), 10 µg per lane was loaded on a 1% agarose gel containing formaldehyde and electrophoresed in MOPS buffer according to standard techniques (Sambrook et al. 1989). The gel was washed twice for 20 minutes in 0.1M NH4-acetate, once in 50 mM NaPi buffer pH 6.8, in 2 gel volumes each, and blotted onto Hybond N+ membrane (Amersham) by capillary transfer (Sambrook et al. 1989) using a reservoir of 50 mM NaPi buffer pH 6.8. The filter was UV treated in a UV Stratalinker 2400 (Stratagene) according to Church and Gilbert (1984), hybridized with 2×10$^6$ cpm/ml of the probe pCRt$^{h2}$-161/170 in 0.5M NaPi buffer pH 6.8/7%SDS/25% formamide at 68° C. over night, washed in 50 mM NaPi buffer pH 6.8/1%SDS at 68° C. and exposed on Kodak X-AR5 film using an intensifying screen. The probe fragment was amplified by PCR with the primer pair 161/170 using the cDNA pCRt$^{h2}$-161/144 as template and labeled as described in figure legend 2. To determine the relative amount of RNA in each lane the filter was re-hybridized as above with the cDNA clone pme66 containing a partial cDNA of the GAPDH gene (Kispert 1990).

FIG. 6:

Southern blot hybridization of DNA derived from several mammalian species and the chick, with the probe pCRt$^{h2}$-161/144 demonstrates the presence of T66Bk-related genes in hamster, rabbit, pig, human and chick suggesting the conservation of this gene class during evolution. The DNA was digested with BamHI, blotted on Nylon filter, and hybridized and washed at reduced stringency (58° C.).

Methods:

Genomic DNA was isolated from organs or blood cells (human) as described (Herrmann and Frischauf 1987), cut with BamHI endonuclease, electrophoresed in a 1% agarose gel in TBE buffer and blotted by alkaline capillary transfer as described (Sambrook et al. 1989; Herrmann et al. 1986) onto a Hybond N+ membrane (Amersham). The filter was UV treated in a UV Stratalinker 2400 (Stratagene) according to Church and Gilbert (1984), hybridized with 2×10$^6$ cpm/ml of the probe pCRt$^{h2}$-191/144 in 0.5M NaPi buffer pH 6.8/7%SDS at 58° C. over night, washed in 100 mM NaPi buffer pH 6.8/1%SDS at 58° C. and exposed on Kodak X-AR5 film using an intensifying screen. The probe fragment pCRt$^{h2}$-161/144 was labeled as described in figure legend 2.

FIGS. 7a–7c

The mouse genome contains several members of the T66Bk gene family. a and b) The protein coding exon of one member, T66Bk-2, is located in a tandem duplication arrangement on the centromere-close side of T66Bk, contained in the BamHI fragment B9.1 of the T66B region cosmid cat.15. The nucleotide (SEQ ID NO:4) and putative amino acid sequence (SEQ ID NO:5) of this exon are shown (FIGS. 7a and b). The sequence of primer 232 and 237 used for cDNA detection, mapping and expression studies (see FIG. 8) are indicated by a dashed line. A single base which is deleted in the cDNA T66k-8 (T 1164) is underlined.

c, d, and e) The cDNA T66k-8 was isolated from a testis cDNA library of the genotype t$^{w5}$/t$^{w12}$ The nucleotide (SEQ ID NO:6) and putative amino acid sequence (SEQ ID NO:7) are shown (FIGS. 7c, d, and e). Its nucleotide sequence is identical to that of T66Bk-2 in the region of overlap except for a single base deletion resulting in a shift of the open reading frame from amino acid residue 359 onwards (underlined). The sequences for primer 161 and 237 are indicated (see FIG. 8).

f, g, and h) SEQ ID NO:8: includes the cDNA T66k-7as is derived from an antisense transcript of a T66Bk family member. The 5' end of T66k-7as is closely related to sequences upstream of the T66Bk promoter. Its 3' end is very similar to the 5' intron near the protein coding exon of T66Bk/T66Bk-2 (see FIGS. 7a and b). The location of T66k-7as in the genome has not been determined. Vector sequences are underlined by a dashed line, sequences with a high similarity to the exon encoding the large ORF of T66Bk/T66Bk-2 by a double dashed line, sequences with high similarity to intron sequences upstream or downstream of the protein coding and 3'-untranslated exon, respectively, of T66Bk/T66Bk-2 by "”". The direction of transcription of the T66Bk/T66Bk-2 homology region is indicated.

i, j, and k) The cDNA clone, T66k-20, was isolated from the t$^{w5}$/t$^{w12}$ testis cDNA library. The nucleotide (SEQ ID NO:9) and putative amino acid sequence (SEQ ID NO:10) shows a strong similarity to the above members of the T66Bk gene family.

l) Comparison of the putative amino acid sequences of the members of the 30 T66Bk gene family. Amino acid residues identical to T66Bk are indicated by ". Gaps indicated by_were introduced to allow optimal alignment. Note the strong similarity of all protein sequences as well as the altered protein tail in T66k-8. Note also the closer relationship of T66Bk-2 and T66Bk-20 compared to T66Bk, despite the fact that T66k-20 is longer at the N-terminus. T66Bk, SEQ ID NO:2; T66Bk-2, SEQ ID NO:5; T66Bk-20, SEQ ID NO:10; T66Bk-8, SEQ ID NO:7.

Methods:

The BamHI fragment B9.1 of cosmid cat.15 was isolated by restriction digestion and cloned in the vector pBluescript KS according to standard techniques. The DNA preparation and sequencing was carried out as described in Figure legend 4. The cDNA clones T66k-7as, T66k-8 and T66k-20 were isolated from a cDNA library constructed from testis of a $t^{w5}/t^{w12}$ male, the library plated and screened by hybridization with a cDNA fragment derived from PCR amplification of the cDNA pCRt$^{h2}$-161/144 with the primer pair 155/170. Library screening, probe preparation, hybridization, plasmid preparation, sequencing etc. are described in figure legends 2, 3 and 4.

FIG. 8:

The T66Bk-2 gene is located in the T66B region and is expressed from 22 day p.p. in the testis.

A cDNA fragment of 951 bp derived by RT-PCR amplification of testis RNA and hybridization with a T66Bk-2/T66k-8 specific primer (232) is detectable in RNA derived from mice carrying the t-haplotypes $t^{h2}$, t49, $t^6$ and $t^{w5}$ but not in $t^{h44}$, $t^{h51}$ and $t^{tr1}$. Therefore it maps to the T66B region, in agreement with the mapping data of cosmid cat.15. The signal obtained from $t^{h2}/t^{h2}$ and $t^{h49}/t^{h49}$ is higher than that obtained from $T^{Or}/t^6$ or $T^{Or}/t^{w5}$ in agreement with the fact the former two are homozygous for T66Bk-2, while the latter are heterozygous. A faint signal is obtained in t-haplotypes carrying the T66A region only or in wild type (Balb/c). This is due to a reduced capability of binding of the oligonucleotide 232 to other members of the T66Bk gene family. In testis RNA derived from $t^6$/+ males of different stages (lower panel) T66Bk-2 transcription is first detected at 22 days p.p. However, the signal is very weak, but is significantly increased at 24 days p.p. This suggests that T66Bk-2 may be expressed at a lower level or later than T66Bk. Overall, the transcription level of T66Bk-2 in each testis sample detected by RT-PCR and hybridization correlates well with the number of T66Bk-2 alleles present in each of the samples. This together with the sequence conservation further suggests that the cDNA clone T66k-8 is derived from the locus T66Bk-2 within the T66B region.

Methods:

RNA derived from testis was reverse transcribed, first strand cDNA was amplified by PCR using the primer pair 161/237 (see FIGS. 7a and b, 7c, d, and e), and the products separated by electrophoresis on 1% agarose as described in figure legend 3. The cDNA was transferred to Hybond N+ filters as described in figure legend 2, and hybridized with oligonucleotide 232 labeled using the DIG Oligonucleotide Tailing Kit (Boehringer Mannheim) according to the instructions of the supplier. Hybridization was carried out in 0.5M NaPi pH 6.8/7% SDS at 37° C. The filters were washed 4 times for 5 minutes in prewarmed 40 mM NaPi pH 6.8/1% SDS (37° C.) at room temperature. Prehybridization and oligonucleotide detection were done according to the protocol from Boehringer (Mannheim).

FIGS. 9a–9b:

a and b) Nucleic acid (SEQ ID NO:11) and amino acid sequence (SEQ ID NO:12) of a cDNA encoding the T66Bk gene. The sequence extends the sequence of pCRt$^{h2}$-161/144 shown on FIGS. 4a and b, both at the 5'- and at the 3'-side, but is identical in the region of overlap. The 3'-end of the cDNA pSV-T66Bk ends in an intron of the mouse rsk3 gene and lacks a consensus polyadenylation signal suggesting that it was derived by oligo(dT) priming of incompletely spliced RNA. Asterisks indicate the positions of introns. The asterisk between position 2023 and 2024 indicates the fusion point between MARK- and rsk3-homology regions of T66Bk.

Methods:

Another cDNA library, in addition to the one used to isolate cDNAs presented on FIG. 7, was constructed from testis RNA of a male carrying the complete t-haplotypes $t^6/t^{w5}$ according to the methods described in figure legend 4 and screened as described in figure legends 7, 2, 3 and 4. A total of 500 000 cDNA clones contained in 10 pools were analysed by PCR for the presence of cDNA clones encoding the gene T66Bk using the primer pair 161/144. Four positive clones were identified and one, named pSV-T66Bk, was purified by colony hybridization screening using the cDNA pCRt$^{h2}$-161/144 as probe, and sequenced.

FIGS. 10a–10f:

Nucleic acid and putative amino acid sequences of wild type members of the T66Bk kinase gene family.

a and b) The cDNA pCR.Balb-66k was isolated by RT-PCR from testis RNA of the wild type inbred mouse strain Balb/c. The putative start codon of the open reading frame is located 20 amino acid residues further upstream from the translation start of the T66Bk gene, very similar to the situation observed in T66k-20. The ORF is equal in length to that of T66k-20. Since in both genes, pCR.Balb-66k and T66k-20, the putative translation start does not conform closely with Kozak's rules it is possible that this start codon of translation is not efficiently used. Thus, it might be that either this or the next 3'-located translation start codon or both are utilized. The nucleotide (SEQ ID NO:13) and putative amino acid sequence (SEQ ID NO:14) are shown.

c and d) The cDNA pCR.C3H-66k was isolated by RT-PCR from testis RNA of the wild type inbred mouse strain C3H/N using the primers 161/220. In contrast to the ORF of T66Bk, the ORF of this gene is shorter at the C-terminal end resulting in a putative protein of 433 amino acid residues. The nucleotide (SEQ ID NO:15) and putative amino acid sequence (SEQ ID NO:16) are shown.

e and f) This is also the case for the ORF encoded by the genomic clone fragment pI.129-66k derived from the 129Sv wild type inbred mouse genome. The significance of this alteration of the ORF compared to the gene T66Bk is unclear. However, it is assumed that the length of the ORF and thus the resulting protein sequence may influence the properties of the protein. The nucleotide (SEQ ID NO:17) and putative amino acid sequence (SEQ ID NO:18) are shown.

FIGS. 11a–11c:

Nucleic acid sequence (SEQ ID NO:19) of the putative promoter of the gene T66Bk. The BamHI fragment B9.1 of the cosmid cat.15 contains the protein coding region of T66Bk-2 (see FIGS. 2 and 7) as well as the putative transcription start site and upstream region of T66Bk. The sequence of 3641 bp presented here shows the intron and 3'-untranslated exon of T66Bk-2, located 3' of the T66Bk-2 sequence shown on FIG. 7, followed by the upstream region and putative first exon of T66Bk. Splice donor/acceptor sites are indicated by an asterisk (*). Exon sequences are underlined. The underlined exon sequence of T66Bk shown represents the sequence contained in the cDNA pSV-T66Bk; the transcription start site of T66Bk, however, may be located further upstream. Two consensus TATA boxes are shown in bold type and underlined. The transcription start site of T66Bk has not been determined, but is likely to be located 3' of either of the TATA boxes. It cannot be excluded that both TATA boxes are utilized alternatively for binding of the TATA binding protein complex. The restriction sites for KpnI and PmlI used to isolate the putative promoter fragment utilized in the construction of tg5 are indicated in bold type. The sequence contains a number of potential binding sites for known transcription factors (Faisst and Meyer 1992). However, since none of them have been demonstrated to be functional, they have been omitted on the figure. Their positions can be readily identified by sequence analysis software such as MacMolly's Interpret program (Softgene, Berlin). Regulatory elements conferring tissue and stage specific regulation of transcription are often located just upstream of the transcription initiation sites, but may also be located in the first exon, intron or at a distance either far upstream or downstream. It is not known whether the sequence shown here contains all cis-regulatory elements or only a subset required for specific expression of T66Bk during spermiogenesis. It is also envisaged that the long 5'-untranslated region of T66Bk mostly comprised by exon 1 may have a function in regulating the onset and/or efficiency of translation.

Methods:

Cloning and sequencing of BamHI fragment B9.1 were done as described in figure legend 7.

Figure 12:
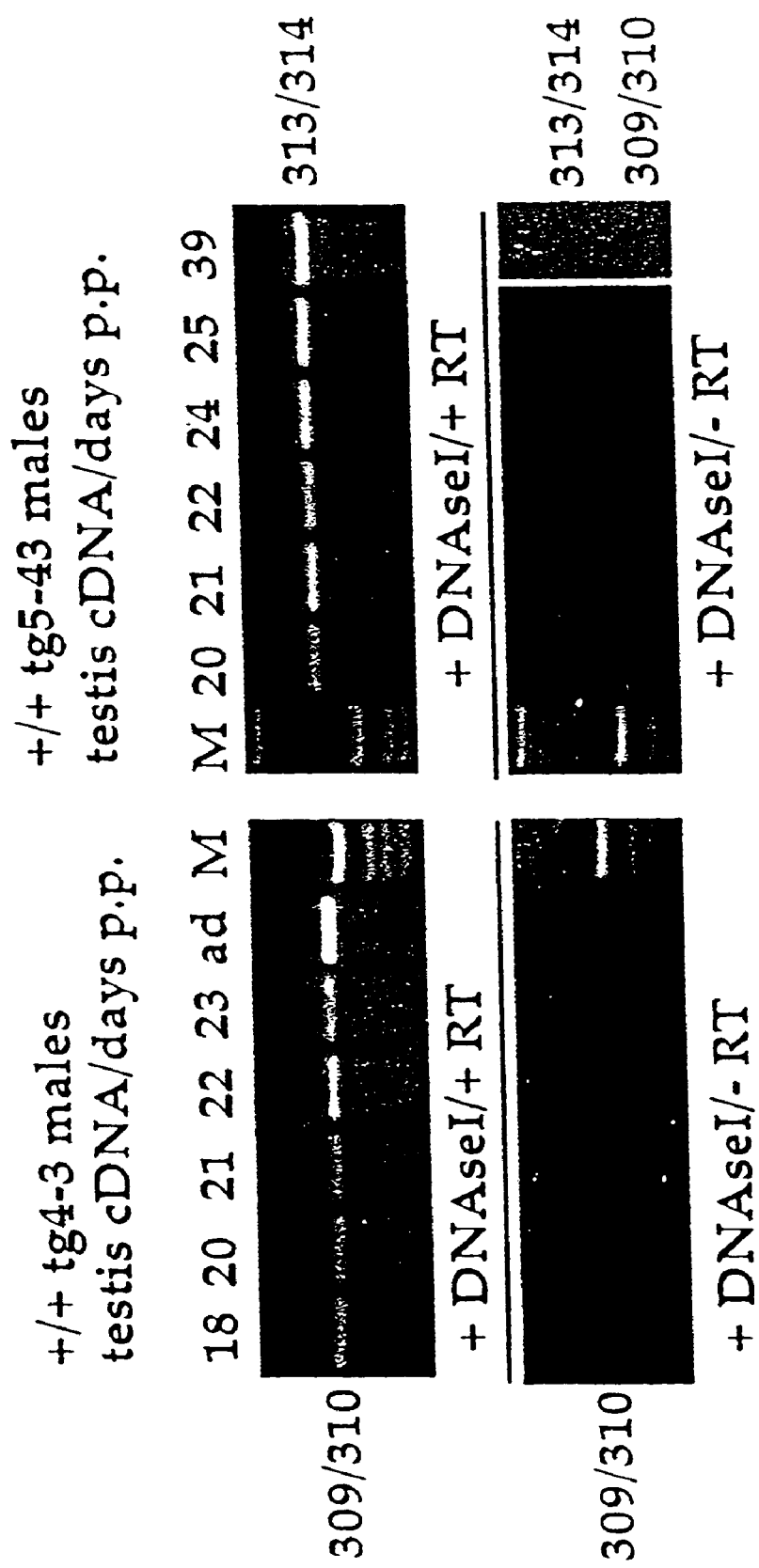

FIGS. 12a–12b:

The transgenes tg4 and tg5 are expressed during spermiogenesis.

To confirm that the transgenes tg4 and tg5 which showed distortion of their transmission from male carriers to their offspring are expressed in the testis, RT-PCR analysis was carried out using a transgene specific primer pair. For tg4 the primer pair 309/310 amplifying a junction fragment between the MARK- and rsk3 homology regions was used. For tg5, the primer pair 313/314 amplifies its 3'-end from hCD24 to the polyadenylation signal sequence. Various post partum stages of testis expected to be in the process of spermatid maturation were analyzed. mRNA was DNAseI treated before reverse transcription and 1 μl of this solution was amplified by PCR (+DNAseI/−RT). After reverse transcription of the remainder, 1 μl of it was amplified in parallel. Tg5-43 was tested with 313/314 except for tg5-43 stage 39 days p.p. which was control tested with the primer pair 309/310.

None of the control reactions showed a PCR product, whereas all samples subjected to reverse transcription yielded the expected fragment after PCR. This demonstrates the expression of tg4 and tg5, respectively, in the testes of male carriers. However, expression occurs earlier than expected from the analysis of c-kit and T66Bk shown on FIG. 3. This might be due to the sensitivity of the RT-PCR assay which might detect basal transcription of the transgenes, or to inappropriate control of transgene expression caused by the promoter fragment used in the construction or caused by influences of the integration sites. On the other hand, the adult male carrying tg4-3 and the tg5-43 39 day p.p. male showed a stronger fragment suggesting an increase of transgene expression during maturation or following mating to females. Abbreviations: ad, adult male (mated); M, marker (1 kb ladder (Gibco/BRL)

Methods:

RT-PCR was carried out essentially as described in figure legend 3 with the following exceptions. Before addition of Reverse Transcriptase to the reaction 1 μl of DNAseI (RNAse free, 10 units/μl) was added and the reaction was incubated at 37° C. for 20 min. 1 μl of the reaction was removed and kept on ice, to the remainder 1 μl of SuperscriptII Reverse Transcriptase (200 units/μl, Gibco/BRL) was added and the reaction was incubated for a further 20 min. each at 37° C. and 55° C. All PCR reactions were set up with the same PCR stock solution to which 1 μl of either the control reaction (+DNAseI/−RT) or the test reaction (+DNAseI/+RT) were added. PCR using the primer pair 309/310 was carried out as described in table 1 legend. The same conditions were used for the primer pair 313: 5'-ATGGGCAGAGCAATGGT-3' (SEQ ID NO:22) and 314: 5'-CAGGTTCAGGGGGAGGT-3' (SEQ ID NO:23).

FIG. 13:

T66Bk contains a second ORF encoding an N-terminal polypeptide of mouse rsk3.

The figure shows the cDNA sequence (SEQ ID NO:20) of pSV-T66Bk emphasizing the ORF encoded by the rsk3 homology region. The putative translation start and stop codons of the MARK-homology region as well as two potential translation start codons of the rsk3 homology region are underlined. The amino acid sequence (SEQ ID NO:21) shown starts at an ATG codon located 3' of the stop codon of the MARK related kinase and 5' of the splice site, indicated by an *. Another potential translation start codon is located in the rsk3 homology region. Although unlikely, there are two possibilities that this ORF is translated. First, the ribosome might not fall off the mRNA after completing translation of the MARK-related kinase and re-start translation at the next ORF. Second, alternative splicing might skip the exon encoding the MARK-related kinase. This would result in a transcript in which the ATG at position 2107–2109 would be the first potential translation start site. The latter is the case observed in the partial cDNA sequence ptlib0.7 shown on FIG. 4c demonstrating that such transcripts exist. However, they are not observed in males carrying the t-haplotypes $t^{h2}$ or $t^{h49}$, but only in complete t-haplotypes suggesting that they are derived from a gene located outside of the region carrying the t-Responder.

The examples illustrate the invention.

EXAMPLE 1

Cloning of a Novel Candidate Gene For The t Complex Responder

Figure 2:
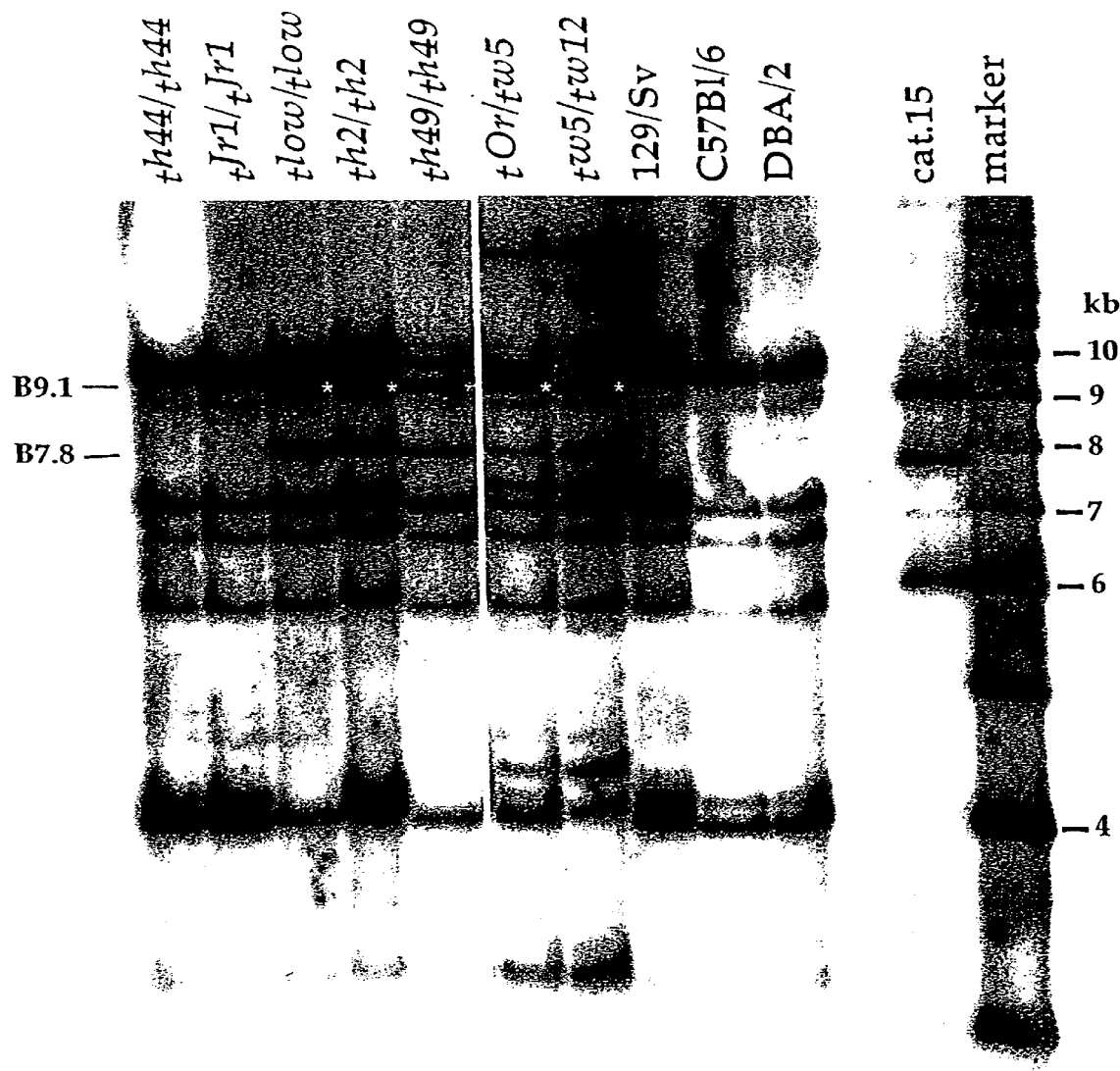

Cosmid clones from the T66B region were isolated and their genomic location within T66B verified by RFLP mapping (FIG. 1). In particular, the fragment pAK34 which is contained within the overlap of the cosmids ct.184 and cat.15 hybridizes to 3 genomic BamHI fragments in complete t-haplotypes, of which one, a 5.5 kb fragment, is located in the T66B region (Kispert 1990). The cosmids ct.184 and cat.15 contain the 5.5 kb BamHI fragment hybridizing to probe pAK34, thus confirming that they are derived from the T66B region. Likewise, the PCR fragment 161/170 derived from the cDNA described here hybridizes to the BamHI fragments B9.1 and B7.8 contained within cosmid cat.15, and both can be mapped to the T66B region (FIGS. 1 and 2).

A gene spanning at least 60 kb of the genomic region contained within the cosmid cluster isolated from the T66B region was identified. This gene is represented in 3 copies in t-haplotypes, one each in the regions T66A, T66B and T66C. The wild type form of it encodes the mouse homologue of human rsk3 (Zhao et al. 1995), a kinase of the pp90 ribosome S6 kinase family (called Tck in Kispert 1990). The gene copy located in the T66B region is altered compared to wild type (Kispert 1990). The 5' end is not contained within cosmid cat.15 and one additional exon. is missing. The fact that one additional exon is missing was detected by RT-PCR of testis RNA derived from a panel of partial and complete t-haplotypes and wild type with the primer pair 145/146. In addition to the expected fragment of 769 bp a smaller fragment was obtained in the t-haplotypes containing the T66B region, but not in those containing only T66A nor in wild type. (FIG. 3a). This demonstrated that the T66B gene copy of rsk3 is expressed in testis. To identify the 5' sequence of this gene, a cDNA library was constructed from mRNA of the testis of a $t^{w5}/t^{w12}$ male mouse. Surprisingly, two clones were isolated from a total of approximately 580000 cDNA clones screened which contain heterologous sequences 5' to base 438 of wild type rsk3 (Kispert 1990). The partial sequence of one of these clones is shown on FIGS. 4c. Primers for polymerase chain reaction (PCR) amplification were designed such that the forward primer (161) is located at the 5' end of this cDNA, that is within the novel sequence, and the reverse primer (144) is located in the rsk3 sequence. PCR amplification of testis cDNA prepared from RNA of the partial t-haplotypes $t^{h2}$ and $t^{h49}$ produced a fragment of 2.1 kb, whereas no band was detected in $t^{h44}$, $t^{h51}$, $t^{jr1}$ or BALB/c (wild type) cDNA. The fragment (pCRt$^{h2}$-161/144) was isolated from $t^{h2}$, cloned and sequenced (FIGS. 4a and b). It comprises yet another novel gene located within the T66B region (see below).

A primer pair (181/144) designed on the basis of the sequence of pCRt$^{h2}$-161/144 allows the amplification of a cDNA fragment of a testis expressed gene which is contained in $t^{h2}$, $t^{h49}$, $t^{w5}$ and $t^6$, but not $t^{h44}$, $t^{h51}$, $t^{jr1}$ or BALB/c (wild type) testis (FIG. 3a). Thus the corresponding transcript is t-specific and derived from a gene mapping to the T66B region. RT-PCR with the primer pair 145/146 for mouse rsk3 also confirmed the quality of the first strand cDNA synthesis. The cDNA-mapping by PCR confirms the genomic localization by Southern blot hybridization (see FIGS. 1 and 2).

EXAMPLE 2

The t Complex Responder Candidate Gene Encodes a Novel Kinase

The sequence of the 2.1 kb cDNA fragment pCRt$^{h2}$-161/144 contains a single long open reading frame (ORF) encoding a protein of 484 amino acid residues (FIGS. 4a and b). Several "in frame" stop codons upstream of the first potential translation start codon (bases 337–339) suggest that the N-terminal end of the putative protein is complete. The translation stop (bases 1789–1791) is still located within the "non-rsk3" sequence; the rsk3 sequence of the fusion transcript starts at base 1837.

Sequence comparisons with protein sequence databases revealed several known motifs within the ORF, most importantly a protein kinase domain and a consensus protein tyrosine kinase active site. However, the pattern of conserved residues is more strongly related to the consensus for serine/threonine kinases, suggesting that the isolated gene encodes a novel Serine/threonine kinase. However, the in vivo specificity remains to be determined experimentally. In accordance with the present invention, the gene is called T66Bk. The best match to known kinases was found to MARK, a recently published serine/threonine kinase which is involved in the regulation of the cytoskeleton (Drewes et al. 1997). The identity to MARK2 is more than 25% and approximately 38% at the amino acid level within the putative kinase domain. The putative protein contains 8 potential phosphorylation sites for casein kinase II, 5 for protein kinase C and 5 potential myristoylation sites.

The data explained above suggest that the T66Bk-rsk3 fusion gene arose by a rearrangement event resulting in the fusion of two gene parts, both derived from a kinase. The 5' region probably including the transcriptional control elements are derived from a MARK related kinase. The 3' end which is derived from the mouse rsk3 gene and may include most of its sequence and probably also its poly(A) addition signal might be around 5 kb long. The Southern blot hybridization data shown in FIG. 2 suggest that the genome may contain several gene family members of the MARK-related kinase.

EXAMPLE 3

Figure 5:
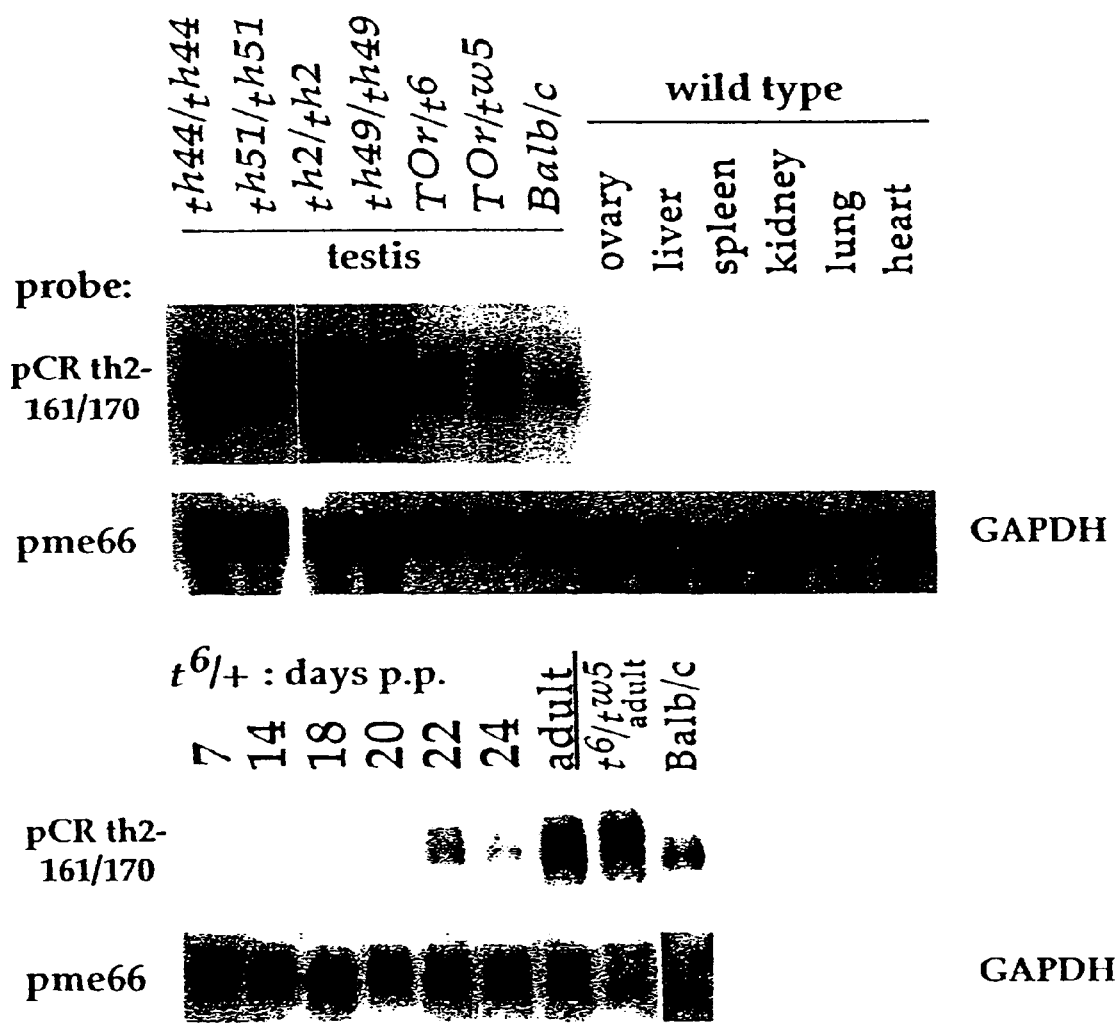

Transcripts Derived from T66Bk-gene Family Members Accumulate During Spermiogenesis In a Northern blot hybridization assay transcripts derived from T66Bk related genes can be detected in 22 day post partum (p.p.) male $t^6$/+ testis or later, using the cDNA fragment pCRt$^{h2}$-161/170 as a probe (FIG. 5). Two transcripts of approximately 2.8 kb and 3.2 kb can be distinguished in $T^{Or}$/$t^6$ and $T^{Or}$/$t^{w5}$ testis RNA. Only the lower band is clearly detectable in BALB/c (wild type) testis RNA. This difference may be caused by differential splicing or different sequence of gene variants which distinguish, for example, t-haplotypes and wild type or various wild type strains. As the expected transcript size of the T66Bk-rsk3 fusion gene is appr. 7 kb, an assignment of one of the observed RNA bands to the T66Bk-rsk3 fusion gene is not possible. The Northern analysis showed that the members of the T66Bk gene family are fairly specifically expressed, and might even be restricted to the testis, as no transcripts were detected in RNA isolated from ovary, liver, spleen, kidney, lung or heart.

In a RT-PCR analysis of testis RNA using the primer pair 155/170, transcripts are detectable as early as day 7 p.p., the earliest stage of spermatogenesis tested (FIG. 3a). This suggests that low level transcription of one or several T66Bk-related kinase genes occurs early during spermatogenesis, but high level transcription detectable by Northern analysis occurs during spermiogenesis.

In agreement with this interpretation, very low (basal) levels of transcripts of the T66Bk-rsk3 fusion gene are detectable by RT-PCR at stage 7, 14 and 20 days p.p., but much higher levels can be seen only from stage 22 d.p.p. onwards (FIG. 3a). This suggests that the T66Bk-rsk3 fusion gene is up-regulated at about the stage when elongating spermatids appear (see below).

The genes mouse protamine 1 (mP1), angiotensin converting enzyme (ACE) and c-kit were analyzed in order to allow a staging of the onset of the T66Bk-rsk3 fusion gene expression during spermatogenesis (FIG. 3b). mP1 has been reported to be first expressed in round spermatids (Peschon et al. 1987), the testis specific promoters of ACE (Howard et al. 1990) and c-kit (Rossi et al. 1992) are first active in elongating spermatids of undefined stage and stage IX–XI, respectively. The analysis of all three promoters has been achieved using transgenic animals (Langford et al. 1991; Albanesi et al. 1996; Peschon et al. 1987). In the RT-PCR analysis shown here, mP1 transcripts were detected as early as day 14 p.p., but a strong band appeared at day 18 p.p. According to Rugh (1990), spermatids appear at day 17 p.p. in male pups. The ACE and c-kit testis transcripts were weakly detectable at 20 days p.p., but a signal comparable to the T66Bk-rsk3 fusion gene band 181/144 first appeared at 22 days p.p. An earlier expression of ACE was detected in day 7 and 14 p.p. testis. Thus, the RT-PCR data are in agreement with the published data showing that ACE and c-kit are expressed in elongating spermatids. This suggests that the expression of the T66Bk-rsk3 fusion gene in testis is up-regulated at about the same time or a little later than that of c-kit and ACE, in elongating spermatids, and that the promoter of the T66Bk-rsk3 fusion gene may be active late enough during spermiogenesis to exclude the distribution of the T66Bk-rsk3 fusion gene products to spermatocytes not containing the T66Bk-rsk3 fusion gene (Willison and Ashworth 1987), thus fulfilling an important criterion for the R function. The low level of expression found in day 7 and 14 p.p., but not in day 18 p.p. testis suggests that the transcripts might be degraded by the end of meiosis.

EXAMLPE 4

T66B-related Genes are Conserved During Evolution

Figure 6:
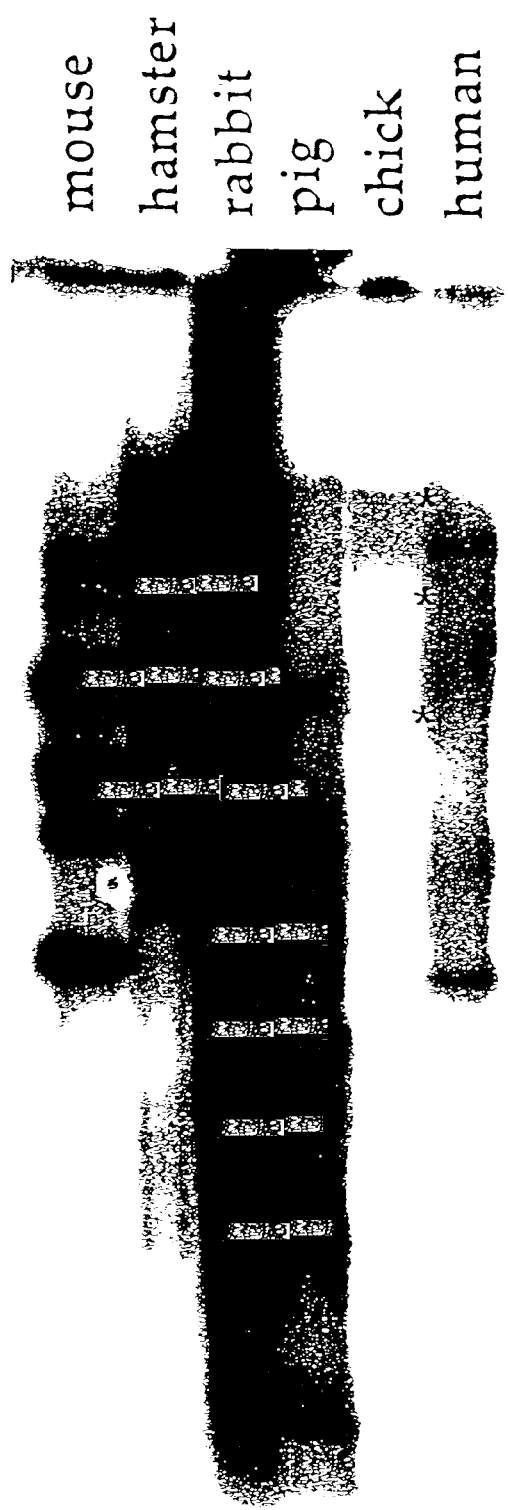

Putative homologs of the T66Bk-related kinases also exist in other species (FIG. 6). A Southern blot hybridization assay at reduced stringency using the cDNA fragment 191/144 as a probe revealed cross-hybridizing fragments in hamster, rabbit, pig, chick and human. This suggests a conservation of the T66Bk-related kinases in other mammals as well as in birds.

EXAMLPE 5

The Mouse T/t-complex Encodes Several Members of the T66Bk Gene Family

In a Southern blot hybridization of cosmid cat.15 with the probe pCRt$^{h2}$-161/170 three hybridizing BamHI fragments, B7.8, B9.1 and a 6.1 kb BamHI fragment are detected (see FIG. 2). Sequencing of the T66Bk or related gene encoding parts of these genomic DNA fragments revealed that each of the BamHI fragments B7.8 and B9.1 contains a large open reading frame (ORF) encoding T66Bk and another member of the T66Bk gene family, respectively. The centromere farthest BamHI fragment (B7.8) contains the T66Bk ORF (FIGS. 1 and 4a and b). Its transcribed part (exon) differs from the corresponding exon contained in the cDNA pCRt$^{h2}$-161/144 by a single point mutation (base 1490 C to T) probably due to an allelic variation between the t-haplotypes t$^{h2}$, and t$^{w12}$ from which cosmid cat.15 was derived, resulting in a single amino acid exchange (Pro to Leu).

The next centromere closer BamHI fragment (B9.1) contains 5'-noncoding sequence and most likely the promoter of T66Bk and, further upstream of it, an ORF encoding exon and a 3'-noncoding exon of another member of the T66Bk gene family, named here T66Bk-2. However, in this case the 3'-noncoding exon is not related to rsk3. The exon sequence of T66Bk-2 encoding a large ORF is shown on FIGS. 7a and b. It differs from the ORF of T66Bk in a number of positions; nevertheless, it is very closely related to T66Bk. In the t$^6$/+ testis cDNA panel, expression of T66Bk-2 is first detected at 22 days p.p. Considerably higher expression is observed from 24 days p.p. onwards (FIG. 8).

The mouse genome contains several more loci of the T66Bk gene family some of which are located in the region of the T/t-complex distal to T66B, probably in T66C. This is based on the observation of several BamHI fragments hybridizing to pCRt$^{h2}$-161/170, other than those described above, contained in the genome of mice carrying partial t-haplotypes or wild type mice. Some of these BamHI fragments are polymorphic and specific to complete t-haplotypes, but are not present in the partial t-haplotypes t$^{h44}$, t$^{Jr1}$, t$^{lowH}$, t$^{h2}$ or t$^{t9}$ nor in wild type (see FIG. 2). Therefore they must be contained in the T/t-complex region distal to T66B. To obtain coding sequences of T66Bk gene family members not contained in the T66B region several cDNA clones were isolated from a testis cDNA library constructed from male mice of the genotype t$^{w5}$/t$^{w12}$, by hybridization with the probe pCRt$^{w5}$-155/170 derived from the T66Bk gene. Several cDNA clones were isolated. All of them have a high sequence similarity to T66Bk or T66Bk-2.

One of them, T66k-8 (FIGS. 7c, d, and e) is almost identical in sequence to T66Bk-2 as far as sequence is available for both genes, except that it contains a single base deletion leading to an alteration of the ORF C-terminally to the protein kinase domain. From the high sequence conservation of T66k-8 to T66Bk-2 it seems not unlikely that T66k-8 is derived from the T66Bk-2 locus. However, it is not clear how the single base change was introduced into the cDNA clone, whether by a mistake in the RNA transcription, processing, reverse transcription, or by another mechanism. For instance, it has been shown that RNA editing resulting in a change of the nucleotide sequence which can alter the ORF, can occur in lower and higher eukaryotes. At the moment, such a mechanism cannot be excluded as the cause of the observed alteration. Nor can it be excluded that T66k-8 derives from a duplicated T66Bk-2 locus. Alternatively, T66k-8 might be derived from the t$^{w5}$ allele of T66Bk-2. Another cDNA was found that also contains a single base deletion at a similar position as T66k-8. The genomic location of the corresponding gene has not been determined. The alteration predicted for the C-terminal tail of either gene product would be expected to result in a change of the regulation and/or level of their protein kinase activity and/or of the location of the protein within the cell.

Another cDNA clone, T66k-7as (FIGS. 7f, g, and h), also isolated from the cDNA library, has a very intriguing sequence and structure. It contains a sequence strongly related to T66BkfT66Bk-2, including intron sequences from either side of the exon containing the single long ORF and additional sequences from further downstream, inserted in antisense orientation in the plasmid cDNA vector. Therefore T66k-7as must be derived from an antisense transcript of a T66Bk family gene. The predicted T66k-7as transcript does not contain a long ORF. The intron sequence 5' to the ORF encoding exon of T66Bk/T66Bk-2 is very A/T rich in antisense direction and apparently serves as transcription stop and polyadenylation signal during the synthesis of this antisense transcript. The sequences contained in the BamHI fragment B9.1 of cat.15 which are related by sequence to the 5' end of T66k-7as map to the vicinity of the promoter of T66Bk suggesting that the promoter region of T66Bk might contain elements controlling in cis the transcription of T66Bk sense RNA as well as the transcription of T66Bk-2 antisense RNA. If that were the case, antisense transcription might be achieved by the same cis-control elements and thus occur at the same stage as sense-RNA transcription. So far, no antisense transcript coming from that locus of the T66B region was identified. Nonetheless, the similarity of the structure and sequence of T66Bk-7as to the head-to-tail arrangement and sequence of T66Bk-2fT66Bk suggests that the T66Bk-2 gene of the T66B region might be transcribed in antisense direction. In addition, another T66Bk locus must exist which is transcribed in antisense direction, gave rise to the cDNA T66k-7as and might be located within the T66B region.

It is obvious that the expression of antisense transcript complementary to mRNA transcribed from members of the T66Bk gene family would be well suited to diminish the level of functional gene products derived from that gene family. This could influence the spermatozoa in two ways. If the antisense transcripts act in both types of spermatids, those carrying the t-Responder and those not carrying it, the former might be protected from that negative action of antisense transcripts by a higher activity of its T66Bk family gene products whereas the latter are not. In the alternative, more likely way the antisense RNA transcripts might be restricted to the former spermatids and lower the expression of T66Bk gene products expressed in them. This would help to protect the former from the negative action of hypermorphic Distorter gene products, whereas the latter would be "poisoned" by them. This "poisoning" would be caused by hyperactivation of the Responder/Distorter signaling cascade.

Antisense RNA derived from (a) T66Bk family member (s) would be expected to attenuate the negative effect of the Distorters and, in that way is envisaged to contribute to the transmission ratio distortion phenotype. Another cDNA clone, T66k-20, isolated from the $t^{w5}/t^{w12}$ testis cDNA library encodes yet another member of the T66Bk gene family (FIGS. 7$i$, $j$, and $k$). Its ORF differs from T66Bk and T66Bk-2 in a number of amino acid residues and in particular at the N-terminal end which is 20 residues longer than that of T66Bk and T66Bk-2 (FIG. 7$e$). Most likely, T66k-20 is derived from a gene located in the T66A region, and thus may provide wild type Responder activity.

The analysis of the transmission ratios of $t^{lowH}$ or $t^{low3H}$ heterozygous with $t^{h51}t^{h18}$ by Lyon (1984), showed a strong difference between the transmission ratio of $t^{lowH}$ and $t^{low3H}$. In addition, neither t-haplotype reached the high value of a complete t-haplotype heterozygous with a wild type chromosome. These data suggest the involvement of several loci in the t-Responder function. At the present level of analysis it is speculated that T66Bk, T66Bk-2, T66k-8, T66k-20 and T66k-7as may cooperatively contribute to the t-Responder function.

The testis cDNA library prepared from RNA of a male carrying the t-haplotypes $t^{w5}/t^{w12}$ did not contain a cDNA clone derived from the T66Bk gene. Therefore another testis cDNA library was constructed from RNA of a male carrying the t-haplotypes $t^6/t^{w5}$. Four clones containing a fragment of the size expected from PCR amplification with the primer pair 161/144 were identified and one of them was purified and sequenced (FIG. 9). The sequence is identical to that of the cDNA pCR$t^{h2}$-161/144 (FIGS. 4$a$ and $b$) in the region of overlap and extends it at the 5' as well as the 3'-end. It is worth noting that the sequence ends in an intron of the rsk3 locus in the T66B region and has no consensus polyadenylation signal suggesting that the cDNA is not derived from a properly processed mRNA molecule, but from a, possibly rare, transcript which has not been spliced completely and may contain a dA-rich intron sequence. This finding leaves open the possibility that the T66Bk gene transcript might include the complete rsk3 locus in T66B from bp 438 of the coding region to the 3'-end.

In addition to the T66Bk family members encoded in the t-haplotype, three more family members derived from the wild type inbred strains Balb/c, C3H/N and 129/Sv were isolated either by RT-PCR or on a genomic clone (FIG. 10). Again, high sequence conservation to the t-haplotype family members was observed. The gene pCR.Balb-66k has the same feature as the gene T66k-20, namely a potential translation start site upstream of the one utilized by T66Bk coding for additional 20 amino acid residues. It is not clear, however, whether this translation start is efficiently used since it does not conform with Kozak's rules demanding an A or a G at position-3 upstream of the ATG codon.

In contrast, the genes pCR.C3H-66k and pλ.129-66k differ significantly from all other T66Bk family members at their C-terminus. Both genes contain a translation stop codon at triplet position 434 resulting in a truncated protein of only 433 amino acid residues whereas the remaining nucleic acid sequence is not significantly different from those of the other members. The truncation occurs outside the kinase domain suggesting that the protein might still be able to function as a kinase. However, the alteration of the C-terminus might influence the regulation and/or level of kinase activity. In this context it is interesting to note that on the C3H background t-haplotypes are transmitted at a very high ratio, whereas e.g. $t^o$ is transmitted at a reduced ratio from males carrying the T/t-complex from Balb/c compared to the ratio obtained by males of the genotype $t^o$/C3H (Bennett et al. 1983). The 129Sv background also enhances the transmission ratio of t-haplotypes similar to C3H (our observations). The shortened ORFs in pCR.C3H-66k and pλ.129-66k might have an influence on this behaviour. On the other hand, other T66Bk family members encoding proteins of the same length as T66Bk might exist in these strains in addition to the ones shown here.

Therefore, and in general, it is to be noted that the genetic background of the animal strain involved may significantly contribute to the expression of the phenotype in terms of the level of distortion of the transmission ratio.

EXAMLPE 6

Transmission Ratio Distortion in Males Carrying Transgene Insertions Encoding the T66Bk Kinase To prove the involvement of T66Bk in the Responder phenotype transgene constructs were made expressing the kinase gene T66Bk (FIGS. 4$a$ and $b$) either under control of the testis promoter of c-kit (tg4-3; tg4-13) or of the putative endogenous promoter of T66Bk (FIG. 11) in transgenic mice (tg5-43; tg5-25). Mice carrying the trangene integration were mated to mice carrying either the t-haplotype $t^{h51}$-$t^{h18}$ expressing the t-Distorters D1 and D2 or the wild type chromosomes C57BL/6 or Ttf/+tf (Lyon 1984). Males of the appropriate genotype were mated to NMRI outbred females and their offspring tested for carriers of the transgene. The expectation based on the experiments of Lyon (1984) was that, if T66Bk encodes a protein involved in transmission ratio distortion the t-Distorters should enhance the transmission ratio of the transgene, as is the case in the genotype +$t^{lowH}$+/$t^{h51}$+$t^{h18}$, whereas in males carrying wild type chromosomes the transmission ratio of the transgene should be lowered. Table 1 shows the data obtained so far. Interestingly, one of the transgene integrations (tg4-3) must have occurred on the Y chromosome since it is only observed in males. In this case offspring were examined for external sexual characteristics after birth, the other transgene integrations were examined by PCR analysis. The data demonstrate a significant distortion of the transmission of the transgene confirming that T66Bk encodes t-Responder activity. The data also demonstrate the potential of the T66Bk gene in breeding strategies selecting for specific genetic traits, in particular sex. In addition the data show the usefulness of both promoters as control elements in achieving a Responder phenotype.

However, the transmission distortion effect obtained is considerably smaller than that observed with the genotype +$t^{lowH}$+/$t^{h51}$+$t^{h18}$ or +$t^{lowH}$+/++tf (Lyon 1984). This suggests that either the expression level of the T66Bk kinase from the transgene constructs is not adequate or that the expression of wild type Responder loci in spermatozoa carrying the transgene diminishes the effect of the T66Bk gene. It should be taken into consideration that the $t^{lowH}$ chromosome is carrying loci selected by nature for an optimal effect on transmission ratio distortion. In Lyon's analyses (1984) sperm carrying this chromosome compete with sperm carrying either a wild type chromosome or the t-Distorters $t^{h51}$-$t^{h18}$ probably in combination with (a) wild type Responder locus (loci). In contrast, the trangene integrations occurred outside of chromosome 17. Therefore, transgene expression always occurs in sperm expressing in addition (a) wild type Responder locus (loci). These sperm are competing with sperm carrying either a wild type chromosome or the t-Distorters $t^{h51}$–$t^{h18}$ probably in combination with (a) wild type Responder locus (loci). The combination of T66Bk expressed from the transgene with expression products from (a) wild type Responder locus (loci) might be less effective in distorting the transmission ratio than the combination of products expressed by members of the T66Bk gene family, in particular T66Bk and T66Bk-2, in the $t^{lowH}$ t-haplotype. Also, it has been demonstrated that the genetic background has a considerable effect on the ratio of transmission distortion achieved by various t-haplotypes (Bennett et al., 1983). It is quite clear that the expression level and/or activity of the T66Bk gene has to be optimized in future experiments in order to obtain a stronger transmission ratio distortion effect.

Also, control elements affecting the expression level such as elements regulating transcription efficiency, transcript processing and stability and translation efficiency, used for transgene expression have to be optimised to achieve a maximal effect. It would be convenient to select a tissue and stage specific promoter such as the one. controlling the expression of T66k-20 preferably including its 5'-untranslated region, first intron and 3'-untranslated region. Alternatively, an 3'-untranslated region known to increase the stability of the corresponding mRNA could be used. We have noticed that transcripts derived from T66k-20 are respresented at a high ratio in cDNA isolated from a testis cDNA library constructed from RNA of mice carrying $t^{w5}/t^{w12}$. In contrast, cDNAs derived from T66Bk were not found and cDNAs derived from T66Bk-2 were highly underrepresented, suggesting that the transcription level of T66k-20 is considerably higher than that of the former loci.

However, transfer of this system for distortion of the transmission of genetic traits, in particular of sex, to farm animals might be achievable without a major effort since it is not expected that amplification of T66Bk related genes also occurred in farm animals which have not evolved transmission ratio distortion. Therefore, T66Bk might have a much stronger effect on transmission ratio when introduced into farm animals. The data presented here open the prospect of producing farm animals fathering preferentially or even exclusively offspring of the same sex, e.g. only or predominantly females.

EXAMLPE 7

Cloning of Wild Type Members of the T66Bk Kinase Gene Family

The cDNAs pCR.Balb-66k and pCR.C3H-66k were isolated by RT-PCR using the primer pairs 161/220 (220: 5'-CTTCCCCCTGGCTGGAC-3' (SEQ ID NO:24)) from testis RNA of the inbred strain Balb/c and C3H/N, respectively, cloned in the plasmid vector pCR2.1 (Invitrogen) and analyzed using the methods described in figure legends 3 and 4. The extension step in the PCR was performed for 2 min. at 72° C. The sequence of p__.129-66k was derived from an EcoRI subclone in pBluescriptKS made from a lambda-FixII clone isolated from a genomic lambda-FixII library using a cDNA fragment of T66Bk as probe. The lambda-library was constructed from genomic DNA of the ES-cell line R1 (Nagy et al. 1993), according to the instructions of the supplier for the lambda cloning and packaging kits (Stratagene). Library construction, plating and screening by hybridization was according to standard techniques (Sambrook et al. 1989) and the methods described in figure legends 2, 3 and 4.

Primer Sequences:

ACE

5'GC CAA CCA GGG GAT A 3'(SEQ ID NO:25); 5'CT GTC CGG TCA TAC TCT T 3'(SEQ ID NO:26)

c-kit

5'CTT GTG TCC TTG GGA GAA 3'(SEQ ID NO:27); 5'GGT GCC ATC CAC TTC AC 3'(SEQ ID NO:28)

mP1

5'CGC AGC AAA AGC AGG AGC AG 3'(SEQ ID NO:29); 5'CAT CGG ACG GTG GCA TTT TT 3'(SEQ ID NO:30)

mouse rsk3

144: 5'TGC TCA AGC CAA AAT CTG TG 3'(SEQ ID NO:31)

145: 5'ATG GCC TGG GGA TCA TCT AC 3'(SEQ ID NO:32)

146: 5'CAC CGC TTG CAC ACT GAG TA 3'(SEQ ID NO:33)

cDNA pCRt$^{h2}$-161/144

155: 5'ATC GAT GTG TGG GGT CTT 3'(SEQ ID NO:34)

161: 5'GTT TGG GAG GAG CTT GTG 3'(SEQ ID NO:35)

170: 5'CTA GTC CAG CCC TTG ATG 3'(SEQ ID NO:36)

181: 5'TGG CAT CTT ATT GTC TAC 3'(SEQ ID NO:37)

191: 5'CCA AGC CCC UT TTC TGA 3'(SEQ ID NO:38)

pSV-Sport1 seq5lib: 5'ATTTAGGTGACACTATAGAAGGTA 3'(SEQ ID NO:39)

Oligonucleotide Sequences:

232: 5'CCC CCT TTA TCT GAC 3'(SEQ ID NO:40)

237: 5'TAT GCT GGC AGC ATC AAA 3'(SEQ ID NO:41)

TABLE 1

| tg4 males | genotype | # female | # male | % male |
|---|---|---|---|---|
| 4-3/5 | th51-th18/C57BL | 42 | 71 | 62.8 |
| 4-3/36 | th51-th18/C57BL | 33 | 55 | 62.5 |
| 4-3/39 | th51-th18/C57BL | 50 | 67 | 57.2 |
| | total: | 125 | 193 | 60.7% |
| 4-3/37 | +tf/C57BL | 42 | 29 | 40.8 |
| 4-3/187 | C57BL/C57BL | 52 | 37 | 41.6 |
| | total: | 94 | 66 | 41.2% |

| tg4 males | genotype | # −tg | # +tg | % tg |
|---|---|---|---|---|
| 4-13/80 | th51-th18/C57BL | 41 | 58 | 58.6 |
| 4-13/86 | th51-th18/C57BL | 45 | 55 | 55 |
| 4-13/97 | th51-th18/C57BL | 44 | 56 | 56 |
| | total: | 130 | 169 | 56.5% |
| 4-13/53 | +tf/C57BL | 56 | 47 | 45.6 |
| 4-13/96 | +tf/C57BL | 70 | 67 | 48.9 |
| 4-13/100 | +tf/C57BL | 53 | 47 | 47 |
| | total: | 179 | 161 | 47.3% |

| tg5 males | genotype | # −tg | # +tg | % tg |
|---|---|---|---|---|
| 5-43/100 | th51-th18/C57BL | 13 | 29 | 69.0 |
| 5-43/101 | th51-th18/C57BL | 12 | 16 | 57.1 |
| 5-43/104 | th51-th18/C57BL | 26 | 28 | 51.8 |
| 5-43/105 | th51-th18/C57BL | 12 | 25 | 67.5 |
| | total: | 63 | 98 | 60.8% |
| 5-25/83 | Ttf/C57BL | 43 | 29 | 40.3 |
| 5-25/84 | +tf/C57BL | 37 | 24 | 39.3 |
| | total: | 80 | 53 | 39.8% |

Table 1

Transmission ratio distortion in mice carrying transgenes encoding the kinase gene T66Bk.

Two transgene constructs, tg4 and tg5 containing the protein coding region of T66Bk were constructed in vitro and introduced into the germ line by injection of DNA into one pronucleus of fertilized eggs of the genotype ((C57BU6 ×C3H/N)F1 ×C57BU6) female ×NMRI male and retransfer of the zygotes or 2-cell embryos into NMRI foster mothers. Male or female carriers of either transgene were mated to mice carrying either the t-Distorters D1 and D2 on a single t-haplotype chromosome ($t^{h51}$–$t^{h18}$) over Ttf, +tf or C57BL/6, or either the wild type genotype Ttf/+tf or C57BL/C57BL. Males carrying the appropriate genotype were identified by PCR analysis and set up for test matings with NMRI outbred females. In most cases, late embryonic stages were used as source of DNA for testing individual offspring for the presence or absence of the transgene, the remainder were tested using a tail piece as DNA source. A chromosome 17 marker locus was tested in parallel to control the quality of the DNA solution. The transgene tg4 of the line 4-3 segregates with the Y-chromosome, suggesting that tg4 is integrated on the Y chromosome. Therefore, in this case, offspring were examined after birth for their sex using external sexual characteristics. The breeding data demonstrate non-mendelian inheritance of the transgene and, in the case of tg4-3, of sex. The deviation from the expected 50% depends on the presence or absence of t-Distorter loci, being significantly higher than 50% in the presence and lower than 50% in the absence of t-Distorter loci, as expected from the t-haplotype Responder locus Tcr. This confirms the finding that T66Bk encodes t-Responder activity.

Methods:

Tg4 consists of the testis promoter of c-kit, base 45 to the StyI site at base 683 (Rossi et al. 1992; Albanesi et al. 1996), the cDNA $t^{h2}$-161/144 and additional mouse rsk3 sequence comprising bp 438 up to bp 998 of rsk3 (Kispert, 1990), and IRES-βgeo containing the internal ribosome entry site IRES (Ghattas et al. 1991) and the βgal-neo fusion gene and SV40 polyadenylation signal (Friedrich and Soriano 1991). In brief, the testis promoter of c-kit was isolated by RT-PCR from testis RNA using the primer pair 5'-ATGTAAGTGGCATGGAGT-3' (SEQ ID NO:42) and 5'-GCACACCGAAAATAAAA-3' (SEQ ID NO:43) and cloned into the plasmid vector pCR2.1 (Invitrogen). A NotI-BstEII fragment comprising the cDNA $t^{h2}$-161/144 from a vector NotI site at the 5'-end to a BstEII site in the rsk3 homology region was ligated to NotI and BstEII sites in the plasmid IRES-βgeo containing the rsk3 homology region from the BstEII site to bp 998, 5' of the IRES-βgeo gene. The 5'-end of the resulting construct containing an EcoRV site from the vector pCR2.1 just 3' of the NotI site was replaced by a NotI-StyI fragment containing the testis promoter of c-kit cloned in the vector pCR2.1 by ligation of the NotI-StyI(blunt; the StyI site was blunt-ended by treatment with the Klenow-fragment of E.coli DNA polymerase I) fragment comprising bp 45 to bp 683 of the c-kit promoter into the NotI and EcoRV sites of the construct. The final transgene construct was released from the vector by digestion with NotI and SalI.

Tg5 consists of 2637 bp (KpnI to PmII fragment) of the genomic region upstream of the putative transcription start site of T66Bk including most of the 5'-untranslated region and the putative promoter of T66Bk (FIG. 11), the cDNA $t^{h2}$-161/144 from the HincII site (bp 293) to the EcoRI site in vector pCR2.1 including the complete protein coding region and a HA-tag constructed into the start site of translation, the IRES sequence and coding region of human CD24 (Kay et al. 1991), and the modified intron and polyadenylation signal of SV40-t (Huang and Gorman 1990). Tg5 was constructed in several steps. First, an HA-tag encoding the peptide sequence YPYDVPDYA was introduced at the translation start of the cDNA $t^{h2}$-161/144.

Second, the putative promoter of T66Bk was isolated as a 2.6 kb KpnI(blunt)-PmII fragment from the genomic BamHI fragment B9.1 of cosmid cat.15, and ligated into EcoRV and HincII sites of the vector containing the HA-tagged cDNA $t^{h2}$-161/144. The EcoRV site stems from the vector pCR2.1 while the HincII site is contained in the 5'-untranslated region of the cDNA $t^{h2}$-161/144. In the third step the IRES sequence and hCD24 coding sequence was cut as an EcoRI-EagI(blunted) fragment from the plasmid pSLV-1, the modified intron and polyadenylation signal of SV40-t were cut as a SnaBI-BamHI fragment from the Vector pSV-Sport1 (Gibco/BRL), and both fragments were ligated together into the previous construct opened at the vector sites EcoRI and BamHI located at the 3'-end of the insert. The construction of an HA-tag into the translation start site of T66Bk was done as follows. First, two fragments of the cDNA $t^{h2}$-161/144 were amplified by PCR using the primer 5'-GGCGTAGTCTGGGACGTCGTATGGGTACA TGTCAGAAAAAGG-3' (SEQ ID NO:44) and 5'-ATG TACCCATACGACGTCCCAGACTACGCCATGGAGA AATTTCAT-3' (SEQ ID NO:45), respectively, in combination with the upstream primer 161 or the downstream primer 188 (5'-ACCCTGGTTGTGGCAGTA-3'(SEQ ID NO:46)), respectively, creating an overlapping region encoding the HA-tag sequence coding for the peptide YPYDVPDYA (SEQ ID NO:53), in frame with the translation start site of T66Bk. The PCR was performed as described in figure legend 3 except that 15 cycles were performed and 50 ng template were added. Then, both fragments were isolated from an agarose gel and used as template together in a second PCR. First 15 cycles of 30 sec. 94° C., 2 min. 72° C. were performed without primers, the flanking primers 161 and 188 were added and a further 25 cycles of 30 sec. 94° C., 30 sec. 50° C., 30 sec. 72° C. were performed. The resulting fragment containing the HA-tag sequence was purified from an agarose gel, cut with HincII-EcoNI and ligated in place of the HincII-EcoNI fragment of the original cDNA clone $t^{h2}$-161/144.

Testing of offspring for carriers of the transgene insertion was done by first digesting a tissue sample of individual embryos or mice in lysis buffer (100 mM Tris-HCI pH8.5/5 mM EDTA/0.2% SDS/200 mM NaCl/200 μg/ml Proteinase K) over night at 55° C., diluting an aliquot 20 fold in water followed by inactivation of the Proteinase K by incubation at 80° C. for 30 min., and assaying 1 μl in a 20 μl PCR reaction as described in figure legend 3 using the primer pair 309: 5'-CAGCCCATGAATCCATC-3' (SEQ ID NO:47) and 310: 5'-TGCCTTCGGTCTGAAAG-3' (SEQ ID NO:48) and the cycling conditions 2 min. 94° C., 35 cycles 30 sec. 94° C., 30 sec. 50° C., 1 min. 72° C. A control PCR reaction assaying for the genotype at the locus Hba-4ps in the distal region of the mouse T/t-complex was performed where appropriate using the primer pair Hb.1/Hb.2 and conditions as published (Schimenti and Hammer 1990). This PCR reaction was also used to test for the presence of the distal t-haplotype region $t^{h18}$ containing the t-Distorter D2. Likewise, presence of the proximal t-Distorter D1 in the t-haplotype $t^{h51}$ was assayed by testing for the presence of a t-specific fragment at the Tcp1 locus. This was done by PCR using the primer pair 5'-AGGAAAGCTT GCCCMGAGAATAGTTMTGC-3' (SEQ ID NO:49) and 5'-AGGCGAATTCCATATCATCAATGCCACCAG-3' (SEQ ID NO:50). The cycling conditions were 40 sec. 94° C., 40 sec. 60° C., 1 min. 30 sec. 72° C., 35 cycles. Different wild type alleles at the locus D17Mit46 from the middle of the T/t-complex were distinguished by PCR using the primers Left: 5'-TCCACCCCACTACCTGACTC-3' (SEQ ID NO:51) and Right: 5'-CCCTTCTGATGACCACAGGT-3' (SEQ ID NO:52). Cycling conditions were 40 sec. 94° C., 40 sec. 50° C., 40 sec. 72° C., 35 cycles. This marker allows to distinguish between the allelic variants of the strains C57BU6, NMRI and Ttf/+tf.

All cloning procedures were performed according to standard techniques (Sambrook et al. 1989), the production of transgenic mice was done according to the methods described in Methods in Enzymology, Vol. 225, Guides to Techniques in Mouse Development, 1993 (ed. P. M. Wassarman and M. L. DePamphilis). Mice carrying the t-haplotype $t^{h51}$–$t^{h18}$ were obtained from Dr. M. F. Lyon (Harwell, England), mice with the genotype Ttf/+tf were a gift of Dr. K. Artzt (Austin, Tex.).

References

Albanesi C., Geremia R., Giorgio M., Dolci S., Sette C., Rossi P. (1996) A cell- and developmental stage-specific promoter drives the expression of a truncated c-kit protein during mouse spermatid elongation. Development 122, 1291–1302

Auffray C., Rougeon F. (1980) Purification of mouse immunoglobulin heavy-chain messenger RNAs from total myeloma tumor RNA. Eur. J. Biochem. 107, 303–314

Bennett D., Alton A. K., and Artzt K. (1983) Genetic analysis of transmission ratio distortion by t-haplotypes in the mouse. Genet. Res. Camb. 41, 29–45

Bullard D. C., Ticknor C., Schimenti J. C. (1992) Functional analysis of a t complex Responder locus transgene in mice. Mammalian Genome 3, 579–587

Cebra-Thomas J. A., Decker C. L., Snyder L. C., Pilder S. H., Silver L. M. (1991) Allele- and haploid-specific product generated by alternative splicing from a mouse t complex Responder locus candidate. Nature 349, 239–241

Church G. M and Gilbert W. (1984) Genomic Sequencing. Proc. Natl. Acad. Sci. USA 81,1991–1995

Drewes G., Ebneth A., Preuss U., Mandelkow E. M., Mandelkow E. (1997) MARK, a novel family or protein kinases that phosphorylate microtubule-associated proteins and trigger microtubule disruption. Cell 89, 297–308

Ehrich E., Craig A., Poustka A., Frischauf A. M., Lehrach H. (1987) A family of cosmid vectors with the multi-copy R6K replication origin. Gene 57, 229–237

Ewulonu U. K., Schimenti K., Kuemerle B., Magnuson T., Schimenti J. (1996) Targeted mutagenesis of a candidate t complex Responder gene in mouse t haplotypes does not eliminate transmission ration distortion. Genetics 144, 785–792

Faisst S., and Meyer S. (1992) Compilation of vertebrate-encoded transcription factors. Nucleic Acids Res. 20, 3–26

Fox H. S., Martin G. R., Lyon M. F., Herrmann B. G., Frischauf A. M., Lehrach H., Silver L. M. (1985) Molecular Probes define different regions of the mouse t complex. Cell 40, 63–69

Friedrich G., and Soriano P. (1991) Promoter traps in embryonic stem cells: a genetic screen to identify and mutate developmental genes in mice. Genes. Dev. 5,1513–1523

Ghattas I. R., Sanes J. R., Majors J. E. (1991) The encephalomyocarditis virus internal ribosome entry site allows efficient coexpression of two genes from a recombinant provirus in cultured cells and in embryos. Mol. Cell. Biol. 11, 2548–2559

Herrmann B. G., Bucan M., Mains P. E., Frischauf A. M., Silver L., Lehrach H. (1986) Genetic analysis of the proximal portion of the mouse t complex: evidence for a second inversion within t haplotypes. Cell 44, 469–476

Herrmann B. G., Barlow D. P., Lehrach H. (1987) A large inverted duplication allows homologous recombination between chromosomes heterozygous for the proximal t complex inversion. Cell 48, 813–825

Herrmann B. G. and Frischauf A. M. (1987) Isolation of Genomic DNA. Methods in Enzymology Vol.152, 180–183 (ed. Berger and Kimmel)

Howard T. E., Shai S. Y., Langford K. G., Martin B. M., Bernstein K. E. (1990) Transcription of testicular angiotensin-converting enzyme (ACE) is initiated within the 12th intron of the somatic ACE gene. Mol. Cell. Biol. 10, 4294–4302

Huang M. T. F., and Gorman C. M. (1990) The Simian Virus 40 small-t intron, present in many common expression vectors, leads to aberrant splicing. Mol. Cell. Biol. 10, 1805–1810

Kay R., Rosten, P. M., and Humphries R. K. (1991) CD24, a signal transducer modulating B cell responses, is a very short peptide with a glycosyl phosphatidylinositol membrane anchor. J. Immunology 147, 1412–1416

Kispert A. (1990) Isolierung und Charakterisierung eines S6 Kinase II-homologen Gens (Tck) aus dem T/t-Komplex der Maus. Diplomarbeit, Universität Tübingen (Germany)

Langford K. G., Shai S. Y., Howard T. E., Kovac M. J., Overbeek P. A., Bemstein K. E. (1991) Transgenic mice demonstrate a testis-specific promoter for angiotensin-converting enzyme. J. Biol. Chem. 266, 15559–15562

Lyon M. F. (1984) Transmission ratio distortion in mouse t-haplotypes is due to multiple Distorter genes acting on a Responder locus. Cell 37, 621–628

Lyon M. F. (1986) Male sterility of the mouse t-complex is due to homozygosity of the Distorter genes. Cell 44, 357–363

Nadeau J. H., Varnum D., Burkart D. (1989) Genetic evidence for two t complex tail interaction (tct) loci in t haplotypes. Genetics 122, 895–903

Nagy A., Rossant J., Nagy R., Abramov-Newerly W., and Roder J. C. (1993) Derivation of completely cell culture-derived mice from early-passage embryonic stem cells. Proc. Natl. Acad. Sci. USA 90, 8424–8428

Peschon J. J., Behringer R. R., Brinster R. L., Palmiter R. D. (1987) Spermatid-specific expression of protamine 1 in transgenic mice. Proc. Natl. Acad. Sci. USA 84, 5316–5319

Rackwitz H. R., Zehetner G., Murialdo H., Delius H., Chai C. H., Poustka A., Frischauf A., Lehrach H. (1985) Analysis of cosmids using linearization by phage lambda terminase. Gene 40, 259–266

Rosen L. L., Bullard D. C., Silver L. M., Schimenti J. C. (1990) Molecular cloning of the t complex Responder genetic locus. Genomics 8, 134–140

Rossi P., Marziali G., Albanesi C., Charlesworth A., Geremia R., Sorrentino V. (1992) A novel c-kit transcript, potentially encoding a truncated receptor, originates within a kit gene intron in mouse spermatids. Dev. Biol. 152, 203–207

Rugh R. (1990) The Mouse, Its Reproduction and Development (Oxford University Press, Oxford)

Sambrook J., Fritsch E. F., Maniatis T. (1989) Molecular Cloning, A Laboratory Manual (Cold Spring Harbor Laboratory Press)

Schimenti J., and Hammer M. (1990) Rapid identification of mouse t-haplotypes by PCR polymorphism (PCRP). Mouse Genome 87,108

Schimenti J., Vold L., Socolow D., Silver L. M. (1987) An unstable family of large DNA elements in the center of the mouse t complex. J. Mol. Biol. 194, 583–594

Schimenti J., Cebra-Thomas J. A., Decker C. L., Islam S. D., Pilder S. H., Silver L. M. (1988) A candidate gene family for the mouse t complex Responder (Tcr) locus responsible for haploid effects on sperm function. Cell 55, 71–78

Silver L. M. and Remis D. (1987) Five of nine genetically defined regions of mouse t haplotypes are involved in transmission ratio distortion. Genet. Res. Camb. 49, 51–56

Willison K., Ashworth A. (1987) Mammalian spermatogenic gene expression. Trends Genet. 3, 351–355

Zhao Y., Bjorbaek C., Weremowicz S., Morton C. C., Moller D. E. (1995) RSK3 encodes a novel pp90-rsk isoform with a unique N-terminal sequence: growth factor-stimulated kinase function and nuclear translocation. Mol. Cell. Biol. 15, 4353–4363.

Zlokamik G., Negulescu P. A., Knapp T. E., Mere L., Burres N., Feng L., Whitney M., Roemer K., Tsien R. Y. (1998) Quantitation of transcription and clonal selection of single living cells with β-lactamase as reporter. Science 279, 84–88.

What is claimed is:

1. An isolated nucleic acid molecule comprising a nucleotide sequence selected from the group consisting of SEQ ID NO:1, SEQ ID NO:4, SEQ ID NO:6, SEQ ID NO:8, SEQ ID NO:9, SEQ ID NO:11, and complements thereof.

2. A vector comprising the isolated nucleic acid molecule of claim 1.

3. A host cell comprising the vector of claim 2.

4. A method of producing an expression product encoded by an isolated nucleic acid molecule comprising a nucleotide sequence selected from the group consisting of SEQ ID NO:1, SEQ ID NO:4, SEQ ID NO:6, SEQ ID NO:8, SEQ ID NO:9, SEQ ID NO:11, the method comprising culturing a host cell comprising the isolated nucleic acid molecule under conditions to cause expression of the expression product.

5. An isolated nucleic acid molecule consisting essentially of a nucleotide sequence selected from the group consisting of SEQ ID NO:1, SEQ ID NO:4, SEQ ID NO:6, SEQ ID NO:8, SEQ ID NO:9, SEQ ID NO:11, and complements thereof, wherein the isolated nucleic acid molecule encodes an expression product.

6. A vector comprising the isolated nucleic acid molecule of claim 5.

7. A host cell comprising the vector of claim 6.

8. A method of producing an expression product encoded by an isolated nucleic acid molecule consisting essentially of a nucleotide sequence selected from the group consisting of SEQ ID NO:1, SEQ ID NO:4, SEQ ID NO:6, SEQ ID NO:8, SEQ ID NO:9, SEQ ID NO:11, the method comprising culturing a host cell comprising the isolated nucleic acid molecule under conditions to cause expression of the expression product.

9. A recombinant DNA molecule comprising the nucleic acid molecule of claim 1 or 5.

* * * * *

UNITED STATES PATENT AND TRADEMARK OFFICE
CERTIFICATE OF CORRECTION

PATENT NO. : 6,642,369 B1
DATED : November 4, 2003
INVENTOR(S) : Bernhard Herrmann, Birgit Koschorz and Andreas Kispert It is certified that error appears in the above-identified patent and that said Letters Patent is hereby corrected as shown below:

Column 19,
Line 14, "contraceptive" should read -- contraceptiva --.

Column 24,
Line 52, "1.44" should be -- 144 --.
Line 57, "$t^{w5}/tw^{12}$" should be -- $t^{w5}/t^{w12}$ --.

Column 26,
Line 24, "$t^{w5}/w^{12}$" should be -- $t^{w5}/t^{w12}$ --.
Line 51, delete "30".

Column 27,
Line 13, "t49" should be -- $t^{h49}$ --.

Column 39,
Line 7, "(C57BU6 x C3H/N)F1 x C57BU6)" should be -- ((C57BL/6 x C3H/N)F1 x (57BL/6) --.

Column 41,
Line 10, "C57BU6" should be -- C57BL/6 --.

Signed and Sealed this

Twenty-eighth Day of September, 2004

JON W. DUDAS
*Director of the United States Patent and Trademark Office*

SEQUENCE LISTING

```
<160> NUMBER OF SEQ ID NOS: 53

<210> SEQ ID NO 1
<211> LENGTH: 2076
<212> TYPE: DNA
<213> ORGANISM: Mus musculus
<220> FEATURE:
<221> NAME/KEY: CDS
<222> LOCATION: (337)..(1788)
<223> OTHER INFORMATION:

<400> SEQUENCE: 1
gtttgggagg agcttgtgtg tgtgagttgt gttttaagtt tatttgcgtg tgagtacctt      60
tgggtttttg tgtgtgtctg tgtgtgtttg tgtgtgtata actgtgggtg actgtaagtg    120
cacctgtgtg tttgtacgtg agtgtgtaag actgtgtgtg tgcacaagag cgtgtgtagg    180
tgcacgtgtt gtaggtgtga gaacacctgt tgtgtttagg ccatcagtca gcttggtcat    240
tgtttctaag gtagcattta tactttgtta cctcaagtgg gctctgggag tcaacagaag    300
tcagaaaagc tcagatccaa gcccccttt  tctgac atg gag aaa ttt cat gct      354
                                        Met Glu Lys Phe His Ala
                                        1               5 caa tat gag atg cta gag act att ggc cag gga ggc tgc gcc cag gtg      402
Gln Tyr Glu Met Leu Glu Thr Ile Gly Gln Gly Gly Cys Ala Gln Val
            10                  15                  20 aag ctg gcc cga cac cgc ctc aca ggc acc cac gtg gct gtc aaa gtg      450
Lys Leu Ala Arg His Arg Leu Thr Gly Thr His Val Ala Val Lys Val
        25                  30                  35 att gta aag agg gag tgt tgg ttc aac cct gtc atg tct gag gca gag      498
Ile Val Lys Arg Glu Cys Trp Phe Asn Pro Val Met Ser Glu Ala Glu
    40                  45                  50 tta ctg atg atg acc gat cat ccg aat atc atc tct ctc ctt caa gtc      546
Leu Leu Met Met Thr Asp His Pro Asn Ile Ile Ser Leu Leu Gln Val
55                  60                  65                  70 att gag acc aag aag aaa gta tac ctc att atg gag ttg tgc gag ggt      594
Ile Glu Thr Lys Lys Lys Val Tyr Leu Ile Met Glu Leu Cys Glu Gly
                75                  80                  85 aaa tca ctt tac caa cac atc caa aat gct ggc tac ctg cag gag gat      642
Lys Ser Leu Tyr Gln His Ile Gln Asn Ala Gly Tyr Leu Gln Glu Asp
            90                  95                  100 gaa gca cgc cca tta ttc aag cag ctc tta agt gct atg aac tac tgc      690
Glu Ala Arg Pro Leu Phe Lys Gln Leu Leu Ser Ala Met Asn Tyr Cys
        105                 110                 115 cac aac cag ggt ata gtt cac agg gac ctg aca cct gac aat att atg      738
```

```
          His Asn Gln Gly Ile Val His Arg Asp Leu Thr Pro Asp Asn Ile Met
              120                 125                 130 gta gaa aaa gat ggg aaa gtg aag atc att gat ttt gga ctc ggc acc          786
Val Glu Lys Asp Gly Lys Val Lys Ile Ile Asp Phe Gly Leu Gly Thr
135                 140                 145                 150 caa gag aag cca ggg caa aac cac aac tta ttc tgt gag att tac cca          834
Gln Glu Lys Pro Gly Gln Asn His Asn Leu Phe Cys Glu Ile Tyr Pro
                155                 160                 165 ttt agt act cct gag gtg ctc ttt aac aga ccc tat gat atg cgc aag          882
Phe Ser Thr Pro Glu Val Leu Phe Asn Arg Pro Tyr Asp Met Arg Lys
            170                 175                 180 atc gat gtg tgg ggt ctt gga gtt gtg ctg tat ttt atg gta act gga          930
Ile Asp Val Trp Gly Leu Gly Val Val Leu Tyr Phe Met Val Thr Gly
        185                 190                 195 aag att ctg ttt gat act gcc agc gta gaa aag ctg cga aag caa att          978
Lys Ile Leu Phe Asp Thr Ala Ser Val Glu Lys Leu Arg Lys Gln Ile
    200                 205                 210 gtt gca gaa aag tgt tct gtt ccc tgt aga ctg tca gta gag ctc caa         1026
Val Ala Glu Lys Cys Ser Val Pro Cys Arg Leu Ser Val Glu Leu Gln
215                 220                 225                 230 gac ctg att aga ctt tta atg acg gac atc ccc gaa ctt agg ccc act         1074
Asp Leu Ile Arg Leu Leu Met Thr Asp Ile Pro Glu Leu Arg Pro Thr
                235                 240                 245 gtt gct gaa gtt atg gtg cat ccc tgg gtc aca gaa ggc tca ggg gtg         1122
Val Ala Glu Val Met Val His Pro Trp Val Thr Glu Gly Ser Gly Val
            250                 255                 260 tta cca gat cct tgt gaa gaa cat ata ccc ctc aag cca gac cct gcg         1170
Leu Pro Asp Pro Cys Glu Glu His Ile Pro Leu Lys Pro Asp Pro Ala
        265                 270                 275 att gca aaa gca atg gga ttt atc ggg ttc caa gct caa gac att gaa         1218
Ile Ala Lys Ala Met Gly Phe Ile Gly Phe Gln Ala Gln Asp Ile Glu
    280                 285                 290 gat tcg tta tgt cag aga aaa ttc aac gaa acc atg gca tct tat tgt         1266
Asp Ser Leu Cys Gln Arg Lys Phe Asn Glu Thr Met Ala Ser Tyr Cys
295                 300                 305                 310 cta ctg aaa aaa cag att ctt aag gaa tgt gac agg cca atc cgg gct         1314
Leu Leu Lys Lys Gln Ile Leu Lys Glu Cys Asp Arg Pro Ile Arg Ala
                315                 320                 325 cag ccc atg aat cca tct gtg acc cca ctc tct tcc ctt gtt gat gct         1362
Gln Pro Met Asn Pro Ser Val Thr Pro Leu Ser Ser Leu Val Asp Ala
            330                 335                 340 cct act ttc cat ctc gga ctt cgg agg aca gag act gaa ccc aca ggt         1410
Pro Thr Phe His Leu Gly Leu Arg Arg Thr Glu Thr Glu Pro Thr Gly
        345                 350                 355 ctc aga tta tct gac aat aag gaa gtg cct gtc tgt ggc aat agt act         1458
Leu Arg Leu Ser Asp Asn Lys Glu Val Pro Val Cys Gly Asn Ser Thr
    360                 365                 370 agt aag aaa aga gag aga agt ttc agt ggg ccg ggt gtt ctc agc agg         1506
Ser Lys Lys Arg Glu Arg Ser Phe Ser Gly Pro Gly Val Leu Ser Arg
375                 380                 385                 390 ccg att aac aca aca ccc aca atg gac caa aca cac acc cgt act tgg         1554
Pro Ile Asn Thr Thr Pro Thr Met Asp Gln Thr His Thr Arg Thr Trp
                395                 400                 405 agt ggt ccc tgc att tac tca aat gtt tgc aca atc cat cca aac agc         1602
Ser Gly Pro Cys Ile Tyr Ser Asn Val Cys Thr Ile His Pro Asn Ser
            410                 415                 420 atc aat gag agt aca gaa ggc cac atc agt acc tca gca gag gat aag         1650
Ile Asn Glu Ser Thr Glu Gly His Ile Ser Thr Ser Ala Glu Asp Lys
        425                 430                 435
```

-continued

```
cct gtc cac agc aga ggc tgg ccc aga ggc atc aag ggc tgg act agg      1698
Pro Val His Ser Arg Gly Trp Pro Arg Gly Ile Lys Gly Trp Thr Arg
    440                 445                 450 aag ata gga aat gca atg agg aag ctc tgt tgc tgt atc cca tcc aaa      1746
Lys Ile Gly Asn Ala Met Arg Lys Leu Cys Cys Cys Ile Pro Ser Lys
455                 460                 465                 470 gag aca tct cac ctg ggg cag aga aga gtc tgc cca aaa att              1788
Glu Thr Ser His Leu Gly Gln Arg Arg Val Cys Pro Lys Ile
                475                 480 taagacacag gaaggatgtc aggagaatga gcatccagca tggcccagcc tttcagaccg    1848
aaggcaagct ctacctgatc ctggacttcc tgcggggagg tgacctcttc accaggcttt    1908
ccaaagaggt gatgttcacg gaggaggatg tcaagttcta cctggctgag ctggccttgg    1968
ctctagacca cctccatggc ctggggatca tctacaggga tctgaagcca gagaatatcc    2028
tcctggatga agagggacat attaagatca cagattttgg cttgagca                2076
```

<210> SEQ ID NO 2
<211> LENGTH: 484
<212> TYPE: PRT
<213> ORGANISM: Mus musculus

<400> SEQUENCE: 2

```
Met Glu Lys Phe His Ala Gln Tyr Glu Met Leu Glu Thr Ile Gly Gln
1               5                   10                  15

Gly Gly Cys Ala Gln Val Lys Leu Ala Arg His Arg Leu Thr Gly Thr
            20                  25                  30

His Val Ala Val Lys Val Ile Val Lys Arg Glu Cys Trp Phe Asn Pro
        35                  40                  45

Val Met Ser Glu Ala Glu Leu Leu Met Met Thr Asp His Pro Asn Ile
    50                  55                  60

Ile Ser Leu Leu Gln Val Ile Glu Thr Lys Lys Lys Val Tyr Leu Ile
65                  70                  75                  80

Met Glu Leu Cys Glu Gly Lys Ser Leu Tyr Gln His Ile Gln Asn Ala
                85                  90                  95

Gly Tyr Leu Gln Glu Asp Glu Ala Arg Pro Leu Phe Lys Gln Leu Leu
            100                 105                 110

Ser Ala Met Asn Tyr Cys His Asn Gln Gly Ile Val His Arg Asp Leu
        115                 120                 125

Thr Pro Asp Asn Ile Met Val Glu Lys Asp Gly Lys Val Lys Ile Ile
    130                 135                 140

Asp Phe Gly Leu Gly Thr Gln Glu Lys Pro Gly Gln Asn His Asn Leu
145                 150                 155                 160

Phe Cys Glu Ile Tyr Pro Phe Ser Thr Pro Glu Val Leu Phe Asn Arg
                165                 170                 175

Pro Tyr Asp Met Arg Lys Ile Asp Val Trp Gly Leu Gly Val Val Leu
            180                 185                 190

Tyr Phe Met Val Thr Gly Lys Ile Leu Phe Asp Thr Ala Ser Val Glu
        195                 200                 205

Lys Leu Arg Lys Gln Ile Val Ala Glu Lys Cys Ser Val Pro Cys Arg
    210                 215                 220

Leu Ser Val Glu Leu Gln Asp Leu Ile Arg Leu Leu Met Thr Asp Ile
225                 230                 235                 240

Pro Glu Leu Arg Pro Thr Val Ala Glu Val Met Val His Pro Trp Val
                245                 250                 255

Thr Glu Gly Ser Gly Val Leu Pro Asp Pro Cys Glu Glu His Ile Pro
```

-continued

```
                        260                 265                 270
Leu Lys Pro Asp Pro Ala Ile Ala Lys Ala Met Gly Phe Ile Gly Phe
            275                 280                 285
Gln Ala Gln Asp Ile Glu Asp Ser Leu Cys Gln Arg Lys Phe Asn Glu
        290                 295                 300
Thr Met Ala Ser Tyr Cys Leu Leu Lys Lys Gln Ile Leu Lys Glu Cys
305                 310                 315                 320
Asp Arg Pro Ile Arg Ala Gln Pro Met Asn Pro Ser Val Thr Pro Leu
                325                 330                 335
Ser Ser Leu Val Asp Ala Pro Thr Phe His Leu Gly Leu Arg Arg Thr
            340                 345                 350
Glu Thr Glu Pro Thr Gly Leu Arg Leu Ser Asp Asn Lys Glu Val Pro
        355                 360                 365
Val Cys Gly Asn Ser Thr Ser Lys Lys Arg Glu Arg Ser Phe Ser Gly
370                 375                 380
Pro Gly Val Leu Ser Arg Pro Ile Asn Thr Thr Pro Thr Met Asp Gln
385                 390                 395                 400
Thr His Thr Arg Thr Trp Ser Gly Pro Cys Ile Tyr Ser Asn Val Cys
                405                 410                 415
Thr Ile His Pro Asn Ser Ile Asn Glu Ser Thr Glu Gly His Ile Ser
            420                 425                 430
Thr Ser Ala Glu Asp Lys Pro Val His Ser Arg Gly Trp Pro Arg Gly
        435                 440                 445
Ile Lys Gly Trp Thr Arg Lys Ile Gly Asn Ala Met Arg Lys Leu Cys
    450                 455                 460
Cys Cys Ile Pro Ser Lys Glu Thr Ser His Leu Gly Gln Arg Arg Val
465                 470                 475                 480
Cys Pro Lys Ile
```

<210> SEQ ID NO 3
<211> LENGTH: 503
<212> TYPE: DNA
<213> ORGANISM: Mus musculus

<400> SEQUENCE: 3

```
gtgtatcagt gtgtgtttgg gaggagcttg tgtgtgtgag ttgtgtttta agtttatttg    60
tgtgttagta cctttgggtt tgtgtgtgtg tctctgtgtg tttgtgtgtg tataactgtg   120
ggtgactgta agtgcacctg tgtgtttgta cgtgagtgtg taagactgtg tgtgtgcaca   180
agagcgtgtg taggtgctcg tgttgtaggt gtgagaacac ctgttgtgtt taggccatca   240
ttcagcttgg ccattgtttc taagctgcga gaccgggtca gatctaagat ggagagagac   300
atcctggcag aggtgaatca ccctttcatt gtcaagctgc attatgcctt tcagaccgaa   360
ggcaagctct acctgatcct ggacttcctg cggggaggtg acctcttcac caggctttcc   420
aaagaggtga tgttcacgga ggaggatgtc aagttctacc tggctgagct ggccttggct   480
ctagaccacc tccatggcct ggg                                           503
```

<210> SEQ ID NO 4
<211> LENGTH: 1590
<212> TYPE: DNA
<213> ORGANISM: Mus musculus
<220> FEATURE:
<221> NAME/KEY: CDS
<222> LOCATION: (91)..(1542)
<223> OTHER INFORMATION:

-continued

```
<400> SEQUENCE: 4
gtagcattta tactttgtta cctcaaatgg gctctgggag tcaacagaag tcagaaaagc          60
tcagatccaa gcccccttta tctgactgac atg gag aaa ttt cat gct caa tat         114
                                 Met Glu Lys Phe His Ala Gln Tyr
                                  1               5 gag atg cta gag act att ggc cag gga ggc tgc gca aag gtg aag ctg         162
Glu Met Leu Glu Thr Ile Gly Gln Gly Gly Cys Ala Lys Val Lys Leu
 10                  15                  20 gcc cga cac cgc ctc aca ggc acc cac gtg gct gtc aaa atg att cca         210
Ala Arg His Arg Leu Thr Gly Thr His Val Ala Val Lys Met Ile Pro
 25                  30                  35                  40 aag agg gag tat tgg tgc aaa ctt ctg atg ttt gag gca gag tta ctg         258
Lys Arg Glu Tyr Trp Cys Lys Leu Leu Met Phe Glu Ala Glu Leu Leu
                 45                  50                  55 atg atg ttc aat cat cct aat atc atc tct ctc ctt caa gtc att gag         306
Met Met Phe Asn His Pro Asn Ile Ile Ser Leu Leu Gln Val Ile Glu
             60                  65                  70 acc aag aag aaa gta tat ctc att atg gag ttg tgc gag ggt aaa tca         354
Thr Lys Lys Lys Val Tyr Leu Ile Met Glu Leu Cys Glu Gly Lys Ser
         75                  80                  85 ctt tac caa cac atc caa aat gct ggc tac ctg cag gag gat gaa gca         402
Leu Tyr Gln His Ile Gln Asn Ala Gly Tyr Leu Gln Glu Asp Glu Ala
     90                  95                 100 cgc cca tta ttc aag cag ctc tta agt gct atg aac tac tgc cac aac         450
Arg Pro Leu Phe Lys Gln Leu Leu Ser Ala Met Asn Tyr Cys His Asn
105                 110                 115                 120 cag ggt ata gtt cac agg gac ctg aca cct gac aat att atg gta gaa         498
Gln Gly Ile Val His Arg Asp Leu Thr Pro Asp Asn Ile Met Val Glu
                125                 130                 135 aaa gat ggg aga gtg aag aac att gat ttt gga ctc agc acc cac gtg         546
Lys Asp Gly Arg Val Lys Asn Ile Asp Phe Gly Leu Ser Thr His Val
            140                 145                 150 aaa cca ggg caa aaa ctc aac tta ttc tgt ggg act tac cca ttt agt         594
Lys Pro Gly Gln Lys Leu Asn Leu Phe Cys Gly Thr Tyr Pro Phe Ser
        155                 160                 165 gct cct gag gtg ctc ctt agc aga ccc tat ggt ggg ccc aag atc gat         642
Ala Pro Glu Val Leu Leu Ser Arg Pro Tyr Gly Gly Pro Lys Ile Asp
170                 175                 180 gta tgg act ctt gga gtt gtg ttg tat ttt atg gta att gga aag atc         690
Val Trp Thr Leu Gly Val Val Leu Tyr Phe Met Val Ile Gly Lys Ile
185                 190                 195                 200 cca ttt gat gct gcc agc ata gaa aag ctg cgg aag caa att gtt gca         738
Pro Phe Asp Ala Ala Ser Ile Glu Lys Leu Arg Lys Gln Ile Val Ala
                205                 210                 215 gga aag tat tct gct ccc tgt aga ctg tca gta aag ctt caa cac ctg         786
Gly Lys Tyr Ser Ala Pro Cys Arg Leu Ser Val Lys Leu Gln His Leu
            220                 225                 230 att aat ctt tta atg acg gac aac ccc gaa ctt agg ccc act gtt gct         834
Ile Asn Leu Leu Met Thr Asp Asn Pro Glu Leu Arg Pro Thr Val Ala
        235                 240                 245 gaa gtt atg gtg cat ccc tgg atc aca aaa ggc tca ggg gtg ttc cca         882
Glu Val Met Val His Pro Trp Ile Thr Lys Gly Ser Gly Val Phe Pro
250                 255                 260 gat cct tgt gaa gaa cag ata ccc ctc aag cca gac cct gcg att gta         930
Asp Pro Cys Glu Glu Gln Ile Pro Leu Lys Pro Asp Pro Ala Ile Val
265                 270                 275                 280 aaa cca atg gga cat att ggg ttc caa gct caa gac att gaa gat tcg         978
Lys Pro Met Gly His Ile Gly Phe Gln Ala Gln Asp Ile Glu Asp Ser
                285                 290                 295
```

```
tta cgt cag aga aaa ttc aat gaa acc atg gca tct tat tgt cta ctg      1026
Leu Arg Gln Arg Lys Phe Asn Glu Thr Met Ala Ser Tyr Cys Leu Leu
            300                 305                 310 aaa aaa cag att ctt aag gaa tgt gac agg cca atc cgg gat cag ccc      1074
Lys Lys Gln Ile Leu Lys Glu Cys Asp Arg Pro Ile Arg Asp Gln Pro
        315                 320                 325 atg aat cca tca gtg acc cca ttc cct tcc ctt gtt gat act cct act      1122
Met Asn Pro Ser Val Thr Pro Phe Pro Ser Leu Val Asp Thr Pro Thr
    330                 335                 340 ttc cat ctc gga ctt cgg agg aga gag act gaa ccc aca ggt ctc aga      1170
Phe His Leu Gly Leu Arg Arg Arg Glu Thr Glu Pro Thr Gly Leu Arg
345                 350                 355                 360 tta tct gcc aat agg caa gtg tct gtc tgt gga aaa agt aca agt aag      1218
Leu Ser Ala Asn Arg Gln Val Ser Val Cys Gly Lys Ser Thr Ser Lys
                365                 370                 375 aaa aga gac aga agt ttc att tgg ccc ggt gtt ctc agc agg ccg att      1266
Lys Arg Asp Arg Ser Phe Ile Trp Pro Gly Val Leu Ser Arg Pro Ile
            380                 385                 390 aac aca aca ccc aca atg gac caa aca cac acc cgt act agg agt gtt      1314
Asn Thr Thr Pro Thr Met Asp Gln Thr His Thr Arg Thr Arg Ser Val
        395                 400                 405 ccc tgc att tac tca aat gtt tgc aca atc cat cca aac agc atc gat      1362
Pro Cys Ile Tyr Ser Asn Val Cys Thr Ile His Pro Asn Ser Ile Asp
    410                 415                 420 gag agt aca gaa ggc cac acc agt gcc tca gca gag gat aag cct gtc      1410
Glu Ser Thr Glu Gly His Thr Ser Ala Ser Ala Glu Asp Lys Pro Val
425                 430                 435                 440 cac agc aga ggc tgg ccc aga ggc atc aag ggc tgg act agg aag ata      1458
His Ser Arg Gly Trp Pro Arg Gly Ile Lys Gly Trp Thr Arg Lys Ile
                445                 450                 455 gga aat gca atg agg aag ctc tgt tgc tgt atc cca tcc aaa gag aca      1506
Gly Asn Ala Met Arg Lys Leu Cys Cys Cys Ile Pro Ser Lys Glu Thr
            460                 465                 470 tct cac ctg ggg cag agc aga gtc tgc cca aaa aaa taagacacag           1552
Ser His Leu Gly Gln Ser Arg Val Cys Pro Lys Lys
        475                 480 gaagggtgtc aggagaacga gcatccggca cggcccag                            1590

<210> SEQ ID NO 5
<211> LENGTH: 484
<212> TYPE: PRT
<213> ORGANISM: Mus musculus

<400> SEQUENCE: 5

Met Glu Lys Phe His Ala Gln Tyr Glu Met Leu Glu Thr Ile Gly Gln
1               5                   10                  15

Gly Gly Cys Ala Lys Val Lys Leu Ala Arg His Arg Leu Thr Gly Thr
            20                  25                  30

His Val Ala Val Lys Met Ile Pro Lys Arg Glu Tyr Trp Cys Lys Leu
        35                  40                  45

Leu Met Phe Glu Ala Glu Leu Met Met Phe Asn His Pro Asn Ile
    50                  55                  60

Ile Ser Leu Leu Gln Val Ile Glu Thr Lys Lys Val Tyr Leu Ile
65                  70                  75                  80

Met Glu Leu Cys Glu Gly Lys Ser Leu Tyr Gln His Ile Gln Asn Ala
                85                  90                  95

Gly Tyr Leu Gln Glu Asp Glu Ala Arg Pro Leu Phe Lys Gln Leu Leu
            100                 105                 110
```

```
Ser Ala Met Asn Tyr Cys His Asn Gln Gly Ile Val His Arg Asp Leu
        115                 120                 125

Thr Pro Asp Asn Ile Met Val Glu Lys Asp Gly Arg Val Lys Asn Ile
130                 135                 140

Asp Phe Gly Leu Ser Thr His Val Lys Pro Gly Gln Lys Leu Asn Leu
145                 150                 155                 160

Phe Cys Gly Thr Tyr Pro Phe Ser Ala Pro Glu Val Leu Leu Ser Arg
                165                 170                 175

Pro Tyr Gly Gly Pro Lys Ile Asp Val Trp Thr Leu Gly Val Val Leu
            180                 185                 190

Tyr Phe Met Val Ile Gly Lys Ile Pro Phe Asp Ala Ala Ser Ile Glu
        195                 200                 205

Lys Leu Arg Lys Gln Ile Val Ala Gly Lys Tyr Ser Ala Pro Cys Arg
210                 215                 220

Leu Ser Val Lys Leu Gln His Leu Ile Asn Leu Met Thr Asp Asn
225                 230                 235                 240

Pro Glu Leu Arg Pro Thr Val Ala Glu Val Met Val His Pro Trp Ile
                245                 250                 255

Thr Lys Gly Ser Gly Val Phe Pro Asp Pro Cys Glu Glu Gln Ile Pro
            260                 265                 270

Leu Lys Pro Asp Pro Ala Ile Val Lys Pro Met Gly His Ile Gly Phe
        275                 280                 285

Gln Ala Gln Asp Ile Glu Asp Ser Leu Arg Gln Arg Lys Phe Asn Glu
290                 295                 300

Thr Met Ala Ser Tyr Cys Leu Leu Lys Lys Gln Ile Leu Lys Glu Cys
305                 310                 315                 320

Asp Arg Pro Ile Arg Asp Gln Pro Met Asn Pro Ser Val Thr Pro Phe
                325                 330                 335

Pro Ser Leu Val Asp Thr Pro Phe His Leu Gly Leu Arg Arg Arg
            340                 345                 350

Glu Thr Glu Pro Thr Gly Leu Arg Leu Ser Ala Asn Arg Gln Val Ser
        355                 360                 365

Val Cys Gly Lys Ser Thr Ser Lys Lys Arg Asp Arg Ser Phe Ile Trp
370                 375                 380

Pro Gly Val Leu Ser Arg Pro Ile Asn Thr Thr Pro Thr Met Asp Gln
385                 390                 395                 400

Thr His Thr Arg Thr Arg Ser Val Pro Cys Ile Tyr Ser Asn Val Cys
                405                 410                 415

Thr Ile His Pro Asn Ser Ile Asp Glu Ser Thr Glu Gly His Thr Ser
            420                 425                 430

Ala Ser Ala Glu Asp Lys Pro Val His Ser Arg Gly Trp Pro Arg Gly
        435                 440                 445

Ile Lys Gly Trp Thr Arg Lys Ile Gly Asn Ala Met Arg Lys Leu Cys
        450                 455                 460

Cys Cys Ile Pro Ser Lys Glu Thr Ser His Leu Gly Gln Ser Arg Val
465                 470                 475                 480

Cys Pro Lys Lys

<210> SEQ ID NO 6
<211> LENGTH: 2257
<212> TYPE: DNA
<213> ORGANISM: Mus musculus
<220> FEATURE:
<221> NAME/KEY: CDS
```

<222> LOCATION: (434)..(1798)
<223> OTHER INFORMATION:

<400> SEQUENCE: 6

```
ggagtttggt ggagttggtg gagttggtgg tgcccttttgt gatttcgttg tatctagtga        60
gttgtgtgtg tgtgtgtgtg tgtgtgtgtg tagttcagtg tgtgtttggg aggagcttgt       120
gtgtgtgagt tgtgaattaa gtttacttgc gtgtgaatac ctttgtgttt ttgtgtgtgt       180
ctgtgtgtat ccatgtgggt gactgtaagt gcacctgtgt gatagttcga aagtgtatga       240
gagagtgtgt gtgggcacaa gagtgtgtgt aggtgcacgt gtggtaggtg tgagaacacc       300
tcttgtgttg aggccgtcag tcagcttggc cattgtttct aaggtagcat ttatactttg       360
ttacctcaaa tgggctctgg gagtcaacag aagtcagaaa agctcagatc caagcccct         420
```

| | | | | | | | | | | | | |
|---|---|---|---|---|---|---|---|---|---|---|---|---|
| ttatctgact gac | atg | gag | aaa | ttt | cat | gct | caa | tat | gag | atg | cta | gag | 469 |
| | Met | Glu | Lys | Phe | His | Ala | Gln | Tyr | Glu | Met | Leu | Glu | |
| | 1 | | | 5 | | | | | 10 | | | | |

```
act att ggc cag gga ggc tgc gca aag gtg aag ctg gcc cga cac cgc        517
Thr Ile Gly Gln Gly Gly Cys Ala Lys Val Lys Leu Ala Arg His Arg
    15                  20                  25 ctc aca ggc acc cac gtg gct gtc aaa atg att cca aag agg gag tat        565
Leu Thr Gly Thr His Val Ala Val Lys Met Ile Pro Lys Arg Glu Tyr
 30                  35                  40 tgg tgc aaa ctt ctg atg ttt gag gca gag tta ctg atg atg ttc aat        613
Trp Cys Lys Leu Leu Met Phe Glu Ala Glu Leu Leu Met Met Phe Asn
45                  50                  55                  60 cat cct aat atc atc tct ctc ctt caa gtc att gag acc aag aag aaa        661
His Pro Asn Ile Ile Ser Leu Leu Gln Val Ile Glu Thr Lys Lys Lys
             65                  70                  75 gta tat ctc att atg gag ttg tgc gag ggt aaa tca ctt tac caa cac        709
Val Tyr Leu Ile Met Glu Leu Cys Glu Gly Lys Ser Leu Tyr Gln His
         80                  85                  90 atc caa aat gct ggc tac ctg cag gag gat gaa gca cgc cca tta ttc        757
Ile Gln Asn Ala Gly Tyr Leu Gln Glu Asp Glu Ala Arg Pro Leu Phe
     95                  100                 105 aag cag ctc tta agt gct atg aac tac tgc cac aac cag ggt ata gtt        805
Lys Gln Leu Leu Ser Ala Met Asn Tyr Cys His Asn Gln Gly Ile Val
110                 115                 120 cac agg gac ctg aca cct gac aat att atg gta gaa aaa gat ggg aga        853
His Arg Asp Leu Thr Pro Asp Asn Ile Met Val Glu Lys Asp Gly Arg
125                 130                 135                 140 gtg aag aac att gat ttt gga ctc agc acc cac gtg aaa cca ggg caa        901
Val Lys Asn Ile Asp Phe Gly Leu Ser Thr His Val Lys Pro Gly Gln
             145                 150                 155 aaa ctc aac tta ttc tgt ggg act tac cca ttt agt gct cct gag gtg        949
Lys Leu Asn Leu Phe Cys Gly Thr Tyr Pro Phe Ser Ala Pro Glu Val
         160                 165                 170 ctc ctt agc aga ccc tat ggt ggg ccc aag atc gat gta tgg act ctt        997
Leu Leu Ser Arg Pro Tyr Gly Gly Pro Lys Ile Asp Val Trp Thr Leu
     175                 180                 185 gga gtt gtg ttg tat ttt atg gta att gga aag atc cca ttt gat gct       1045
Gly Val Val Leu Tyr Phe Met Val Ile Gly Lys Ile Pro Phe Asp Ala
190                 195                 200 gcc agc ata gaa aag ctg cgg aag caa att gtt gca gga aag tat tct       1093
Ala Ser Ile Glu Lys Leu Arg Lys Gln Ile Val Ala Gly Lys Tyr Ser
205                 210                 215                 220 gct ccc tgt aga ctg tca gta aag ctt caa cac ctg att aat ctt tta       1141
Ala Pro Cys Arg Leu Ser Val Lys Leu Gln His Leu Ile Asn Leu Leu
             225                 230                 235
```

-continued

| | | |
|---|---|---|
| atg acg gac aac ccc gaa ctt agg ccc act gtt gct gaa gtt atg gtg<br>Met Thr Asp Asn Pro Glu Leu Arg Pro Thr Val Ala Glu Val Met Val<br>240 245 250 | 1189 |
| cat ccc tgg atc aca aaa ggc tca ggg gtg ttc cca gat cct tgt gaa<br>His Pro Trp Ile Thr Lys Gly Ser Gly Val Phe Pro Asp Pro Cys Glu<br>255 260 265 | 1237 |
| gaa cag ata ccc ctc aag cca gac cct gcg att gta aaa cca atg gga<br>Glu Gln Ile Pro Leu Lys Pro Asp Pro Ala Ile Val Lys Pro Met Gly<br>270 275 280 | 1285 |
| cat att ggg ttc caa gct caa gac att gaa gat tcg tta cgt cag aga<br>His Ile Gly Phe Gln Ala Gln Asp Ile Glu Asp Ser Leu Arg Gln Arg<br>285 290 295 300 | 1333 |
| aaa ttc aat gaa acc atg gca tct tat tgt cta ctg aaa aaa cag att<br>Lys Phe Asn Glu Thr Met Ala Ser Tyr Cys Leu Leu Lys Lys Gln Ile<br>305 310 315 | 1381 |
| ctt aag gaa tgt gac agg cca atc cgg gat cag ccc atg aat cca tca<br>Leu Lys Glu Cys Asp Arg Pro Ile Arg Asp Gln Pro Met Asn Pro Ser<br>320 325 330 | 1429 |
| gtg acc cca ttc cct tcc ctt gtt gat act cct act ttc cat ctc gga<br>Val Thr Pro Phe Pro Ser Leu Val Asp Thr Pro Thr Phe His Leu Gly<br>335 340 345 | 1477 |
| ctt cgg agg aga gag act gaa ccc aca ggc tca gat tat ctg cca ata<br>Leu Arg Arg Arg Glu Thr Glu Pro Thr Gly Ser Asp Tyr Leu Pro Ile<br>350 355 360 | 1525 |
| ggc aag tgt ctg tct gtg gaa aaa gta caa gta aga aaa gag aca gaa<br>Gly Lys Cys Leu Ser Val Glu Lys Val Gln Val Arg Lys Glu Thr Glu<br>365 370 375 380 | 1573 |
| gtt tca ttt ggc ccg gtg ttc tca gca ggc cga tta aca caa cac cca<br>Val Ser Phe Gly Pro Val Phe Ser Ala Gly Arg Leu Thr Gln His Pro<br>385 390 395 | 1621 |
| caa tgg acc aaa cac aca ccc gta cta gga gtg ttc cct gca ttt act<br>Gln Trp Thr Lys His Thr Pro Val Leu Gly Val Phe Pro Ala Phe Thr<br>400 405 410 | 1669 |
| caa atg ttt gca caa tcc atc caa aca gca tcg atg aga gta cag aag<br>Gln Met Phe Ala Gln Ser Ile Gln Thr Ala Ser Met Arg Val Gln Lys<br>415 420 425 | 1717 |
| gcc aca cca gtg cct cag cag agg ata agc ctg tcc aca gca gag gct<br>Ala Thr Pro Val Pro Gln Gln Arg Ile Ser Leu Ser Thr Ala Glu Ala<br>430 435 440 | 1765 |
| ggc cca gag gca tca agg gct gga cta gga aga taggaaatgc aatgaggaag<br>Gly Pro Glu Ala Ser Arg Ala Gly Leu Gly Arg<br>445 450 455 | 1818 |
| ctctgttgct gtatcccatc caaagagaca tctcacctgg ggcagagcag agtctgccca | 1878 |
| aaaaaataag acacaggaag ggtgtcagga gaacagagcat ccggcacggc ccagaagatc | 1938 |
| accagaggat gccggatgct acgattcaac agttataata ttggaaagga cccatgtata | 1998 |
| gacatggacc tgcaaaaggg aaccttgtgg aaaggcatca tgttctgggt tcagcatgtt | 2058 |
| tcactcagag ccccgggtcc agccaggggg aagaaagcaa atgatgaaat cccagatggt | 2118 |
| gtctgggatc accattcaga gcaggggctg aaagcctgtc caaagctggt agagacagaa | 2178 |
| gcccctctgc ctacccaggg tcataatcag actcctgctc tgagaataaa atagatgttt | 2238 |
| gtgaaagatg aaaaaaaaa | 2257 |

<210> SEQ ID NO 7
<211> LENGTH: 455
<212> TYPE: PRT
<213> ORGANISM: Mus musculus

<400> SEQUENCE: 7

```
Met Glu Lys Phe His Ala Gln Tyr Glu Met Leu Glu Thr Ile Gly Gln
1               5                   10                  15
Gly Gly Cys Ala Lys Val Lys Leu Ala Arg His Arg Leu Thr Gly Thr
            20                  25                  30
His Val Ala Val Lys Met Ile Pro Lys Arg Glu Tyr Trp Cys Lys Leu
            35                  40                  45
Leu Met Phe Glu Ala Glu Leu Leu Met Met Phe Asn His Pro Asn Ile
        50                  55                  60
Ile Ser Leu Leu Gln Val Ile Glu Thr Lys Lys Lys Val Tyr Leu Ile
65                  70                  75                  80
Met Glu Leu Cys Glu Gly Lys Ser Leu Tyr Gln His Ile Gln Asn Ala
                85                  90                  95
Gly Tyr Leu Gln Glu Asp Glu Ala Arg Pro Leu Phe Lys Gln Leu Leu
            100                 105                 110
Ser Ala Met Asn Tyr Cys His Asn Gln Gly Ile Val His Arg Asp Leu
            115                 120                 125
Thr Pro Asp Asn Ile Met Val Glu Lys Asp Gly Arg Val Lys Asn Ile
            130                 135                 140
Asp Phe Gly Leu Ser Thr His Val Lys Pro Gly Gln Lys Leu Asn Leu
145                 150                 155                 160
Phe Cys Gly Thr Tyr Pro Phe Ser Ala Pro Glu Val Leu Leu Ser Arg
            165                 170                 175
Pro Tyr Gly Gly Pro Lys Ile Asp Val Trp Thr Leu Gly Val Val Leu
            180                 185                 190
Tyr Phe Met Val Ile Gly Lys Ile Pro Phe Asp Ala Ala Ser Ile Glu
            195                 200                 205
Lys Leu Arg Lys Gln Ile Val Ala Gly Lys Tyr Ser Ala Pro Cys Arg
            210                 215                 220
Leu Ser Val Lys Leu Gln His Leu Ile Asn Leu Leu Met Thr Asp Asn
225                 230                 235                 240
Pro Glu Leu Arg Pro Thr Val Ala Glu Val Met Val His Pro Trp Ile
            245                 250                 255
Thr Lys Gly Ser Gly Val Phe Pro Asp Pro Cys Glu Glu Gln Ile Pro
            260                 265                 270
Leu Lys Pro Asp Pro Ala Ile Val Lys Pro Met Gly His Ile Gly Phe
            275                 280                 285
Gln Ala Gln Asp Ile Glu Asp Ser Leu Arg Gln Arg Lys Phe Asn Glu
            290                 295                 300
Thr Met Ala Ser Tyr Cys Leu Leu Lys Lys Gln Ile Leu Lys Glu Cys
305                 310                 315                 320
Asp Arg Pro Ile Arg Asp Gln Pro Met Asn Pro Ser Val Thr Pro Phe
            325                 330                 335
Pro Ser Leu Val Asp Thr Pro Thr Phe His Leu Gly Leu Arg Arg Arg
            340                 345                 350
Glu Thr Glu Pro Thr Gly Ser Asp Tyr Leu Pro Ile Gly Lys Cys Leu
            355                 360                 365
Ser Val Glu Lys Val Gln Val Arg Lys Glu Thr Glu Val Ser Phe Gly
            370                 375                 380
Pro Val Phe Ser Ala Gly Arg Leu Thr Gln His Pro Gln Trp Thr Lys
385                 390                 395                 400
His Thr Pro Val Leu Gly Val Phe Pro Ala Phe Thr Gln Met Phe Ala
            405                 410                 415
```

Gln Ser Ile Gln Thr Ala Ser Met Arg Val Gln Lys Ala Thr Pro Val
        420                 425                 430

Pro Gln Gln Arg Ile Ser Leu Ser Thr Ala Glu Ala Gly Pro Glu Ala
        435                 440                 445

Ser Arg Ala Gly Leu Gly Arg
        450                 455

<210> SEQ ID NO 8
<211> LENGTH: 2596
<212> TYPE: DNA
<213> ORGANISM: Mus musculus

<400> SEQUENCE: 8

| | | | | | | |
|---|---|---|---|---|---|---|
| gaattcccgg | gtcgacccac | gcgtccggca | ggaattcaca | gagttaccgt | gcttgcctct | 60 |
| gtggaagtgg | gtcaagctga | tggtatctaa | tattctctct | ggtccttctg | atcatgctgc | 120 |
| tgggtccaga | agtacccaga | ttccacaccc | agcttctaca | ctcccccact | tcaggtacct | 180 |
| gaaagcttgg | tcccttcaaa | ggcactttta | atgatctggt | ggtttggggt | gtgaagttat | 240 |
| tctacctggg | gcttttgtac | accacaggaa | caatttttcct | cttacttctc | ccacttcctc | 300 |
| tccctagcat | ggtcagttct | cctccttgtt | caacgtgcat | gatacacaca | ggagatactt | 360 |
| tctgggatgt | tagatctgtt | ggcaggttcg | atttaaccac | catcccatgg | tgtctagacc | 420 |
| tagcttcccc | atgcatcaca | ccatatacat | atacataagt | ataatctgcc | agtttacaca | 480 |
| gacatgagta | acatagatac | attcaaatac | agaaatgtac | ctgggccgtg | ccagatgctc | 540 |
| attctcctga | caaccttcct | gtgtcttatt | ttttggggag | actctgctgt | gccccacgtg | 600 |
| agctgtctct | tttgatggga | tacagcaaca | gagtttcctc | attgcatttc | ctatcttcct | 660 |
| agtccagccc | ttgatgcctc | tgggccagcc | tctgctgcgg | acaggcttat | cctctgctga | 720 |
| ggcactggtg | tggccttctg | tactctcatc | actgctattt | ggatggattg | tgcaaacatt | 780 |
| tgagtaaatg | cagggaacac | tcctagtatg | ggtgtgtctg | tggtccattg | tggatgttat | 840 |
| gtggagtggc | ctgccggaaa | cactgggcca | actgaatctt | ctgtctcttt | ttttactagt | 900 |
| acacttgcca | cagacagaca | cttgcctatt | gccagatgac | cagagacctg | tgggttcagt | 960 |
| ctctcccctc | caaagtctga | gatggaaagt | aggagtatca | acaagggaag | ggaatggggt | 1020 |
| cagcgacaga | ttcatgggct | gagcccggat | tggcctgtca | cattccttaa | gaatctgttt | 1080 |
| tttcagtaga | caataagatg | ccatggtttc | attgaatttt | ctctgacata | acgaatcttc | 1140 |
| aatgtcttga | gcttggaacc | cgatatatcc | cattgctttt | acaatcgcag | ggtctggctt | 1200 |
| gaggggtatc | tgttcttcac | aaggatctgg | gaacacgcct | gagccttctg | tgacccaggg | 1260 |
| atgcaccata | acttcagcaa | cagtgggcct | aagttcgggg | ttgtccgtca | ttaaaagtct | 1320 |
| aatcaggtct | tggagctcta | ctgacagtct | acagggaaca | gaacactttc | ctgcaacaat | 1380 |
| ttgctttcgc | agcttttcta | tgctggcagc | atcaaacaga | atctttccag | ttaccataaa | 1440 |
| atacagcaca | actctaagac | cccacacatc | gatcttgcgc | atatcatagg | gtctgctaag | 1500 |
| gagcacctca | ggagtactaa | atgggtaagt | ctcacagaat | aagttgagtt | tttgccctgg | 1560 |
| cttctcttgg | gtgccgagtc | caaaatcaat | gatcttcact | ttcccatctt | tttctaccat | 1620 |
| aatattgtca | ggtgtcaggt | ccctggttgt | ggcagtagtt | catagcactt | aagagctgct | 1680 |
| tgaataatgg | gcgtgcttca | tcctcctgca | ggtagccagc | gtttcagatg | tgttggtaaa | 1740 |
| gtgatttacc | ctctcacaac | tccataatga | ggtacttttt | cttcttggtc | tcaatgactt | 1800 |
| gaaggagaga | gatgatattt | ggatgatcgg | ccatcatcag | taactctgcc | tcagacatga | 1860 |

-continued

```
cagggttgca ccaatactcc ctctttcgaa tcactttgac agccacgtgg gtgcctgtga    1920
ggcggtgcct ggccagcttc accttggcac agcctccatc gccgatagtc tctagcatct    1980
catattgagc atgaaatttc gccatgtcag agaaaggggg cttggatctg agcttttctg    2040
atttctgttg actcccagag cccacttgag gtaacaaagt ataaatgcta cctaaggggg    2100
cggggagaaa taagggaag aaagaaaggt aagataaaaa ttaaaatagt gaaaataag     2160 caaaacagaa aattaaaacc caacaaaaaa taataacagc agaaacccag aagagcaaaa    2220
ccacacacaa agccaagaaa atccaaatta aaaaacctag ctgcaagtcc ctaggagaga    2280
ggggcacagc tcagcaacac taagaagaaa tattactaag tgaggagcca agtgtgttgg    2340
cgcacacctt taatcccctg actcgggagg ccgaggcagg tggatttctg agttcggggc    2400
cagcctggtc tacagagtga attccaggac agccagagct atacagagaa atcctatctc    2460
aaaaaacaaa caaacaaaca aacaaaaaac tctactagga aatatataaa tgattagtat    2520
aacaaactca tcaaaacttc tagaatatac aaagaactaa aaaaaaaaaa aaagggcgg    2580 ccgctctaga ggatcc                                                    2596
```

<210> SEQ ID NO 9
<211> LENGTH: 2738
<212> TYPE: DNA
<213> ORGANISM: Mus musculus
<220> FEATURE:
<221> NAME/KEY: CDS
<222> LOCATION: (439)..(1950)
<223> OTHER INFORMATION:

<400> SEQUENCE: 9

```
agttggtgga gttggtggag tttggtggag ttggtggtgc cctttgcgat ttcgttgtat     60
ctagtgagct gtgtgtggat tttgtgtttg attggtttgt gtgtgagctt gtgtgtgtgt    120
gtgtgtgtgt gtgtgtgtgt gtgtctagat cagtgtgtgt ttgggaggag cgttgcttgt    180
gtttgtgagt tgagttttaa gtttacttgc gtgtgagtaa cttttgtgttg tgtgtgggtg    240 tgtgtgtgta ggtatacccg tgggtgactc taagtgcacc tgtgtgtttg tgaccgagtg    300
tgtgagagtg tgtgtgtgtg agcacacaag agtgtgtgta ggtgcacgtg tagcaggtgt    360
gagaacatct gttgtgttga ggccgtcagt cagcttggcc attgtttcta aggtagcatt    420
tatacttggt tacctcaa atg ggc cct ggg agt caa cag aag tca gaa aag       471
                     Met Gly Pro Gly Ser Gln Gln Lys Ser Glu Lys
                      1               5                  10 ctc aga tcc aag tcc cct ttg gct gac atg gat ggt ttg cat gct caa       519
Leu Arg Ser Lys Ser Pro Leu Ala Asp Met Asp Gly Leu His Ala Gln
            15                  20                  25 tat gtg atg cta gag act atc ggc cat gga ggc tgt gcc aca gtg aag       567
Tyr Val Met Leu Glu Thr Ile Gly His Gly Gly Cys Ala Thr Val Lys
        30                  35                  40 ctg gcc cag cac cgc ctc aca ggc act cac gtg gct gtc aaa acg att       615
Leu Ala Gln His Arg Leu Thr Gly Thr His Val Ala Val Lys Thr Ile
    45                  50                  55 cga aag agg gag tat tgg tgc aac cgt gtc att tct gag gta gag tta       663
Arg Lys Arg Glu Tyr Trp Cys Asn Arg Val Ile Ser Glu Val Glu Leu
60                  65                  70                  75 ctg atg atg gcc gat cat ccg aat atc atc tct ctc ctt caa gtc att       711
Leu Met Met Ala Asp His Pro Asn Ile Ile Ser Leu Leu Gln Val Ile
                80                  85                  90 gag acc aag aag aaa gta tac ctc att atg gag ttg tgc aag ggt aaa       759
Glu Thr Lys Lys Lys Val Tyr Leu Ile Met Glu Leu Cys Lys Gly Lys
            95                 100                 105
```

| | | |
|---|---|---|
| tca ctt tac caa cac atc cga aaa gct ggc tac ctg cag gag cat gaa<br>Ser Leu Tyr Gln His Ile Arg Lys Ala Gly Tyr Leu Gln Glu His Glu<br>          110                    115                    120 | 807 |
| gca cgc gca tta ttc aag cag ctc tta agt gct atg aac tac tgc cac<br>Ala Arg Ala Leu Phe Lys Gln Leu Leu Ser Ala Met Asn Tyr Cys His<br>125                    130                    135 | 855 |
| aac cag ggt ata gtt cac agg gac ctg aaa ccg gac aat atc atg gtt<br>Asn Gln Gly Ile Val His Arg Asp Leu Lys Pro Asp Asn Ile Met Val<br>140                    145                    150                    155 | 903 |
| gaa aaa gat ggg aaa gtg aag atc att gat ttt gga ctc ggc acc aaa<br>Glu Lys Asp Gly Lys Val Lys Ile Ile Asp Phe Gly Leu Gly Thr Lys<br>                    160                    165                    170 | 951 |
| gtg aag cca ggg caa aaa ctc aac tta ttc tgt ggg act tac cca ttt<br>Val Lys Pro Gly Gln Lys Leu Asn Leu Phe Cys Gly Thr Tyr Pro Phe<br>          175                    180                    185 | 999 |
| agt gct cct gag gtg ctc ctt agc aca ccc tat gat ggg ccc aag atc<br>Ser Ala Pro Glu Val Leu Leu Ser Thr Pro Tyr Asp Gly Pro Lys Ile<br>          190                    195                    200 | 1047 |
| gat gta tgg act ctt gga gtt gtg ctg tat ttt atg gta act gga aag<br>Asp Val Trp Thr Leu Gly Val Val Leu Tyr Phe Met Val Thr Gly Lys<br>          205                    210                    215 | 1095 |
| atc ccg ttt gat gct tgc agc ata aaa aag ctg gta aag cga att ctt<br>Ile Pro Phe Asp Ala Cys Ser Ile Lys Lys Leu Val Lys Arg Ile Leu<br>220                    225                    230                    235 | 1143 |
| gca gga aag tat tct att ccc tct aga ctg tca gca gag ctc caa gac<br>Ala Gly Lys Tyr Ser Ile Pro Ser Arg Leu Ser Ala Glu Leu Gln Asp<br>                    240                    245                    250 | 1191 |
| ctg ctt agt ctt tta atg acg gcc aac ccc aaa ctc agg ccc act gtt<br>Leu Leu Ser Leu Leu Met Thr Ala Asn Pro Lys Leu Arg Pro Thr Val<br>          255                    260                    265 | 1239 |
| gct gag gtt atg gtg cat ccc tgg gtc aca gaa ggc tca ggg gtg ttc<br>Ala Glu Val Met Val His Pro Trp Val Thr Glu Gly Ser Gly Val Phe<br>          270                    275                    280 | 1287 |
| cca gat cct tgt gaa gaa cag acc ccc ctc aag cca gac cct gca att<br>Pro Asp Pro Cys Glu Glu Gln Thr Pro Leu Lys Pro Asp Pro Ala Ile<br>285                    290                    295 | 1335 |
| gta aaa gca atg gga cat atc ggg ttc caa gct caa gat att gaa gat<br>Val Lys Ala Met Gly His Ile Gly Phe Gln Ala Gln Asp Ile Glu Asp<br>300                    305                    310                    315 | 1383 |
| tcg tta cgt cag aga aaa ttc aac caa acc atg gcg tct tat tgt cta<br>Ser Leu Arg Gln Arg Lys Phe Asn Gln Thr Met Ala Ser Tyr Cys Leu<br>                    320                    325                    330 | 1431 |
| ctg aaa aaa cag att ctt aag gaa tgt gac agg cca acc cgg gct agg<br>Leu Lys Lys Gln Ile Leu Lys Glu Cys Asp Arg Pro Thr Arg Ala Arg<br>          335                    340                    345 | 1479 |
| ccc gtg aac cca tcg gtg acc cca ttc cct tcc ctt gtt gat act gct<br>Pro Val Asn Pro Ser Val Thr Pro Phe Pro Ser Leu Val Asp Thr Ala<br>          350                    355                    360 | 1527 |
| act acc cgt ctc gga ctt cgc agg aga gag aat gaa ccc aca tgt ccc<br>Thr Thr Arg Leu Gly Leu Arg Arg Arg Glu Asn Glu Pro Thr Cys Pro<br>          365                    370                    375 | 1575 |
| tgg tca tcc gcc aat agg caa gtg tct gtc tgt ggc aag agt act agt<br>Trp Ser Ser Ala Asn Arg Gln Val Ser Val Cys Gly Lys Ser Thr Ser<br>380                    385                    390                    395 | 1623 |
| aag aaa aga gac aga aga gtc agt tgg ccc agt gtt ctc ggc agg cca<br>Lys Lys Arg Asp Arg Arg Val Ser Trp Pro Ser Val Leu Gly Arg Pro<br>                    400                    405                    410 | 1671 |
| cgc cac acg gca ccc aca atg gac cac aca cgc acc cgt act agg agt<br>Arg His Thr Ala Pro Thr Met Asp His Thr Arg Thr Arg Thr Arg Ser | 1719 |

-continued

```
            415                 420                 425
gta ccc tgc att tgc tca atg ttt tgc aca gtc cag cca aac agc agc    1767
Val Pro Cys Ile Cys Ser Met Phe Cys Thr Val Gln Pro Asn Ser Ser
        430                 435                 440 gaa gag agc aca caa ggc cac acc aga gcc tca gca gca gat aag cct    1815
Glu Glu Ser Thr Gln Gly His Thr Arg Ala Ser Ala Ala Asp Lys Pro
        445                 450                 455 gtc cac agc agg ggc tgg ccc aga ggc atc aag ggc tgg acg agg atg    1863
Val His Ser Arg Gly Trp Pro Arg Gly Ile Lys Gly Trp Thr Arg Met
460                 465                 470                 475 ata gga aat gcg atg agg aag ctc tgt tgc tgt atc cca tcc aaa gag    1911
Ile Gly Asn Ala Met Arg Lys Leu Cys Cys Cys Ile Pro Ser Lys Glu
                480                 485                 490 aca tct cac ctg ggg cag aac aga gtc tcc ccc aaa aaa taagacacag    1960
Thr Ser His Leu Gly Gln Asn Arg Val Ser Pro Lys Lys
            495                 500 gaagggtgtc aggagaacaa gcatccggca cggcccaggt acatttctgc atttgaatgt    2020
atctatgtta ctcatgtctg tgtcaactgg cagatgatac ttatgtatat ggtgcaaagc    2080
atggggaagc taggtgtaga caccgtggga tgatgggtaa atcgaacctg ccaacagacc    2140
tagcatccca gaaggtatct cctgcgtgta tcctgcatgt tgaacaagga ggggaactga    2200
ccatgctagg gggaggaagt gggagaagga agaggaggag atgctgaggg aggagaggat    2260
ggtatgtgat gggagctagg agatgggggg aagaggttga dacaggagga ggcaacttgg    2320
```

```
ggtatgtgat gggagctagg agatgggggg aagaggttga acaggagga ggcaacttgg    2320 gggagcagtg tgaaacaggg taaccacagc tggagagatg ccctgtgcag ctgaggttct    2380
cagagtccct ctcacgtgtg ctttgcattt tagaagatca ccagaggatg ccggatgcta    2440
cgattctaca gttatagtat tggaaaggac ccgtgtatag acacggacct gaaaaaggga    2500
accttgtgga aaggcatcat gttctgggtt cagcgtgctt cactcagagc ccccagtcca    2560 gccaggggc aagaaagcaa atgatgaaat cccagatggg ctctgggatc accattcaga    2620
gaagtggctt aaagcatgtc caaagctgat agagacagcc cctctgcctg cccaagctca    2680
taatcagact cctcctctga gaataaaata gatgtttgtg aaaaaaaaaa aaaaaaa    2738
```

<210> SEQ ID NO 10
<211> LENGTH: 504
<212> TYPE: PRT
<213> ORGANISM: Mus musculus

<400> SEQUENCE: 10

```
Met Gly Pro Gly Ser Gln Gln Lys Ser Glu Lys Leu Arg Ser Lys Ser
1               5                   10                  15

Pro Leu Ala Asp Met Asp Gly Leu His Ala Gln Tyr Val Met Leu Glu
            20                  25                  30

Thr Ile Gly His Gly Gly Cys Ala Thr Val Lys Leu Ala Gln His Arg
        35                  40                  45

Leu Thr Gly Thr His Val Ala Val Lys Thr Ile Arg Lys Arg Glu Tyr
    50                  55                  60

Trp Cys Asn Arg Val Ile Ser Glu Val Glu Leu Met Met Ala Asp
65                  70                  75                  80

His Pro Asn Ile Ile Ser Leu Leu Gln Val Ile Glu Thr Lys Lys Lys
                85                  90                  95

Val Tyr Leu Ile Met Glu Leu Cys Lys Gly Lys Ser Leu Tyr Gln His
            100                 105                 110

Ile Arg Lys Ala Gly Tyr Leu Gln Glu His Glu Ala Arg Ala Leu Phe
        115                 120                 125
```

-continued

```
Lys Gln Leu Leu Ser Ala Met Asn Tyr Cys His Asn Gln Gly Ile Val
    130                 135                 140
His Arg Asp Leu Lys Pro Asp Asn Ile Met Val Glu Lys Asp Gly Lys
145                 150                 155                 160
Val Lys Ile Ile Asp Phe Gly Leu Gly Thr Lys Val Lys Pro Gly Gln
                165                 170                 175
Lys Leu Asn Leu Phe Cys Gly Thr Tyr Pro Phe Ser Ala Pro Glu Val
            180                 185                 190
Leu Leu Ser Thr Pro Tyr Asp Gly Pro Lys Ile Asp Val Trp Thr Leu
        195                 200                 205
Gly Val Val Leu Tyr Phe Met Val Thr Gly Lys Ile Pro Phe Asp Ala
    210                 215                 220
Cys Ser Ile Lys Lys Leu Val Lys Arg Ile Leu Ala Gly Lys Tyr Ser
225                 230                 235                 240
Ile Pro Ser Arg Leu Ser Ala Glu Leu Gln Asp Leu Leu Ser Leu Leu
                245                 250                 255
Met Thr Ala Asn Pro Lys Leu Arg Pro Thr Val Ala Glu Val Met Val
            260                 265                 270
His Pro Trp Val Thr Glu Gly Ser Gly Val Phe Pro Asp Pro Cys Glu
        275                 280                 285
Glu Gln Thr Pro Leu Lys Pro Asp Pro Ala Ile Val Lys Ala Met Gly
    290                 295                 300
His Ile Gly Phe Gln Ala Gln Asp Ile Glu Asp Ser Leu Arg Gln Arg
305                 310                 315                 320
Lys Phe Asn Gln Thr Met Ala Ser Tyr Cys Leu Leu Lys Lys Gln Ile
                325                 330                 335
Leu Lys Glu Cys Asp Arg Pro Thr Arg Ala Arg Pro Val Asn Pro Ser
            340                 345                 350
Val Thr Pro Phe Pro Ser Leu Val Asp Thr Ala Thr Arg Leu Gly
        355                 360                 365
Leu Arg Arg Arg Glu Asn Glu Pro Thr Cys Pro Trp Ser Ser Ala Asn
    370                 375                 380
Arg Gln Val Ser Val Cys Gly Lys Ser Thr Ser Lys Lys Arg Asp Arg
385                 390                 395                 400
Arg Val Ser Trp Pro Ser Val Leu Gly Arg Pro Arg His Thr Ala Pro
                405                 410                 415
Thr Met Asp His Thr Arg Thr Arg Thr Arg Ser Val Pro Cys Ile Cys
            420                 425                 430
Ser Met Phe Cys Thr Val Gln Pro Asn Ser Ser Glu Glu Ser Thr Gln
        435                 440                 445
Gly His Thr Arg Ala Ser Ala Ala Asp Lys Pro Val His Ser Arg Gly
    450                 455                 460
Trp Pro Arg Gly Ile Lys Gly Trp Thr Arg Met Ile Gly Asn Ala Met
465                 470                 475                 480
Arg Lys Leu Cys Cys Cys Ile Pro Ser Lys Glu Thr Ser His Leu Gly
                485                 490                 495
Gln Asn Arg Val Ser Pro Lys Lys
            500

<210> SEQ ID NO 11
<211> LENGTH: 2827
<212> TYPE: DNA
<213> ORGANISM: Mus musculus
<220> FEATURE:
```

-continued

```
<221> NAME/KEY: CDS
<222> LOCATION: (524)..(1975)
<223> OTHER INFORMATION:

<400> SEQUENCE: 11
```

| | |
|---|---|
| gagaggagtt ggtggagttg gtggagtttg gtggatttgg tggagttggt ggtgcccttt | 60 |
| gcgatttcgt tgtatctagt gagccgtgtg tggattttgt gtttgattgg ttcgtgtgtg | 120 |
| agcttttgtg tgtgtgtgtg tgtgtgtgtg tgtgtgtgtg tgtgtgtgtg tgtgtagatc | 180 |
| agtgtgtgtt tgggaggagc ttgtgtgtgt gagttgtgtt ttaagtttat ttgcgtgtga | 240 |
| gtacctttgg gttttttgtgt gtgtctgtgt gtgtttgtgt gtgtataact gtgggtgact | 300 |
| gtaagtgcac ctgtgtgttt gtacgtgagt gtgtaagact gtgtgtgtgc acaagagcgt | 360 |
| gtgtaggtgc acgtgttgta ggtgtgagaa cacctgttgt gtttaggcca tcagtcagct | 420 |
| tggtcattgt ttctaaggta gcatttatac tttgttacct caagtgggct ctgggagtca | 480 |
| acagaagtca gaaaagctca gatccaagcc cccttttcct gac atg gag aaa ttt                                                                                                  Met Glu Lys Phe<br>                                                                                                                1 | 535 |
| cat gct caa tat gag atg cta gag act att ggc cag gga ggc tgc gcc<br>His Ala Gln Tyr Glu Met Leu Glu Thr Ile Gly Gln Gly Gly Cys Ala<br>5                    10                   15                 20 | 583 |
| cag gtg aag ctg gcc cga cac cgc ctc aca ggc acc cac gtg gct gtc<br>Gln Val Lys Leu Ala Arg His Arg Leu Thr Gly Thr His Val Ala Val<br>                   25                   30                   35 | 631 |
| aaa gtg att gta aag agg gag tgt tgg ttc aac cct gtc atg tct gag<br>Lys Val Ile Val Lys Arg Glu Cys Trp Phe Asn Pro Val Met Ser Glu<br>        40                   45                   50 | 679 |
| gca gag tta ctg atg atg acc gat cat ccg aat atc atc tct ctc ctt<br>Ala Glu Leu Leu Met Met Thr Asp His Pro Asn Ile Ile Ser Leu Leu<br>55                    60                   65 | 727 |
| caa gtc att gag acc aag aag aaa gta tac ctc att atg gag ttg tgc<br>Gln Val Ile Glu Thr Lys Lys Lys Val Tyr Leu Ile Met Glu Leu Cys<br>        70                   75                   80 | 775 |
| gag ggt aaa tca ctt tac caa cac atc caa aat gct ggc tac ctg cag<br>Glu Gly Lys Ser Leu Tyr Gln His Ile Gln Asn Ala Gly Tyr Leu Gln<br>85                    90                   95                 100 | 823 |
| gag gat gaa gca cgc cca tta ttc aag cag ctc tta agt gct atg aac<br>Glu Asp Glu Ala Arg Pro Leu Phe Lys Gln Leu Leu Ser Ala Met Asn<br>                  105                 110                 115 | 871 |
| tac tgc cac aac cag ggt ata gtt cac agg gac ctg aca cct gac aat<br>Tyr Cys His Asn Gln Gly Ile Val His Arg Asp Leu Thr Pro Asp Asn<br>            120                   125                 130 | 919 |
| att atg gta gaa aaa gat ggg aaa gtg aag atc att gat ttt gga ctc<br>Ile Met Val Glu Lys Asp Gly Lys Val Lys Ile Ile Asp Phe Gly Leu<br>135                  140                   145 | 967 |
| ggc acc caa gag aag cca ggg caa aac cac aac tta ttc tgt gag att<br>Gly Thr Gln Glu Lys Pro Gly Gln Asn His Asn Leu Phe Cys Glu Ile<br>          150                   155                 160 | 1015 |
| tac cca ttt agt act cct gag gtg ctc ttt aac aga ccc tat gat atg<br>Tyr Pro Phe Ser Thr Pro Glu Val Leu Phe Asn Arg Pro Tyr Asp Met<br>165                  170                   175                 180 | 1063 |
| cgc aag atc gat gtg tgg ggt ctt gga gtt gtg ctg tat ttt atg gta<br>Arg Lys Ile Asp Val Trp Gly Leu Gly Val Val Leu Tyr Phe Met Val<br>                  185                 190                 195 | 1111 |
| act gga aag att ctg ttt gat act gcc agc gta gaa aag ctg cga aag<br>Thr Gly Lys Ile Leu Phe Asp Thr Ala Ser Val Glu Lys Leu Arg Lys<br>          200                   205                 210 | 1159 |
| caa att gtt gca gaa aag tgt tct gtt ccc tgt aga ctg tca gta gag | 1207 |

```
                                                                -continued

Gln Ile Val Ala Glu Lys Cys Ser Val Pro Cys Arg Leu Ser Val Glu
            215                 220                 225 ctc caa gac ctg att aga ctt tta atg acg gac atc ccc gaa ctt agg      1255
Leu Gln Asp Leu Ile Arg Leu Leu Met Thr Asp Ile Pro Glu Leu Arg
        230                 235                 240 ccc act gtt gct gaa gtt atg gtg cat ccc tgg gtc aca gaa ggc tca      1303
Pro Thr Val Ala Glu Val Met Val His Pro Trp Val Thr Glu Gly Ser
245                 250                 255                 260 ggg gtg tta cca gat cct tgt gaa gaa cat ata ccc ctc aag cca gac      1351
Gly Val Leu Pro Asp Pro Cys Glu Glu His Ile Pro Leu Lys Pro Asp
                265                 270                 275 cct gcg att gca aaa gca atg gga ttt atc ggg ttc caa gct caa gac      1399
Pro Ala Ile Ala Lys Ala Met Gly Phe Ile Gly Phe Gln Ala Gln Asp
            280                 285                 290 att gaa gat tcg tta tgt cag aga aaa ttc aac gaa acc atg gca tct      1447
Ile Glu Asp Ser Leu Cys Gln Arg Lys Phe Asn Glu Thr Met Ala Ser
        295                 300                 305 tat tgt cta ctg aaa aaa cag att ctt aag gaa tgt gac agg cca atc      1495
Tyr Cys Leu Leu Lys Lys Gln Ile Leu Lys Glu Cys Asp Arg Pro Ile
310                 315                 320 cgg gct cag ccc atg aat cca tct gtg acc cca ctc tct tcc ctt gtt      1543
Arg Ala Gln Pro Met Asn Pro Ser Val Thr Pro Leu Ser Ser Leu Val
325                 330                 335                 340 gat gct cct act ttc cat ctc gga ctt cgg agg aca gag act gaa ccc      1591
Asp Ala Pro Thr Phe His Leu Gly Leu Arg Arg Thr Glu Thr Glu Pro
                345                 350                 355 aca ggt ctc aga tta tct gac aat aag gaa gtg cct gtc tgt ggc aat      1639
Thr Gly Leu Arg Leu Ser Asp Asn Lys Glu Val Pro Val Cys Gly Asn
            360                 365                 370 agt act agt aag aaa aga gag aga agt ttc agt ggg ccg ggt gtt ctc      1687
Ser Thr Ser Lys Lys Arg Glu Arg Ser Phe Ser Gly Pro Gly Val Leu
        375                 380                 385 agc agg ccg att aac aca aca ccc aca atg gac caa aca cac acc cgt      1735
Ser Arg Pro Ile Asn Thr Thr Pro Thr Met Asp Gln Thr His Thr Arg
390                 395                 400 act tgg agt ggt ccc tgc att tac tca aat gtt tgc aca atc cat cca      1783
Thr Trp Ser Gly Pro Cys Ile Tyr Ser Asn Val Cys Thr Ile His Pro
405                 410                 415                 420 aac agc atc aat gag agt aca gaa ggc cac atc agt acc tca gca gag      1831
Asn Ser Ile Asn Glu Ser Thr Glu Gly His Ile Ser Thr Ser Ala Glu
                425                 430                 435 gat aag cct gtc cac agc aga ggc tgg ccc aga ggc atc aag ggc tgg      1879
Asp Lys Pro Val His Ser Arg Gly Trp Pro Arg Gly Ile Lys Gly Trp
            440                 445                 450 act agg aag ata gga aat gca atg agg aag ctc tgt tgc tgt atc cca      1927
Thr Arg Lys Ile Gly Asn Ala Met Arg Lys Leu Cys Cys Cys Ile Pro
        455                 460                 465 tcc aaa gag aca tct cac ctg ggg cag aga aga gtc tgc cca aaa att      1975
Ser Lys Glu Thr Ser His Leu Gly Gln Arg Arg Val Cys Pro Lys Ile
470                 475                 480 taagacacag gaaggatgtc aggagaatga gcatccagca tggcccagcc tttcagaccg    2035
aaggcaagct ctacctgatc ctggacttcc tgcggggagg tgacctcttc accaggcttt    2095
ccaaagaggt gatgttcacg gaggaggatg tcaagttcta cctggctgag ctggccttgg    2155
ctctagacca cctccatggc ctggggatca tctacaggga tctgaagcca gagaatatcc    2215
tcctggatga gagggacat attaagatca cagattttgg cttgagcaag gaggccaccg     2275
accatgacaa gagagcctat tcattttgtg ggactattga atacatggcg cccgaggtgg    2335
```

```
tgaaccggcg tggacacaca cagagtgccg actggtggtc cttcggtgtg ctcatgttcg    2395
agatgctcac aggtccctg ccattccagg ggaaggacag gaaggaaaca atggcccgca    2455
tcctcaaagc aaagctgggt atgccttagt tcctcagtgc ggaggctcag agcctgctca    2515
gggccctttt caagcggaac ccctgcaacc ggctaggtaa gggtccctgt gacaccccca    2575
ccccaggaat gcaatgaggc tgccctctag acccccctta ggaatgtgag aggccaccat    2635
tctgttcccc acgggatgtg gaggacttcc tccttatgcc ccaactctga actgtatgct    2695
tttccttgct aaggttgcag gaagcagagg taccccgacg ctggggaaac actcacatgt    2755
ggcctggcgc ccacaggcac gtggacttat caggattgct gaaaggcatt tgaaaaaaaa    2815 aaaaaaaaa aa                                                         2827

<210> SEQ ID NO 12
<211> LENGTH: 484
<212> TYPE: PRT
<213> ORGANISM: Mus musculus

<400> SEQUENCE: 12

Met Glu Lys Phe His Ala Gln Tyr Glu Met Leu Glu Thr Ile Gly Gln
1               5                   10                  15

Gly Gly Cys Ala Gln Val Lys Leu Ala Arg His Arg Leu Thr Gly Thr
                20                  25                  30

His Val Ala Val Lys Val Ile Val Lys Arg Glu Cys Trp Phe Asn Pro
            35                  40                  45

Val Met Ser Glu Ala Glu Leu Leu Met Met Thr Asp His Pro Asn Ile
        50                  55                  60

Ile Ser Leu Leu Gln Val Ile Glu Thr Lys Lys Lys Val Tyr Leu Ile
65                  70                  75                  80

Met Glu Leu Cys Glu Gly Lys Ser Leu Tyr Gln His Ile Gln Asn Ala
                85                  90                  95

Gly Tyr Leu Gln Glu Asp Glu Ala Arg Pro Leu Phe Lys Gln Leu Leu
                100                 105                 110

Ser Ala Met Asn Tyr Cys His Asn Gln Gly Ile Val His Arg Asp Leu
            115                 120                 125

Thr Pro Asp Asn Ile Met Val Glu Lys Asp Gly Lys Val Lys Ile Ile
        130                 135                 140

Asp Phe Gly Leu Gly Thr Gln Glu Lys Pro Gly Gln Asn His Asn Leu
145                 150                 155                 160

Phe Cys Glu Ile Tyr Pro Phe Ser Thr Pro Glu Val Leu Phe Asn Arg
                165                 170                 175

Pro Tyr Asp Met Arg Lys Ile Asp Val Trp Gly Leu Gly Val Val Leu
                180                 185                 190

Tyr Phe Met Val Thr Gly Lys Ile Leu Phe Asp Thr Ala Ser Val Glu
            195                 200                 205

Lys Leu Arg Lys Gln Ile Val Ala Glu Lys Cys Ser Val Pro Cys Arg
        210                 215                 220

Leu Ser Val Glu Leu Gln Asp Leu Ile Arg Leu Leu Met Thr Asp Ile
225                 230                 235                 240

Pro Glu Leu Arg Pro Thr Val Ala Glu Val Met Val His Pro Trp Val
                245                 250                 255

Thr Glu Gly Ser Gly Val Leu Pro Asp Pro Cys Glu Glu His Ile Pro
                260                 265                 270

Leu Lys Pro Asp Pro Ala Ile Ala Lys Ala Met Gly Phe Ile Gly Phe
            275                 280                 285
```

```
Gln Ala Gln Asp Ile Glu Asp Ser Leu Cys Gln Arg Lys Phe Asn Glu
    290                 295                 300

Thr Met Ala Ser Tyr Cys Leu Leu Lys Lys Gln Ile Leu Lys Glu Cys
305                 310                 315                 320

Asp Arg Pro Ile Arg Ala Gln Pro Met Asn Pro Ser Val Thr Pro Leu
                325                 330                 335

Ser Ser Leu Val Asp Ala Pro Thr Phe His Leu Gly Leu Arg Arg Thr
            340                 345                 350

Glu Thr Glu Pro Thr Gly Leu Arg Leu Ser Asp Asn Lys Glu Val Pro
        355                 360                 365

Val Cys Gly Asn Ser Thr Ser Lys Lys Arg Glu Arg Ser Phe Ser Gly
    370                 375                 380

Pro Gly Val Leu Ser Arg Pro Ile Asn Thr Thr Pro Thr Met Asp Gln
385                 390                 395                 400

Thr His Thr Arg Thr Trp Ser Gly Pro Cys Ile Tyr Ser Asn Val Cys
                405                 410                 415

Thr Ile His Pro Asn Ser Ile Asn Glu Ser Thr Glu Gly His Ile Ser
            420                 425                 430

Thr Ser Ala Glu Asp Lys Pro Val His Ser Arg Gly Trp Pro Arg Gly
        435                 440                 445

Ile Lys Gly Trp Thr Arg Lys Ile Gly Asn Ala Met Arg Lys Leu Cys
    450                 455                 460

Cys Cys Ile Pro Ser Lys Glu Thr Ser His Leu Gly Gln Arg Arg Val
465                 470                 475                 480

Cys Pro Lys Ile

<210> SEQ ID NO 13
<211> LENGTH: 1787
<212> TYPE: DNA
<213> ORGANISM: Mus musculus
<220> FEATURE:
<221> NAME/KEY: CDS
<222> LOCATION: (95)..(1606)
<223> OTHER INFORMATION:

<400> SEQUENCE: 13
cacgtgtggt aggtgtgaga acacctcttg tgttgaggcc gtcagtcagc ttggccattg      60
tttctaaggt agcatttata ctttgttacc tcaa atg ggg tct ggg agt caa cag     115
                                     Met Gly Ser Gly Ser Gln Gln
                                      1               5 aag tca gaa aag ctc aga tcc aag ccc cct ttc tct gaa atg gag aac     163
Lys Ser Glu Lys Leu Arg Ser Lys Pro Pro Phe Ser Glu Met Glu Asn
         10                  15                  20 ttt cat gct caa tat gag atg cta ggg act att ggc cat gga ggc agc     211
Phe His Ala Gln Tyr Glu Met Leu Gly Thr Ile Gly His Gly Gly Ser
 25                  30                  35 aca aag gtg aag ctg gcc cga cac cgc ctc aca ggc acc cac gtg gct     259
Thr Lys Val Lys Leu Ala Arg His Arg Leu Thr Gly Thr His Val Ala
 40                  45                  50                  55 gtc aaa atg att cca aag agg gag tat tgg tgc aaa cct ctc atg tct     307
Val Lys Met Ile Pro Lys Arg Glu Tyr Trp Cys Lys Pro Leu Met Ser
                 60                  65                  70 gag gca gag tta ctg atg atg gcc gat cat ccg aat atc atc tct ctc     355
Glu Ala Glu Leu Leu Met Met Ala Asp His Pro Asn Ile Ile Ser Leu
             75                  80                  85 ctt caa gtc att gag acc aag aag aaa gta tac ctc att atg gag ttg     403
Leu Gln Val Ile Glu Thr Lys Lys Lys Val Tyr Leu Ile Met Glu Leu
```

-continued

```
                        90                        95                            100
tgt gag ggt aaa tca ctt tac caa cac atc aga aac gct ggc tac ctg        451
Cys Glu Gly Lys Ser Leu Tyr Gln His Ile Arg Asn Ala Gly Tyr Leu
            105                 110                 115 cag gag gat gaa gca cga gca tta ttc aag cag ctc tta agt gct ata        499
Gln Glu Asp Glu Ala Arg Ala Leu Phe Lys Gln Leu Leu Ser Ala Ile
120                 125                 130                 135 aac tac tgc cgc aac cag ggt ata gtt cac agg gac ctg aaa ccc gac        547
Asn Tyr Cys Arg Asn Gln Gly Ile Val His Arg Asp Leu Lys Pro Asp
                140                 145                 150 aat att atg gta gaa aaa gat ggg aga gta aag atc att gat ttt ggg        595
Asn Ile Met Val Glu Lys Asp Gly Arg Val Lys Ile Ile Asp Phe Gly
            155                 160                 165 ctt ggc atc caa gtg aag cca ggc caa aaa cta aac tta ttc tgt ggg        643
Leu Gly Ile Gln Val Lys Pro Gly Gln Lys Leu Asn Leu Phe Cys Gly
            170                 175                 180 act tac cca ttt agt gct cct gag gtg ctc ctt agc aga ccc tat gat        691
Thr Tyr Pro Phe Ser Ala Pro Glu Val Leu Leu Ser Arg Pro Tyr Asp
            185                 190                 195 ggg ccc aag atc gat gta tgg act ctt gga gtt gtg cta tac ttt atg        739
Gly Pro Lys Ile Asp Val Trp Thr Leu Gly Val Val Leu Tyr Phe Met
200                 205                 210                 215 gta act gga aag atc cca ttt gat gct gcc agc ata gaa aag ctg cgg        787
Val Thr Gly Lys Ile Pro Phe Asp Ala Ala Ser Ile Glu Lys Leu Arg
            220                 225                 230 aag caa att gtt gca gga aag tat tct gtt ccc tgt aga ctg tca gta        835
Lys Gln Ile Val Ala Gly Lys Tyr Ser Val Pro Cys Arg Leu Ser Val
            235                 240                 245 aag ctt cat cac ctg att act ctt tta atg aca gac aac cct gaa ctt        883
Lys Leu His His Leu Ile Thr Leu Leu Met Thr Asp Asn Pro Glu Leu
            250                 255                 260 agg ccc act gtt gct gaa gtt atg atg cat ccc tgg gtc aca aaa ggc        931
Arg Pro Thr Val Ala Glu Val Met Met His Pro Trp Val Thr Lys Gly
            265                 270                 275 tca ggg gtg ttc cca gat cct tgt gaa gaa cag ata ccc ctc aag cca        979
Ser Gly Val Phe Pro Asp Pro Cys Glu Glu Gln Ile Pro Leu Lys Pro
280                 285                 290                 295 gac cct gcg att gta aaa gca atg gga cat att ggg ttc caa gct caa       1027
Asp Pro Ala Ile Val Lys Ala Met Gly His Ile Gly Phe Gln Ala Gln
            300                 305                 310 gac att gaa gat tct tta cgt cag aga aaa ttc aac gaa acc atg gca       1075
Asp Ile Glu Asp Ser Leu Arg Gln Arg Lys Phe Asn Glu Thr Met Ala
            315                 320                 325 tct tat tgt cta ctg aaa aaa cag ctt ctt aag gaa tgt gac agg cca       1123
Ser Tyr Cys Leu Leu Lys Lys Gln Leu Leu Lys Glu Cys Asp Arg Pro
            330                 335                 340 atc cgg gct cag ccc atg aat cca tcg gtg acc cca ttc ccc tcc ctt       1171
Ile Arg Ala Gln Pro Met Asn Pro Ser Val Thr Pro Phe Pro Ser Leu
345                 350                 355 gtt gat act cct act ttc cat ctc gga ctt cgg agg aga gag act gaa       1219
Val Asp Thr Pro Thr Phe His Leu Gly Leu Arg Arg Arg Glu Thr Glu
360                 365                 370                 375 ccc acg agt ctc aga tta tct gct aat agg caa atg tct gtc tgt gga       1267
Pro Thr Ser Leu Arg Leu Ser Ala Asn Arg Gln Met Ser Val Cys Gly
            380                 385                 390 agg agt act agt aag aaa aga gac aga agt ttc agt tgg ccc ggt gtt       1315
Arg Ser Thr Ser Lys Lys Arg Asp Arg Ser Phe Ser Trp Pro Gly Val
            395                 400                 405 ctc agc agg ccg att aac ata aca ccc aca atg gac caa aca cac acc       1363
```

```
Leu Ser Arg Pro Ile Asn Ile Thr Pro Thr Met Asp Gln Thr His Thr
        410                 415                 420 tgt act agg agt gtt ccc tgc att aac tca aat ttt tgc ata atc cat      1411
Cys Thr Arg Ser Val Pro Cys Ile Asn Ser Asn Phe Cys Ile Ile His
        425                 430                 435 cca aac agc agc gac gag agt aca gaa ggc cac acc agt gcc tca gca      1459
Pro Asn Ser Ser Asp Glu Ser Thr Glu Gly His Thr Ser Ala Ser Ala
440                 445                 450                 455 gag gat aag cct gtc cgc agc aga ggc tgg ccc aga ggc atc aag ggc      1507
Glu Asp Lys Pro Val Arg Ser Arg Gly Trp Pro Arg Gly Ile Lys Gly
                460                 465                 470 tgg act agc aag ata gga aat gcg atg agg aag ctc tgt tgc tgt atc      1555
Trp Thr Ser Lys Ile Gly Asn Ala Met Arg Lys Leu Cys Cys Cys Ile
            475                 480                 485 cca tca aat gag aca tct cac ctg ggg cag agg aga gtc tcc ccc aaa      1603
Pro Ser Asn Glu Thr Ser His Leu Gly Gln Arg Arg Val Ser Pro Lys
        490                 495                 500 aaa taagacacag gaagggtgtc aggagaacga gcattcggct cggcacagaa           1656
Lys gatcactaga ggatgccgga tgctatgatt caacagttat agtattggaa aggacccatg    1716
tatagacatg gacctgcaaa agggaacctt gtggaaaggc atcatgttct gggtccagcc    1776 aggggggaaga a                                                        1787

<210> SEQ ID NO 14
<211> LENGTH: 504
<212> TYPE: PRT
<213> ORGANISM: Mus musculus

<400> SEQUENCE: 14

Met Gly Ser Gly Ser Gln Gln Lys Ser Glu Lys Leu Arg Ser Lys Pro
1               5                   10                  15

Pro Phe Ser Glu Met Glu Asn Phe His Ala Gln Tyr Glu Met Leu Gly
            20                  25                  30

Thr Ile Gly His Gly Gly Ser Thr Lys Val Lys Leu Ala Arg His Arg
        35                  40                  45

Leu Thr Gly Thr His Val Ala Val Lys Met Ile Pro Lys Arg Glu Tyr
    50                  55                  60

Trp Cys Lys Pro Leu Met Ser Glu Ala Glu Leu Leu Met Met Ala Asp
65                  70                  75                  80

His Pro Asn Ile Ile Ser Leu Leu Gln Val Ile Glu Thr Lys Lys Lys
                85                  90                  95

Val Tyr Leu Ile Met Glu Leu Cys Glu Gly Lys Ser Leu Tyr Gln His
            100                 105                 110

Ile Arg Asn Ala Gly Tyr Leu Gln Glu Asp Glu Ala Arg Ala Leu Phe
        115                 120                 125

Lys Gln Leu Leu Ser Ala Ile Asn Tyr Cys Arg Asn Gln Gly Ile Val
    130                 135                 140

His Arg Asp Leu Lys Pro Asp Asn Ile Met Val Glu Lys Asp Gly Arg
145                 150                 155                 160

Val Lys Ile Ile Asp Phe Gly Leu Gly Ile Gln Val Lys Pro Gly Gln
                165                 170                 175

Lys Leu Asn Leu Phe Cys Gly Thr Tyr Pro Phe Ser Ala Pro Glu Val
            180                 185                 190

Leu Leu Ser Arg Pro Tyr Asp Gly Pro Lys Ile Asp Val Trp Thr Leu
        195                 200                 205
```

| | | | | | | | | | | | |
|---|---|---|---|---|---|---|---|---|---|---|---|
|Gly|Val|Val|Leu|Tyr|Phe|Met|Val|Thr|Gly|Lys|Ile|Pro|Phe|Asp|Ala|
| |210| | | |215| | | |220| | | | | | |

Gly Val Val Leu Tyr Phe Met Val Thr Gly Lys Ile Pro Phe Asp Ala
          210                 215                 220

Ala Ser Ile Glu Lys Leu Arg Lys Gln Ile Val Ala Gly Lys Tyr Ser
225                 230                 235                 240

Val Pro Cys Arg Leu Ser Val Lys Leu His His Leu Ile Thr Leu Leu
                245                 250                 255

Met Thr Asp Asn Pro Glu Leu Arg Pro Thr Val Ala Glu Val Met Met
            260                 265                 270

His Pro Trp Val Thr Lys Gly Ser Gly Val Phe Pro Asp Pro Cys Glu
        275                 280                 285

Glu Gln Ile Pro Leu Lys Pro Asp Pro Ala Ile Val Lys Ala Met Gly
    290                 295                 300

His Ile Gly Phe Gln Ala Gln Asp Ile Glu Asp Ser Leu Arg Gln Arg
305                 310                 315                 320

Lys Phe Asn Glu Thr Met Ala Ser Tyr Cys Leu Leu Lys Lys Gln Leu
                325                 330                 335

Leu Lys Glu Cys Asp Arg Pro Ile Arg Ala Gln Pro Met Asn Pro Ser
            340                 345                 350

Val Thr Pro Phe Pro Ser Leu Val Asp Thr Pro Thr Phe His Leu Gly
        355                 360                 365

Leu Arg Arg Arg Glu Thr Glu Pro Thr Ser Leu Arg Leu Ser Ala Asn
    370                 375                 380

Arg Gln Met Ser Val Cys Gly Arg Ser Thr Ser Lys Lys Arg Asp Arg
385                 390                 395                 400

Ser Phe Ser Trp Pro Gly Val Leu Ser Arg Pro Ile Asn Ile Thr Pro
                405                 410                 415

Thr Met Asp Gln Thr His Thr Cys Thr Arg Ser Val Pro Cys Ile Asn
            420                 425                 430

Ser Asn Phe Cys Ile Ile His Pro Asn Ser Ser Asp Glu Ser Thr Glu
        435                 440                 445

Gly His Thr Ser Ala Ser Ala Glu Asp Lys Pro Val Arg Ser Arg Gly
    450                 455                 460

Trp Pro Arg Gly Ile Lys Gly Trp Thr Ser Lys Ile Gly Asn Ala Met
465                 470                 475                 480

Arg Lys Leu Cys Cys Ile Pro Ser Asn Glu Thr Ser His Leu Gly
                485                 490                 495

Gln Arg Arg Val Ser Pro Lys Lys
            500

```
<210> SEQ ID NO 15
<211> LENGTH: 2001
<212> TYPE: DNA
<213> ORGANISM: Mus musculus
<220> FEATURE:
<221> NAME/KEY: CDS
<222> LOCATION: (343)..(1641)
<223> OTHER INFORMATION:

<400> SEQUENCE: 15
gtgtgggagg agcttgtgtg tgtgagttgt gttttaagtt tatttgcgtc tcgtgagtac     60
ctttgggttt gtgtgtgtgt gtctgtgtgt gtttgtgtgt gtataactgt gggtgactgt    120
taagagcacc tgtgtgtttg tacgtgagtg tgtaagactg tgtgtgtgca caagagcgtg    180
tgtaggtgca catgttgtag gtgtgagaac acctgttgtg tttaggccat cagtcagctt    240
ggccattgtt tctaaggtag catttatact ttgttacctc aagtgggctc tgggagtcaa    300
```

-continued

| | |
|---|---|
| gagaaatcag aaaagctcag atccaagccc cctttctctg ac atg gag aaa ttt<br>                                                                                Met Glu Lys Phe<br>                                                                                 1 | 354 |
| cat gct caa tat gaa atg cta gag act atc ggc cag gga ggc tgc gcc<br>His Ala Gln Tyr Glu Met Leu Glu Thr Ile Gly Gln Gly Gly Cys Ala<br>5                        10                       15                      20 | 402 |
| cag gtg aag ctg gcc cag cac cgc ctc aca ggc acc cac gtg gct gtc<br>Gln Val Lys Leu Ala Gln His Arg Leu Thr Gly Thr His Val Ala Val<br>                   25                       30                      35 | 450 |
| aaa gtg att gta aag agg gag tgt tgg ttc aac cct gtc atg tct gag<br>Lys Val Ile Val Lys Arg Glu Cys Trp Phe Asn Pro Val Met Ser Glu<br>                40                       45                      50 | 498 |
| gca gag tta ctg atg atg acc gat cat ccg aat atc atc tct ctc ctt<br>Ala Glu Leu Leu Met Met Thr Asp His Pro Asn Ile Ile Ser Leu Leu<br>      55                       60                       65 | 546 |
| caa gtc atc gag acc aag aag aaa tta tac ctc att atg gag ttg tgc<br>Gln Val Ile Glu Thr Lys Lys Lys Leu Tyr Leu Ile Met Glu Leu Cys<br>70                        75                       80 | 594 |
| gag ggt aaa tca ctt tac caa cac atc caa aat gct ggc tac ctg cag<br>Glu Gly Lys Ser Leu Tyr Gln His Ile Gln Asn Ala Gly Tyr Leu Gln<br>85                       90                      95                 100 | 642 |
| gag gat gaa gca tgc cca tta ttc aag cag ctc tta agt gct gtg aac<br>Glu Asp Glu Ala Cys Pro Leu Phe Lys Gln Leu Leu Ser Ala Val Asn<br>                 105                   110                115 | 690 |
| tac tgc cac aac cag ggt ata gtt cac agg gac ctg aca cct gac aat<br>Tyr Cys His Asn Gln Gly Ile Val His Arg Asp Leu Thr Pro Asp Asn<br>          120                   125                   130 | 738 |
| att atg gta gaa aaa gat ggg aaa gtg aag atc att gat ttt gga ctc<br>Ile Met Val Glu Lys Asp Gly Lys Val Lys Ile Ile Asp Phe Gly Leu<br>               135                   140                   145 | 786 |
| ggc acc caa gag aag cca gcg caa aaa ctc aac tta ttc tgt gag aat<br>Gly Thr Gln Glu Lys Pro Ala Gln Lys Leu Asn Leu Phe Cys Glu Asn<br>150                      155                   160 | 834 |
| tac cca ttt agt acc cct gag gtg ctc ctt agc aga ccc tat gat atg<br>Tyr Pro Phe Ser Thr Pro Glu Val Leu Leu Ser Arg Pro Tyr Asp Met<br>165                      170                   175                180 | 882 |
| cgc aag atc gat gtg tgg ggt ctt gga gtt gtg ctg tat ttt atg gta<br>Arg Lys Ile Asp Val Trp Gly Leu Gly Val Val Leu Tyr Phe Met Val<br>                 185                   190                195 | 930 |
| act gga aag att ctg ttt gat gct gcc agc ata gaa aag ctg cga aag<br>Thr Gly Lys Ile Leu Phe Asp Ala Ala Ser Ile Glu Lys Leu Arg Lys<br>          200                   205                   210 | 978 |
| caa att gtt gca gga aag tgt tct gtt ccc tgt aga ctg tca gta gag<br>Gln Ile Val Ala Gly Lys Cys Ser Val Pro Cys Arg Leu Ser Val Glu<br>               215                   220                   225 | 1026 |
| ctc caa gac ctg att aga ctt tta atg acg gac aac ccc gaa ctt agg<br>Leu Gln Asp Leu Ile Arg Leu Leu Met Thr Asp Asn Pro Glu Leu Arg<br>230                      235                   240 | 1074 |
| ccc act gtt gct gaa gtt atg gtg cat ccc tgg gtc aca gta ggc tca<br>Pro Thr Val Ala Glu Val Met Val His Pro Trp Val Thr Val Gly Ser<br>245                      250                   255                260 | 1122 |
| ggg gtg ttc cca gat cct tgt gaa gaa cag ata tcc ctc aag cca gac<br>Gly Val Phe Pro Asp Pro Cys Glu Glu Gln Ile Ser Leu Lys Pro Asp<br>                 265                   270                275 | 1170 |
| cct gcg att gta aaa gca atg gga tat atc ggg ttc cga gct caa gaa<br>Pro Ala Ile Val Lys Ala Met Gly Tyr Ile Gly Phe Arg Ala Gln Glu<br>          280                   285                   290 | 1218 |
| att gaa gat tcg tta cgt cag aga aaa ttc aac gaa acc atg gca tct<br>Ile Glu Asp Ser Leu Arg Gln Arg Lys Phe Asn Glu Thr Met Ala Ser<br>               295                   300                   305 | 1266 |

-continued

```
tat tgt cta ctg aaa aaa cag att ctt aag gaa tgt gac agg cca atc      1314
Tyr Cys Leu Leu Lys Lys Gln Ile Leu Lys Glu Cys Asp Arg Pro Ile
    310                 315                 320 cgg gct cag ccc atg aat cca tcg ctg acc cca ttc cct tcc ctt gtt      1362
Arg Ala Gln Pro Met Asn Pro Ser Leu Thr Pro Phe Pro Ser Leu Val
325                 330                 335                 340 gat act cct act tcc cat ctc gga ctt cgg agg aga gag act gaa ccc      1410
Asp Thr Pro Thr Ser His Leu Gly Leu Arg Arg Arg Glu Thr Glu Pro
                345                 350                 355 aca ggt ctc agc tta tct gcc aat agg caa gtg tct gtc tgt ggc aag      1458
Thr Gly Leu Ser Leu Ser Ala Asn Arg Gln Val Ser Val Cys Gly Lys
            360                 365                 370 agt act agt aag aaa aga gac aga agt ttc agt tgg ccc ggt gtt cta      1506
Ser Thr Ser Lys Lys Arg Asp Arg Ser Phe Ser Trp Pro Gly Val Leu
        375                 380                 385 ggc agg ccg atc cac aca aca ccc aca atg gac caa aca cac acc cgt      1554
Gly Arg Pro Ile His Thr Thr Pro Thr Met Asp Gln Thr His Thr Arg
    390                 395                 400 act agg agt gtt ccc tgc att tac tca aat ttt tgc aca atc cat cca      1602
Thr Arg Ser Val Pro Cys Ile Tyr Ser Asn Phe Cys Thr Ile His Pro
405                 410                 415                 420 aac agc atc gat gag agt aca gaa ggc cac acc agt gcc taagcagagg       1651
Asn Ser Ile Asp Glu Ser Thr Glu Gly His Thr Ser Ala
                425                 430 ataagcctgt ccgcagcaga ggctggccca gaggcatcaa gggctggact aggaagatag    1711
gaaatgcgat gaggaagctc tgttgctgta tcccatcaaa agagacatct cacctggggc    1771
agagcaaagt ctccccaaaa aaataagaca caggaagggt gtcaggagaa agagcatctg    1831
gcacggccca gaagatcacc agaggatgcc ggatgctatg attcgacagt tataatattg    1891
gaaaggaccc atgtatagac attgtcctgc aaaagggaac cttgtggaaa ggcatcatgt    1951
tctgggttca gcgtgcttca ctcagagccc cgggtccagc caggggggaag              2001
```

<210> SEQ ID NO 16
<211> LENGTH: 433
<212> TYPE: PRT
<213> ORGANISM: Mus musculus

<400> SEQUENCE: 16

```
Met Glu Lys Phe His Ala Gln Tyr Glu Met Leu Glu Thr Ile Gly Gln
1               5                   10                  15

Gly Gly Cys Ala Gln Val Lys Leu Ala Gln His Arg Leu Thr Gly Thr
            20                  25                  30

His Val Ala Val Lys Val Ile Val Lys Arg Glu Cys Trp Phe Asn Pro
        35                  40                  45

Val Met Ser Glu Ala Glu Leu Leu Met Met Thr Asp His Pro Asn Ile
    50                  55                  60

Ile Ser Leu Leu Gln Val Ile Glu Thr Lys Lys Lys Leu Tyr Leu Ile
65                  70                  75                  80

Met Glu Leu Cys Glu Gly Lys Ser Leu Tyr Gln His Ile Gln Asn Ala
                85                  90                  95

Gly Tyr Leu Gln Glu Asp Glu Ala Cys Pro Leu Phe Lys Gln Leu Leu
            100                 105                 110

Ser Ala Val Asn Tyr Cys His Asn Gln Gly Ile Val His Arg Asp Leu
        115                 120                 125

Thr Pro Asp Asn Ile Met Val Glu Lys Asp Gly Lys Val Lys Ile Ile
    130                 135                 140
```

```
Asp Phe Gly Leu Gly Thr Gln Glu Lys Pro Ala Gln Lys Leu Asn Leu
145                 150                 155                 160

Phe Cys Glu Asn Tyr Pro Phe Ser Thr Pro Glu Val Leu Leu Ser Arg
                165                 170                 175

Pro Tyr Asp Met Arg Lys Ile Asp Val Trp Gly Leu Gly Val Val Leu
            180                 185                 190

Tyr Phe Met Val Thr Gly Lys Ile Leu Phe Asp Ala Ala Ser Ile Glu
        195                 200                 205

Lys Leu Arg Lys Gln Ile Val Ala Gly Lys Cys Ser Val Pro Cys Arg
    210                 215                 220

Leu Ser Val Glu Leu Gln Asp Leu Ile Arg Leu Leu Met Thr Asp Asn
225                 230                 235                 240

Pro Glu Leu Arg Pro Thr Val Ala Glu Val Met Val His Pro Trp Val
                245                 250                 255

Thr Val Gly Ser Gly Val Phe Pro Asp Pro Cys Glu Glu Gln Ile Ser
            260                 265                 270

Leu Lys Pro Asp Pro Ala Ile Val Lys Ala Met Gly Tyr Ile Gly Phe
        275                 280                 285

Arg Ala Gln Glu Ile Glu Asp Ser Leu Arg Gln Arg Lys Phe Asn Glu
    290                 295                 300

Thr Met Ala Ser Tyr Cys Leu Leu Lys Lys Gln Ile Leu Lys Glu Cys
305                 310                 315                 320

Asp Arg Pro Ile Arg Ala Gln Pro Met Asn Pro Ser Leu Thr Pro Phe
                325                 330                 335

Pro Ser Leu Val Asp Thr Pro Thr Ser His Leu Gly Leu Arg Arg Arg
            340                 345                 350

Glu Thr Glu Pro Thr Gly Leu Ser Leu Ser Ala Asn Arg Gln Val Ser
        355                 360                 365

Val Cys Gly Lys Ser Thr Ser Lys Lys Arg Asp Arg Ser Phe Ser Trp
    370                 375                 380

Pro Gly Val Leu Gly Arg Pro Ile His Thr Thr Pro Thr Met Asp Gln
385                 390                 395                 400

Thr His Thr Arg Thr Arg Ser Val Pro Cys Ile Tyr Ser Asn Phe Cys
                405                 410                 415

Thr Ile His Pro Asn Ser Ile Asp Glu Ser Thr Glu Gly His Thr Ser
            420                 425                 430

Ala

<210> SEQ ID NO 17
<211> LENGTH: 1591
<212> TYPE: DNA
<213> ORGANISM: Mus musculus
<220> FEATURE:
<221> NAME/KEY: CDS
<222> LOCATION: (92)..(1390)
<223> OTHER INFORMATION:

<400> SEQUENCE: 17
cttaggtagc atttatactt tgttacctca agtgggctct gggagtcaag cgaagtcaga      60
aaagctcaga tccaagcccc ctttctctga c atg gag aaa ttt cat tct caa      112
                                    Met Glu Lys Phe His Ser Gln
                                      1               5 tat gag atg cta gag act atc ggc cag gga agc tgc gcc cag gtg aag      160
Tyr Glu Met Leu Glu Thr Ile Gly Gln Gly Ser Cys Ala Gln Val Lys
       10                  15                  20
```

```
ctg gcc cag cac cgc ctc aca ggc acc cac gtg gct gtc aaa gtg att      208
Leu Ala Gln His Arg Leu Thr Gly Thr His Val Ala Val Lys Val Ile
     25                  30                  35 gta aag agg gag tgt tgg ttc aac cct gtc atg tct gag gca gag tta      256
Val Lys Arg Glu Cys Trp Phe Asn Pro Val Met Ser Glu Ala Glu Leu
 40                  45                  50                  55 ctg atg atg acc gat cat ccg aat atc atc tct ctc ctt caa gtc atc      304
Leu Met Met Thr Asp His Pro Asn Ile Ile Ser Leu Leu Gln Val Ile
                 60                  65                  70 gag acc aag aag aaa tta tac ctc att atg gag ttg tgc gag ggt aaa      352
Glu Thr Lys Lys Lys Leu Tyr Leu Ile Met Glu Leu Cys Glu Gly Lys
             75                  80                  85 tca ctt tac caa cac atc caa aat gct ggc tac ctg cag gag gat gaa      400
Ser Leu Tyr Gln His Ile Gln Asn Ala Gly Tyr Leu Gln Glu Asp Glu
         90                  95                 100 gca tgc cca tta ttc aag cag ctc tta agt gct gtg aac tac tgc cac      448
Ala Cys Pro Leu Phe Lys Gln Leu Leu Ser Ala Val Asn Tyr Cys His
    105                 110                 115 aac cag ggt ata gtt cac agg gac ctg aca cct gac aat att atg gta      496
Asn Gln Gly Ile Val His Arg Asp Leu Thr Pro Asp Asn Ile Met Val
120                 125                 130                 135 gaa aaa gat ggg aaa gtg aag atc att gat ttt gga ctc ggc acc caa      544
Glu Lys Asp Gly Lys Val Lys Ile Ile Asp Phe Gly Leu Gly Thr Gln
                140                 145                 150 gag aag cca gcg caa aaa ctc aac tta ttc tgt gag aat tac cca ttt      592
Glu Lys Pro Ala Gln Lys Leu Asn Leu Phe Cys Glu Asn Tyr Pro Phe
            155                 160                 165 agt acc cct gag gtc ctc ctt agc aga ccc tat gat atg cgc aag atc      640
Ser Thr Pro Glu Val Leu Leu Ser Arg Pro Tyr Asp Met Arg Lys Ile
        170                 175                 180 gat gtg tgg ggt ctt gga gtt gtg ctg tat ttt atg gta act gga aag      688
Asp Val Trp Gly Leu Gly Val Val Leu Tyr Phe Met Val Thr Gly Lys
    185                 190                 195 att ctg ttt gat gct gcc agc ata gaa aag ctg cga aag caa att gtt      736
Ile Leu Phe Asp Ala Ala Ser Ile Glu Lys Leu Arg Lys Gln Ile Val
200                 205                 210                 215 gca gga aag tgt tct gtt ccc tgt aga ctg tca gta gag ctc caa gac      784
Ala Gly Lys Cys Ser Val Pro Cys Arg Leu Ser Val Glu Leu Gln Asp
                220                 225                 230 ctg att aga ctt tta atg acg gac aac ccc gaa ctt agg ccc act gtt      832
Leu Ile Arg Leu Leu Met Thr Asp Asn Pro Glu Leu Arg Pro Thr Val
            235                 240                 245 gct gaa gtt atg gtg cat ccc tgg gtc aca gaa ggc tca ggg gtg ttc      880
Ala Glu Val Met Val His Pro Trp Val Thr Glu Gly Ser Gly Val Phe
        250                 255                 260 cca gat cct tgt gaa gaa cag ata tcc ctc aag cca gac cct gcg att      928
Pro Asp Pro Cys Glu Glu Gln Ile Ser Leu Lys Pro Asp Pro Ala Ile
    265                 270                 275 gta aaa gca atg gga tat atc ggg ttc cga gct caa gaa att gaa gat      976
Val Lys Ala Met Gly Tyr Ile Gly Phe Arg Ala Gln Glu Ile Glu Asp
280                 285                 290                 295 tcg tta cgt cag aga aaa ttc aac gaa acc atg gca tct tat tgt cta     1024
Ser Leu Arg Gln Arg Lys Phe Asn Glu Thr Met Ala Ser Tyr Cys Leu
                300                 305                 310 ctg aaa aaa cag att ctt aag gaa tgt gac agg cca atc cgg gct cag     1072
Leu Lys Lys Gln Ile Leu Lys Glu Cys Asp Arg Pro Ile Arg Ala Gln
            315                 320                 325 ccc atg aat cca tcg ctg acc cca ttc cct tcc ctt gtt gat act cct     1120
Pro Met Asn Pro Ser Leu Thr Pro Phe Pro Ser Leu Val Asp Thr Pro
        330                 335                 340
```

```
act tcc cat ctc gga ctt cgg agg aga gag act gaa ccc aca ggt ctc      1168
Thr Ser His Leu Gly Leu Arg Arg Arg Glu Thr Glu Pro Thr Gly Leu
    345                 350                 355 agc tta tct gcc aat agg caa gtg tct gtc tgt ggc aag agt act agt      1216
Ser Leu Ser Ala Asn Arg Gln Val Ser Val Cys Gly Lys Ser Thr Ser
360                 365                 370                 375 aag aaa aga gac aga agt ttc agt tgg ccc ggt gtt cta ggc agg ccg      1264
Lys Lys Arg Asp Arg Ser Phe Ser Trp Pro Gly Val Leu Gly Arg Pro
                380                 385                 390 atc cac aca aca ccc aca atg gac caa aca cac acc cgt act agg agt      1312
Ile His Thr Thr Pro Thr Met Asp Gln Thr His Thr Arg Thr Arg Ser
            395                 400                 405 gtt ccc tgc att tac tca aat ttt tgc aca atc cat cca aac agc atc      1360
Val Pro Cys Ile Tyr Ser Asn Phe Cys Thr Ile His Pro Asn Ser Ile
        410                 415                 420 gat gag agt aca gaa ggc cac acc agt gcc taagcagagg ataagcctgt        1410
Asp Glu Ser Thr Glu Gly His Thr Ser Ala
    425                 430 ccgcagcaga ggctggccca gaggcatcaa gggctggact aggaagatag gaaatgcgat    1470
gaggaagctc tgttgctgta tcccatcaaa agagacatct cacctggggc agagcagagt   1530
gtccccaaaa aaataagaca caggaagggt gtcaggagaa cgagcatgcg gcacggccca   1590
g                                                                    1591

<210> SEQ ID NO 18
<211> LENGTH: 433
<212> TYPE: PRT
<213> ORGANISM: Mus musculus

<400> SEQUENCE: 18

Met Glu Lys Phe His Ser Gln Tyr Glu Met Leu Glu Thr Ile Gly Gln
1               5                   10                  15

Gly Ser Cys Ala Gln Val Lys Leu Ala Gln His Arg Leu Thr Gly Thr
            20                  25                  30

His Val Ala Val Lys Val Ile Val Lys Arg Glu Cys Trp Phe Asn Pro
        35                  40                  45

Val Met Ser Glu Ala Glu Leu Leu Met Met Thr Asp His Pro Asn Ile
    50                  55                  60

Ile Ser Leu Leu Gln Val Ile Glu Thr Lys Lys Lys Leu Tyr Leu Ile
65                  70                  75                  80

Met Glu Leu Cys Glu Gly Lys Ser Leu Tyr Gln His Ile Gln Asn Ala
                85                  90                  95

Gly Tyr Leu Gln Glu Asp Glu Ala Cys Pro Leu Phe Lys Gln Leu Leu
            100                 105                 110

Ser Ala Val Asn Tyr Cys His His Asn Gln Gly Ile Val His Arg Asp Leu
        115                 120                 125

Thr Pro Asp Asn Ile Met Val Glu Lys Asp Gly Lys Val Lys Ile Ile
    130                 135                 140

Asp Phe Gly Leu Gly Thr Gln Glu Lys Pro Ala Gln Lys Leu Asn Leu
145                 150                 155                 160

Phe Cys Glu Asn Tyr Pro Phe Ser Thr Pro Glu Val Leu Leu Ser Arg
                165                 170                 175

Pro Tyr Asp Met Arg Lys Ile Asp Val Trp Gly Leu Gly Val Val Leu
            180                 185                 190

Tyr Phe Met Val Thr Gly Lys Ile Leu Phe Asp Ala Ala Ser Ile Glu
        195                 200                 205
```

```
Lys Leu Arg Lys Gln Ile Val Ala Gly Lys Cys Ser Val Pro Cys Arg
    210                 215                 220
Leu Ser Val Glu Leu Gln Asp Leu Ile Arg Leu Leu Met Thr Asp Asn
225                 230                 235                 240
Pro Glu Leu Arg Pro Thr Val Ala Glu Val Met Val His Pro Trp Val
                245                 250                 255
Thr Glu Gly Ser Gly Val Phe Pro Asp Pro Cys Glu Glu Gln Ile Ser
            260                 265                 270
Leu Lys Pro Asp Pro Ala Ile Val Lys Ala Met Gly Tyr Ile Gly Phe
        275                 280                 285
Arg Ala Gln Glu Ile Glu Asp Ser Leu Arg Gln Arg Lys Phe Asn Glu
    290                 295                 300
Thr Met Ala Ser Tyr Cys Leu Leu Lys Lys Gln Ile Leu Lys Glu Cys
305                 310                 315                 320
Asp Arg Pro Ile Arg Ala Gln Pro Met Asn Pro Ser Leu Thr Pro Phe
                325                 330                 335
Pro Ser Leu Val Asp Thr Pro Ser His Leu Gly Leu Arg Arg
            340                 345                 350
Glu Thr Glu Pro Thr Gly Leu Ser Leu Ser Ala Asn Arg Gln Val Ser
        355                 360                 365
Val Cys Gly Lys Ser Thr Ser Lys Lys Arg Asp Arg Ser Phe Ser Trp
    370                 375                 380
Pro Gly Val Leu Gly Arg Pro Ile His Thr Thr Pro Thr Met Asp Gln
385                 390                 395                 400
Thr His Thr Arg Thr Arg Ser Val Pro Cys Ile Tyr Ser Asn Phe Cys
                405                 410                 415
Thr Ile His Pro Asn Ser Ile Asp Glu Ser Thr Glu Gly His Thr Ser
            420                 425                 430
Ala

<210> SEQ ID NO 19
<211> LENGTH: 3641
<212> TYPE: DNA
<213> ORGANISM: Mus musculus

<400> SEQUENCE: 19
gtacattctg tatttgaatg tatctatgtt actcatgtct gtgtcaactg gcagattata    60
cttatgtata tgtatatgta tatgtatatg tatatgtata tgtatatgta tatgtatatg   120
tatatgtata tggtgcaatg catggggaag ctaggtctag acaccttggg aaaatagtta   180
aattgaacct gccaacagat ccagcatccc agaaggtatc tcctgtgtgt atcctgcaca   240
ttgaacaagg aggagaactg accatgctag ggagaggaag tgggagaagg aagaggagga   300
gatgctgagg gaggagaggg tggtatgtgg tggaagctag gagaagaggg gaagaggttc   360
agacaggagg aggcaacttg ggggagcagt gtgaaacagg gtaacccag ctggagagat    420
gccctgtgca gctgaggttc tcagagtccc tctcacgtgt gctttggcat tttagaagat   480
caccagagga tgccggatgc tacgattcaa cagttataat attggaaagg acccatgtat   540
agacatggac ctgcaaaagg gaaccttgtg gaaaggcatc atgttctggg ttcagcatgt   600
ttcactcaga gccccgggtc cagccagggg gaagaaagca aatgatgaaa tcccagatgg   660
tgtctgggat caccattcag agcagggggct gaaagcctgt ccaaagctgg tagagacaga   720
agcccctctg cctacccagg gtcataatca gactcctgct ctgagaataa aatagatgtt   780
```

-continued

```
tgtgaaagat gacctcggag gttttcctgc ctcttcttta cataggaaaa acgttcctgt    840
ggtgttcaaa atccccaggt agaacaactt cacaccccaa accaccagat cattaaaagt    900
gcctttgaag ggaccaagct ttcaggtacc tgaagtgggg gagtgtagaa gctgggtgtg    960
gactctgggt ccttctggac ccagcagcat gatcagaagg accagagaga acattagata   1020
caatcagctt gacccacttc cacagaggca agcccggtca ccctgtgaat tcctgcagat   1080
gtggcatgtg ttgcatccca gggtctctgc ctatgtaaga tcagagagcc tggagttagc   1140
taaatatcag tgtcccttgg cctcaaggga aagggaggt tggattccag ccctagcatg   1200
gtcctctaat aagcagtccc cctcaaatgc agacagcaag gtctacatga tgttcacagc   1260
tcccctggcc taaaaccatc ctgtgattga tactacaaac caggaagcag ggacttgaag   1320
ttgagatcac tgactcaggc tagggagggc tccagggcac ctgatctcaa ctacaatatc   1380
agaagctgag ccacaatgac cagtggtggc aggttttctt ttctgctctc aggcccggca   1440
atgaagtcca catatgaggc tctttcctcc cagtcgtact gtctgcagat atgaggttcc   1500
tcaacagtgg attcaaaact ccagaaagga aagagctaca cattgtactc tgaaaagcag   1560
aggcccattc agggtttgag caaatcatcg ctcaatagtt agattccggg tacactatgt   1620
gctcaggagt aacacagcag catggggttct gtgagctgaa tgtggttcaa agtctgtttc   1680
aagtgtgtca gcagcacagc taatctgttc acggtgtcca cagagcttct ggtcctcgaa   1740
tgtgcctgct ccacctttgg accttagagt gtaaagtgag ccctacacgc agcacggact   1800
tggttttcta tacatcatgc caacctctgt gtttgatgac ggggcgggag tgggggtat   1860 gtggtgggag aggtgagaga aaggagagag agagagtcgg gtagagaaag gaaggaagg   1920 agggagggga gaggtaaaag gaaaagcttc tatgtacatg gtcatggata tgtcccacca   1980
tgtgtgtgga ggttagagga cattttctc agatttacct tctactttgt ttgaaactag   2040
gtgtgtggtt tgagactaca tatgccaagg tgcctgcccc acaagctccc agacattttc   2100
ctgtctctaa tgctttccct gcttcctagg agctctgata ttgcaagtgt gtgctcagtg   2160
tccacatgca ttcaatctca ggccctccct ctttgcaggg caggtgttct aaccacttgt   2220
ctatccccta aggcccctcc catgtttttg atgagaatcc aaaaccttgg aaattatgag   2280
aaacacctct ttctgtcatc ctcacaggtg gtaataagct gccctattat atttcataag   2340
cagagttggg gtccaggaat caccccacaa accactcagc catctaagtc aagcagggat   2400
agtttattga acatataccc tgggactgat tgatcaggga tgcagatcag actcagaagt   2460
ttagactgca accctgtttc ccaagggttg cttataaaag gcaaaaacca caggagctca   2520
cggcaaccat aaaagctcac acacaggtgc aggaagtctt gccaggcagt tgggtggctg   2580
gttcgagtcc aaccttattt ttgctaactg tacaaagcaa ttccaactga ctttagttat   2640
tatgattggc cctaaacgag ggcaagggtc ggggtgttt gcaagaacac caaagcataa   2700
agcttaatgg gatatgcagt taatggttag ctgggcatga gaaaggtcct ctgtaataat   2760
ttaagatggc aggctacagg tataaaatga aatggctaca gtaatgtcag aaaggcagca   2820
gccacctacg tcttaatgag taggacccttt ttatttattt atttatttat ttatttattt   2880
atttatttaa tgttaagtgg tggcatcatc ctggacccat cagttggaat gcaaaggtga   2940
cacacagagt gtagacatga ggactttaaa gcaggaggca cagcaaacat tcaaaccaga   3000
gacctaagga catcagcatg gcctagaggt tttgatttct aaaagcctaa tgtcagtctc   3060
catagcccac ttaagccaga gccttgagtc cctcctagcc ctgccaggac aggtcctgat   3120
atgaccacat gaggagtgac tatgatgcgg cccagccagc aggtttaagc tgtggccaca   3180
```

```
cctagatttc tttgagtgtg ttgagaggag ttggtggagt tggtggagtt tggtggattt    3240
ggtggagttg gtggtgccct ttgcgatttc gttgtatcta gtgagccgtg tgtggatttt    3300
gtgtttgatt ggttcgtgtg tgagcttttg tgtgtgtgtg tgtgtgtgtg tgtgtgtgtg    3360
tgtgtgtgtg tgtgtgtgta gatcagtgtg tgtttgggag gagcttgtgt gtgtgagttg    3420
tgttttaagt ttatttgcgt gtgagtacct ttgggttttt gtgtgtgtct gtgtgtgttt    3480
gtgtgtgtat aactgtgggt gactgtaagt gcacctgtgt gtttgtacgt gagtgtgtaa    3540
gactgtgtgt gtgcacaaga gcgtgtgtag gtgcacgtgt tgtaggtgtg agaacacctg    3600
ttgtgtttag gccatcagtc agcttggtca ttgtttctaa g                       3641
```

<210> SEQ ID NO 20
<211> LENGTH: 2827
<212> TYPE: DNA
<213> ORGANISM: Mus musculus
<220> FEATURE:
<221> NAME/KEY: CDS
<222> LOCATION: (2002)..(2481)
<223> OTHER INFORMATION:

<400> SEQUENCE: 20

```
gagaggagtt ggtggagttg gtggagtttg gtggatttgg tggagttggt ggtgcccttt      60
gcgatttcgt tgtatctagt gagccgtgtg tggattttgt gtttgattgg ttcgtgtgtg     120
agcttttgtg tgtgtgtgtg tgtgtgtgtg tgtgtgtgtg tgtgtgtgtg tgtgtagatc     180
agtgtgtgtt tgggaggagc ttgtgtgtgt gagttgtgtt ttaagtttat ttgcgtgtga     240
gtacctttgg gttttgtgt gtgtctgtgt gtgtttgtgt gtgtataact gtgggtgact     300
gtaagtgcac ctgtgtgttt gtacgtgagt gtgtaagact gtgtgtgtgc acaagagcgt     360
gtgtaggtgc acgtgttgta ggtgtgagaa cacctgttgt gtttaggcca tcagtcagct     420
tggtcattgt ttctaaggta gcatttatac tttgttacct caagtgggct ctgggagtca     480
acagaagtca gaaaagctca gatccaagcc ccctttttct gacatggaga aatttcatgc     540
tcaatatgag atgctagaga ctattggcca gggaggctgc gcccaggtga agctggcccg     600
acaccgcctc acaggcaccc acgtggctgt caaagtgatt gtaaagaggg agtgttggtt     660
caaccctgtc atgtctgagg cagagttact gatgatgacc gatcatccga atatcatctc     720
tctccttcaa gtcattgaga ccaagaagaa agtatacctc attatggagt tgtgcgaggg     780
taaatcactt taccaacaca tccaaaatgc tggctacctg caggaggatg aagcacgccc     840
attattcaag cagctcttaa gtgctatgaa ctactgccac aacagggta tagttcacag     900 ggacctgaca cctgacaata ttatggtaga aaaagatggg aaagtgaaga tcattgattt     960
tggactcggc acccaagaga agccagggca aaaccacaac ttattctgtg agatttaccc    1020
atttagtact cctgaggtgc tctttaacag accctatgat atgcgcaaga tcgatgtgtg    1080
gggtcttgga gttgtgctgt attttatggt aactggaaag attctgtttg atactgccag    1140
cgtagaaaag ctgcgaaagc aaattgttgc agaaaagtgt tctgttccct gtagactgtc    1200
agtagagctc caagacctga ttagacttttt aatgacggac atccccgaac ttaggcccac    1260
tgttgctgaa gttatggtgc atccctgggt cacagaaggc tcaggggtgt taccagatcc    1320
ttgtgaagaa catataccc tcaagccaga ccctgcgatt gcaaaagcaa tgggattat    1380 cgggttccaa gctcaagaca ttgaagattc gttatgtcag agaaaattca cgaaaaccat    1440
ggcatcttat tgtctactga aaaaacagat tcttaaggaa tgtgacaggc caatccgggc    1500
```

```
tcagcccatg aatccatctg tgaccccact ctcttccctt gttgatgctc ctactttcca    1560
tctcggactt cggaggacag agactgaacc cacaggtctc agattatctg acaataagga    1620
agtgcctgtc tgtggcaata gtactagtaa gaaaagagag agaagtttca gtgggccggg    1680
tgttctcagc aggccgatta acacaacacc cacaatggac caaacacaca cccgtacttg    1740
gagtggtccc tgcatttact caaatgtttg cacaatccat ccaaacagca tcaatgagag    1800
tacagaaggc cacatcagta cctcagcaga ggataagcct gtccacagca gaggctggcc    1860
cagaggcatc aagggctgga ctaggaagat aggaaatgca atgaggaagc tctgttgctg    1920
tatcccatcc aaagagacat ctcacctggg gcagagaaga gtctgcccaa aaatttaaga    1980
cacaggaagg atgtcaggag a atg agc atc cag cat ggc cca gcc ttt cag     2031
                        Met Ser Ile Gln His Gly Pro Ala Phe Gln
                         1               5                  10 acc gaa ggc aag ctc tac ctg atc ctg gac ttc ctg cgg gga ggt gac     2079
Thr Glu Gly Lys Leu Tyr Leu Ile Leu Asp Phe Leu Arg Gly Gly Asp
             15                  20                  25 ctc ttc acc agg ctt tcc aaa gag gtg atg ttc acg gag gag gat gtc     2127
Leu Phe Thr Arg Leu Ser Lys Glu Val Met Phe Thr Glu Glu Asp Val
         30                  35                  40 aag ttc tac ctg gct gag ctg gcc ttg gct cta gac cac ctc cat ggc     2175
Lys Phe Tyr Leu Ala Glu Leu Ala Leu Ala Leu Asp His Leu His Gly
     45                  50                  55 ctg ggg atc atc tac agg gat ctg aag cca gag aat atc ctc ctg gat     2223
Leu Gly Ile Ile Tyr Arg Asp Leu Lys Pro Glu Asn Ile Leu Leu Asp
 60                  65                  70 gaa gag gga cat att aag atc aca gat ttt ggc ttg agc aag gag gcc     2271
Glu Glu Gly His Ile Lys Ile Thr Asp Phe Gly Leu Ser Lys Glu Ala
75                  80                  85                  90 acc gac cat gac aag aga gcc tat tca ttt tgt ggg act att gaa tac     2319
Thr Asp His Asp Lys Arg Ala Tyr Ser Phe Cys Gly Thr Ile Glu Tyr
                 95                 100                 105 atg gcg ccc gag gtg gtg aac cgg cgt gga cac aca cag agt gcc gac     2367
Met Ala Pro Glu Val Val Asn Arg Arg Gly His Thr Gln Ser Ala Asp
             110                 115                 120 tgg tgg tcc ttc ggt gtg ctc atg ttc gag atg ctc aca ggg tcc ctg     2415
Trp Trp Ser Phe Gly Val Leu Met Phe Glu Met Leu Thr Gly Ser Leu
         125                 130                 135 cca ttc cag ggg aag gac agg aag gaa aca atg gcc cgc atc ctc aaa     2463
Pro Phe Gln Gly Lys Asp Arg Lys Glu Thr Met Ala Arg Ile Leu Lys
     140                 145                 150 gca aag ctg ggt atg cct tagttcctca gtgcggaggc tcagagcctg           2511
Ala Lys Leu Gly Met Pro
155                 160 ctcagggccc tttcaagcg aaccctgc aaccggctag gtaagggtcc ctgtgacacc     2571
cccaccccag gaatgcaatg aggctgccct ctagacccc cttaggaatg tgagaggcca   2631
ccattctgtt ccccacggga tgtggaggac ttcctcctta tgccccaact ctgaactgta  2691 tgctttcct tgctaaggtt gcaggaagca gaggtacccc gacgctgggg aaacactcac   2751
atgtggcctg gcgcccacag gcacgtggac ttatcaggat tgctgaaagg catttgaaaa  2811
aaaaaaaaaa aaaaaa                                                   2827

<210> SEQ ID NO 21
<211> LENGTH: 160
<212> TYPE: PRT
<213> ORGANISM: Mus musculus

<400> SEQUENCE: 21
```

-continued

```
Met Ser Ile Gln His Gly Pro Ala Phe Gln Thr Glu Gly Lys Leu Tyr
1               5                   10                  15
Leu Ile Leu Asp Phe Leu Arg Gly Gly Asp Leu Phe Thr Arg Leu Ser
                20                  25                  30
Lys Glu Val Met Phe Thr Glu Glu Asp Val Lys Phe Tyr Leu Ala Glu
                35                  40                  45
Leu Ala Leu Ala Leu Asp His Leu His Gly Leu Gly Ile Ile Tyr Arg
            50                  55                  60
Asp Leu Lys Pro Glu Asn Ile Leu Leu Asp Glu Glu Gly His Ile Lys
65                  70                  75                  80
Ile Thr Asp Phe Gly Leu Ser Lys Glu Ala Thr Asp His Asp Lys Arg
                85                  90                  95
Ala Tyr Ser Phe Cys Gly Thr Ile Glu Tyr Met Ala Pro Glu Val Val
                100                 105                 110
Asn Arg Arg Gly His Thr Gln Ser Ala Asp Trp Trp Ser Phe Gly Val
                115                 120                 125
Leu Met Phe Glu Met Leu Thr Gly Ser Leu Pro Phe Gln Gly Lys Asp
                130                 135                 140
Arg Lys Glu Thr Met Ala Arg Ile Leu Lys Ala Lys Leu Gly Met Pro
145                 150                 155                 160

<210> SEQ ID NO 22
<211> LENGTH: 17
<212> TYPE: DNA
<213> ORGANISM: Artificial Sequence
<220> FEATURE:
<223> OTHER INFORMATION: Primer

<400> SEQUENCE: 22
atgggcagag caatggt                                                  17

<210> SEQ ID NO 23
<211> LENGTH: 17
<212> TYPE: DNA
<213> ORGANISM: Artificial Sequence
<220> FEATURE:
<223> OTHER INFORMATION: Primer

<400> SEQUENCE: 23
caggttcagg gggaggt                                                  17

<210> SEQ ID NO 24
<211> LENGTH: 17
<212> TYPE: DNA
<213> ORGANISM: Artificial Sequence
<220> FEATURE:
<223> OTHER INFORMATION: Primer

<400> SEQUENCE: 24
cttccccctg gctggac                                                  17

<210> SEQ ID NO 25
<211> LENGTH: 15
<212> TYPE: DNA
<213> ORGANISM: Artificial Sequence
<220> FEATURE:
<223> OTHER INFORMATION: Primer

<400> SEQUENCE: 25
gccaaccagg ggata                                                    15
```

<210> SEQ ID NO 26
<211> LENGTH: 18
<212> TYPE: DNA
<213> ORGANISM: Artificial Sequence
<220> FEATURE:
<223> OTHER INFORMATION: Primer

<400> SEQUENCE: 26
ctgtccggtc atactctt                                               18

<210> SEQ ID NO 27
<211> LENGTH: 18
<212> TYPE: DNA
<213> ORGANISM: Artificial Sequence
<220> FEATURE:
<223> OTHER INFORMATION: Primer

<400> SEQUENCE: 27
cttgtgtcct tgggagaa                                               18

<210> SEQ ID NO 28
<211> LENGTH: 17
<212> TYPE: DNA
<213> ORGANISM: Artificial Sequence
<220> FEATURE:
<223> OTHER INFORMATION: Primer

<400> SEQUENCE: 28
ggtgccatcc acttcac                                                17

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
cgcagcaaaa gcaggagcag                                             20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
catcggacgg tggcattttt                                             20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
tgctcaagcc aaaatctgtg                                             20

<210> SEQ ID NO 32
<211> LENGTH: 20
<212> TYPE: DNA
<213> ORGANISM: Artificial Sequence
<220> FEATURE:
<223> OTHER INFORMATION: Primer

```
<400> SEQUENCE: 32
atggcctggg gatcatctac                                              20

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
caccgcttgc acactgagta                                              20

<210> SEQ ID NO 34
<211> LENGTH: 18
<212> TYPE: DNA
<213> ORGANISM: Artificial Sequence
<220> FEATURE:
<223> OTHER INFORMATION: Primer

<400> SEQUENCE: 34
atcgatgtgt ggggtctt                                                18

<210> SEQ ID NO 35
<211> LENGTH: 18
<212> TYPE: DNA
<213> ORGANISM: Artificial Sequence
<220> FEATURE:
<223> OTHER INFORMATION: Primer

<400> SEQUENCE: 35
gtttgggagg agcttgtg                                                18

<210> SEQ ID NO 36
<211> LENGTH: 18
<212> TYPE: DNA
<213> ORGANISM: Artificial Sequence
<220> FEATURE:
<223> OTHER INFORMATION: Primer

<400> SEQUENCE: 36
ctagtccagc ccttgatg                                                18

<210> SEQ ID NO 37
<211> LENGTH: 18
<212> TYPE: DNA
<213> ORGANISM: Artificial Sequence
<220> FEATURE:
<223> OTHER INFORMATION: Primer

<400> SEQUENCE: 37
tggcatctta ttgtctac                                                18

<210> SEQ ID NO 38
<211> LENGTH: 18
<212> TYPE: DNA
<213> ORGANISM: Artificial Sequence
<220> FEATURE:
<223> OTHER INFORMATION: Primer

<400> SEQUENCE: 38
ccaagcccct ttttctga                                                18

<210> SEQ ID NO 39
```

```
<211> LENGTH: 24
<212> TYPE: DNA
<213> ORGANISM: Artificial Sequence
<220> FEATURE:
<223> OTHER INFORMATION: Primer

<400> SEQUENCE: 39
atttaggtga cactatagaa ggta                                              24

<210> SEQ ID NO 40
<211> LENGTH: 15
<212> TYPE: DNA
<213> ORGANISM: Artificial Sequence
<220> FEATURE:
<223> OTHER INFORMATION: Primer

<400> SEQUENCE: 40 cccccttttat ctgac                                                       15

<210> SEQ ID NO 41
<211> LENGTH: 18
<212> TYPE: DNA
<213> ORGANISM: Artificial Sequence
<220> FEATURE:
<223> OTHER INFORMATION: Primer

<400> SEQUENCE: 41
tatgctggca gcatcaaa                                                     18

<210> SEQ ID NO 42
<211> LENGTH: 18
<212> TYPE: DNA
<213> ORGANISM: Artificial Sequence
<220> FEATURE:
<223> OTHER INFORMATION: Primer

<400> SEQUENCE: 42
atgtaagtgg catggagt                                                     18

<210> SEQ ID NO 43
<211> LENGTH: 17
<212> TYPE: DNA
<213> ORGANISM: Artificial Sequence
<220> FEATURE:
<223> OTHER INFORMATION: Primer

<400> SEQUENCE: 43
gcacaccgaa aataaaa                                                      17

<210> SEQ ID NO 44
<211> LENGTH: 42
<212> TYPE: DNA
<213> ORGANISM: Artificial Sequence
<220> FEATURE:
<223> OTHER INFORMATION: Primer

<400> SEQUENCE: 44
ggcgtagtct gggacgtcgt atgggtacat gtcagaaaaa gg                          42

<210> SEQ ID NO 45
<211> LENGTH: 45
<212> TYPE: DNA
<213> ORGANISM: Artificial Sequence
<220> FEATURE:
<223> OTHER INFORMATION: Primer

<400> SEQUENCE: 45
```
atgtacccat acgacgtccc agactacgcc atggagaaat ttcat        45

<210> SEQ ID NO 46
<211> LENGTH: 18
<212> TYPE: DNA
<213> ORGANISM: Artificial Sequence
<220> FEATURE:
<223> OTHER INFORMATION: Primer

<400> SEQUENCE: 46
accctggttg tggcagta        18

<210> SEQ ID NO 47
<211> LENGTH: 17
<212> TYPE: DNA
<213> ORGANISM: Artificial Sequence
<220> FEATURE:
<223> OTHER INFORMATION: Primer

<400> SEQUENCE: 47
cagcccatga atccatc        17

<210> SEQ ID NO 48
<211> LENGTH: 17
<212> TYPE: DNA
<213> ORGANISM: Artificial Sequence
<220> FEATURE:
<223> OTHER INFORMATION: Primer

<400> SEQUENCE: 48
tgccttcggt ctgaaag        17

<210> SEQ ID NO 49
<211> LENGTH: 31
<212> TYPE: DNA
<213> ORGANISM: Artificial Sequence
<220> FEATURE:
<223> OTHER INFORMATION: Primer

<400> SEQUENCE: 49
aggaaagctt gcccaagaga atagttaatg c        31

<210> SEQ ID NO 50
<211> LENGTH: 30
<212> TYPE: DNA
<213> ORGANISM: Artificial Sequence
<220> FEATURE:
<223> OTHER INFORMATION: Primer

<400> SEQUENCE: 50
aggcgaattc catatcatca atgccaccag        30

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
tccaccccac tacctgactc        20

<210> SEQ ID NO 52
<211> LENGTH: 20
<212> TYPE: DNA

—continued

```
<213> ORGANISM: Artificial Sequence
<220> FEATURE:
<223> OTHER INFORMATION: Primer

<400> SEQUENCE: 52
cccttctgat gaccacaggt                                              20

<210> SEQ ID NO 53
<211> LENGTH: 9
<212> TYPE: PRT
<213> ORGANISM: Artificial Sequence
<220> FEATURE:
<223> OTHER INFORMATION: Peptide

<400> SEQUENCE: 53

Tyr Pro Tyr Asp Val Pro Asp Tyr Ala
1               5
```